(12) United States Patent
Tanaka et al.

(10) Patent No.: US 9,306,169 B2
(45) Date of Patent: Apr. 5, 2016

(54) ELECTRONIC DEVICE, POLYMER COMPOUND, ORGANIC COMPOUND, AND METHOD OF PRODUCING POLYMER COMPOUND

(75) Inventors: Masanobu Tanaka, Ibaraki (JP); Rui Ishikawa, Ibaraki (JP); Ken Sakakibara, Ibaraki (JP); Hideyuki Higashimura, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/007,668

(22) PCT Filed: Mar. 27, 2012

(86) PCT No.: PCT/JP2012/058021
§ 371 (c)(1),
(2), (4) Date: Sep. 26, 2013

(87) PCT Pub. No.: WO2012/133465
PCT Pub. Date: Oct. 4, 2012

(65) Prior Publication Data
US 2014/0024785 A1 Jan. 23, 2014

(30) Foreign Application Priority Data
Mar. 28, 2011 (JP) .................. 2011-070410

(51) Int. Cl.
*H01L 51/00* (2006.01)
*C07C 69/94* (2006.01)
*C08G 61/02* (2006.01)
*C08G 61/12* (2006.01)
(Continued)

(52) U.S. Cl.
CPC ............ *H01L 51/0039* (2013.01); *C07C 69/76* (2013.01); *C07C 69/94* (2013.01); *C08G 61/02* (2013.01); *C08G 61/12* (2013.01); *C08G 61/122* (2013.01); *H01L 51/0035* (2013.01); *H01L 51/0043* (2013.01); *C07C 2103/18* (2013.01); *C08G 2261/124* (2013.01); *C08G 2261/142* (2013.01); *C08G 2261/1424* (2013.01); *C08G 2261/1426* (2013.01); *C08G 2261/3142* (2013.01); *C08G 2261/3221* (2013.01); *C08G 2261/411* (2013.01); *C08G 2261/512* (2013.01); *H01L 51/5056* (2013.01); *H01L 51/5088* (2013.01)

(58) Field of Classification Search
CPC ...... C08F 12/34; C08F 112/34; C08F 212/34; H01L 51/0039; H01L 51/0043; H01L 51/0035; H01L 51/5088; H01L 51/5056; C07C 69/76; C07C 69/94; C07C 2103/18; C08G 61/02; C08G 61/122; C08G 61/12; C08G 2261/3221; C08G 2261/1424; C08G 2261/142; C08G 2261/411; C08G 2261/124; C08G 2261/3142; C08G 2261/1426; C08G 2261/512
USPC ......... 526/239, 240, 242, 274, 280, 286, 287, 526/290, 293, 296, 299, 336
See application file for complete search history.

(56) References Cited

U.S. PATENT DOCUMENTS

| 6,259,201 | B1 | 7/2001 | Lee et al. |
| 6,538,263 | B1 | 3/2003 | Park et al. |
| 7,118,810 | B2 | 10/2006 | Park et al. |

(Continued)

FOREIGN PATENT DOCUMENTS

| CN | 101085857 A | 12/2007 |
| CN | 101437865 A | 5/2009 |

(Continued)

OTHER PUBLICATIONS

Extended European Search Report issued Jul. 28, 2014 in EP Application No. 12764423.5.

(Continued)

*Primary Examiner* — Robert Jones, Jr.
(74) *Attorney, Agent, or Firm* — Panitch Schwarze Belisario & Nadel LLP

(57) ABSTRACT

An electronic device that serves as a high-brightness electroluminescent device includes a layer containing a polymer compound having one or more structural units selected from a structural unit represented by formula (1) and a structural unit represented by formula (7) as a charge injection layer and/or a charge transport layer:

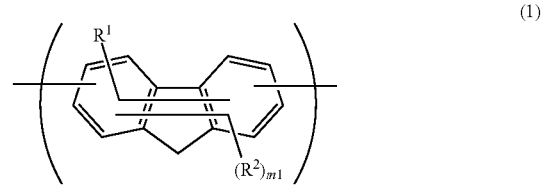

(1)

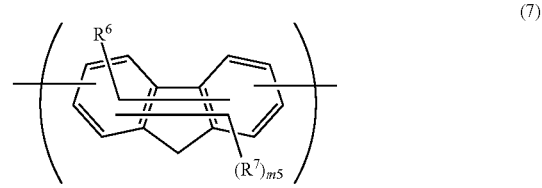

(7)

Wherein $R^1$, $R^2$, $R^6$ and $R^7$ represent certain groups; m1 and m5 represent an integer of 0 or more; when $R^2$ and $R^7$ are plurally present, they may be the same or different; and a hydrogen atom in formula (1) or (7) may be replaced with a substituent other than the certain groups.

10 Claims, No Drawings

(51) Int. Cl.
*C07C 69/76* (2006.01)
*H01L 51/50* (2006.01)

(56) References Cited

U.S. PATENT DOCUMENTS

| | | |
|---|---|---|
| 7,436,649 B2 | 10/2008 | Omura |
| 8,158,444 B2 | 4/2012 | Gaylord et al. |
| 8,354,239 B2 | 1/2013 | Gaylord et al. |
| 8,815,414 B2 | 8/2014 | Kobayashi et al. |
| 2002/0037432 A1 | 3/2002 | Park et al. |
| 2006/0094859 A1 | 5/2006 | Marrocco et al. |
| 2008/0020208 A1 | 1/2008 | Lee et al. |
| 2008/0265756 A1 | 10/2008 | McKiernan et al. |
| 2009/0152531 A1 | 6/2009 | Towns et al. |
| 2011/0006294 A1 | 1/2011 | Tanaka et al. |
| 2012/0032121 A1 | 2/2012 | Higashimura et al. |
| 2012/0181529 A1 | 7/2012 | Tanaka et al. |
| 2013/0018155 A1 | 1/2013 | Tanaka et al. |
| 2013/0099224 A1 | 4/2013 | Iljima et al. |

FOREIGN PATENT DOCUMENTS

| | | |
|---|---|---|
| CN | 101516960 A | 8/2009 |
| EP | 2597932 A1 | 5/2013 |
| EP | 2692796 A1 | 2/2014 |
| JP | 2003-530676 A | 10/2003 |
| JP | 2007-327058 A | 12/2007 |
| JP | 2008516040 A | 5/2008 |
| JP | 2008-519140 A | 6/2008 |
| JP | 2009501259 A | 1/2009 |
| JP | 2010261102 A | 11/2010 |
| JP | 2010-540885 A | 12/2010 |
| WO | 2005064702 A1 | 7/2005 |
| WO | 2006128352 A1 | 12/2006 |
| WO | 2011126063 A1 | 10/2011 |
| WO | 2012002284 A1 | 1/2012 |
| WO | 2012011418 A1 | 1/2012 |
| WO | 2012046736 A1 | 4/2012 |

OTHER PUBLICATIONS

Int'l Search Report issued Jun. 5, 2012 in Int'l Application No. PCT/JP2012/058021.
Liu et al, "Anionic benzothiadiazole containing polyfluorene and oligofluorene as organic sensitizers for dye-sensitized solar cells," Chem. Commun., vol. 32, pp. 3789-3791 (Jun. 23, 2008).
Burrows et al, "Aqueous Solution Behavior of Anionic Fluorene-co-thiophene-Based Conjugated Polyelectrolytes," Applied Materials & Interfaces, vol. 1, No. 4, pp. 864-874 (2009).
Office Action issued Jul. 10, 2015 in Cn Application No. 201280015865.4.
Office Action issued Dec. 2, 2015 in TW Application No. 101110519.
Office Action issued Dec. 15, 2015 in JP Application No. 2012072604.

ELECTRONIC DEVICE, POLYMER COMPOUND, ORGANIC COMPOUND, AND METHOD OF PRODUCING POLYMER COMPOUND

CROSS-REFERENCE TO RELATED APPLICATION

This application is a Section 371 of International Application No. PCT/JP2012/058021, filed Mar. 27, 2012, which was published in the Japanese language on Oct. 4, 2012, under International Publication No. WO 2012/133465 A1, and the disclosure of which is incorporated herein by reference.

TECHNICAL FIELD

The present invention relates to an electronic device and a polymer compound for use in the electronic device.

BACKGROUND ART

In order to improve the characteristics of an electroluminescent device, disposing various types of layers between a light-emitting layer and an electrode is under study. For example, it is known that an electroluminescent device has a layer formed of a non-conjugated polymer compound containing a substituent having a cation and two hetero atoms between a light-emitting layer and an electrode (Patent Literature 1).

PRIOR ART DOCUMENT

Patent Literature

Patent Literature 1: Patent application laid-open publication No. 2003-530676

SUMMARY OF INVENTION

Problem to be Solved by the Invention

However, the brightness of the above electroluminescent device is still insufficient.

An object of the present invention is to provide an electronic device that serves as a high-brightness electroluminescent device.

Means for Solving Problem

The present inventors have found that the above object can be achieved by the electronic device or the like below to achieve the present invention.

Accordingly, the present invention provides an electronic device including a layer comprising a polymer compound comprising one or more structural units selected from the group consisting of a structural unit represented by formula (1) and a structural unit represented by formula (7) as a charge injection layer and/or a charge transport layer; and the like. The structural unit represented by formula (1) and the structural unit represented by formula (7) are each a divalent structural unit.

The structural unit represented by formula (1) is:

[Chemical Formula 1]

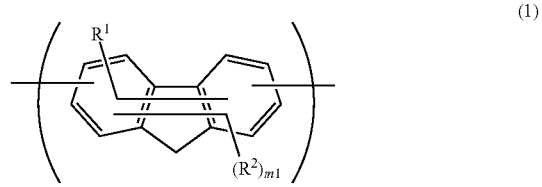

(1)

wherein
$R^1$ represents a group represented by formula (2) or formula (3);
$R^2$ represents a group represented by formula (4);
m1 represents an integer of 0 or more;
when $R^2$ is plurally present, they may be the same or different; and
a hydrogen atom in formula (1) may be replaced with a substituent other than $R^1$ or $R^2$;
wherein the group represented by formula (2) is:

$$-R^3-\{(Q^1)_{n1}-Y^1(M^1)_{a1}(Z^1)_{b1}\}_{m2} \qquad (2)$$

wherein
$R^3$ represents a single bond, or a (1+m2)-valent organic group that optionally has a substituent;
$Q^1$ represents a divalent organic group;
$Y^1$ represents $-CO_2^-$, $-SO_3^-$, $-SO_2^-$, $-PO_3^{2-}$ or $-B(R^\alpha)_3^-$;
$M^1$ represents a metallic cation, or represents an ammonium cation that optionally has a substituent;
$Z^1$ represents $F^-$, $Cl^-$, $Br^-$, $I^-$, $OH^-$, $B(R^a)_4^-$, $R^aSO_3^-$, $R^aCOO^-$, $ClO^-$, $ClO_2^-$, $ClO_3^-$, $ClO_4^-$, $SCN^-$, $CN^-$, $NO_3^-$, $SO_4^{2-}$, $HSO_4^-$, $PO_4^{3-}$, $HPO_4^{2-}$, $H_2PO_4^-$, $BF_4^-$, or $PF_6^-$;
n1 represents an integer of 0 or more;
a1 represents an integer of 1 or more, and b1 represents an integer of 0 or more, wherein a1 and b1 are selected such that a charge of the group represented by formula (2) is zero;
$R^\alpha$ represents an alkyl group having 1 to 30 carbon atoms that optionally has a substituent, or an aryl group having 6 to 50 carbon atoms that optionally has a substituent;
$R^a$ represents an alkyl group having 1 to 30 carbon atoms that optionally has a substituent, or an aryl group having 6 to 50 carbon atoms that optionally has a substituent;
m2 represents an integer of 1 or more, and when $R^3$ is a single bond, m2 represents 1; and
when $Q^1$, $Y^1$, $M^1$, $Z^1$, n1, a1 and b1 are each plurally present, they each may be the same or different;
wherein the group represented by formula (3) is:

$$-R^4-\{(Q^2)_{n2}-Y^2(M^2)_{a2}(Z^2)_{b2}\}_{m3} \qquad (3)$$

wherein
$R^4$ represents a single bond, or a (1+m3)-valent organic group that optionally has a substituent;
$Q^2$ represents a divalent organic group;
$Y^2$ represents a carbocation, an ammonium cation, a phosphonium cation, a sulfonium cation, or an iodonium cation;
$M^2$ represents $F^-$, $Cl^-$, $Br^-$, $I^-$, $OH^-$, $B(R^b)_4^-$, $R^bSO_3^-$, $R^bCOO^-$, $ClO^-$, $ClO_2^-$, $ClO_3^-$, $ClO_4^-$, $SCN^-$, $CN^-$, $NO_3^-$, $SO_4^{2-}$, $HSO_4^-$, $PO_4^{3-}$, $HPO_4^{2-}$, $H_2PO_4^-$, $BF_4^-$ or $PF_6^-$;
$Z^2$ represents a metallic cation, or represents an ammonium cation that optionally has a substituent;
n2 represents an integer of 0 or more;

a2 represents an integer of 1 or more, and b2 represents an integer of 0 or more, wherein a2 and b2 are selected such that a charge of the group represented by formula (3) is zero;

$R^b$ represents an alkyl group having 1 to 30 carbon atoms that optionally has a substituent, or an aryl group having 6 to 50 carbon atoms that optionally has a substituent;

m3 represents an integer of 1 or more, and when $R^4$ is a single bond, m3 represents 1; and when $Q^2$, $Y^2$, $M^2$, $Z^2$, n2, a2 and b2 are each plurally present, they each may be the same or different;

wherein the group represented by formula (4) is:

(4)

wherein $R^5$ represents a single bond, or a (1+m4)-valent organic group that optionally has a substituent;

$Q^3$ represents a divalent organic group;

$Y^3$ represents a group represented by formula (5) or formula (6);

n3 represents an integer of 0 or more;

m4 represents an integer of 1 or more, and when $R^5$ is a single bond, m4 is 1; and when $Q^3$, $Y^3$ and n3 are each plurally present, they each may be the same or different;

wherein the group represented by formula (5) or formula (6) are:

—O—(R'O)$_{a3}$—R''  (5)

[Chemical Formula 2]

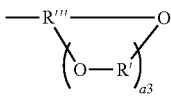

(6)

wherein

R' represents a divalent hydrocarbon group that optionally has a substituent;

R'' represents a hydrogen atom, a monovalent hydrocarbon group that optionally has a substituent, a carboxyl group, a sulfo group, a hydroxy group, a mercapto group, —NR$^C{}_2$, a cyano group or —C(=O)NR$^C{}_2$;

R''' represents a trivalent hydrocarbon group that optionally has a substituent;

a3 represents an integer of 1 or more;

$R^c$ represents an alkyl group having 1 to 30 carbon atoms that optionally has a substituent, or an aryl group having 6 to 50 carbon atoms that optionally has a substituent; and when R', R'' and R''' are each plurally present, they each may be the same or different.

The structural unit represented by formula (7) is:

[Chemical Formula 3]

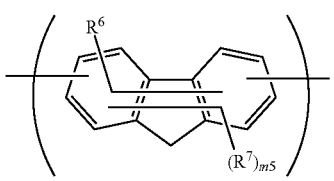

(7)

wherein $R^6$ represents a group represented by formula (8) or formula (9);

$R^7$ represents the group represented by formula (4);

m5 represents an integer of 0 or more;

when $R^7$ is plurally present, they may be the same or different; and a hydrogen atom in formula (7) may be replaced with a substituent other than $R^6$ or $R^7$;

wherein the group represented by formula (8) is:

[Chemical Formula 4]

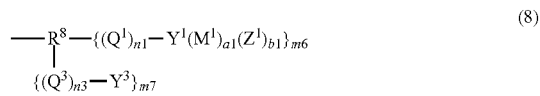

(8)

wherein $R^8$ represents a (1+m6+m7)-valent organic group that optionally has a substituent;

$Q^1$, $Q^3$, $Y^1$, $Y^3$, $M^1$, $Z^1$, n1, n3, a1 and b1 are the same as the corresponding definitions above;

m6 and m7 each independently represent an integer of 1 or more; and when $Q^1$, $Q^3$, $Y^1$, $Y^3$, $M^1$, n1, n3, a1 and b1 are each plurally present, they each may be the same or different;

wherein the group represented by formula (9) is:

[Chemical Formula 5]

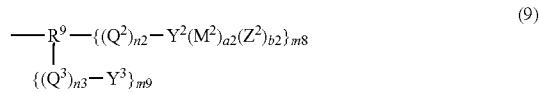

(9)

wherein $R^9$ represents a (1+m8+m9)-valent organic group that optionally has a substituent;

$Q^2$, $Q^3$, $Y^2$, $Y^3$, $M^2$, $Z^2$, n2, n3, a2 and b2 are the same as the corresponding definitions above;

m8 and m9 each independently represent an integer of 1 or more; and when $Q^2$, $Q^3$, $Y^2$, $Y^3$, $M^2$, $Z^2$, n2, n3, a2 and b2 are each plurally present, they each may be the same or different.

Effect of the Invention

The electronic device of the present invention serves as a high-brightness electroluminescent device.

MODE(S) FOR CARRYING OUT THE INVENTION

The present invention will be described in detail below.

<Polymer Compound>

The polymer compound of the present invention is a polymer compound having one or more structural units selected from the group consisting of a structural unit represented by Formula (1) and a structural unit represented by Formula (7). The polymer compound has preferably 15 to 100% by mole of the structural unit represented by Formula (1) and/or the structural unit represented by Formula (7) based on all structural units.

—Structural Unit Represented by Formula (1)

In Formula (1), $R^1$ represents a group represented by Formula (2) or Formula (3); $R^2$ represents the group represented by Formula (4); and m1 represents an integer of 0 or more. m1 is preferably 0 to 3 and more preferably 0 to 2.

The structural unit represented by Formula (1) may include two or more types of groups represented by Formula (2), may include two or more types of groups represented by Formula (3), and may include two or more types of groups represented by Formula (4).

A hydrogen atom in Formula (1) may be replaced with a substituent other than $R^1$ or $R^2$. Examples of the substituent may include an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, an amido group, an acid imide group, a monovalent heterocyclic group, a hydroxy group, a substituted carboxy group, a cyano group, a nitro group, and a cross-linkable group. When the substituent is plurally present, they may be the same or different.

The substituent will be described below. The term "$C_m$ to $C_n$" (m and n are positive integers satisfying m<n) represents that the number of carbon atoms of the organic group described with this term is m to n. For example, a $C_m$ to $C_n$ alkyl group represents that the number of carbon atoms of the alkyl group is m to n; a $C_m$ to $C_n$ alkylaryl group represents that the number of carbon atoms of the alkyl group is m to n; and an aryl-$C_m$ to $C_n$ alkyl group represents that the number of carbon atoms of the alkyl group is m to n. The following term may be used for groups other than the above substituents. A certain group that optionally has a substituent means a certain group having a substituent or a certain group having no substituent.

The alkyl group may be linear or branched, or may also be a cycloalkyl group. The number of carbon atoms of the alkyl group is usually 1 to 20 (usually 3 to 20 for a cycloalkyl group) and preferably 1 to 10 (3 to 10 for a cycloalkyl group). The alkyl group may have a substituent, and the number of carbons of the substituent is not included in the above number of carbons.

Examples of the alkyl group may include a methyl group, an ethyl group, a propyl group, an isopropyl group, a butyl group, an isobutyl group, a sec-butyl group, a tert-butyl group, a pentyl group, a hexyl group, a cyclohexyl group, a heptyl group, an octyl group, a nonyl group, a decyl group, and a lauryl group. A hydrogen atom in the alkyl group may be substituted with a fluorine atom. Examples of such a fluorine atom-substituted alkyl group may include a trifluoromethyl group, a pentafluoroethyl group, a perfluorobutyl group, a perfluorohexyl group, and a perfluorooctyl group. Examples of the $C_1$ to $C_{12}$ alkyl group may include a methyl group, an ethyl group, a propyl group, an isopropyl group, a butyl group, an isobutyl group, a sec-butyl group, a tert-butyl group, a pentyl group, an isoamyl group, a hexyl group, a cyclohexyl group, a heptyl group, an octyl group, a nonyl group, a decyl group, and a lauryl group.

The alkoxy group (also referred to as an alkyloxy group) may be linear or branched, or may also be a cycloalkyloxy group. The number of carbon atoms of the alkoxy group is usually 1 to 20 (usually 3 to 20 for a cycloalkyloxy group) and preferably 1 to 10 (3 to 10 for a cycloalkyloxy group). The alkoxy group may have a substituent, and the number of carbons of the substituent is not included in the above number of carbons.

Examples of the alkoxy group may include a methoxy group, an ethoxy group, a propyloxy group, an isopropyloxy group, a butoxy group, an isobutoxy group, a sec-butoxy group, a tert-butoxy group, a pentyloxy group, a hexyloxy group, a cyclohexyloxy group, a heptyloxy group, an octyloxy group, a nonyloxy group, a decyloxy group, and a lauryloxy group. A hydrogen atom in the alkoxy group may be substituted with a fluorine atom. Examples of such a fluorine atom-substituted alkoxy group may include a trifluoromethoxy group, a pentafluoroethoxy group, a perfluorobutoxy group, a perfluorohexyloxy group and a perfluorooctyloxy group. Examples of the alkoxy group may also include a methoxymethyloxy group and a 2-methoxyethyloxy group. Examples of the $C_1$ to $C_{12}$ alkoxy group may include a methoxy group, an ethoxy group, a propyloxy group, an isopropyloxy group, a butoxy group, an isobutoxy group, a sec-butoxy group, a tert-butoxy group, a pentyloxy group, a hexyloxy group, a cyclohexyloxy group, a heptyloxy group, an octyloxy group, a 2-ethylhexyloxy group, a nonyloxy group, a decyloxy group, a 3,7-dimethyloctyloxy group, and a lauryloxy group.

The alkylthio group may be linear or branched, or may also be a cycloalkylthio group. The number of carbon atoms of the alkylthio group is usually 1 to 20 (usually 3 to 20 for a cycloalkylthio group) and preferably 1 to 10 (3 to 10 for a cycloalkylthio group). The alkylthio group may have a substituent, and the number of carbons of the substituent is not included in the above number of carbons.

Examples of the alkylthio group may include a methylthio group, an ethylthio group, a propylthio group, an isopropylthio group, a butylthio group, an isobutylthio group, a sec-butylthio group, a tert-butylthio group, a pentylthio group, a hexylthio group, a cyclohexylthio group, a heptylthio group, an octylthio group, a nonylthio group, a decylthio group, and a laurylthio group. A hydrogen atom in the alkylthio group may be substituted with a fluorine atom. Examples of such a fluorine atom-substituted alkylthio group may include a trifluoromethylthio group.

The aryl group is an atomic group remaining after removing one hydrogen atom that is bonded to a carbon atom constituting a ring (preferably, an aromatic ring) from an aromatic hydrocarbon, and also includes a group having a benzene ring, a group having a fused ring, and a group in which two or more independent benzene rings or fused rings are bonded through a single bond or a divalent organic group, for example, an alkenylene group such as a vinylene group. The aryl group has usually 6 to 60 carbon atoms and preferably 6 to 48 carbon atoms. The aryl group may have a substituent, and the number of carbons of the substituent is not included in the above number of carbons.

Examples of the aryl group may include a phenyl group, a $C_1$ to $C_{12}$ alkoxyphenyl group, a $C_1$ to $C_{12}$ alkylphenyl group, a 1-naphthyl group, a 2-naphthyl group, a 1-anthracenyl group, a 2-anthracenyl group, and a 9-anthracenyl group. A hydrogen atom in the aryl group may be substituted with a fluorine atom. Examples of such a fluorine atom-substituted aryl group may include a pentafluorophenyl group. Among the aryl groups, a phenyl group, a $C_1$ to $C_{12}$ alkoxyphenyl group, and a $C_1$ to $C_{12}$ alkylphenyl group are preferred.

Among the aryl groups, examples of the $C_1$ to $C_{12}$ alkoxyphenyl group may include a methoxyphenyl group, an ethoxyphenyl group, a propyloxyphenyl group, an isopropyloxyphenyl group, a butoxyphenyl group, an isobutoxyphenyl group, a sec-butoxyphenyl group, a tert-butoxyphenyl group, a pentyloxyphenyl group, a hexyloxyphenyl group, a cyclohexyloxyphenyl group, a heptyloxyphenyl group, an octyloxyphenyl group, a 2-ethylhexyloxyphenyl group, a nonyloxyphenyl group, a decyloxyphenyl group, a 3,7-dimethyloctyloxyphenyl group, and a lauryloxyphenyl group.

Among the aryl groups, examples of the $C_1$ to $C_{12}$ alkylphenyl group may include a methylphenyl group, an ethylphenyl group, a dimethylphenyl group, a propylphenyl group, a mesityl group, a methylethylphenyl group, an isopropylphenyl group, a butylphenyl group, an isobutylphenyl group, a tert-butylphenyl group, a pentylphenyl group, an isoamylphenyl group, a hexylphenyl group, a heptylphenyl group, an octylphenyl group, a nonylphenyl group, a decylphenyl group, and a dodecylphenyl group.

The aryloxy group has usually 6 to 60 carbon atoms and preferably 6 to 48 carbon atoms. The aryloxy group may have a substituent, and the number of carbons of the substituent is not included in the above number of carbons.

Examples of the aryloxy group may include a phenoxy group, a $C_1$ to $C_{12}$ alkoxyphenoxy group, a $C_1$ to $C_{12}$ alkylphenoxy group, a 1-naphthyloxy group, a 2-naphthyloxy group, and a pentafluorophenyloxy group. Among the aryloxy group, a phenoxy group, a $C_1$ to $C_{12}$ alkoxyphenoxy group and a $C_1$ to $C_{12}$ alkylphenoxy group are preferred.

Among the aryloxy groups, examples of the $C_1$ to $C_{12}$ alkoxyphenoxy group may include a methoxyphenoxy group, an ethoxyphenoxy group, a propyloxyphenoxy group, an isopropyloxyphenoxy group, a butoxyphenoxy group, an isobutoxyphenoxy group, a sec-butoxyphenoxy group, a tert-butoxyphenoxy group, a pentyloxyphenoxy group, a hexyloxyphenoxy group, a cyclohexyloxyphenoxy group, a heptyloxyphenoxy group, an octyloxyphenoxy group, a 2-ethylhexyloxyphenoxy group, a nonyloxyphenoxy group, a decyloxyphenoxy group, a 3,7-dimethyloctyloxyphenoxy group, and a lauryloxyphenoxy group.

The arylthio group is a group in which the above aryl group is bonded to a sulfur atom. The arylthio group has usually 6 to 60 carbon atoms and preferably 6 to 30 carbon atoms. The arylthio group may have a substituent on an aromatic ring of the aryl group, and the number of carbons of the substituent is not included in the above number of carbons.

Examples of the arylthio group may include a phenylthio group, a $C_1$ to $C_{12}$ alkoxyphenylthio group, a $C_1$ to $C_{12}$ alkylphenylthio group, a 1-naphthylthio group, a 2-naphthylthio group, and a pentafluorophenylthio group.

The arylalkyl group is a group in which the above aryl group is bonded to the above alkyl group. The arylalkyl group has usually 7 to 60 carbon atoms and preferably 7 to 30 carbon atoms. The arylalkyl group may have a substituent, and the number of carbons of the substituent is not included in the above number of carbons.

Examples of the arylalkyl group may include a phenyl-$C_1$ to $C_{12}$ alkyl group, a $C_1$ to $C_{12}$ alkoxyphenyl-$C_1$ to $C_{12}$ alkyl group, a $C_1$ to $C_{12}$ alkylphenyl-$C_1$ to $C_{12}$ alkyl group, a 1-naphthyl-$C_1$ to $C_{12}$ alkyl group, and a 2-naphthyl-$C_1$ to $C_{12}$ alkyl group.

The arylalkoxy group (also referred to as an arylalkyloxy group) is a group in which the above aryl group is bonded to the above alkoxy group. The arylalkoxy group has usually 7 to 60 carbon atoms and preferably 7 to 30 carbon atoms. The arylalkoxy group may have a substituent, and the number of carbons of the substituent is not included in the above number of carbons.

Examples of the arylalkoxy group may include a phenyl-$C_1$ to $C_{12}$ alkoxy group, a $C_1$ to $C_{12}$ alkoxyphenyl-$C_1$ to $C_{12}$ alkoxy group, a $C_1$ to $C_{12}$ alkylphenyl-$C_1$ to $C_{12}$ alkoxy group, a 1-naphthyl-$C_1$ to $C_{12}$ alkoxy group, and a 2-naphthyl-$C_1$ to $C_{12}$ alkoxy group.

The arylalkylthio group is a group in which the above aryl group is bonded to the above alkylthio group. The arylalkylthio group has usually 7 to 60 carbon atoms and preferably 7 to 30 carbon atoms. The arylalkylthio group may have a substituent, and the number of carbons of the substituent is not included in the above number of carbons.

Examples of the arylalkylthio group may include a phenyl-$C_1$ to $C_{12}$ alkylthio group, a $C_1$ to $C_{12}$ alkoxyphenyl-$C_1$ to $C_{12}$ alkylthio group, a $C_1$ to $C_{12}$ alkylphenyl-$C_1$ to $C_{12}$ alkylthio group, a 1-naphthyl-$C_1$ to $C_{12}$ alkylthio group, and a 2-naphthyl-$C_1$ to $C_{12}$ alkylthio group.

The arylalkenyl group is a group in which the above aryl group is bonded to an alkenyl group. The arylalkenyl group has usually 8 to 60 carbon atoms and preferably 8 to 30 carbon atoms. The arylalkenyl group may have a substituent, and the number of carbons of the substituent is not included in the above number of carbons.

Examples of the arylalkenyl group may include a phenyl-$C_2$ to $C_{12}$ alkenyl group, a $C_1$ to $C_{12}$ alkoxyphenyl-$C_2$ to $C_{12}$ alkenyl group, a $C_1$ to $C_{12}$ alkylphenyl-$C_2$ to $C_{12}$ alkenyl group, a 1-naphthyl-$C_2$ to $C_{12}$ alkenyl group, and a 2-naphthyl-$C_2$ to $C_{12}$ alkenyl group, and a $C_1$ to $C_{12}$ alkoxyphenyl-$C_2$ to $C_{12}$ alkenyl group and a $C_2$ to $C_{12}$ alkylphenyl-$C_2$ to $C_{12}$ alkenyl group are preferred. Examples of the $C_2$ to $C_{12}$ alkenyl group may include a vinyl group, a 1-propenyl group, a 2-propenyl group, a 1-butenyl group, a 2-butenyl group, a 1-pentenyl group, a 2-pentenyl group, a 1-hexenyl group, a 2-hexenyl group, and a 1-octenyl group.

The arylalkynyl group is a group in which the above aryl group is bonded to an alkynyl group. The arylalkynyl group has usually 8 to 60 carbon atoms and preferably 8 to 30 carbon atoms. The arylalkynyl group may have a substituent, and the number of carbons of the substituent is not included in the above number of carbons.

Examples of the arylalkynyl group may include a phenyl-$C_2$ to $C_{12}$ alkynyl group, a $C_1$ to $C_{12}$ alkoxyphenyl-$C_2$ to $C_{12}$ alkynyl group, a $C_1$ to $C_{12}$ alkylphenyl-$C_2$ to $C_{12}$ alkynyl group, a 1-naphthyl-$C_2$ to $C_{12}$ alkynyl group, and a 2-naphthyl-$C_2$ to $C_{12}$ alkynyl group, and a $C_1$ to $C_{12}$ alkoxyphenyl-$C_2$ to $C_{12}$ alkynyl group and a $C_1$ to $C_{12}$ alkylphenyl-$C_2$ to $C_{12}$ alkynyl group are preferred. Examples of the $C_2$ to $C_{12}$ alkynyl group may include an ethynyl group, a 1-propynyl group, a 2-propynyl group, a 1-butynyl group, a 2-butynyl group, a 1-pentynyl group, a 2-pentynyl group, a 1-hexynyl group, a 2-hexynyl group, and a 1-octynyl group.

The substituted amino group means an amino group in which at least one hydrogen atom in an amino group is substituted with one or two groups selected from the group consisting of an alkyl group, an aryl group, an arylalkyl group, and a monovalent heterocyclic group. The alkyl group, the aryl group, the arylalkyl group, or the monovalent heterocyclic group may have a substituent, and the number of carbons of the substituent is not included in the above number of carbons of the substituted amino group. The carbon number of the substituted amino group is usually 1 to 60 and preferably 2 to 48, without including the number of carbon atoms of the substituent that the alkyl group, the aryl group, the arylalkyl group, or the monovalent heterocyclic group may have.

Examples of the substituted amino group may include a methylamino group, a dimethylamino group, an ethylamino group, a diethylamino group, a propylamino group, a dipropylamino group, an isopropylamino group, a diisopropylamino group, a butylamino group, an isobutylamino group, a sec-butylamino group, a tert-butylamino group, a pentylamino group, a hexylamino group, a cyclohexylamino group, a heptylamino group, an octylamino group, a 2-ethylhexylamino group, a nonylamino group, a decylamino group, a 3,7-dimethyloctylamino group, a laurylamino group, a cyclopentylamino group, a dicyclopentylamino group, a cyclohexylamino group, a dicyclohexylamino group, a ditrifluoromethylamino group, a phenylamino group, a diphenylamino group, a ($C_1$ to $C_{12}$ alkoxyphenyl)amino group, a di($C_1$ to $C_{12}$ alkoxyphenyl)amino group, a di($C_1$ to $C_{12}$ alkylphenyl)amino group, a 1-naphthylamino group, a 2-naphthylamino group, a pentafluorophenylamino group, a pyridylamino group, a pyridazinylamino group, a pyrimidinylamino group, a pyrazinylamino group, a triazinylamino group, a (phenyl-$C_1$ to $C_{12}$ alkyl)amino group, a ($C_1$ to $C_{12}$ alkoxyphenyl-$C_1$ to $C_{12}$ alkyl)amino group, a ($C_1$ to $C_{12}$ alkylphenyl-$C_1$ to $C_{12}$ alkyl)amino group, a di($C_1$ to $C_{12}$ alkoxyphenyl-$C_1$ to $C_{12}$ alkyl]amino group, a di($C_1$ to $C_{12}$ alkylphenyl-$C_1$ to $C_{12}$ alkyl)amino group, a 1-naphthyl-$C_1$ to $C_{12}$ alkylamino group, and a 2-naphthyl-$C_1$ to $C_{12}$ alkylamino group.

The substituted silyl group means a silyl group in which at least one hydrogen atom in a silyl group is substituted with one to three groups selected from the group consisting of an alkyl group, an aryl group, an arylalkyl group, and a monovalent heterocyclic group. The alkyl group, the aryl group, the arylalkyl group, or the monovalent heterocyclic group may have a substituent, and the number of carbons of the substituent is not included in the number of carbons of the substituted silyl group. The number of carbon atoms of the substituted silyl group is usually 1 to 60 and preferably 3 to 48, without including the number of carbon atoms of the substituent that the alkyl group, the aryl group, the arylalkyl group, or the monovalent heterocyclic group may have.

Examples of the substituted silyl group may include a trimethylsilyl group, a triethylsilyl group, a tripropylsilyl group, a triisopropylsilyl group, an isopropyldimethylsilyl group, an isopropyldiethylsilyl group, a tert-butyldimethylsilyl group, a pentyldimethylsilyl group, a hexyldimethylsilyl group, a heptyldimethylsilyl group, an octyldimethylsilyl group, a 2-ethylhexyldimethylsilyl group, a nonyldimethylsilyl group, a decyldimethylsilyl group, a 3,7-dimethyloctyldimethylsilyl group, a laurydimethylsilyl group, a (phenyl-$C_1$ to $C_{12}$ alkyl) silyl group, a ($C_1$ to $C_{12}$ alkoxyphenyl-$C_1$ to $C_{12}$ alkyl) silyl group, a ($C_1$ to $C_{12}$ alkylphenyl-$C_1$ to $C_{12}$ alkyl)silyl group, a (1-naphthyl-$C_1$ to $C_{12}$ alkyl)silyl group, a (2-naphthyl-$C_1$ to $C_{12}$ alkyl)silyl group, a (phenyl-$C_1$ to $C_{12}$ alkyl)dimethylsilyl group, a triphenylsilyl group, a tri(p-xylyl)silyl group, a tribenzylsilyl group, a diphenylmethylsilyl group, a tert-butyldiphenylsilyl group, and a dimethylphenylsilyl group.

Examples of the halogen atom may include a fluorine atom, a chlorine atom, a bromine atom, and an iodine atom.

The acyl group (also referred to as an alkyl carbonyl group) has usually 2 to 20 carbon atoms and preferably 2 to 18 carbon atoms. The acyl group may have a substituent, and the number of carbons of the substituent is not included in the above number of carbons.

Examples of the acyl group may include an acetyl group, a propionyl group, a butyryl group, an isobutyryl group, a pivaloyl group, a benzoyl group, a trifluoroacetyl group, and a pentafluorobenzoyl group.

The acyloxy group (also referred to as an alkyl carbonyloxy group) has usually 2 to 20 carbon atoms and preferably 2 to 18 carbon atoms. The acyloxy group may have a substituent, and the number of carbons of the substituent is not included in the above number of carbons.

Examples of the acyloxy group may include an acetoxy group, a propionyloxy group, a butyryloxy group, an isobutyryloxy group, a pivaloyloxy group, a benzoyloxy group, a trifluoroacetyloxy group, and a pentafluorobenzoyloxy group.

The imine residue means a group remaining after removing one hydrogen atom from an imine compound having a structure represented by at least any one of formula: H—N=C< and formula: —N=CH—. Examples of such an imine compound may include aldimine; ketimine; and a compound in which a hydrogen atom that is bonded to a nitrogen atom in aldimine is substituted with a group such as an alkyl group, an aryl group, an arylalkyl group, an arylalkenyl group, and an arylalkynyl group. The number of carbon atoms of the imine residue is usually 2 to 20 and preferably 2 to 18. The imine residue may have a substituent, and the number of carbons of the substituent is not included in the above number of carbons.

Examples of the imine residue may include a group represented by general formula: —$CR^{\beta}$=N—$R^{\gamma}$ or general formula: —N=C($R^{\gamma}$)$_2$, (where $R^{\beta}$ represents a hydrogen atom, an alkyl group, an aryl group, an arylalkyl group, an arylalkenyl group, or an arylalkynyl group; and $R^{\gamma}$ independently represents an alkyl group, an aryl group, an arylalkyl group, an arylalkenyl group, or an arylalkynyl group, and when two $R^{\gamma}$ are present, the two $R^{\gamma}$ may be combined with each other to form a ring as a divalent group (e.g., an alkylene group having 2 to 18 carbon atoms such as an ethylene group, a trimethylene group, a tetramethylene group, a pentamethylene group, and a hexamethylene group). Examples of the imine residue may include the following groups.

[Chemical Formula 6]

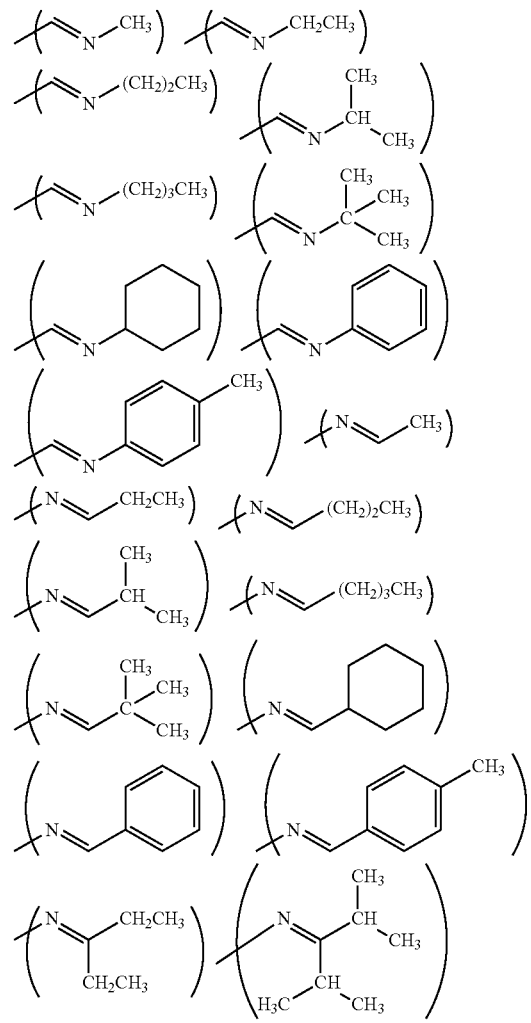

-continued

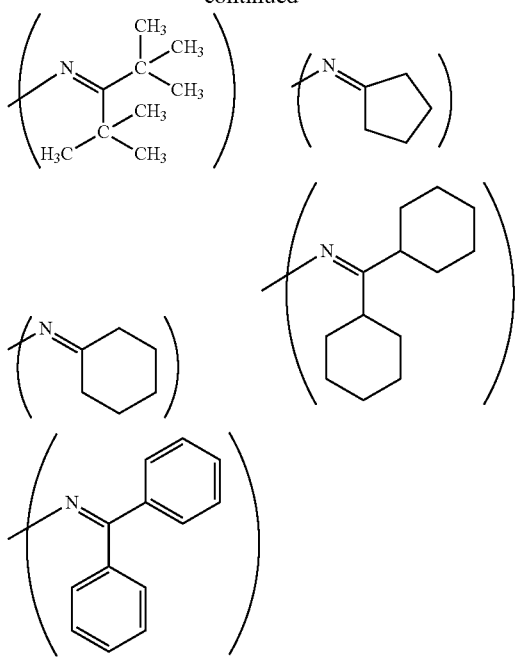

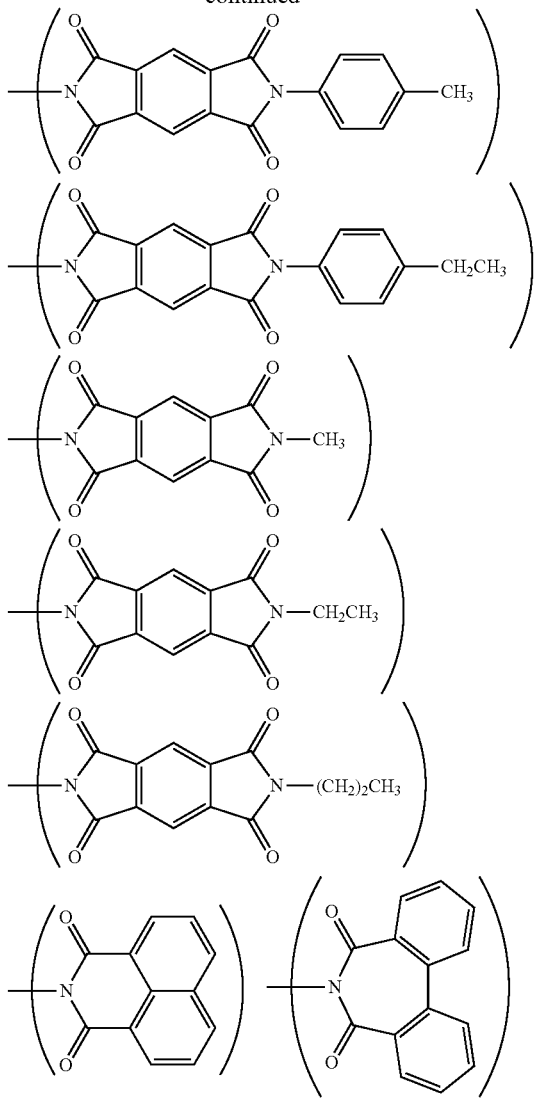

The amido group has usually 1 to 20 carbon atoms and preferably 2 to 18 carbon atoms. The amido group may have a substituent, and the number of carbons of the substituent is not included in the above number of carbons.

Examples of the amido group may include a formamido group, an acetamido group, a propioamido group, a butyramido group, a benzamido group, a trifluoroacetamido group, a pentafluorobenzamido group, a diformamido group, a diacetamido group, a dipropioamido group, a dibutyramido group, a dibenzamido group, a ditrifluoroacetamido group, and a dipentafluorobenzamido group.

The acid imido group means a group obtained by removing a hydrogen atom that is bonded to a nitrogen atom from an acid imide. The acid imido group has usually 4 to 20 carbon atoms and preferably 4 to 18 carbon atoms. The acid imido group may have a substituent, and the number of carbons of the substituent is not included in the above number of carbons.

Examples of the acid imido group may include the following groups.

[Chemical Formula 7]

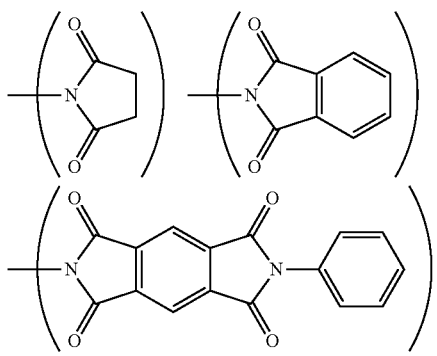

The monovalent heterocyclic group means an atomic group remaining after removing one hydrogen atom that is bonded to a carbon atom constituting a ring from a heterocyclic compound. The heterocyclic compound refers to an organic compound containing not only a carbon atom, but also a hetero atom such as an oxygen atom, a sulfur atom, a nitrogen atom, a phosphorus atom, a boron atom, a silicon atom, a selenium atom, a tellurium atom, and an arsenic atom as an element constituting the ring, among organic compounds having a cyclic structure. The monovalent heterocyclic group has usually 3 to 60 carbon atoms and preferably 3 to 20 carbon atoms. The number of carbon atoms of the monovalent heterocyclic group does not include the number of carbon atoms of the substituent. The monovalent heterocyclic group may have a substituent, and the number of carbons of the substituent is not included in the above number of carbons.

Examples of such a monovalent heterocyclic group may include a thienyl group, a $C_1$ to $C_{12}$ alkylthienyl group, a pyrrolyl group, a furyl group, a pyridyl group, a $C_1$ to $C_{12}$ alkylpyridyl group, a pyridazinyl group, a pyrimidyl group, a pyrazinyl group, a triazinyl group, a pyrrolidyl group, a piperidyl group, a quinolyl group, and an isoquinolyl group, and among them, a thienyl group, a $C_1$ to $C_{12}$ alkylthienyl group, a pyridyl group, a $C_1$ to $C_{12}$ alkylpyridyl group, and a triazinyl group are preferred. The monovalent heterocyclic group is preferably a monovalent aromatic heterocyclic group.

The substituted carboxy group means a carboxy group in which a hydrogen atom in a carboxy group is substituted with an alkyl group, an aryl group, an arylalkyl group, or a monovalent heterocyclic group, that is, a group represented by formula: —C(=O)OR* (where R* is an alkyl group, an aryl group, an arylalkyl group, or a monovalent heterocyclic group). The substituted carboxy group has usually 2 to 60 carbon atoms and preferably 2 to 48 carbon atoms. The alkyl group, the aryl group, the arylalkyl group, or the monovalent heterocyclic group may have a substituent, and the number of carbons of the substituent is not included in the above number of carbons.

Examples of the substituted carboxy group may include a methoxycarbonyl group, an ethoxycarbonyl group, a propyloxycarbonyl group, an isopropyloxycarbonyl group, a butoxycarbonyl group, an isobutoxycarbonyl group, a sec-butoxycarbonyl group, a tert-butoxycarbonyl group, a pentyloxycarbonyl group, a hexyloxycarbonyl group, a cyclohexyloxycarbonyl group, a heptyloxycarbonyl group, an octyloxycarbonyl group, a 2-ethylhexyloxycarbonyl group, a nonyloxycarbonyl group, a decyloxycarbonyl group, a 3,7-dimethyloctyloxycarbonyl group, a dodecyloxycarbonyl group, a trifluoromethoxycarbonyl group, a pentafluoroethoxycarbonyl group, a perfluorobutoxycarbonyl group, a perfluorohexyloxycarbonyl group, a perfluorooctyloxycarbonyl group, a phenoxycarbonyl group, a naphthoxycarbonyl group, and a pyridyloxycarbonyl group.

The cross-linkable group means a group that can form bonds among two or more molecules by causing a polymerization reaction through the action of heat, light, a thermal polymerization initiator, or a photopolymerization initiator.

Examples of the cross-linkable group may include an ethenyl group, an ethynyl group, a butenyl group, an acryloyl group, an acrylate group, an acrylamidyl group, a methacryl group, a methacrylate group, a methacrylamidyl group, an ethenyloxy group, an ethenylamino group, a hydroxysilyl group, a functional group containing a structure of a small ring (e.g., cyclopropane, cyclobutane, benzocyclobutene, epoxide, oxetane, diketene, thiirane, lactone, and lactam), and a functional group having a structure of a siloxane derivative. In addition to the above groups, a combination of groups that can form an ester bond or an amide bond may be used. Examples of the combination of groups that can form an ester bond or an amide bond may include a combination of an ester group and an amino group and a combination of an ester group and a hydroxy group.

—Group Represented by Formula (2)—

In Formula (2), $R^3$ represents a single bond or a (1+m2)-valent organic group that optionally has a substituent. The group represented by Formula (2) is a monovalent group.

In Formula (2), examples of the (1+m2)-valent organic group that optionally has a substituent represented by $R^3$ may include: a group remaining after removing m2 hydrogen atoms from an alkyl group having 1 to 20 carbon atoms that optionally has a substituent, such as a methyl group, an ethyl group, a propyl group, an isopropyl group, a butyl group, an isobutyl group, a sec-butyl group, a tert-butyl group, a pentyl group, a hexyl group, a cyclohexyl group, a heptyl group, an octyl group, a nonyl group, a decyl group, a lauryl group, and a group in which at least one hydrogen atom in these groups is substituted with a substituent; a group remaining after removing m2 hydrogen atoms from an aryl group having 6 to 30 carbon atoms that optionally has a substituent, such as a phenyl group, a 1-naphthyl group, a 2-naphthyl group, a 1-anthracenyl group, a 2-anthracenyl group, a 9-anthracenyl group, and a group in which at least one hydrogen atom in these groups is substituted with a substituent; a group remaining after removing m2 hydrogen atoms from an alkoxy group having 1 to 50 carbon atoms that optionally has a substituent, such as a methoxy group, an ethoxy group, a propyloxy group, a butoxy group, a pentyloxy group, a hexyloxy group, a nonyloxy group, a dodecyloxy group, a cyclopropyloxy group, a cyclobutyloxy group, a cyclopentyloxy group, a cyclohexyloxy group, a cyclononyloxy group, a cyclododecyloxy group, a norbornyloxy group, an adamantyloxy group, and a group in which at least one hydrogen atom in these groups is substituted with a substituent; a group remaining after removing m2 hydrogen atoms from an amino group having a substituent containing a carbon atom; and a group remaining after removing m2 hydrogen atoms from a silyl group having a substituent containing a carbon atom. The number of carbons of the substituent is not included in the above number of carbons. Because the synthesis of the raw material monomer is simplified, preferred examples are a group remaining after removing m2 hydrogen atoms from an alkyl group, a group remaining after removing m2 hydrogen atoms from an aryl group, and a group remaining after removing m2 hydrogen atoms from an alkoxy group.

Examples of the above substituent may include the same as the substituent exemplified in the description with respect to Formula (1). When the substituent is plurally present, they may be the same or different.

In Formula (2), m2 represents an integer of 1 or more (e.g., 1, 2, or 3), and when $R^3$ is a single bond, m2 represents 1.

In Formula (2), examples of the divalent organic group represented by $Q^1$ may include: a divalent chain saturated hydrocarbon group having 1 to 50 carbon atoms that optionally has a substituent, such as a methylene group, an ethylene group, a 1,2-propylene group, a 1,3-propylene group, a 1,2-butylene group, a 1,3-butylene group, a 1,4-butylene group, a 1,5-pentylene group, a 1,6-hexylene group, a 1,9-nonylene group, a 1,12-dodecylene group, and a group in which at least one hydrogen atom in these groups is substituted with a substituent; a divalent chain unsaturated hydrocarbon group having 2 to 50 carbon atoms that optionally has a substituent including an alkenylene group having 2 to 50 carbon atoms that optionally has a substituent, such as an ethenylene group, a propenylene group, a 3-butenylene group, a 2-butenylene group, a 2-pentenylene group, a 2-hexenylene group, a 2-nonenylene group, a 2-dodecenylene group, and a group in which at least one hydrogen atom in these groups is substituted with a substituent and an ethynylene group; a divalent saturated cyclic hydrocarbon group having 3 to 50 carbon atoms that optionally has a substituent, such as a cyclopropylene group, a cyclobutylene group, a cyclopentylene group, a cyclohexylene group, a cyclononylene group, a cyclododecylene group, a norbornylene group, an adamantylene group, and a group in which at least one hydrogen atom in these groups is substituted with a substituent; an arylene group having 6 to 50 carbon atoms that optionally has a substituent, such as a 1,3-phenylene group, a 1,4-phenylene group, a 1,4-naphthylene group, a 1,5-naphthylene group, a 2,6-naphthylene group, a biphenyl-4,4'-diyl group, and a group in which at least one hydrogen atom in these groups is substituted with a substituent; an alkyleneoxy group having 1 to 50 carbon atoms that optionally has a substituent, such as a methyleneoxy group, an ethyleneoxy group, a propyleneoxy group, a butyleneoxy group, a pentyleneoxy group, a hexyleneoxy group, and a group in which at least one hydrogen atom in these groups is substituted with a substituent (that is, a divalent organic group represented by formula: —R$^d$—O— (where R$^d$ is an alkylene group having 1 to 50 carbon atoms that optionally has a substituent, such as a methylene group, an ethylene group, a propylene group, a butylene group, a pentylene group, a hexylene group, and a group in which at least one hydrogen atom in these groups is substituted with a substituent)); an imino group having a substituent containing a carbon atom; and a silylene group having a substituent containing a carbon atom. The number of carbons of the substituent is not included in the above number of carbons. Because the synthesis of a monomer that is a raw material of the macromolecule compound (referred to as the "raw material monomer" in this specification) is simplified, preferred examples are a divalent chain saturated hydrocarbon group, an arylene group, and an alkyleneoxy group.

The group exemplified for the divalent organic group represented by Q$^1$ may have a substituent. Examples of the substituent may include the same as the substituent exemplified in the description with respect to Formula (1). When the substituent is plurally present, they may be the same or different.

In Formula (2), Y$^1$ represents —CO$_2^-$, —SO$_3^-$, —SO$_2^-$, —PO$_3^{2-}$, or —B(R$^\alpha$)$_3^-$. In view of the acidity of the polymer compound, Y$^1$ is preferably, —CO$_2^-$, —SO$_2^-$, or —PO$_3^{2-}$ and more preferably —CO$_2^-$. In view of the stability of the polymer compound, Y$^1$ is preferably —CO$_2^-$, —SO$_3^-$, —SO$_2^-$, or —PO$_3^{2-}$. R$^\alpha$ represents an alkyl group having 1 to 30 carbon atoms that optionally has a substituent or an aryl group having 6 to 50 carbon atoms that optionally has a substituent. The number of carbons of the substituent is not included in the above number of carbons. Examples of the substituent may include the same as the substituent exemplified in the description with respect to Formula (1). When the substituent is plurally present, they may be the same or different. Examples of R$^\alpha$ may include: an alkyl group having 1 to 20 carbon atoms such as a methyl group, an ethyl group, a propyl group, an isopropyl group, a butyl group, an isobutyl group, a sec-butyl group, a tert-butyl group, a pentyl group, a hexyl group, a cyclohexyl group, a heptyl group, an octyl group, a nonyl group, a decyl group, and a lauryl group; and an aryl group having 6 to 30 carbon atoms such as a phenyl group, a 1-naphthyl group, a 2-naphthyl group, a 1-anthracenyl group, a 2-anthracenyl group, and a 9-anthracenyl group.

In Formula (2), M$^1$ represents a metal cation or an ammonium cation that optionally has a substituent. The metal cation is preferably a monovalent, divalent, or trivalent ion. Examples of the metal cation may include an ion of Li, Na, K, Cs, Be, Mg, Ca, Ba, Ag, Al, Bi, Cu, Fe, Ga, Mn, Pb, Sn, Ti, V, W, Y, Yb, Zn, Zr, and Li$^+$, Na$^+$, K$^+$, Rb$^+$, Cs$^+$, Ag$^+$, Mg$^{2+}$, and Ca$^{2+}$ are preferred. Examples of the substituent that the ammonium cation may have may include: an alkyl group having 1 to 10 carbon atoms such as a methyl group, an ethyl group, a propyl group, an isopropyl group, an n-butyl group, an i-butyl group, and a tert-butyl group; and an aryl group having 6 to 60 carbon atoms such as a phenyl group, a 1-naphthyl group, and a 2-naphthyl group.

In Formula (2), Z$^1$ represents F$^-$, Cl$^-$, Br$^-$, I$^-$, OH$^-$, B(R$^a$)$_4^-$, R$^a$SO$_3^-$, R$^a$COO$^-$, ClO$^-$, ClO$_2^-$, ClO$_3^-$, ClO$_4^-$, SCN$^-$, CN$^-$, NO$_3^-$, SO$_4^{2-}$, HSO$_4^-$, PO$_4^{3-}$, HPO$_4^{2-}$, H$_2$PO$_4^-$, BF$_4^-$, or PF$_6^-$. R$^a$ represents an alkyl group having 1 to 30 carbon atoms that optionally has a substituent or an aryl group having 6 to 50 carbon atoms that optionally has a substituent. The number of carbons of the substituent is not included in the above number of carbons. Examples of the substituent may include the same as the substituent exemplified in the description with respect to Formula (1). When the substituent is plurally present, they may be the same or different. Examples of R$^a$ may include: an alkyl group having 1 to 20 carbon atoms such as a methyl group, an ethyl group, a propyl group, an isopropyl group, a butyl group, an isobutyl group, a sec-butyl group, a tert-butyl group, a pentyl group, a hexyl group, a cyclohexyl group, a heptyl group, an octyl group, a nonyl group, a decyl group, and a lauryl group; and an aryl group having 6 to 30 carbon atoms such as a phenyl group, a 1-naphthyl group, a 2-naphthyl group, a 1-anthracenyl group, a 2-anthracenyl group, and a 9-anthracenyl group.

In Formula (2), n1 represents an integer of 0 or more, and in view of the synthesis of the raw material monomer, n1 is preferably an integer of from 0 to 8, and more preferably an integer of from 0 to 2.

In Formula (2), a1 represents an integer of 1 or more (e.g., an integer of from 1 to 10), and b1 represents an integer of 0 or more (e.g., an integer of from 1 to 10).

a1 and b1 are selected so that the electric charge of the group represented by Formula (2) is zero. For example, when Y$^1$ is —CO$_2^-$, —SO$_3^-$, —SO$_2^-$, —PO$_3^{2-}$, or —B(R$^\alpha$)$_3^-$; M$^1$ is a monovalent metal cation or an ammonium cation that optionally has a substituent; and Z$^1$ is F$^-$, Cl$^-$, Br$^-$, I$^-$, OH$^-$, B(R$^a$)$_4^-$, R$^a$SO$_3^-$, R$^a$COO$^-$, ClO$^-$, ClO$_2^-$, ClO$_3^-$, ClO$_4^-$, SCN$^-$, CN$^-$, NO$_3^-$, HSO$_4^-$, H$_2$PO$_4^-$, BF$_4^-$, or PF$_6^-$, a1 and b1 are selected so as to satisfy a1=b1+1. When Y$^1$ is —CO$_2^-$, —SO$_3^-$, —SO$_2^-$, —PO$_3^{2-}$, or —B(R$^\alpha$)$_3^-$; M$^1$ is a divalent metal cation; and Z$^1$ is F$^-$, Cl$^-$, Br$^-$, I$^-$, OH$^-$, B(R$^a$)$_4^-$, R$^a$SO$_3^-$, R$^a$COO$^-$, ClO$^-$, ClO$_2^-$, ClO$_3^-$, ClO$_4^-$, SCN$^-$, CN$^-$, NO$_3^-$, HSO$_4^-$, H$_2$PO$_4^-$, BF$_4^-$, or PF$_6^-$, a1 and b1 are selected so as to satisfy b1=2×a1−1. When Y$^1$ is —CO$_2^-$, —SO$_3^-$, —SO$_2^-$, or —PO$_3^{2-}$; M$^1$ is a trivalent metal cation; and Z$^1$ is F$^-$, Cl$^-$, Br$^-$, I$^-$, OH$^-$, B(R$^a$)$_4^-$, R$^a$SO$_3^-$, R$^a$COO$^-$, ClO$^-$, ClO$_2^-$, ClO$_3^-$, ClO$_4^-$, SCN$^-$, CN$^-$, NO$_3^-$, HSO$_4^-$, H$_2$PO$_4^-$, BF$_4^-$, or PF$_6^-$, a1 and b1 are selected so as to satisfy b1=3×a1−1. When Y$^1$ is —CO$_2^-$, —SO$_3^-$, —SO$_2^-$, —PO$_3^{2-}$, or —B(R$^\alpha$)$_3^-$; M$^1$ is a monovalent metal cation or an ammonium cation that optionally has a substituent; and Z$^1$ is SO$_4^{2-}$ or HPO$_4^{2-}$, a1 and b1 are selected so as to satisfy a1=2×b1+1. In any one of the above numerical formulae expressing the relationship between a1 and b1, a1 is preferably an integer of from 1 to 5, and more preferably 1 or 2.

Examples of the group represented by Formula (2) may include groups represented by the following formulae (where M represents Li, Na, K, Rb, Cs, or N(CH$_3$)$_4$).

[Chemical Formula 8]

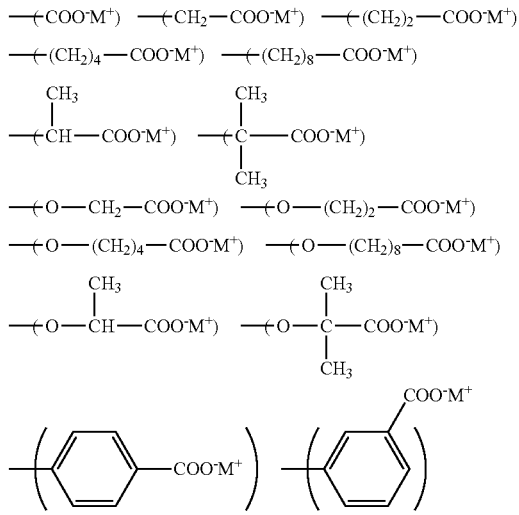

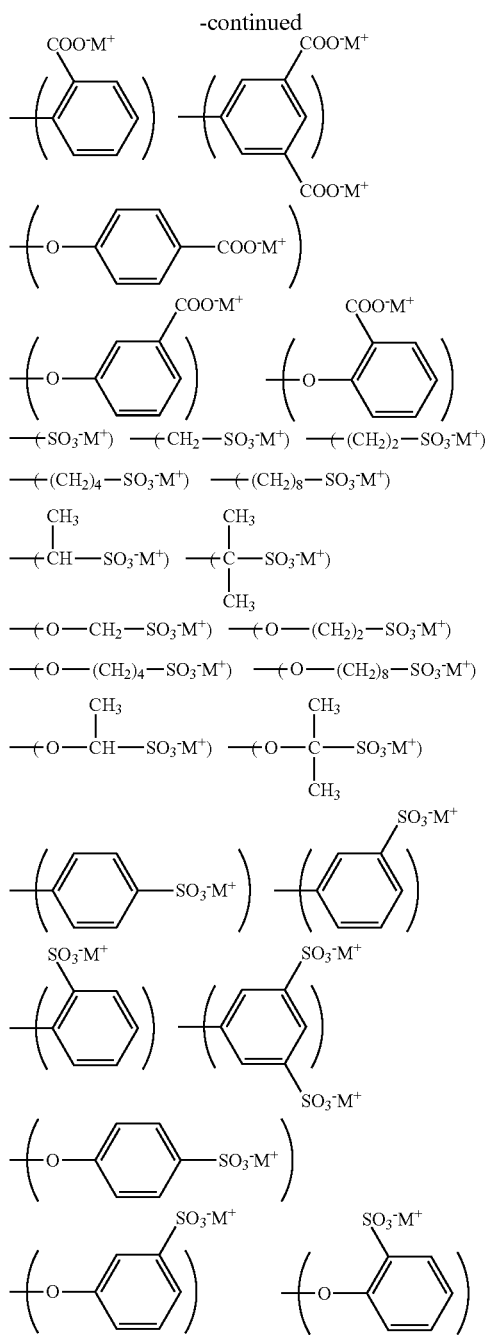

—Group Represented by Formula (3)—

In Formula (3), $R^4$ represents a single bond or a (1+m3)-valent organic group that optionally has a substituent. The group represented by Formula (3) is a monovalent group.

In Formula (3), examples of the (1+m3)-valent organic group that optionally has a substituent represented by $R^4$ may include a group remaining after removing m3 hydrogen atoms from an alkyl group having 1 to 20 carbon atoms that optionally has a substituent, such as a methyl group, an ethyl group, a propyl group, an isopropyl group, a butyl group, an isobutyl group, a sec-butyl group, a tert-butyl group, a pentyl group, a hexyl group, a cyclohexyl group, a heptyl group, an octyl group, a nonyl group, a decyl group, a lauryl group, and a group in which at least one hydrogen atom in these groups is substituted with a substituent; a group remaining after removing m3 hydrogen atoms from an aryl group having 6 to 30 carbon atoms that optionally has a substituent, such as a phenyl group, a 1-naphthyl group, a 2-naphthyl group, a 1-anthracenyl group, a 2-anthracenyl group, a 9-anthracenyl group, and a group in which at least one hydrogen atom in these groups is substituted with a substituent; a group remaining after removing m3 hydrogen atoms from an alkoxy group having 1 to 50 carbon atoms that optionally has a substituent, such as a methoxy group, an ethoxy group, a propyloxy group, a butoxy group, a pentyloxy group, a hexyloxy group, a nonyloxy group, a dodecyloxy group, a cyclopropyloxy group, a cyclobutyloxy group, a cyclopentyloxy group, a cyclohexyloxy group, a cyclononyloxy group, a cyclododecyloxy group, a norbornyloxy group, an adamantyloxy group, and a group in which at least one hydrogen atom in these groups is substituted with a substituent; a group remaining after removing m3 hydrogen atoms from an amino group having a substituent containing a carbon atom; and a group remaining after removing m3 hydrogen atoms from a silyl group having a substituent containing a carbon atom. The number of carbons of the substituent is not included in the above number of carbons. Because the synthesis of the raw material monomer is simplified, preferred examples are a group remaining after removing m3 hydrogen atoms from an alkyl group, a group remaining after removing m3 hydrogen atoms from an aryl group, and a group remaining after removing m3 hydrogen atoms from an alkoxy group.

Examples of the above substituent may include the same as the substituent exemplified in the description with respect to Formula (1). When the substituent is plurally present, they may be the same or different.

In Formula (3), m3 represents an integer of 1 or more (e.g., 1, 2, or 3), and when $R^4$ is a single bond, m3 represents 1.

In Formula (3), examples of the divalent organic group represented by $Q^2$ may include the same as the group exemplified with respect to the divalent organic group represented by $Q^1$. Because the synthesis of the raw material monomer is simplified, preferred examples are a divalent chain saturated hydrocarbon group, an arylene group, and an alkyleneoxy group.

The group exemplified for the divalent organic group represented by $Q^2$ may have a substituent. Examples of the substituent may include the same as the substituent exemplified in the description with respect to Formula (1). When the substituent is plurally present, they may be the same or different.

In Formula (3), $Y^2$ represents a carbocation, an ammonium cation, a phosphonium cation, a sulfonium cation, or an iodonium cation.

Examples of the carbonation may include a group represented by:

$$-C^+R_2$$

(where R represents the above alkyl group or aryl group; R that is plurally present may be the same or different).

Examples of the ammonium cation may include a group represented by:

$$-N^+R_3$$

(where R represents the same meaning as described above; R that is plurally present may be the same or different).

Examples of the phosphonium cation may include a group represented by:

$$-P^+R_3$$

(where R represents the same meaning as described above; R that is plurally present may be the same or different).

Examples of the sulfonium cation may include a group represented by:

—S⁺R₂

(where R represents the same meaning as described above; R that is plurally present may be the same or different).

Examples of the iodonium cation may include a group represented by:

—I⁺R₂

(where R represents the same meaning as described above; R that is plurally present may be the same or different).

In Formula (2), because of the simplicity of the synthesis of the raw material monomer and the stability of the raw material monomer and the polymer compound against air, moisture, or heat, $Y^2$ is preferably a carbocation, an ammonium cation, a phosphonium cation, or a sulfonium cation, and more preferably an ammonium cation.

In Formula (3), $M^2$ represents $F^-$, $Cl^-$, $Br^-$, $I^-$, $OH^-$, $B(R^b)_4^-$, $R^bSO_3^-$, $R^bCOO^-$, $ClO^-$, $ClO_2^-$, $ClO_3^-$, $ClO_4^-$, $SCN^-$, $CN^-$, $NO_3^-$, $SO_4^{2-}$, $HSO_4^-$, $PO_4^{3-}$, $HPO_4^{2-}$, $H_2PO_4^-$, $BF_4^-$, or $PF_6^-$. $R^b$ represents an alkyl group having 1 to 30 carbon atoms that optionally has a substituent or an aryl group having 6 to 50 carbon atoms that optionally has a substituent. The number of carbons of the substituent is not included in the above number of carbons. Examples of the substituent may include the same as the substituent exemplified in the description with respect to Formula (1). When the substituent is plurally present, they may be the same or different. More specifically, examples of $R^b$ may include: an alkyl group having 1 to 20 carbon atoms such as a methyl group, an ethyl group, a propyl group, an isopropyl group, a butyl group, an isobutyl group, a sec-butyl group, a tert-butyl group, a pentyl group, a hexyl group, a cyclohexyl group, a heptyl group, an octyl group, a nonyl group, a decyl group, and a lauryl group; and an aryl group having 6 to 30 carbon atoms such as a phenyl group, a 1-naphthyl group, a 2-naphthyl group, a 1-anthracenyl group, a 2-anthracenyl group, and a 9-anthracenyl group.

In Formula (3), $Z^2$ represents a metal cation or an ammonium cation that optionally has a substituent. Examples of the metal cation or ammonium cation that optionally has a substituent represented by $Z^2$ may include the same as exemplified with respect to the metal cation or ammonium cation that optionally has a substituent represented by the above $M^1$.

In Formula (3), n2 represents an integer of 0 or more, preferably an integer of from 0 to 6, and more preferably an integer of from 0 to 2.

In Formula (3), a2 represents an integer of 1 or more (e.g., an integer of from 1 to 10), and b2 represents an integer of 0 or more (e.g., an integer of from 0 to 10). a2 is preferably an integer of from 1 to 5 and more preferably 1 or 2.

a2 and b2 are selected so that the electric charge of the group represented by Formula (3) is zero, as is the case with a1 and b1 with respect to Formula (2).

Examples of the group represented by Formula (3) may include groups represented by the following formulae. In the following formulae, X represents F, Cl, Br, I, $B(C_6H_5)_4$, $CH_3COO$, or $CF_3SO_3$.

[Chemical Formula 9]

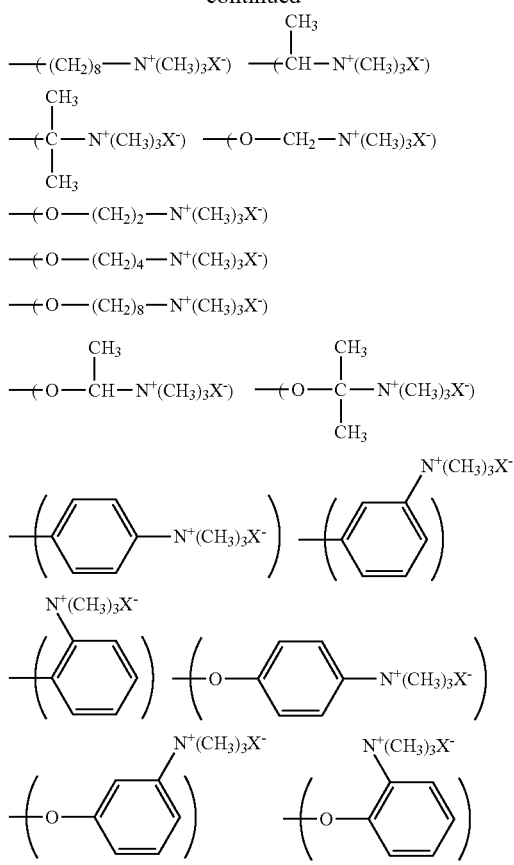

[Chemical Formula 10]

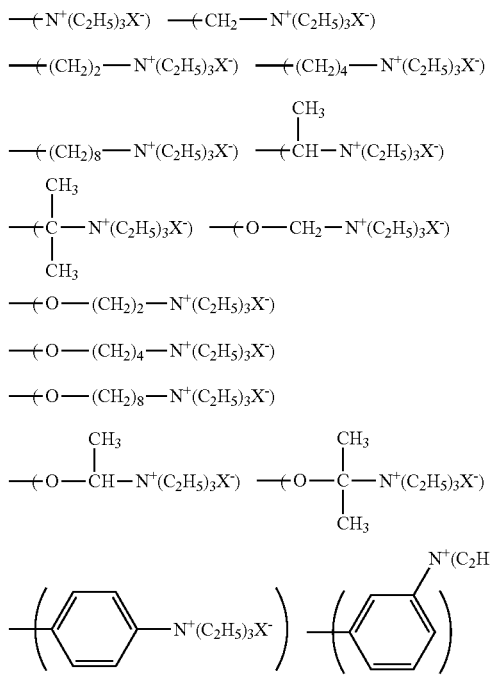

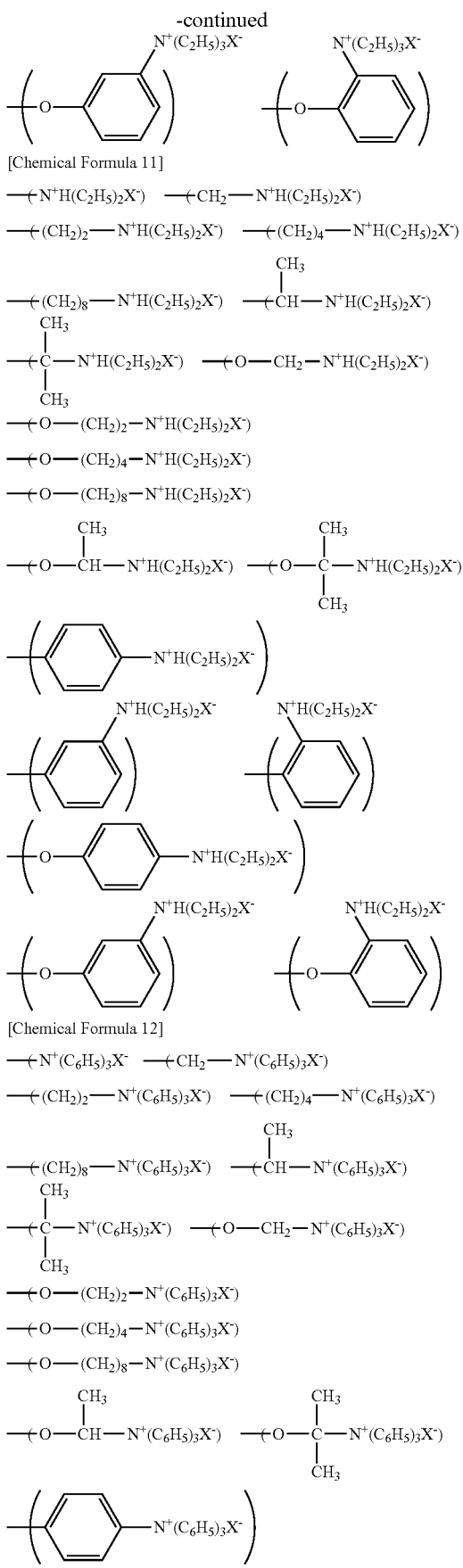

[Chemical Formula 11]

[Chemical Formula 12]

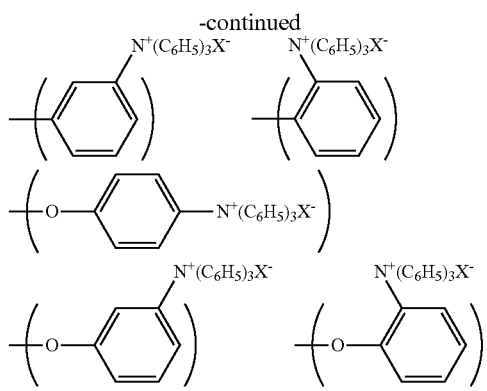

—Group Represented by Formula (4)—

In Formula (4), $R^5$ represents a single bond or a (1+m4)-valent organic group that optionally has a substituent. The group represented by Formula (4) is a monovalent group.

In Formula (4), examples of the (1+m4)-valent organic group that optionally has a substituent represented by $R^5$ may include a group remaining after removing m4 hydrogen atoms from an alkyl group having 1 to 20 carbon atoms that optionally has a substituent, such as a methyl group, an ethyl group, a propyl group, an isopropyl group, a butyl group, an isobutyl group, a sec-butyl group, a tert-butyl group, a pentyl group, a hexyl group, a cyclohexyl group, a heptyl group, an octyl group, a nonyl group, a decyl group, a lauryl group, and a group in which at least one hydrogen atom in these groups is substituted with a substituent; a group remaining after removing m4 hydrogen atoms from an aryl group having 6 to 30 carbon atoms that optionally has a substituent, such as a phenyl group, a 1-naphthyl group, a 2-naphthyl group, a 1-anthracenyl group, a 2-anthracenyl group, a 9-anthracenyl group, and a group in which at least one hydrogen atom in these groups is substituted with a substituent; a group remaining after removing m4 hydrogen atoms from an alkoxy group having 1 to 50 carbon atoms that optionally has a substituent, such as a methoxy group, an ethoxy group, a propyloxy group, a butoxy group, a pentyloxy group, a hexyloxy group, a nonyloxy group, a dodecyloxy group, a cyclopropyloxy group, a cyclobutyloxy group, a cyclopentyloxy group, a cyclohexyloxy group, a cyclononyloxy group, a cyclododecyloxy group, a norbornyloxy group, an adamantyloxy group, and a group in which at least one hydrogen atom in these groups is substituted with a substituent; a group remaining after removing m4 hydrogen atoms from an amino group having a substituent containing a carbon atom; and a group remaining after removing m4 hydrogen atoms from a silyl group having a substituent containing a carbon atom. The number of carbons of the substituent is not included in the above number of carbons. Because the synthesis of the raw material monomer is simplified, preferred examples are a group remaining after removing m4 hydrogen atoms from an alkyl group, a group remaining after removing m4 hydrogen atoms from an aryl group, and a group remaining after removing m4 hydrogen atoms from an alkoxy group.

Examples of the substituent may include the same as the substituent exemplified in the description with respect to Formula (1). When the substituent is plurally present, they may be the same or different.

In Formula (4), m4 represents an integer of 1 or more (e.g., 1, 2, or 3), and when $R^5$ is a single bond, m4 represents 1.

In Formula (4), examples of the divalent organic group represented by $Q^3$ may include the same as the group exemplified with respect to the divalent organic group represented by $Q^1$. Because the synthesis of the raw material monomer is simplified, preferred examples are a divalent chain saturated hydrocarbon group, an arylene group, and an alkyleneoxy group.

The group exemplified for the divalent organic group represented by $Q^3$ may have a substituent. Examples of the substituent may include the same as the substituent exemplified in the description with respect to Formula (1). When the substituent is plurally present, they may be the same or different.

In Formula (4), n3 represents an integer of 0 or more, preferably an integer of from 0 to 20, and more preferably an integer of from 0 to 8.

In Formula (4), $Y^3$ represents a cyano group or a group represented by Formula (5) or Formula (6). The group represented by Formula (5) or Formula (6) is a monovalent group.

Examples of the divalent hydrocarbon group that optionally has a substituent represented by R' in Formulae (5) and (6) may include: a divalent chain saturated hydrocarbon group having 1 to 50 carbon atoms that optionally has a substituent, such as a methylene group, an ethylene group, a 1,2-propylene group, a 1,3-propylene group, a 1,2-butylene group, a 1,3-butylene group, a 1,4-butylene group, a 1,5-pentylene group, a 1,6-hexylene group, a 1,9-nonylene group, a 1,12-dodecylene group, and a group in which at least one hydrogen atom in these groups is substituted with a substituent; a divalent chain unsaturated hydrocarbon group having 2 to 50 carbon atoms that optionally has a substituent including an alkenylene group having 2 to 50 carbon atoms that optionally has a substituent, such as an ethenylene group, a propenylene group, a 3-butenylene group, a 2-butenylene group, a 2-pentenylene group, a 2-hexenylene group, a 2-nonenylene group, a 2-dodecenylene group, and a group in which at least one hydrogen atom in these groups is substituted with a substituent, and an ethynylene group; a divalent saturated cyclic hydrocarbon group having 3 to 50 carbon atoms that optionally has a substituent, such as a cyclopropylene group, a cyclobutylene group, a cyclopentylene group, a cyclohexylene group, a cyclononylene group, a cyclododecylene group, a norbornylene group, an adamantylene group, and a group in which at least one hydrogen atom in these groups is substituted with a substituent; and an arylene group having 6 to 50 carbon atoms that optionally has a substituent, such as a 1,3-phenylene group, a 1,4-phenylene group, a 1,4-naphthylene group, a 1,5-naphthylene group, a 2,6-naphthylene group, a biphenyl-4,4'-diyl group, and a group in which at least one hydrogen atom in these groups is substituted with a substituent. The number of carbons of the substituent is not included in the above number of carbons.

Examples of the substituent may include the same as the substituent exemplified in the description with respect to Formula (1). When the substituent is plurally present, they may be the same or different.

In Formula (5), examples of the monovalent hydrocarbon group that optionally has a substituent represented by R" may include: an alkyl group having 1 to 20 carbon atoms that optionally has a substituent, such as a methyl group, an ethyl group, a propyl group, an isopropyl group, a butyl group, an isobutyl group, a sec-butyl group, a tert-butyl group, a pentyl group, a hexyl group, a cyclohexyl group, a heptyl group, an octyl group, a nonyl group, a decyl group, a lauryl group, and a group in which at least one hydrogen atom in these groups is substituted with a substituent; and an aryl group having 6 to 30 carbon atoms that optionally has a substituent, such as a phenyl group, a 1-naphthyl group, a 2-naphthyl group, a 1-anthracenyl group, a 2-anthracenyl group, a 9-anthracenyl group, and a group in which at least one hydrogen atom in these groups is substituted with a substituent. The number of carbons of the substituent is not included in the above number of carbons. In view of the solubility of the polymer compound, preferred examples are a methyl group, an ethyl group, a phenyl group, a 1-naphthyl group, and 2-naphthyl group. Examples of the substituent may include the same as the substituent exemplified in the description with respect to Formula (1). When the substituent is plurally present, they may be the same or different.

In Formula (6), examples of the trivalent hydrocarbon group that optionally has a substituent represented by R'" may include: an alkanetriyl group having 1 to 20 carbon atoms that optionally has a substituent, such as a methanetriyl group, an ethanetriyl group, a 1,2,3-propanetriyl group, a 1,2,4-butanetriyl group, a 1,2,5-pentanetriyl group, a 1,3,5-pentanetriyl group, a 1,2,6-hexanetriyl group, a 1,3,6-hexanetriyl group, and a group in which at least one hydrogen atom in these groups is substituted with a substituent; and an arenetriyl group having 6 to 30 carbon atoms that optionally has a substituent, such as a 1,2,3-benzenetriyl group, a 1,2,4-benzenetriyl group, a 1,3,5-benzenetriyl group, and a group in which at least one hydrogen atom in these groups is substituted with a substituent. The number of carbons of the substituent is not included in the above number of carbons. In view of the solubility of the polymer compound, preferred examples are a methanetriyl group, an ethanetriyl group, a 1,2,4-benzenetriyl group, and a 1,3,5-benzenetriyl group. Examples of the substituent may include the same as the substituent exemplified in the description with respect to Formula (1). When the substituent is plurally present, they may be the same or different.

With respect to —$NR^C_2$ and —$C(=O)NR^C_2$ that are examples of R", $R^c$ represents an alkyl group having 1 to 30 carbon atoms that optionally has a substituent or an aryl group having 6 to 50 carbon atoms that optionally has a substituent. The number of carbons of the substituent is not included in the above number of carbons. Examples of the substituent may include the same as the substituent exemplified in the description with respect to Formula (1). In Formula (5), in view of the solubility of the polymer compound, preferred examples of $R^c$ are a methyl group, an ethyl group, a phenyl group, a 1-naphthyl group, and 2-naphthyl group.

In Formulae (5) and (6), a3 represents an integer of 1 or more, preferably an integer of from 3 to 10.

Because the synthesis of the raw material monomer is simplified, $Y^3$ is particularly preferably the following groups.

[Chemical Formula 13]

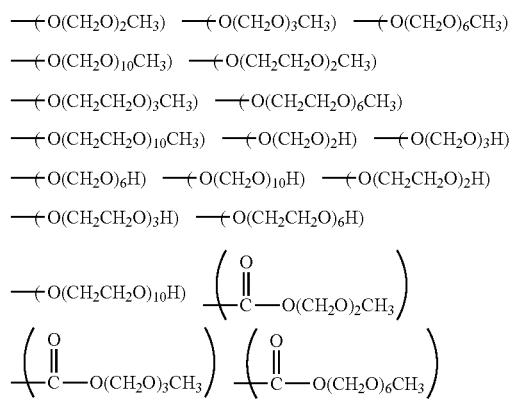

-continued

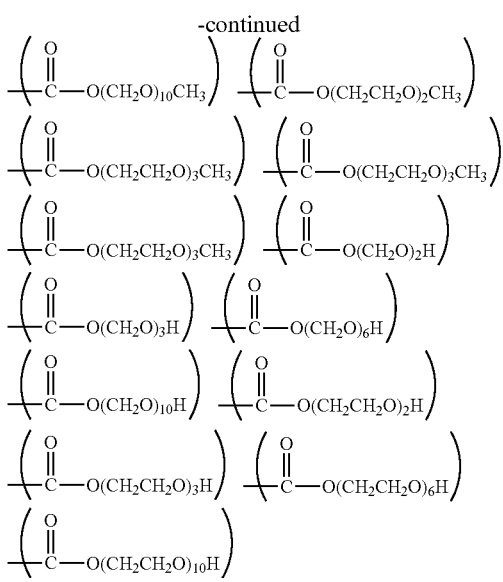

[Specific Examples of Group Represented by Formula (4)]

Examples of the group represented by Formula 4 may include groups represented by the following formulae.

[Chemical Formula 14]

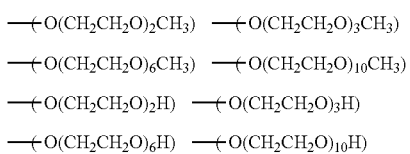

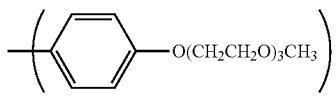

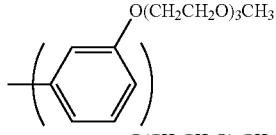

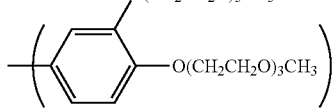

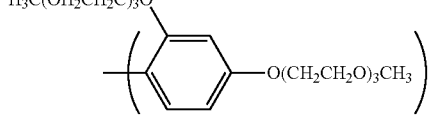

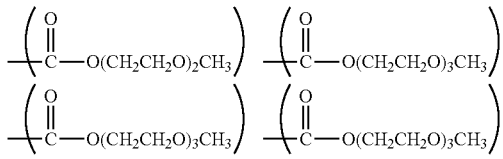

-continued

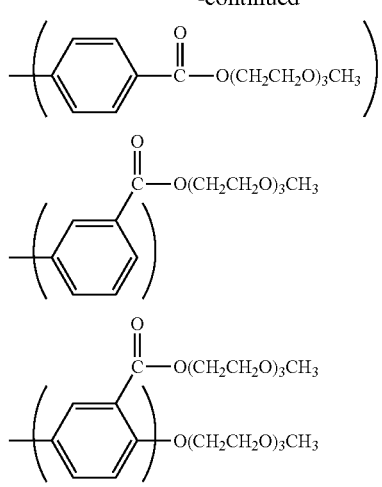

The structural unit represented by Formula (1) is preferably a structural unit represented by Formula (10), in view of the stability of the polymer compound. The structural unit represented by Formula (10) is a divalent structural unit.

[Chemical Formula 15]

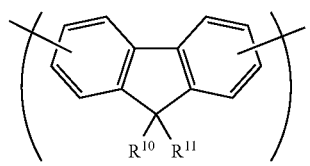

(10)

In Formula (10), $R^{10}$ is a group represented by Formula (2) or Formula (3), preferably the group represented by Formula (2), in view of the stability of the polymer compound according to the present invention against an electronic current. $R^{11}$ is a group represented by Formula (4). A hydrogen atom in Formula (10) may be replaced with a substituent that is the same as the substituent exemplified in the description with respect to Formula (1) other than $R^{10}$ or $R^{11}$. When the substituent is plurally present, they may be the same or different.

Examples of the structural unit represented by Formula (10) may include structural units that optionally has a substituent represented by the following formulae. In the following formulae, M represents the same meaning as described above. Examples of the substituent may include the same as the substituent exemplified in the description with respect to Formula (1). When the substituent is plurally present, they may be the same or different.

[Chemical Formula 16]

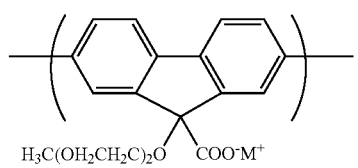

-continued

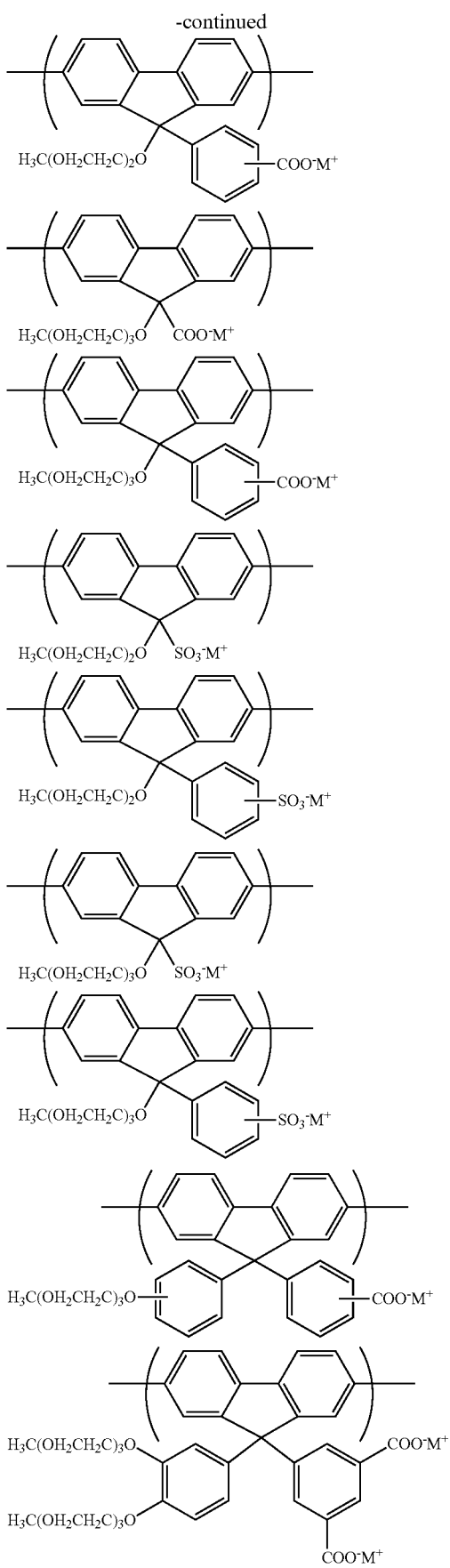

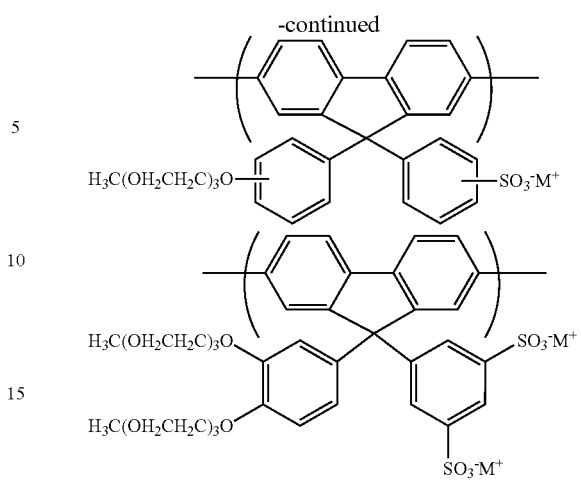

—Structural Unit Represented by Formula (7)

In Formula (7), $R^6$ is a group represented by Formula (8) or Formula (9), $R^7$ is a group represented by Formula (4), and m5 represents an integer of 0 or more. m5 is preferably 0 to 3 and more preferably 0 to 2.

The structural unit represented by Formula (7) may contain two or more types of groups represented by Formula (8), may contain two or more types of groups represented by Formula (9), and may contain two or more types of groups represented by Formula (4).

A hydrogen atom in Formula (7) may be replaced with a substituent other than $R^6$ or $R^7$. Examples of the substituent may include the same as the substituent exemplified in the description with respect to Formula (1). In view of solubility, preferred examples of the substituent are an alkyl group, an alkoxy group, an aryl group, and aryloxy group. When the substituent is plurally present, they may be the same or different.

—Group Represented by Formula (8)—

In Formula (8), $R^8$ represents a (1+m6+m7)-valent organic group that optionally has a substituent. The group represented by Formula (8) is a monovalent group.

In Formula (8), the (1+m6+m7)-valent organic group that optionally has a substituent represented by $R^8$ may include: a group remaining after removing (m6+m7) hydrogen atoms from an alkyl group having 1 to 20 carbon atoms that optionally has a substituent, such as a methyl group, an ethyl group, a propyl group, an isopropyl group, a butyl group, an isobutyl group, a sec-butyl group, a tert-butyl group, a pentyl group, a hexyl group, a cyclohexyl group, a heptyl group, an octyl group, a nonyl group, a decyl group, a lauryl group, and a group in which at least one hydrogen atom in these groups is substituted with a substituent; a group remaining after removing (m6+m7) hydrogen atoms from an aryl group having 6 to 30 carbon atoms that optionally has a substituent, such as a phenyl group, a 1-naphthyl group, a 2-naphthyl group, a 1-anthracenyl group, a 2-anthracenyl group, a 9-anthracenyl group, and a group in which at least one hydrogen atom in these groups is substituted with a substituent; a group remaining after removing (m6+m7) hydrogen atoms from an alkoxy group having 1 to 50 carbon atoms that optionally has a substituent, such as a methoxy group, an ethoxy group, a propyloxy group, a butoxy group, a pentyloxy group, a hexyloxy group, a nonyloxy group, a dodecyloxy group, a cyclopropyloxy group, a cyclobutyloxy group, a cyclopentyloxy group, a cyclohexyloxy group, a cyclononyloxy group, a cyclododecyloxy group, a norbornyloxy group, an adamantyloxy group, and a group in which at least one hydrogen atom in these groups is substituted with a substituent; a group remaining after removing (m6+m7) hydrogen atoms from an amino group having a substituent containing a carbon atom; and a group remaining after removing (m6+m7) hydrogen atoms from a silyl group having a substituent containing a carbon atom. The number of carbons of the substituent is not included in the above number of carbons. Because the synthesis of the raw material monomer is simplified, preferred examples are a group remaining after removing (m6+m7) hydrogen atoms from an alkyl group, a group remaining after removing (m6+m7) hydrogen atoms from an aryl group, and a group remaining after removing (m6+m7) hydrogen atoms from an alkoxy group.

Examples of the above substituent may include the same as the substituent exemplified in the description with respect to Formula (1). When the substituent is plurally present, they may be the same or different.

In Formula (8), m6 and m7 each independently represent an integer of 1 or more (e.g., 1, 2, or 3 for each).

In Formula (8), $Q^1$, $Q^3$, $Y^1$, $Y^3$, $M^1$, $Z^1$, n1, n3, a1, and b1 are the same as the corresponding definitions above.

[Specific Examples of Group Represented by Formula (8)]

Examples of the group represented by Formula (8) may include groups represented by the following formulae. In the following formulae, M represents the same meaning as described above.

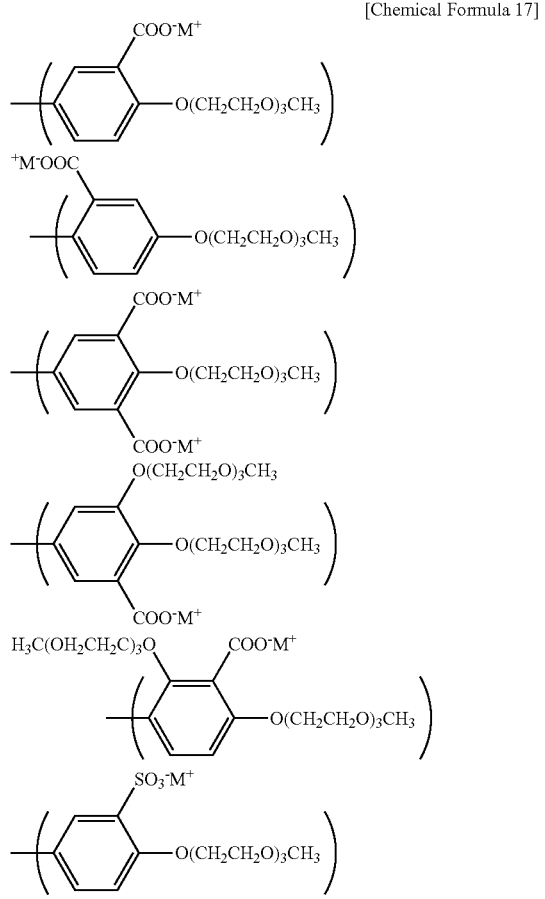

[Chemical Formula 17]

—Group Represented by Formula (9)—

In Formula (9), $R^9$ represents a (1+m8+m9)-valent organic group that optionally has a substituent. The group represented by Formula (9) is a monovalent group.

In Formula (9), the (1+m8+m9)-valent organic group that optionally has a substituent represented by $R^9$ may include: a group remaining after removing (m8+m9) hydrogen atoms from an alkyl group having 1 to 20 carbon atoms that optionally has a substituent, such as a methyl group, an ethyl group, a propyl group, an isopropyl group, a butyl group, an isobutyl group, a sec-butyl group, a tert-butyl group, a pentyl group, a hexyl group, a cyclohexyl group, a heptyl group, an octyl group, a nonyl group, a decyl group, a lauryl group, and a group in which at least one hydrogen atom in these groups is substituted with a substituent; a group remaining after removing (m8+m9) hydrogen atoms from an aryl group having 6 to 30 carbon atoms that optionally has a substituent, such as a phenyl group, a 1-naphthyl group, a 2-naphthyl group, a 1-anthracenyl group, a 2-anthracenyl group, a 9-anthracenyl group, and a group in which at least one hydrogen atom in these groups is substituted with a substituent; a group remaining after removing (m8+m9) hydrogen atoms from an alkoxy group having 1 to 50 carbon atoms that optionally has a substituent, such as a methoxy group, an ethoxy group, a propyloxy group, a butoxy group, a pentyloxy group, a hexyloxy group, a nonyloxy group, a dodecyloxy group, a cyclopropyloxy group, a cyclobutyloxy group, a cyclopentyloxy group, a cyclohexyloxy group, a cyclononyloxy group, a cyclododecyloxy group, a norbornyloxy group, an adamantyloxy group, and a group in which at least one hydrogen atom in these groups is substituted with a substituent; a group remaining after removing (m8+m9) hydrogen atoms from an amino group having a substituent containing a carbon atom; and a group remaining after removing (m8+m9) hydrogen atoms from a silyl group having a substituent containing a carbon atom. The number of carbons of the substituent is not included in the above number of carbons. Because the synthesis of the raw material monomer is simplified, preferred examples are a group remaining after removing (m8+m9) hydrogen atoms from an alkyl group, a group remaining after removing (m8+m9) hydrogen atoms from an aryl group, and a group remaining after removing (m8+m9) hydrogen atoms from an alkoxy group.

Examples of the above substituent may include the same as the substituent exemplified in the description with respect to Formula (1). When the substituent is plurally present, they may be the same or different.

In Formula (9), m8 and m9 each independently represent an integer of 1 or more (e.g., 1, 2, or 3 for each).

In Formula (9), $Q^2$, $Q^3$, $Y^2$, $Y^3$, $M^2$, $Z^2$, n2, n3, a2, and b2 are the same as the corresponding definitions above.

[Specific Examples of Group Represented by Formula (9)]

Examples of the group represented by Formula (9) may include groups represented by the following formulae. In the following formulae, X represents the same meaning as described above.

[Chemical Formula 18]

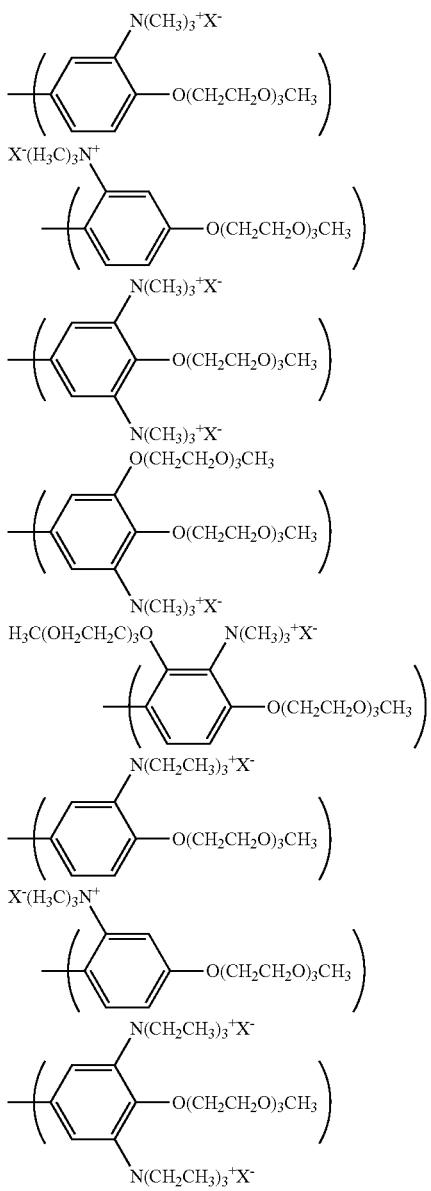

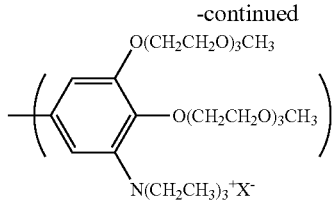

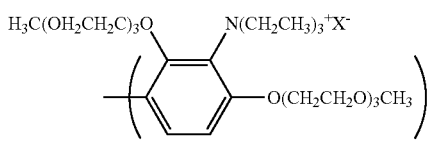

The structural unit represented by Formula (7) is preferably a structural unit represented by Formula (11), in view of the stability of the polymer compound. The structural unit represented by Formula (11) is a divalent structural unit.

[Chemical Formula 19]

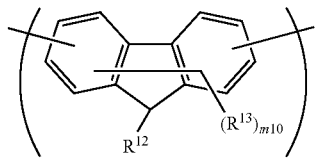

(11)

In Formula (11), $R^{12}$ is a group represented by Formula (8) or Formula (9), preferably the group represented by Formula (8), in view of the stability of the polymer compound according to the present invention against an electronic current; $R^{13}$ is a group represented by Formula (4); m10 represents an integer of 0 or more; a hydrogen atom in Formula (11) may be replaced with a substituent that is the same as the substituent exemplified in the description with respect to Formula (1) other than $R^{12}$ or $R^{13}$; and when the substituent is plurally present, they may be the same or different. m10 is preferably 0 to 3 and more preferably 0 to 2.

Examples of the structural unit represented by Formula (11) may include structural units that optionally has a substituent represented by the following formulae. In the following formulae, M represents the same meaning as described above. Examples of the above substituent may include the same as the substituent exemplified in the description with respect to Formula (1). When the substituent is plurally present, they may be the same or different.

[Chemical Formula 20]

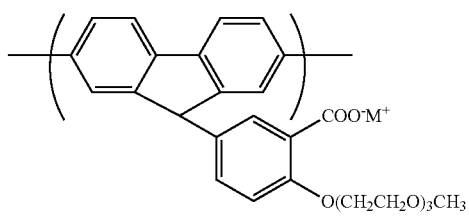

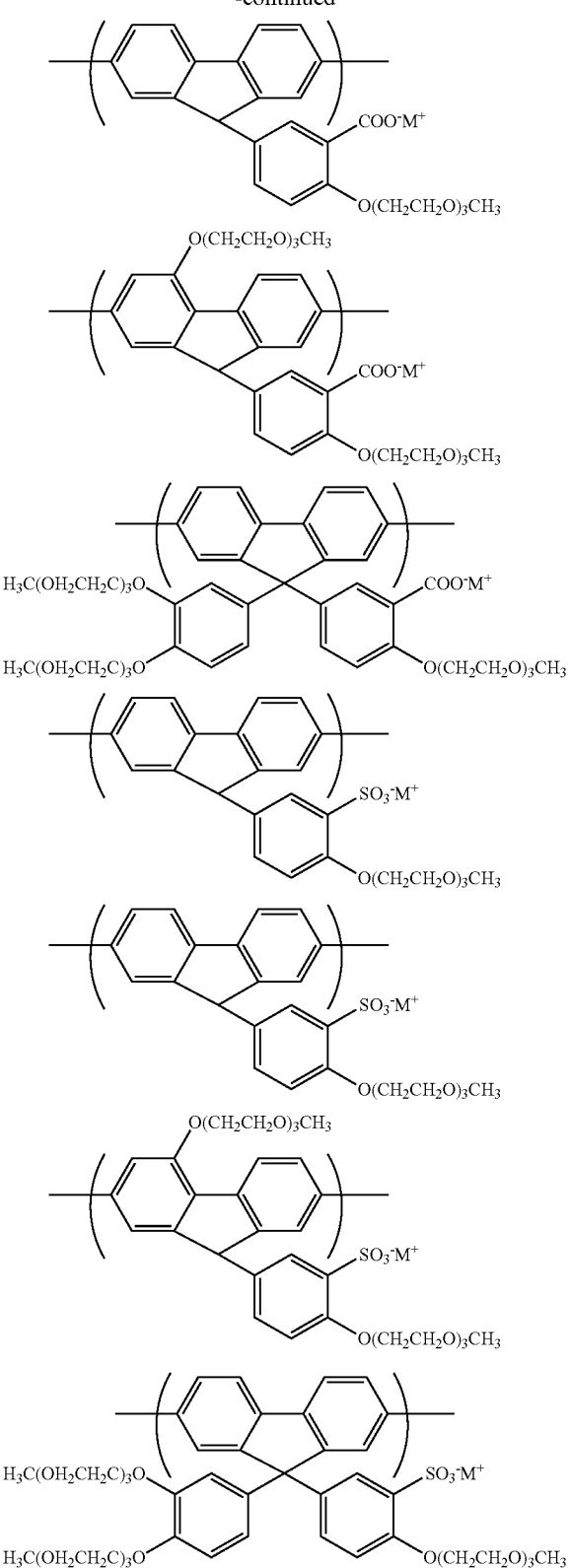

Other Structural Units

The polymer compound according to the present invention may have one or more structural units represented by Formula (15).

[Chemical Formula 21]

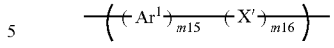

(15)

(In Formula (15), $Ar^1$ represents a divalent aromatic group that optionally has a substituent or a divalent aromatic amine residue that optionally has a substituent; X' represents an imino group that optionally has a substituent, a silylene group that optionally has a substituent, or an ethenylene group that optionally has a substituent or ethynylene group; m15 and m16 each independently represent 0 or 1; and at least either one of m15 and m16 is 1.)

Examples of the divalent aromatic group represented by $Ar^1$ in Formula (15) may include divalent aromatic hydrocarbon groups and divalent aromatic heterocyclic groups. Examples of the divalent aromatic group may include: a divalent group remaining after removing two hydrogen atoms that are boned to a carbon atom constituting a ring from a monocyclic aromatic ring such as a benzene ring, a pyridine ring, a 1,2-diazine ring, a 1,3-diazine ring, a 1,4-diazine ring, a 1,3,5-triazine ring, a furan ring, a pyrrole ring, a thiophene ring, a pyrazole ring, an imidazole ring, an oxazole ring, an oxadiazole ring, and an azadiazole ring; a divalent group remaining after removing two hydrogen atoms that are bonded to a carbon atom constituting a ring from a fused polycyclic aromatic ring in which two or more rings selected from the group consisting of the above monocyclic aromatic rings are fused; a divalent group remaining after removing two hydrogen atoms that are bonded to a carbon atom constituting a ring from an aromatic ring assembly in which two or more aromatic rings selected from the group consisting of the above monocyclic aromatic rings and the above fused polycyclic aromatic rings are linked through a single bond, an ethenylene group, or an ethynylene group; and a divalent group remaining after removing two hydrogen atoms that are bonded to a carbon atom constituting a ring from a bridged polycyclic aromatic ring having a bridge in which two aromatic rings adjacent to each other of the above fused polycyclic aromatic ring or the above aromatic ring assembly are bridged through a divalent group such as a methylene group, an ethylene group, a carbonyl group, and an imino group.

In the fused polycyclic aromatic ring, the number of monocyclic aromatic rings to be fused is preferably 2 to 4, more preferably 2 to 3, and further preferably 2, in view of the solubility of the polymer compound. In the aromatic ring assembly, the number of aromatic rings to be linked is preferably 2 to 4, more preferably 2 to 3, and further preferably 2, in view of the solubility. In the bridged polycyclic aromatic ring, the number of aromatic rings to be bridged is preferably 2 to 4, more preferably 2 to 3, and further preferably 2, in view of the solubility of the polymer compound.

Examples of the monocyclic aromatic ring may include the following rings.

[Chemical Formula 22]

52

Examples of the fused polycyclic aromatic ring may include the following rings.
[Chemical Formula 23]
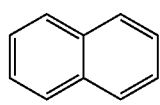
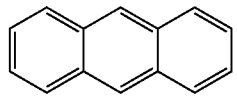
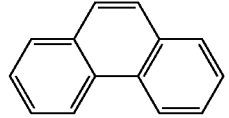
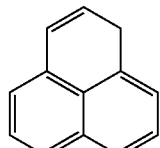
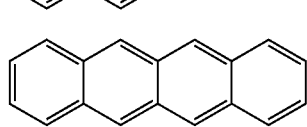
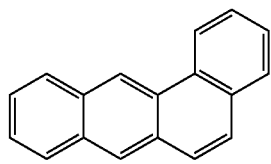
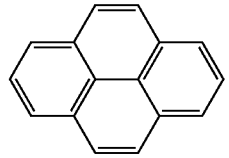
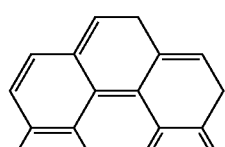
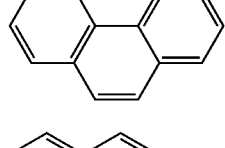
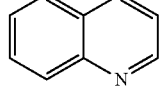

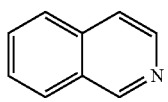
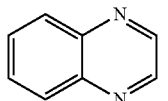
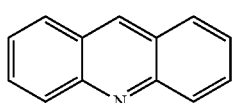
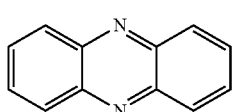
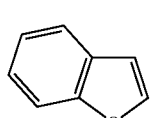
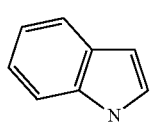
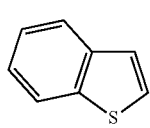
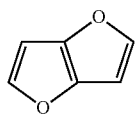
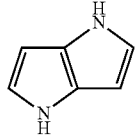
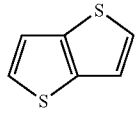
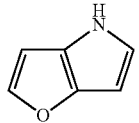
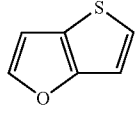
Examples of the aromatic ring assembly may include the following rings.
[Chemical Formula 24]
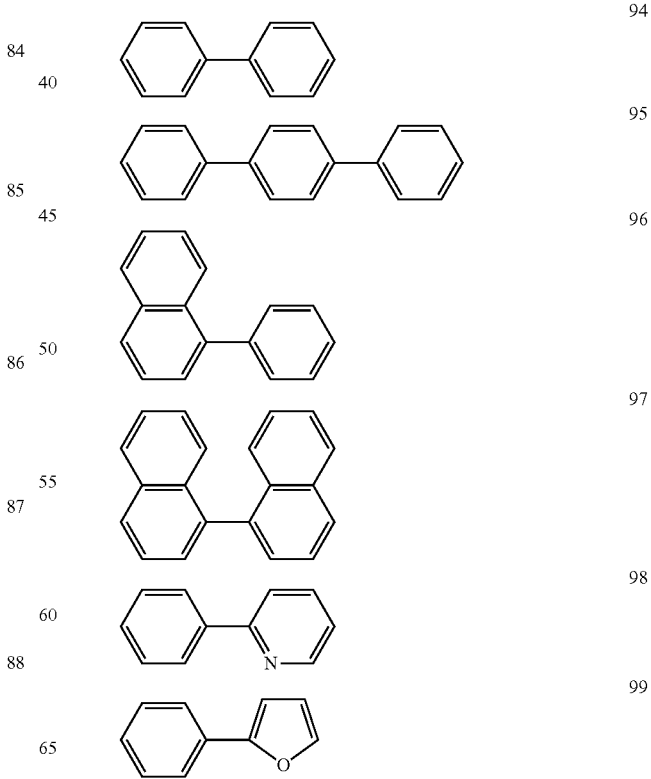

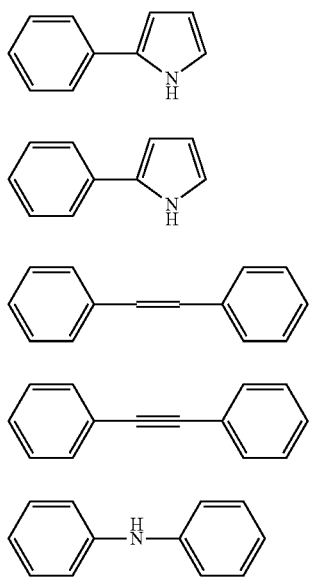

Examples of the bridged polycyclic aromatic ring may include the following rings.

[Chemical Formula 25]

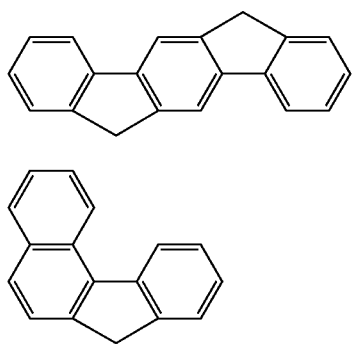

In view of any one of or both of the electron acceptability and the hole acceptability of the polymer compound, the divalent aromatic group represented by $Ar^1$ is preferably a divalent group remaining after removing two hydrogen atoms from a ring represented by a Formula from 52 to 67, 68 to 83, 89 to 93, 104 to 106, 108, and 109, and more preferably a divalent group remaining after removing two hydrogen atoms from a ring represented by a Formula from 52 to 57, 66, 67, 89, 91, 93, 104, 105, 108, and 109.

The divalent aromatic group may have a substituent. Examples of the substituent may include the same as the substituent exemplified in the description with respect to Formula (1).

Examples of the divalent aromatic amine residue represented by $Ar^1$ in Formula (15) may include a group represented by Formula (16).

[Chemical Formula 26]

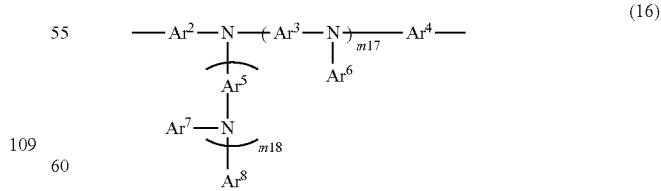

(16)

(In Formula (16), $Ar^2$, $Ar^3$, $Ar^4$, and $Ar^5$ each independently represent an arylene group that optionally has a substituent or a divalent heterocyclic group that optionally has a substituent; $Ar^6$, $Ar^7$, and $Ar^8$ each independently represent an aryl group that optionally has a substituent or a monovalent heterocyclic group that optionally has a substituent; and m17 and m18 each independently represent 0 or 1.)

Examples of the substituent that the arylene group, the aryl group, the divalent heterocyclic group or the monovalent heterocyclic group may have may include a halogen atom, an alkyl group, an alkyloxy group, an alkylthio group, an aryl group, an aryloxy group, an arylthio group, an arylalkyl group, an arylalkyloxy group, an arylalkylthio group, an alkenyl group, an alkynyl group, an arylalkenyl group, an arylalkynyl group, an acyl group, an acyloxy group, an amido group, an acid imido group, an imine residue, a substituted amino group, a substituted silyl group, a substituted silyloxy group, a substituted silylthio group, a substituted silylamino group, a cyano group, a nitro group, a monovalent heterocyclic group, a heteroaryloxy group, a heteroarylthio group, an alkyloxycarbonyl group, an aryloxycarbonyl group, an arylalkyloxycarbonyl group, a heteroaryloxycarbonyl group, and a carboxy group. The substituent may also be a cross-linkable group such as a vinyl group, an acetylene group, a butenyl group, an acryl group, an acrylate group, an acrylamido group, a methacryl group, a methacrylate group, a methacrylamido group, a vinyl ether group, a vinyl amino group, a silanol group, a group having a small ring (such as a cyclopropyl group, a cyclobutyl group, an epoxy group, an oxetane group, a diketene group, and an episulfide group), a lactone group, a lactam group, and a group containing a structure of a siloxane derivative.

When m17 is 0, a carbon atom in $Ar^2$ and a carbon atom in $Ar^4$ may be bonded to each other directly or may be bonded to each other through a divalent group such as —O— and —S—.

The aryl group and the monovalent heterocyclic group represented by $Ar^6$, $Ar^7$ and $Ar^8$ are the same as the aryl group and the monovalent heterocyclic group described and exemplified above as the substituent.

Examples of the arylene group represented by $Ar^2$, $Ar^3$, $Ar^4$, and $Ar^5$ may include an atomic group remaining after removing two hydrogen atoms that are bonded to a carbon atom constituting a ring (preferably, an aromatic ring) from an aromatic hydrocarbon, and examples of the arylene group may include a group having a benzene ring, a group having a fused ring, and a group in which two or more independent benzene rings or fused rings are bonded with each other through a single bond or a divalent organic group, for example, an alkenylene group such as a vinylene group. The arylene group has usually 6 to 60 carbon atoms and preferably 7 to 48 carbon atoms. Specific examples of the arylene group may include a phenylene group, a biphenylene group, a $C_1$ to $C_{17}$ alkoxyphenylene group, a $C_1$ to $C_{17}$ alkylphenylene group, a 1-naphthylene group, a 2-naphthylene group, a 1-anthracenylene group, a 2-anthracenylene group, and a 9-anthracenylene group. A hydrogen atom in the aryl group may be substituted with a fluorine atom. Examples of such a fluorine atom-substituted aryl group may include a tetrafluorophenylene group. Among the aryl groups, a phenylene group, a biphenylene group, a $C_1$ to $C_{12}$ alkoxyphenylene group, and a $C_1$ to $C_{12}$ alkylphenylene group are preferred.

Examples of the divalent heterocyclic group represented by $Ar^2$, $Ar^3$, $Ar^4$, and $Ar^5$ may include an atomic group remaining after removing two hydrogen atoms that are bonded to a carbon atom constituting a ring from a heterocyclic compound. The heterocyclic compound refers to an organic compound containing not only a carbon atom, but also a hetero atom such as an oxygen atom, a sulfur atom, a nitrogen atom, a phosphorus atom, a boron atom, a silicon atom, a selenium atom, a tellurium atom, and an arsenic atom as an element constituting the ring, among organic compounds having a cyclic structure. The divalent heterocyclic group may have a substituent. The divalent heterocyclic group has usually 4 to 60 carbon atoms and preferably 4 to 20 carbon atoms. The number of carbon atoms of the divalent heterocyclic group does not include the number of carbon atoms of the substituent. Examples of such a divalent heterocyclic group may include a thiophenediyl group, a $C_1$ to $C_{12}$ alkylthiophenediyl group, a pyrroldiyl group, a furandiyl group, a pyridinediyl group, a $C_1$ to $C_{12}$ alkylpyridinediyl group, a pyridazinediyl group, a pyrimidinediyl group, a pyrazinediyl group, a triazinediyl group, a pyrrolidinediyl group, a piperidinediyl group, a quinolinediyl group, and an isoquinolinediyl group, and among them, a thiophenediyl group, a $C_1$ to $C_{12}$ alkylthiophenediyl group, a pyridinediyl group, and a $C_1$ to $C_{12}$ alkylpyridinediyl group are more preferred.

The polymer compound containing a divalent aromatic amine residue as a structural unit may further have other structural units. Examples of the other structural unit may include an arylene group such as a phenylene group and a fluorenediyl group.

Examples of the divalent aromatic amine residue represented by Formula (16) may include a group remaining after removing two hydrogen atoms from an aromatic amine represented by a Formula from 115 to 124 below. In view of the stability of the polymer compound against a hole current, a group remaining after removing two hydrogen atoms from an aromatic amine represented by Formula 115, 116, 117, or 120 is preferred.

[Chemical Formula 27]

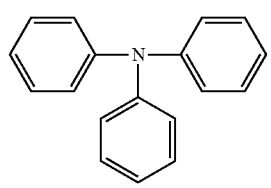

115

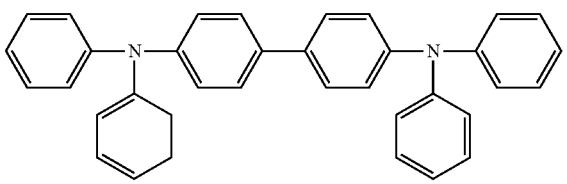

116

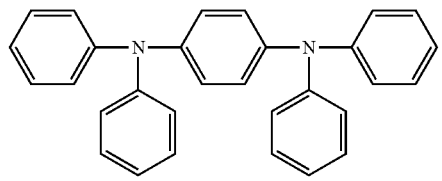

117

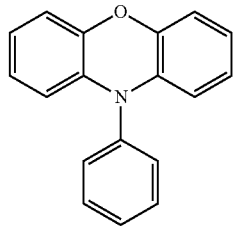

118

-continued

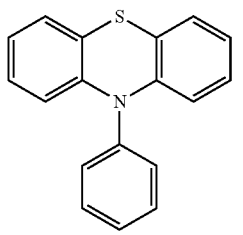
119

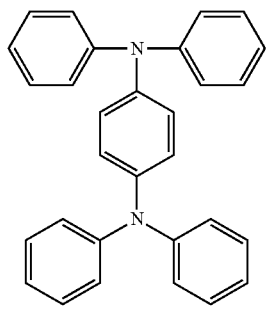
120

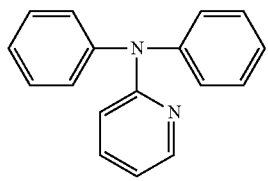
121

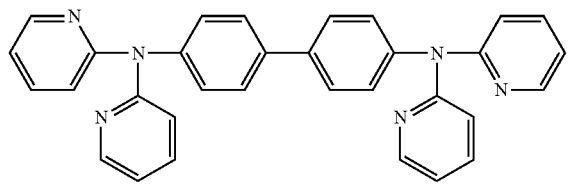
122

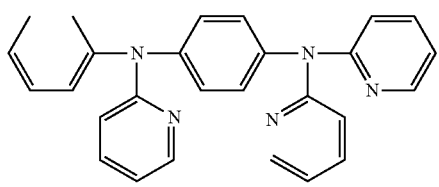
123

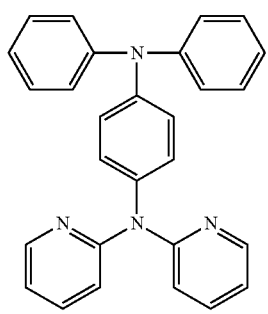
124

The aromatic amine represented by a Formula from 115 to 124 may have a substituent so long as the aromatic amine can generate a divalent aromatic amine residue. Examples of the substituent may include the same substituent exemplified in the above description with respect to Formula (1). When the substituent is plurally present, they may be the same or different.

In Formula (15), X' represents an imino group that optionally has a substituent, a silylene group that optionally has a substituent, an ethenylene group that optionally has a substituent, or an ethynylene group. Examples of the substituent that an imino group, a silyl group, or an ethenylene group may have may include: an alkyl group having 1 to 20 carbon atoms such as a methyl group, an ethyl group, a propyl group, an isopropyl group, a butyl group, an isobutyl group, a sec-butyl group, a tert-butyl group, a pentyl group, a hexyl group, a cyclohexyl group, a heptyl group, an octyl group, a 2-ethylhexyl group, a nonyl group, a decyl group, a 3,7-dimethyloctyl group, and a lauryl group; and an aryl group having 6 to 30 carbon atoms such as a phenyl group, a 1-naphthyl group, a 2-naphthyl group, a 1-anthracenyl group, a 2-anthracenyl group, and a 9-anthracenyl group. When the substituent is plurally present, they may be the same or different.

In view of the stability of the polymer compound against air, moisture, or heat, X' is preferably an imino group, an ethenylene group, or an ethynylene group.

In view of the electron transport property of the polymer compound, it is preferable that m15 is 1 and m16 is 0.

Ratio of Structural Units

In view of the light-emitting efficiency of the electroluminescent device, the ratio of the sum of the structural unit represented by Formula (1), the structural unit represented by Formula (7), the structural unit represented by Formula (10), and the structural unit represented by Formula (11) contained in the polymer compound according to the present invention is more preferably 30 to 100% by mole, based on all structural units contained in the polymer compound with the terminal structural unit excluded.

Terminal Structural Unit

Examples of the terminal structural unit (terminal group) of the polymer compound according to the present invention may include a hydrogen atom, a methyl group, an ethyl group, a propyl group, an isopropyl group, a butyl group, an isobutyl group, a sec-butyl group, a tert-butyl group, a pentyl group, an isoamyl group, a hexyl group, a cyclohexyl group, a heptyl group, an octyl group, a nonyl group, a decyl group, a lauryl group, a methoxy group, an ethoxy group, a propyloxy group, an isopropyloxy group, a butoxy group, an isobutoxy group, a sec-butoxy group, a tert-butoxy group, a pentyloxy group, a hexyloxy group, a cyclohexyloxy group, a heptyloxy group, an octyloxy group, a 2-ethylhexyloxy group, a nonyloxy group, a decyloxy group, a 3,7-dimethyloctyloxy group, a lauryloxy group, a methylthio group, an ethylthio group, a propylthio group, an isopropylthio group, a butylthio group, an isobutylthio group, a sec-butylthio group, a tert-butylthio group, a pentylthio group, a hexylthio group, a cyclohexylthio group, a heptylthio group, an octylthio group, a nonylthio group, a decylthio group, a laurylthio group, a methoxyphenyl group, an ethoxyphenyl group, a propyloxyphenyl group, an isopropyloxyphenyl group, a butoxyphenyl group, an isobutoxyphenyl group, a sec-butoxyphenyl group, a tert-butoxyphenyl group, a pentyloxyphenyl group, a hexyloxyphenyl group, a cyclohexyloxyphenyl group, a heptyloxyphenyl group, an octyloxyphenyl group, a 2-ethylhexyloxyphenyl group, a nonyloxyphenyl group, a decyloxyphenyl group, a 3,7-dimethyloctyloxyphenyl group, a lauryloxyphenyl group, a methylphenyl group, an ethylphenyl group, a dimethylphenyl group, a propylphenyl group, a mesityl group, a methylethylphenyl group, an isopropylphenyl group, a butylphenyl group, an isobutylphenyl group, a tert-butylphenyl group, a pentylphenyl group, an isoamylphenyl group, a hexylphenyl group, a heptylphenyl group, an octylphenyl group, a nonylphenyl group, a decylphenyl group, a dodecylphenyl group, a methylamino group, a dimethylamino group, an ethylamino group, a diethylamino group, a propylamino group, a dipropylamino group, an isopropylamino group, a diisopropylamino group, a butylamino group, an isobutylamino group, a sec-butylamino group, a tert-butylamino group, a pentylamino group, a hexylamino group, a cyclohexylamino group, a heptylamino group, an octylamino group, a 2-ethylhexylamino group, a nonylamino group, a decylamino group, a 3,7-dimethyloctylamino group, a laurylamino group, a cyclopentylamino group, a dicyclopentylamino group, a cyclohexylamino group, a dicyclohexylamino group, a ditrifluoromethylamino group, a phenylamino group, a diphenylamino group, a ($C_1$ to $C_{12}$ alkoxyphenyl)amino group, a di($C_1$ to $C_{12}$ alkoxyphenyl)amino group, a di($C_1$ to $C_{12}$ alkylphenyl)amino group, a 1-naphthylamino group, a 2-naphthylamino group, a pentafluorophenylamino group, a pyridylamino group, a pyridazinylamino group, a pyrimidylamino group, a pyrazinylamino group, a triazinylamino group, a (phenyl-$C_1$ to $C_{12}$ alkyl)amino group, a ($C_1$ to $C_{12}$ alkoxyphenyl-$C_1$ to $C_{12}$ alkyl)amino group, a ($C_1$ to $C_{12}$ alkylphenyl-$C_1$ to $C_{12}$ alkyl) amino group, a di($C_1$ to $C_{12}$ alkoxyphenyl-$C_1$ to $C_{12}$ alkyl) amino group, a di($C_1$ to $C_{12}$ alkylphenyl-$C_1$ to $C_{12}$ alkyl) amino group, a 1-naphthyl-$C_1$ to $C_{12}$ alkylamino group, a 2-naphthyl-$C_1$ to $C_{12}$ alkylamino group, a trimethylsilyl group, a triethylsilyl group, a tripropylsilyl group, a triisopropylsilyl group, an isopropyldimethylsilyl group, an isopropyldiethylsilyl group, a tert-butyldimethylsilyl group, a pentyldimethylsilyl group, a hexyldimethylsilyl group, a heptyldimethylsilyl group, an octyldimethylsilyl group, a 2-ethylhexyldimethylsilyl group, a nonyldimethylsilyl group, a decyldimethylsilyl group, a 3,7-dimethyloctyldimethylsilyl group, a lauryldimethylsilyl group, a (phenyl-$C_1$ to $C_{12}$ alkyl)silyl group, a ($C_1$ to $C_{12}$ alkoxyphenyl-$C_1$ to $C_{12}$ alkyl)silyl group, a ($C_1$ to $C_{12}$ alkylphenyl-$C_1$ to $C_{12}$ alkyl) silyl group, a (1-naphthyl-$C_1$ to $C_{12}$ alkyl)silyl group, a (2-naphthyl-$C_1$ to $C_{12}$ alkyl)silyl group, a (phenyl-$C_1$ to $C_{12}$ alkyl)dimethylsilyl group, a triphenylsilyl group, a tri(p-xylyl)silyl group, a tribenzylsilyl group, a diphenylmethylsilyl group, a tert-butyldiphenylsilyl group, a dimethylphenylsilyl group, a thienyl group, a $C_1$ to $C_{12}$ alkylthienyl group, a pyrrolyl group, a furyl group, a pyridyl group, a $C_1$ to $C_{12}$ alkylpyridyl group, a pyridazinyl group, a pyrimidyl group, a pyrazinyl group, a triazinyl group, a pyrrolidyl group, a piperidyl group, a quinolyl group, an isoquinolyl group, a hydroxy group, a mercapto group, a fluorine atom, a chlorine atom, a bromine atom, and an iodine atom. When the terminal structural unit is plurally present, they may be the same or different.

—Characteristics of Polymer Compound—

The polymer compound refers to a compound whose polystyrene-equivalent weight-average molecular weight is $1\times10^3$ or more.

In view of the film forming property by the application of the polymer compound according to the present invention, polystyrene-equivalent weight-average molecular weight of the polymer compound is preferably $1\times10^3$ or more, more preferably $2\times10^3$ or more, further preferably $3\times10^3$ or more, and particularly preferably $5\times10^3$ or more; the upper limit of the weight-average molecular weight is preferably $1\times10^8$ or less and more preferably $1\times10^7$ or less; and the range of the weight-average molecular weight is preferably $1\times10^3$ to $1\times10^8$, more preferably $2\times10^3$ to $1\times10^7$, further preferably $3\times10^3$ to $1\times10^7$, and particularly preferably $5\times10^3$ to $1\times10^7$. In view of the purity of the polymer compound, polystyrene-equivalent number-average molecular weight is preferably $1\times10^3$ or more; the upper limit of the number-average molecular weight is preferably $5\times10^7$ or less, more preferably $1\times10^7$ or less, and further preferably $5\times10^6$ or less; and the range of the number-average molecular weight is preferably $1\times10^3$ to $5\times10^7$, more preferably $1\times10^3$ to $1\times10^7$, and further preferably $1\times10^3$ to $5\times10^6$. In view of the solubility of the polymer compound, polystyrene-equivalent weight-average molecular weight is preferably $1\times10^3$ or more; the upper limit of the weight-average molecular weight is preferably $5\times10^5$ or less, more preferably $5\times10^4$ or less, and further preferably $3\times10^3$ or less; and the range of the weight-average molecular weight is preferably $1\times10^3$ to $5\times10^5$, more preferably $1\times10^3$ to $5\times10^4$, and further preferably $1\times10^3$ to $3\times10^3$. Polystyrene-equivalent number-average molecular weight and polystyrene-equivalent weight-average molecular weight of the polymer compound according to the present invention can be determined using, for example, gel permeation chromatography (GPC).

The polymer compound used in the present invention is preferably a conjugated polymer compound. That the polymer compound used in the present invention is a conjugated polymer compound means that the polymer compound contains, in the main chain thereof, a region in which multiple bonds or unshared electron pairs possessed by a nitrogen atom, an oxygen atom, or the like are linked through a single bond. When the polymer compound is a conjugated polymer compound, in view of the electron transport property of the conjugated polymer compound, the polymer compound has a ratio calculated by a formula of {(the number of atoms on the main chain contained in the region in which multiple bonds or unshared electron pairs possessed by a nitrogen atom, an oxygen atom, or the like are linked through a single bond)/(the number of all atoms on the main chain)}×100% of preferably 50% or more, more preferably 60% or more, further preferably 70% or more, particularly preferably 80% or more, and most of all preferably 90% or more.

In view of the electron acceptability and the hole acceptability of the polymer compound according to the present invention, the orbital energy of the lowest unoccupied molecular orbital (LUMO) of the polymer compound is preferably −5.0 eV or more and more preferably −4.5 eV or less; the upper limit of the orbital energy of LUMO is preferably −2.0 eV or less; and the range of the orbital energy of LUMO is preferably −5.0 eV or more and −2.0 eV or less, and more preferably −4.5 eV or more and −2.0 eV or less. In view of the same, the orbital energy of the highest occupied molecular orbital (HOMO) of the polymer compound is preferably −6.0 eV or more and more preferably −5.5 eV or more; the upper limit of the orbital energy of HOMO is preferably −3.0 eV or less; and the range of the orbital energy of HOMO is preferably −6.0 eV or more and −3.0 eV or less, and more preferably −5.5 eV or more and −3.0 eV or less, provided that the orbital energy of HOMO is lower than the orbital energy of LUMO. The orbital energy of HOMO of the polymer compound is determined by measuring the ionization potential of the polymer compound, and regarding the obtained ionization potential as the orbital energy. On the other hand, the orbital energy of LUMO of the polymer compound is determined by measuring the energy difference between HOMO and LUMO, and regarding the sum of the value and the above measured ionization potential as the orbital energy. For measuring the ionization potential, a photoelectron spectrophotometer is used. The energy difference between HOMO and LUMO is determined by measuring an absorption spectrum of the polymer compound using an ultraviolet-visible-near infrared spectrophotometer through its absorption edge.

In view of the stability of the polymer compound according to the present invention, the polymer compound is preferably: a polymer compound comprising the structural unit represented by Formula (10); a polymer compound comprising the structural unit represented by Formula (10) and one or more structural units selected from the group consisting of structural units remaining after removing two hydrogen atoms from the compound represented by a Formula from 52 to 57, 66, 67, 89, 91, 93, 104, 105, 108, 109, 115, 116, 117, and 120; a polymer compound comprising the structural unit represented by Formula (11); and a polymer compound comprising the structural unit represented by Formula (11) and one or more structural units selected from the group consisting of structural units remaining after removing two hydrogen atoms from the compound represented by a Formula from 52 to 57, 66, 67, 89, 91, 93, 104, 105, 108, 109, 115, 116, 117, and 120.

Examples of the polymer compound may include the polymer compounds having structural units represented by the following formulae. Among these polymer compounds, in polymer compounds having structural units represented by a formula in which a plurality of structures are delimited by a slash "/," the ratio of the left-hand structural unit is p % by mole and the ratio of the right-hand structural unit is (100−p) % by mole, and these structural units are arranged at random. Structural units other than the structural units represented by the following formulae may be further contained, and also in this case, they can be represented in the same manner as below. In the following formulae, M represents the same meaning as described above; n represents the degree of polymerization; and any hydrogen atom in the formulae may be replaced with a substituent to the extent of capable of being synthesized. Examples of the substituent may include the same as the group that may be substituted in Formula (1).

[Chemical Formula 28]

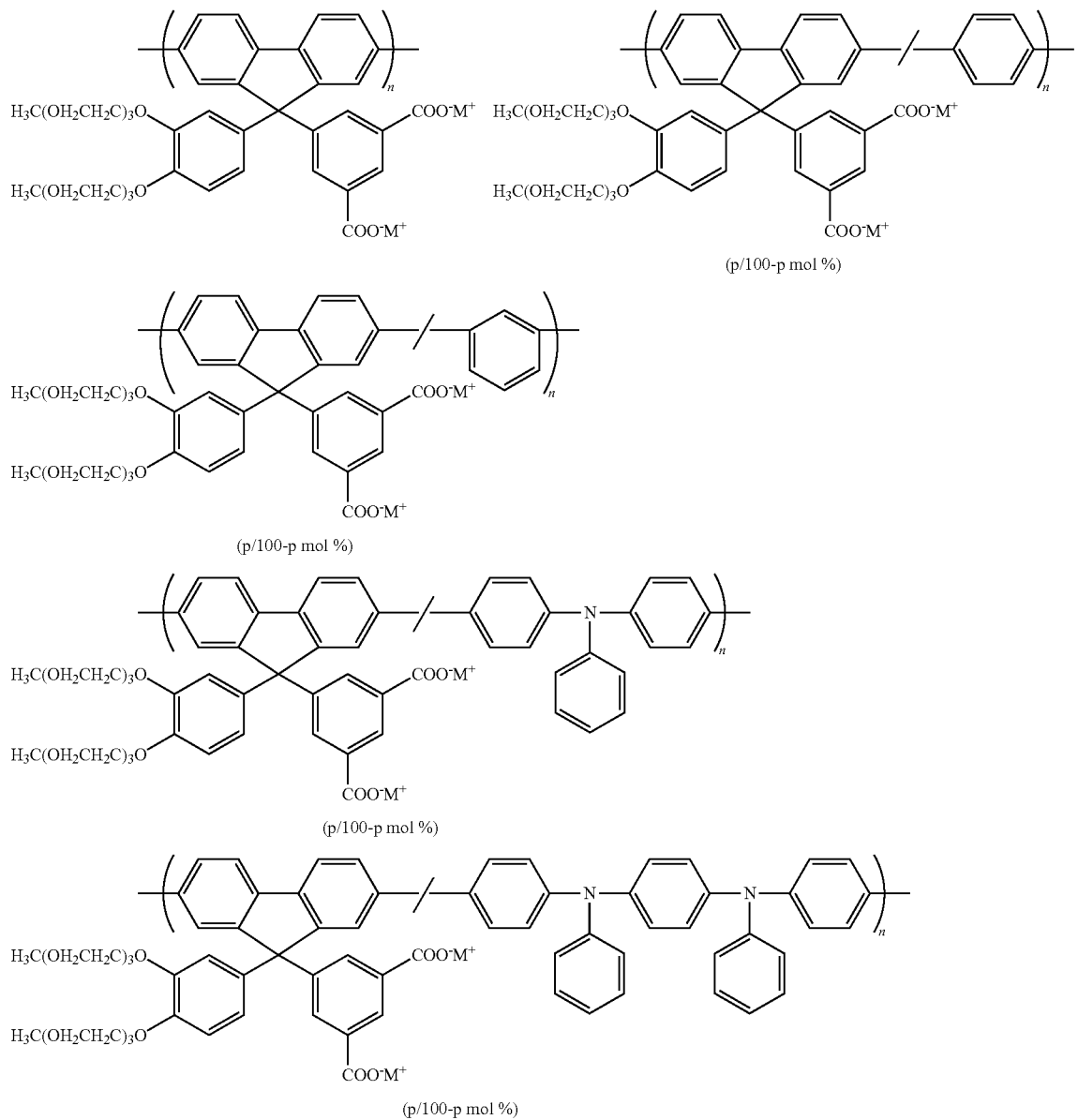

-continued
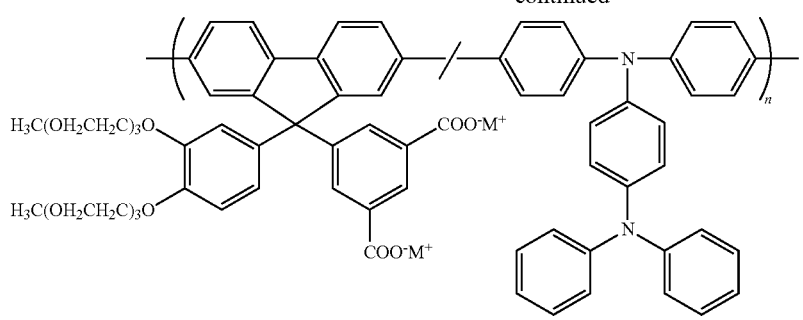
(p/100-p mol %)
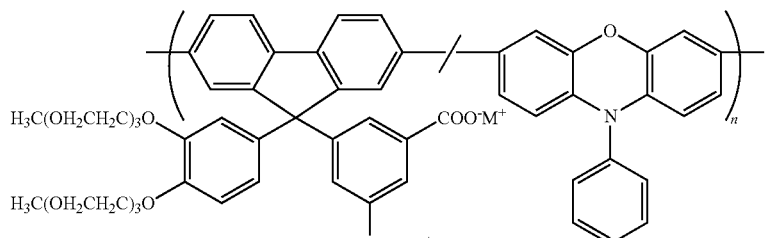
(p/100-p mol %)
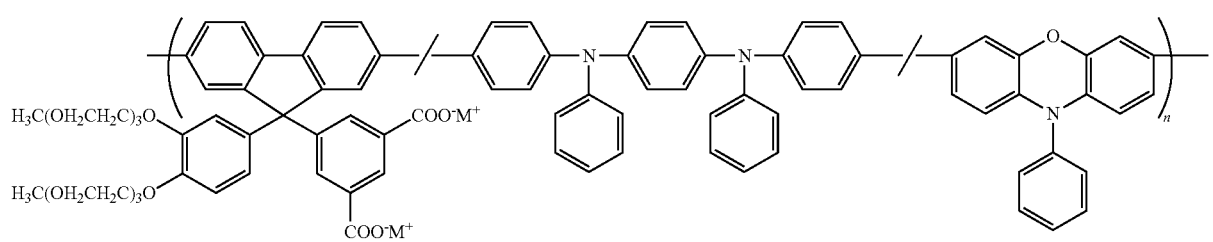
(p/q/100-p-q mol %)
[Chemical Formula 29]
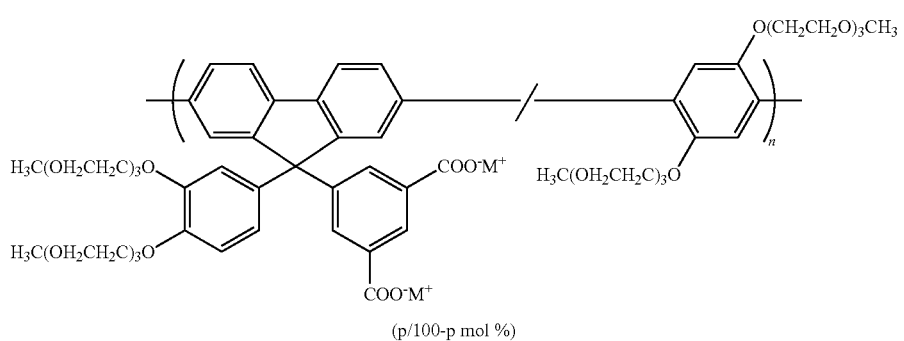
(p/100-p mol %)
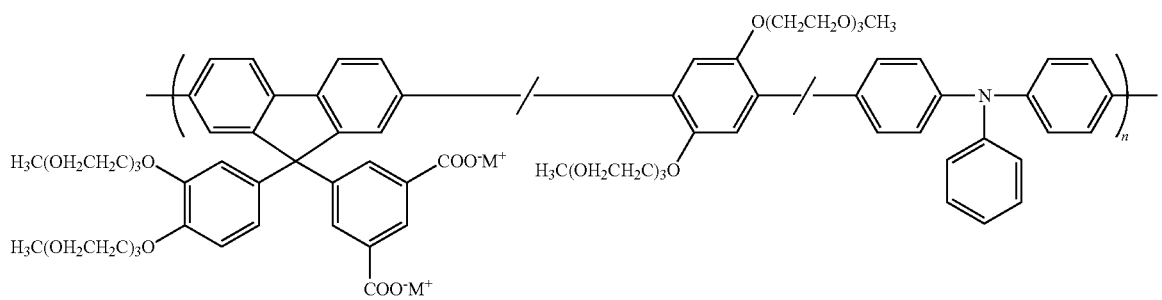
(p/q/100-p-q mol %)

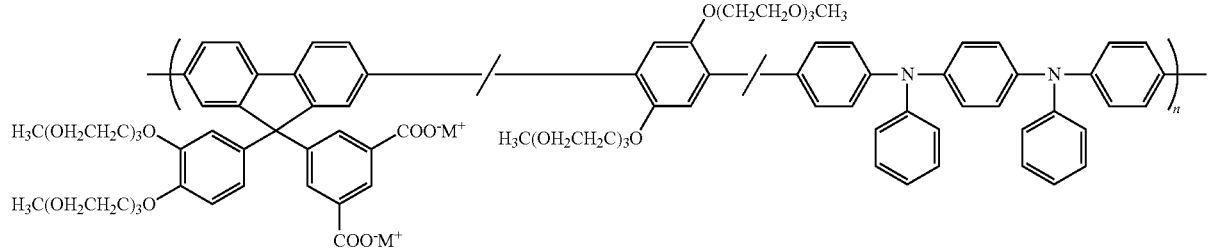
(p/q/100-p-q mol %)
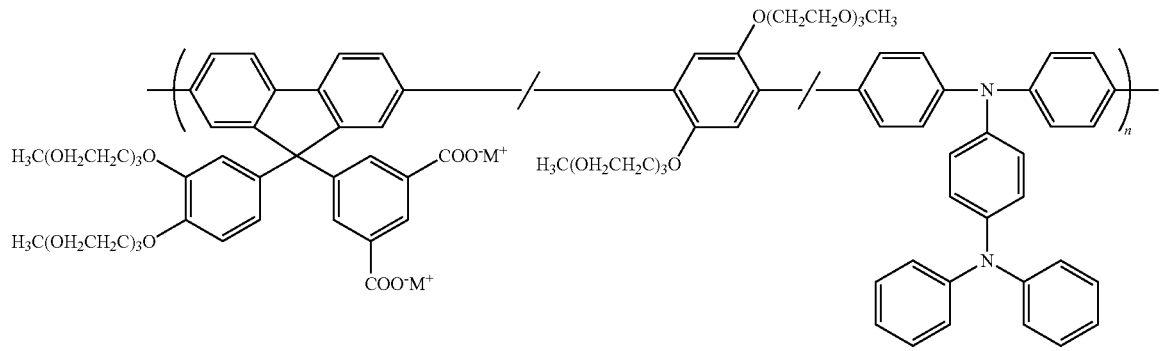
(p/q/100-p-q mol %)
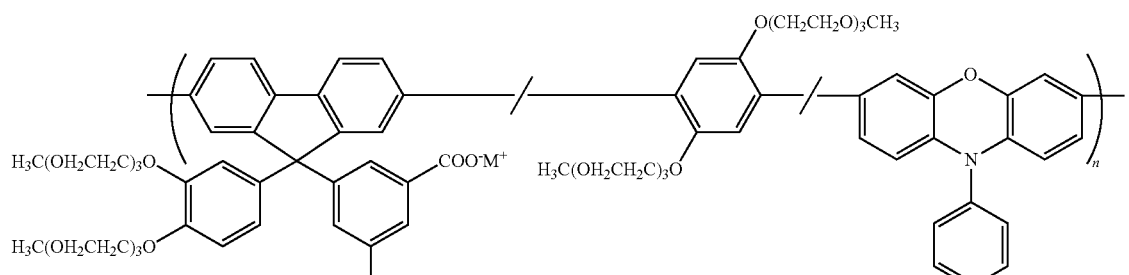
(p/q/100-p-q mol %)
[Chemical Formula 30]
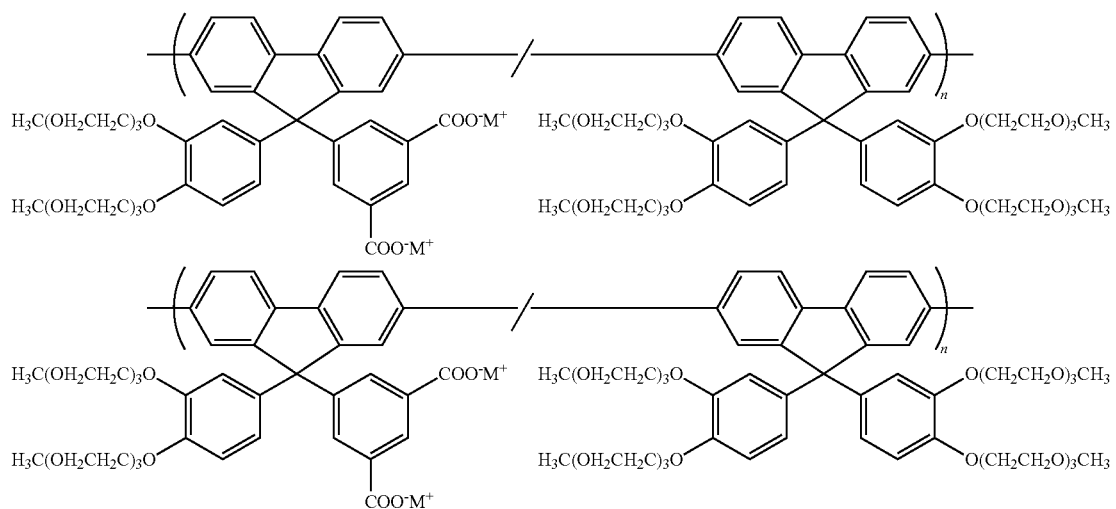
(p/100-p mol %)

-continued
53
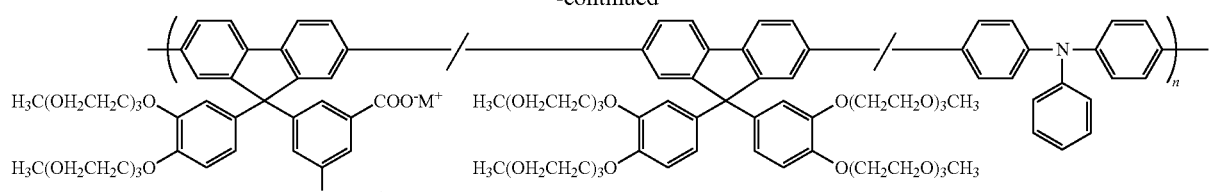
(p/q/100-p-q mol %)
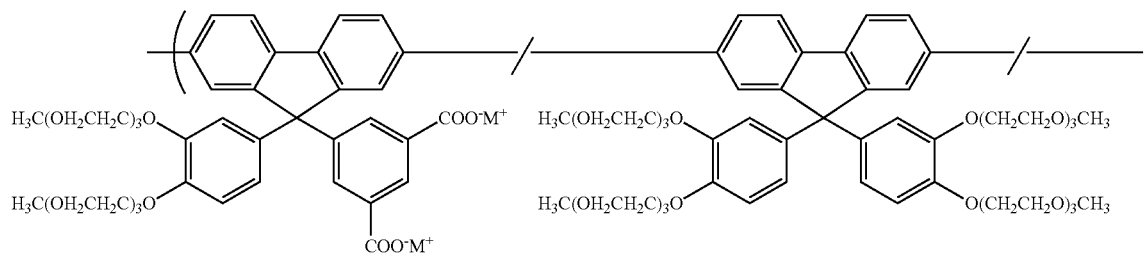
(p/q/100-p-q mol %)
54
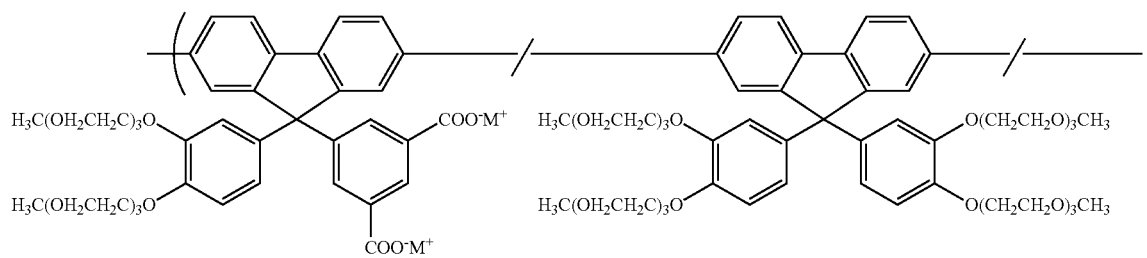
(p/q/100-p-q mol %)
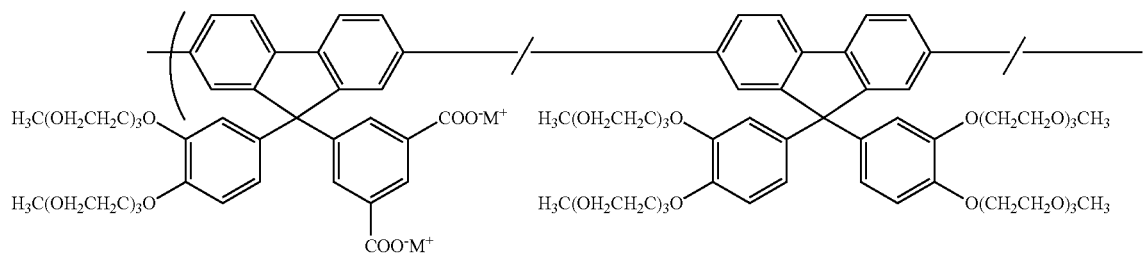

-continued
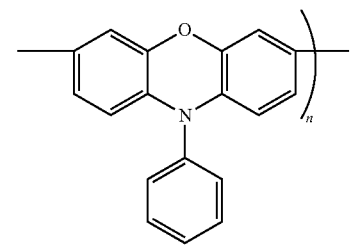
(p/q/100-p-q mol %)
[Chemical Formula 31]
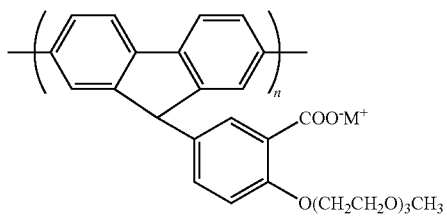
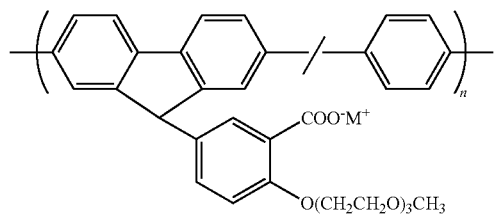
(p/100-p mol %)
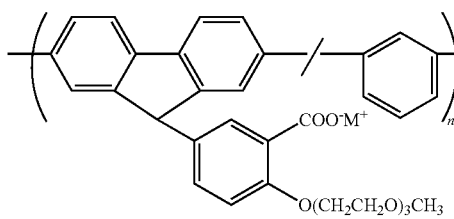
(p/100-p mol %)
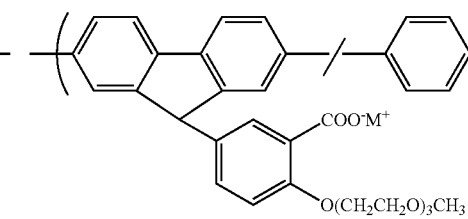
(p/100-p mol %)
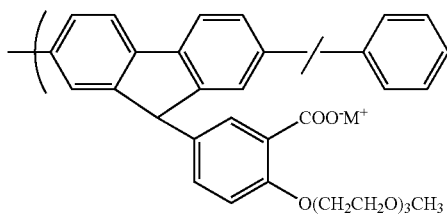
(p/100-p mol %)
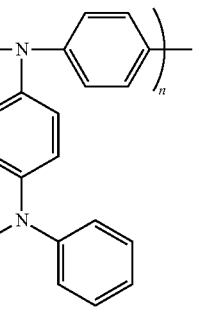
(p/100-p mol %)
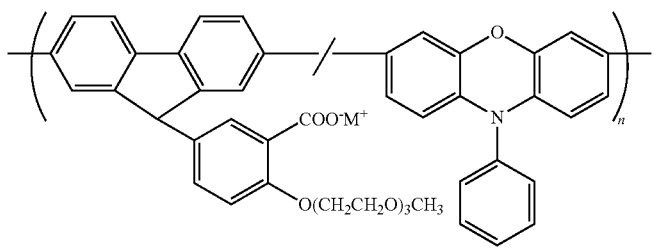
(p/100-p mol %)

[Chemical Formula 32]
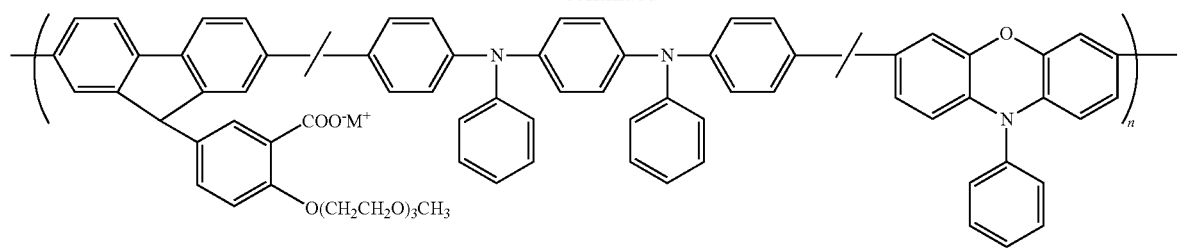
(p/q/100-p-q mol %)
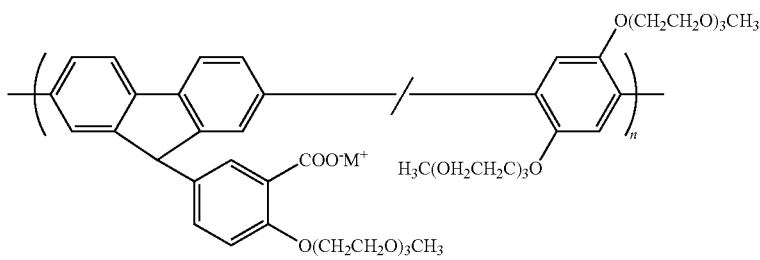
(p/100-p mol %)
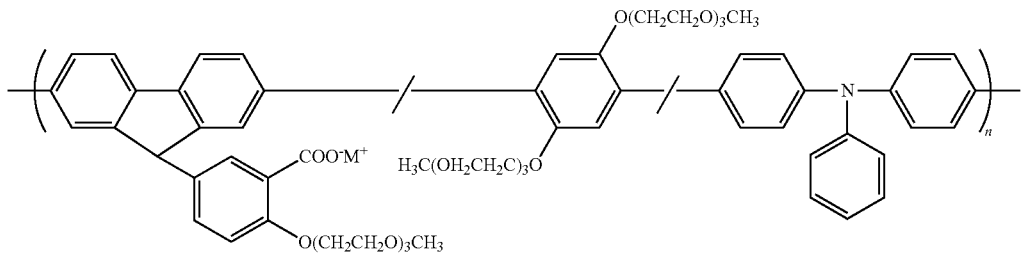
(p/q/100-p-q mol %)
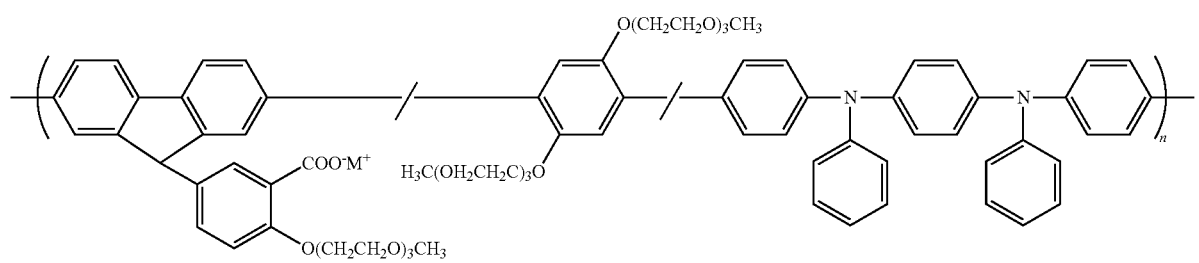
(p/q/100-p-q mol %)
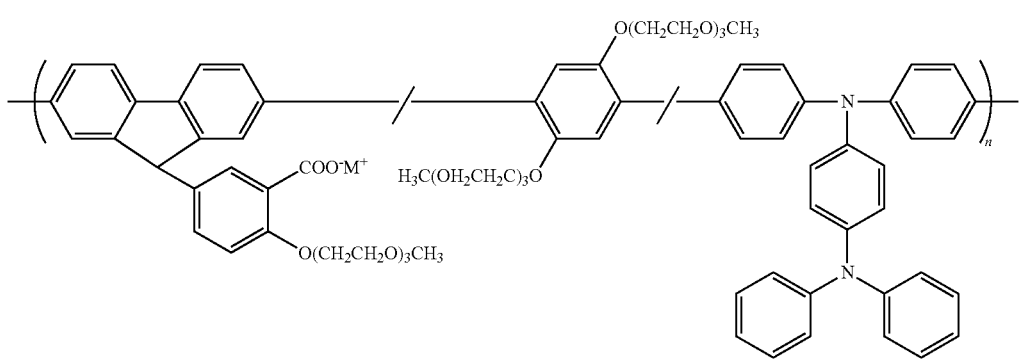
(p/q/100-p-q mol %)

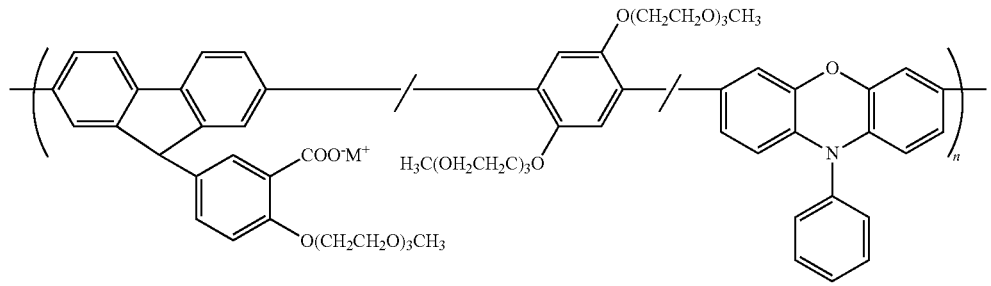
(p/q/100-p-q mol %)
[Chemical Formula 33]
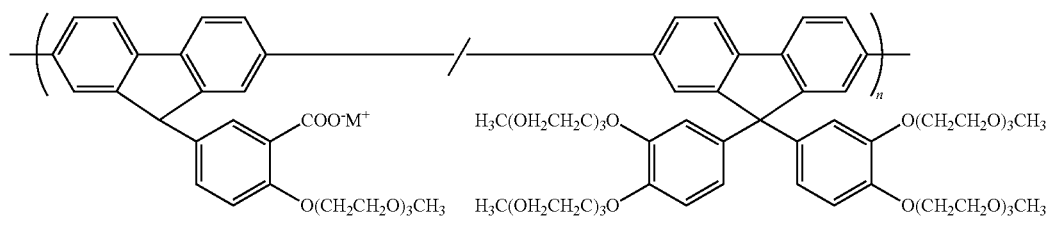
(p/100-p mol %)
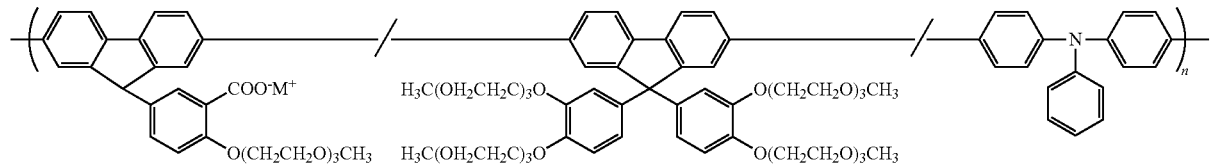
(p/q/100-p-q mol %)
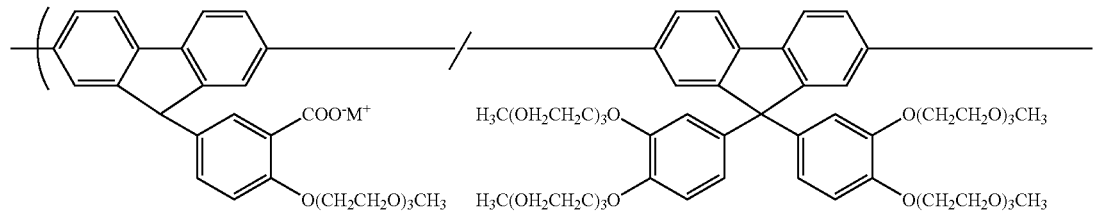
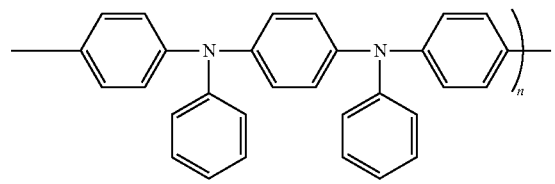
(p/q/100-p-q mol %)
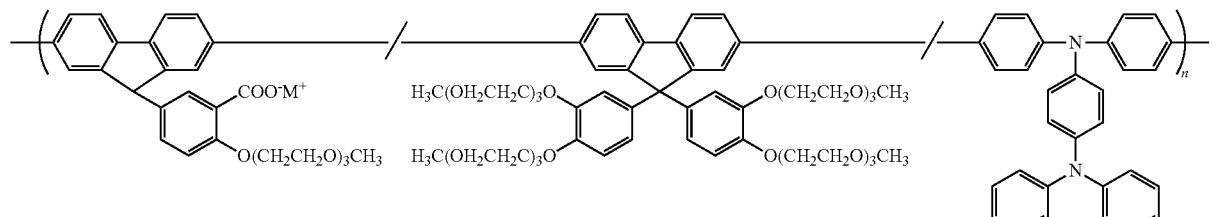
(p/q/100-p-q mol %)

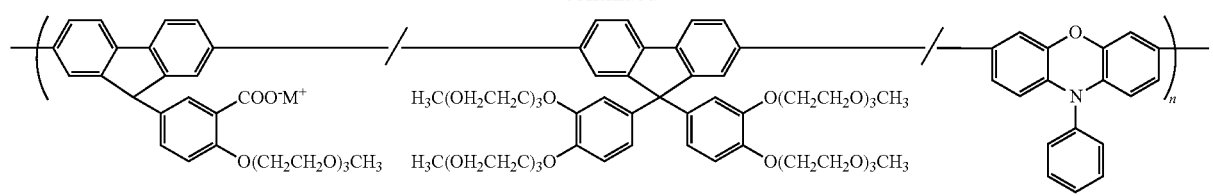
(p/q/100-p-q mol %)
[Chemical Formula 34]
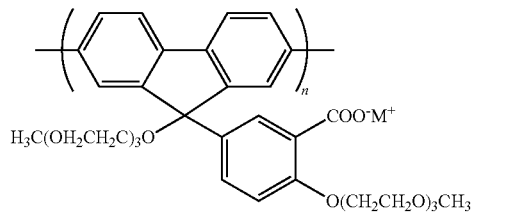
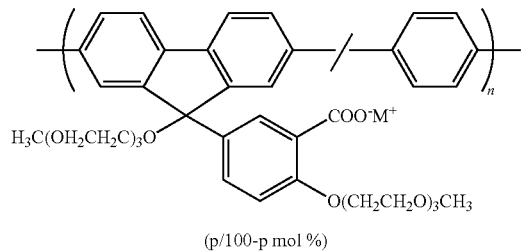
(p/100-p mol %)
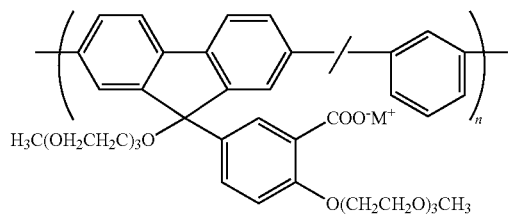
(p/100-p mol %)
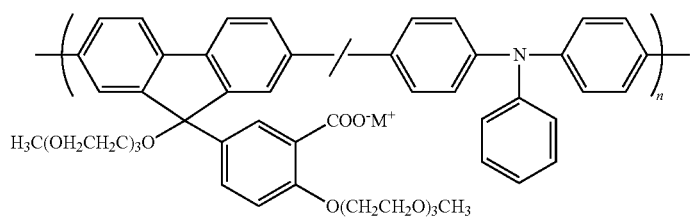
(p/100-p mol %)
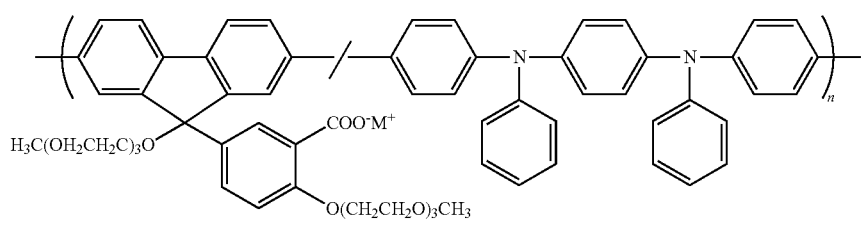
(p/100-p mol %)
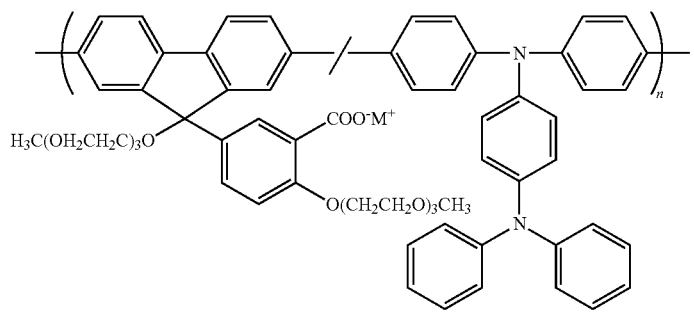
(p/100-p mol %)

-continued
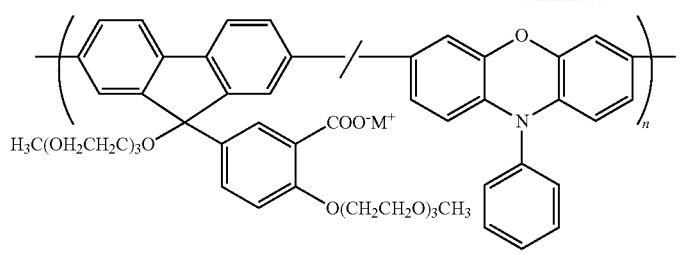
(p/100-p mol %)
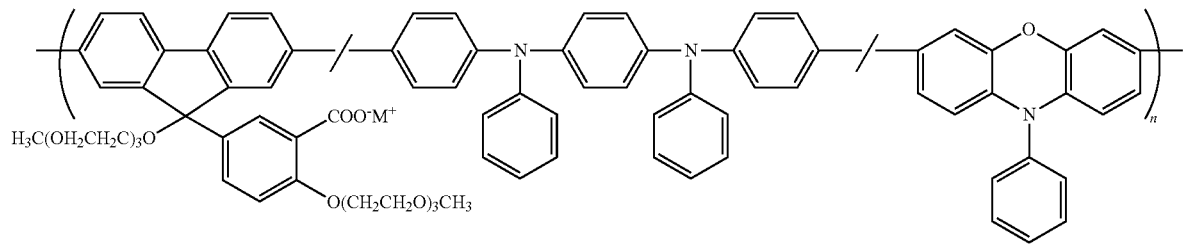
(p/q/100-p-q mol %)
[Chemical Formula 35]
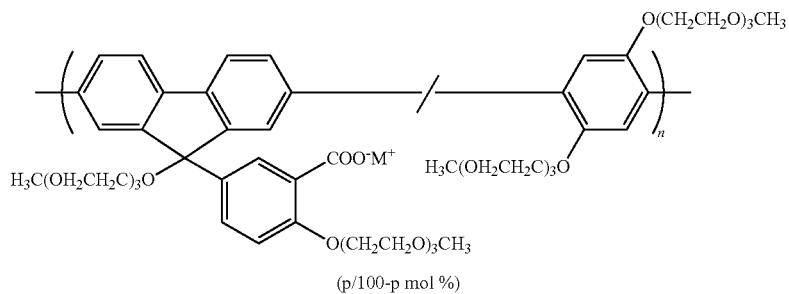
(p/100-p mol %)
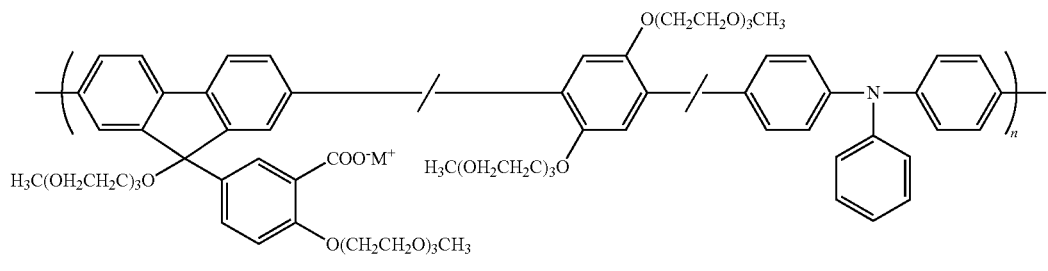
(p/q/100-p-q mol %)
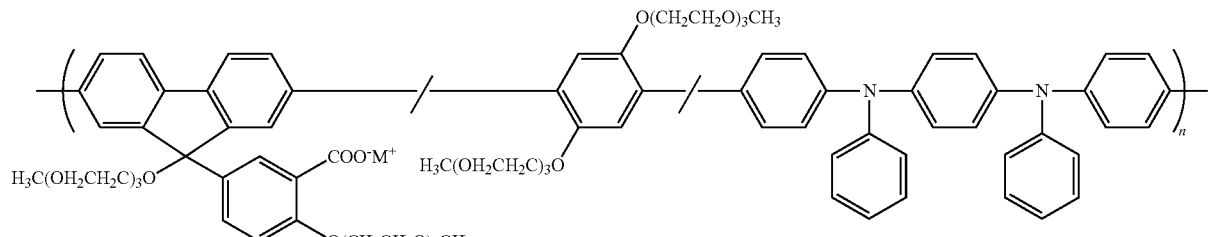
(p/q/100-p-q mol %)

-continued
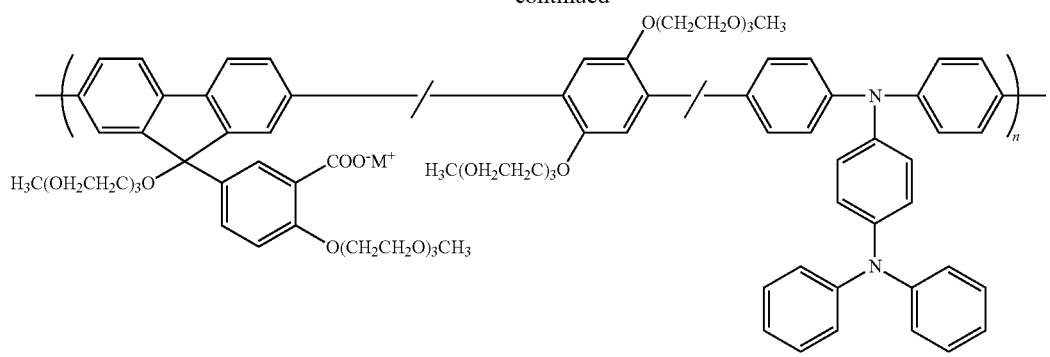
(p/q/100-p-q mol %)
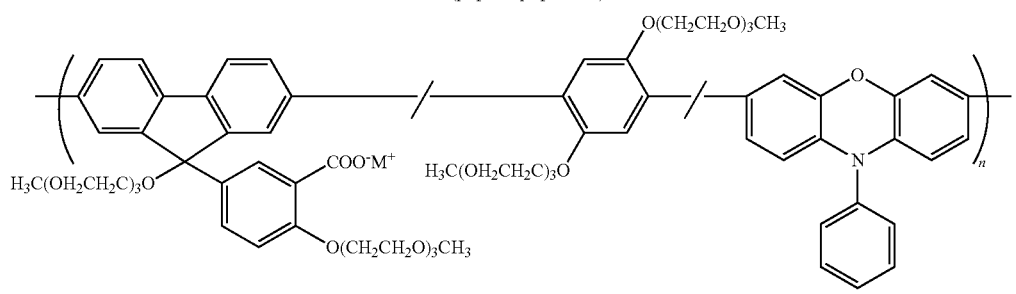
(p/q/100-p-q mol %)
[Chemical Formula 36]
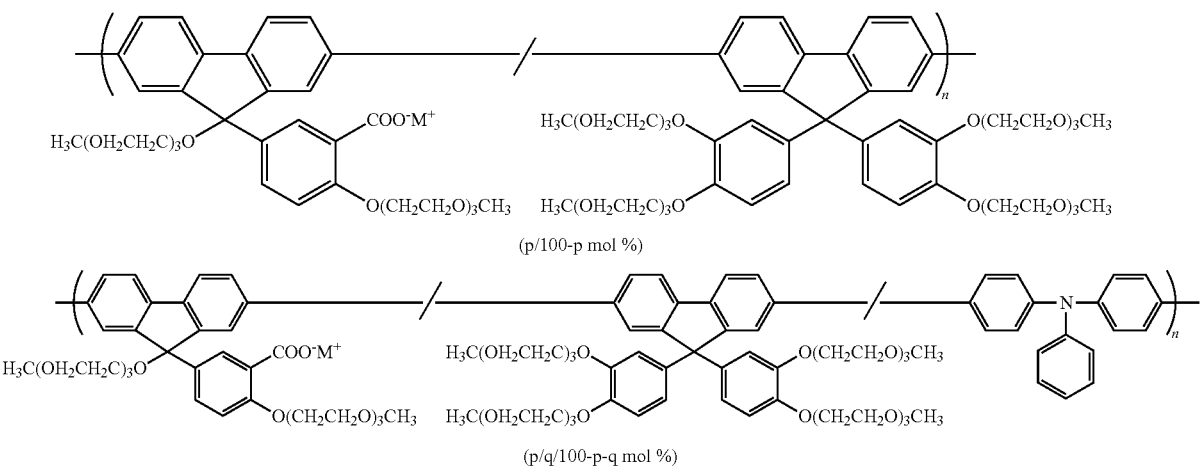
(p/100-p mol %)
(p/q/100-p-q mol %)
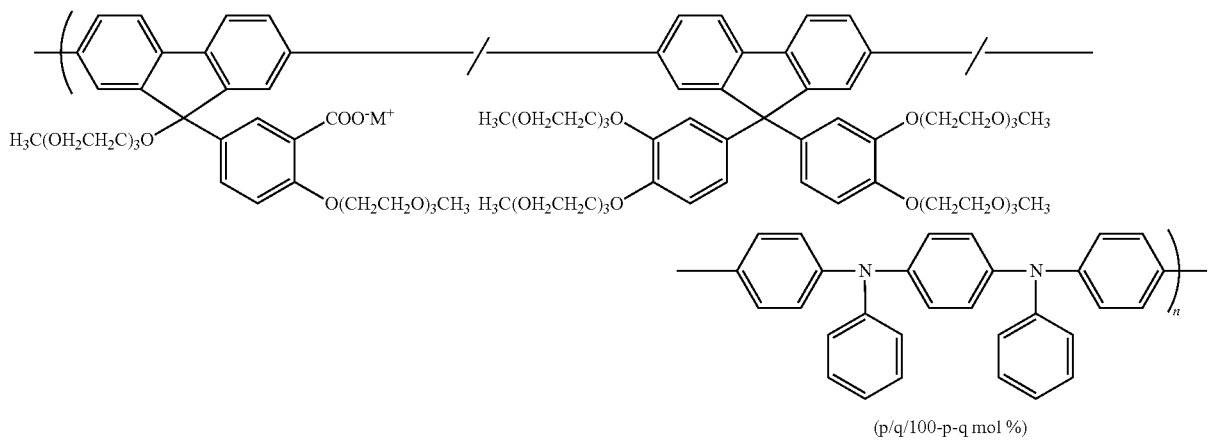
(p/q/100-p-q mol %)

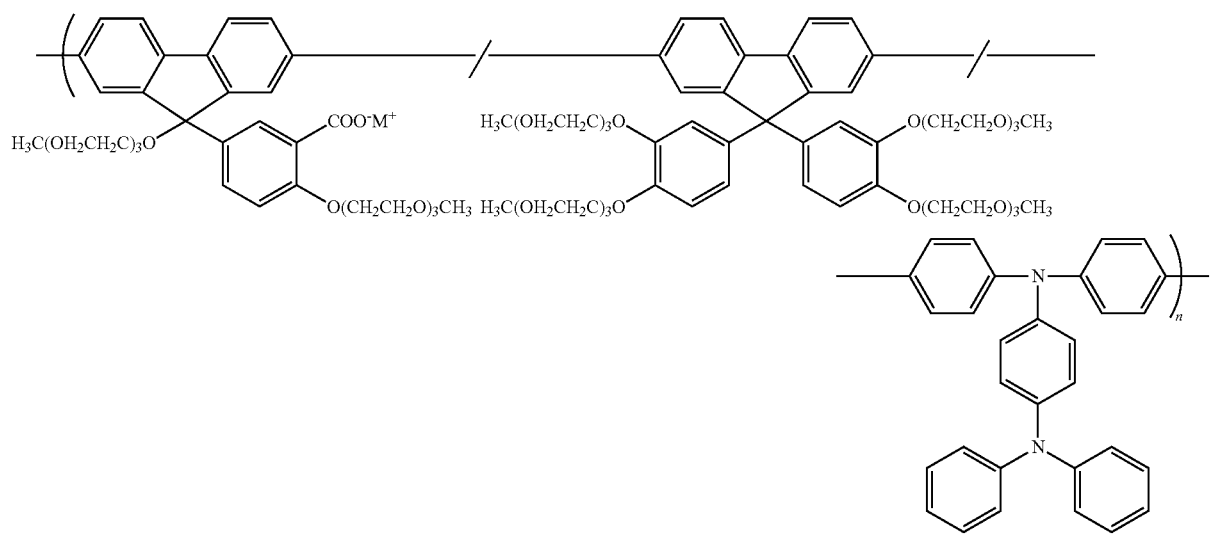
(p/q/100-p-q mol %)
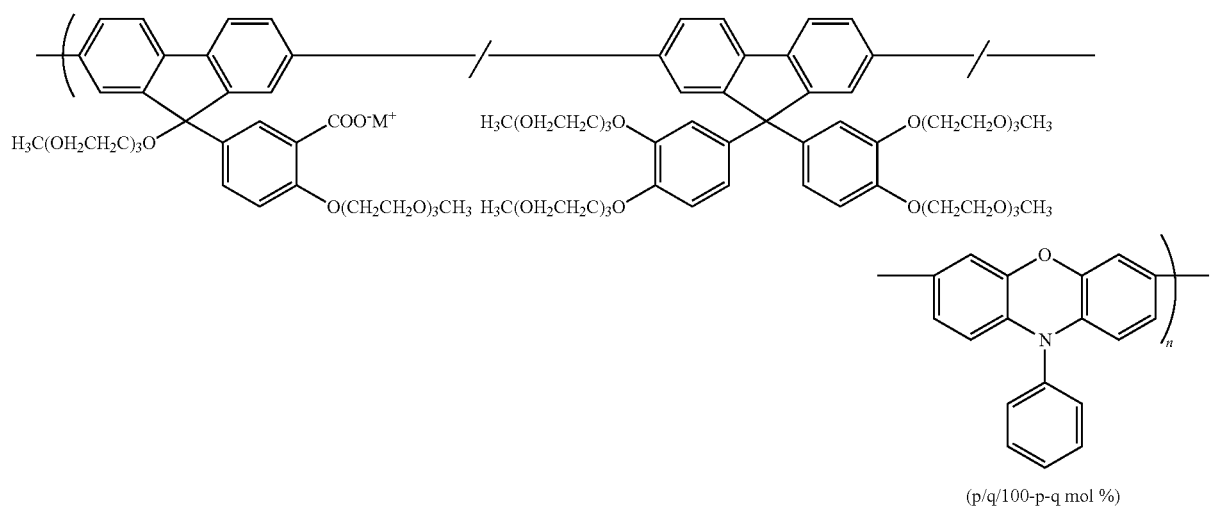
(p/q/100-p-q mol %)
[Chemical Formula 37]
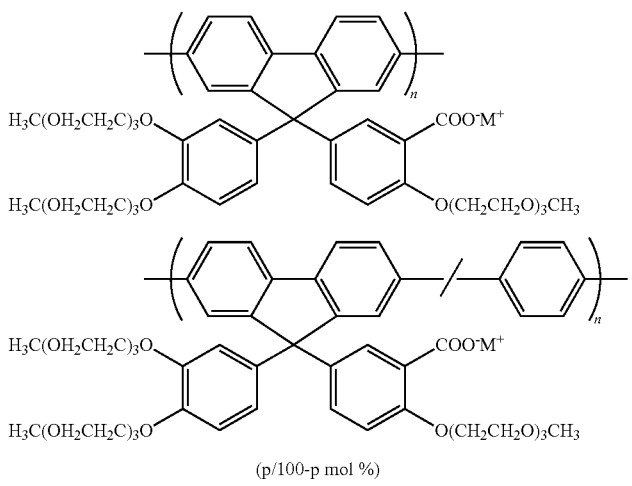
(p/100-p mol %)

-continued
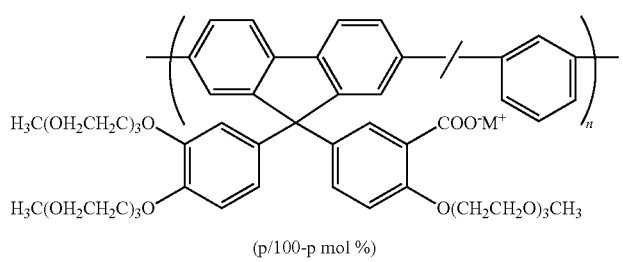
(p/100-p mol %)
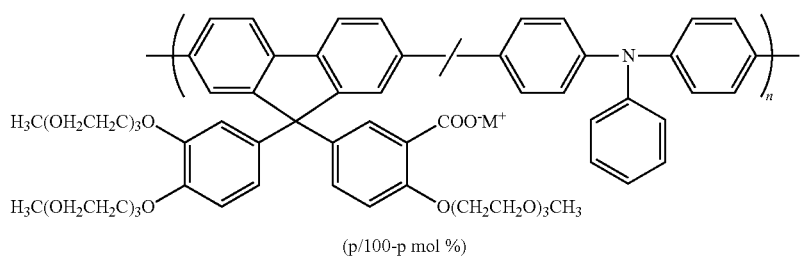
(p/100-p mol %)
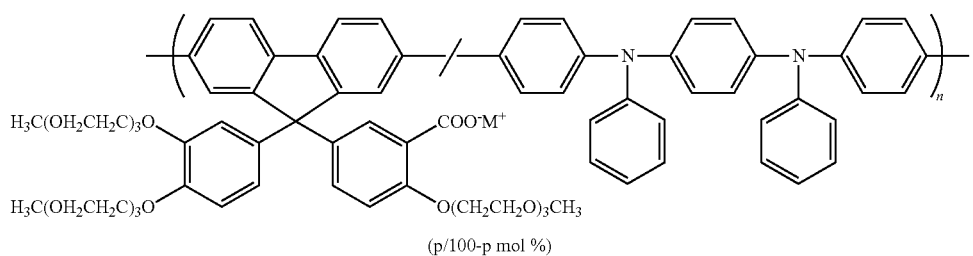
(p/100-p mol %)
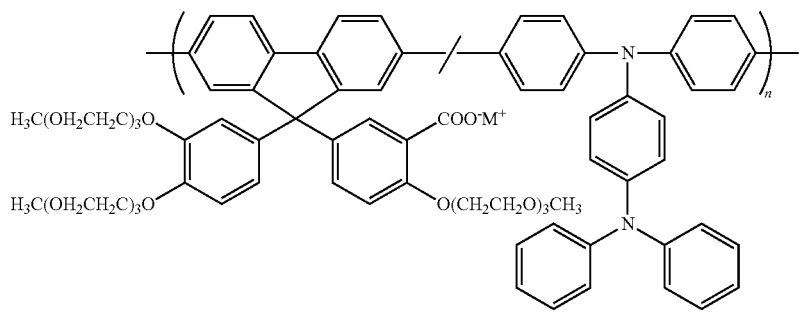
(p/100-p mol %)
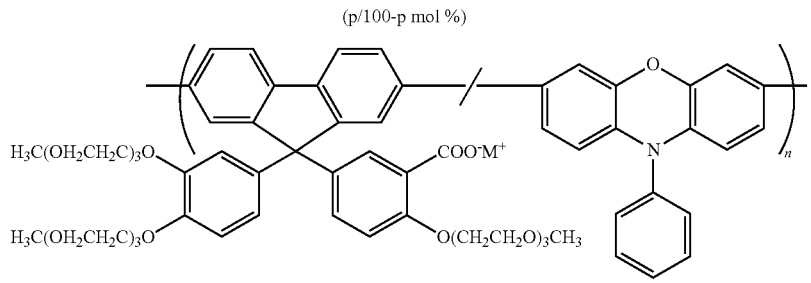
(p/100-p mol %)
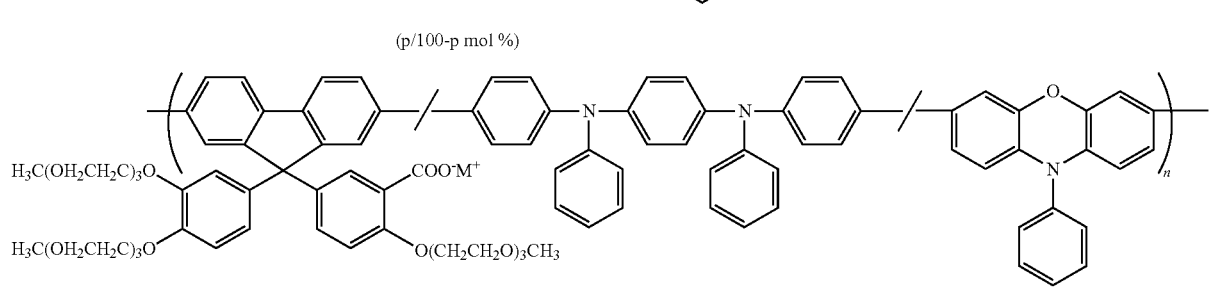
(p/q/100-p-q mol %)

[Chemical Formula 38]
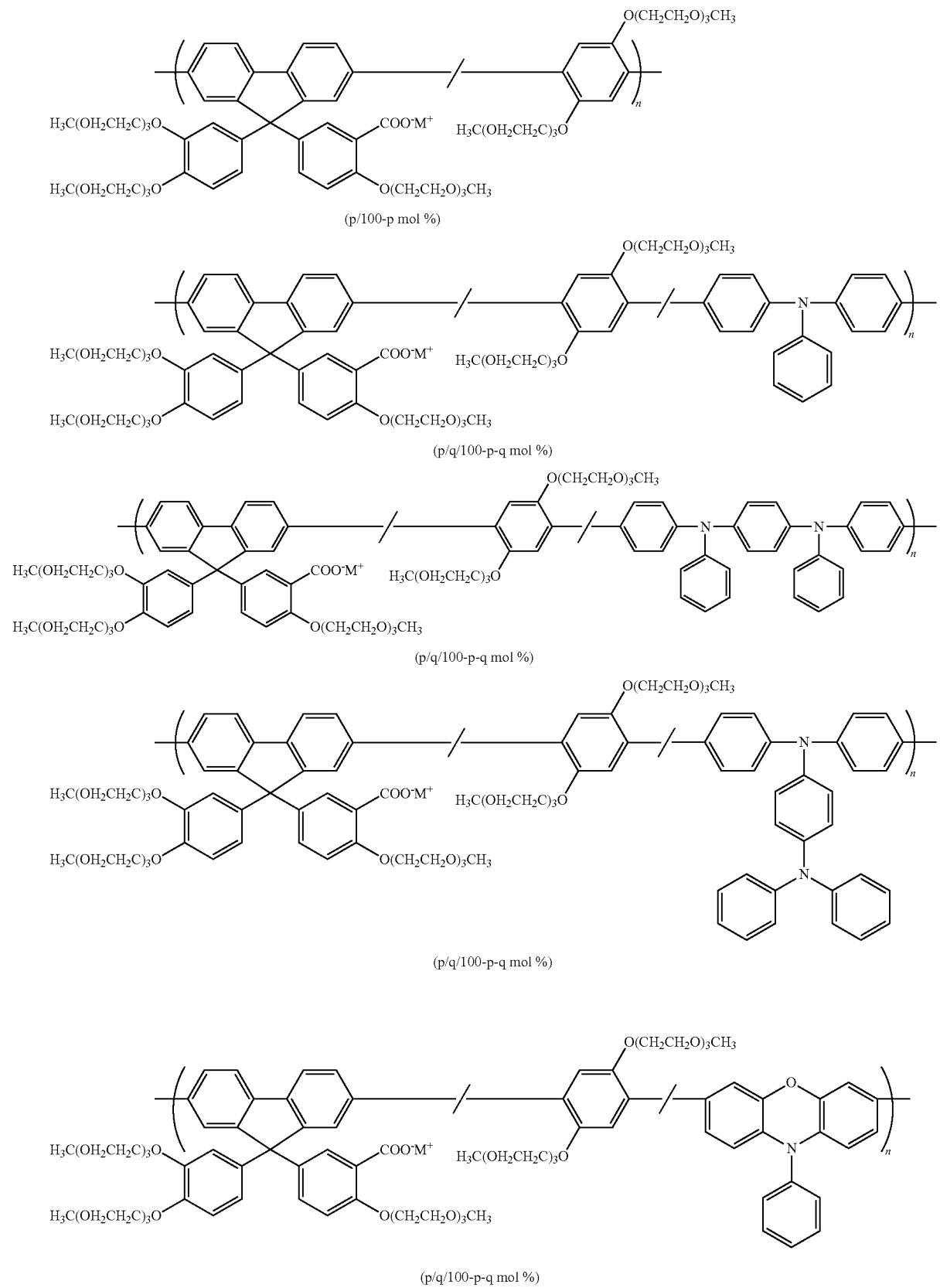

[Chemical Formula 39]
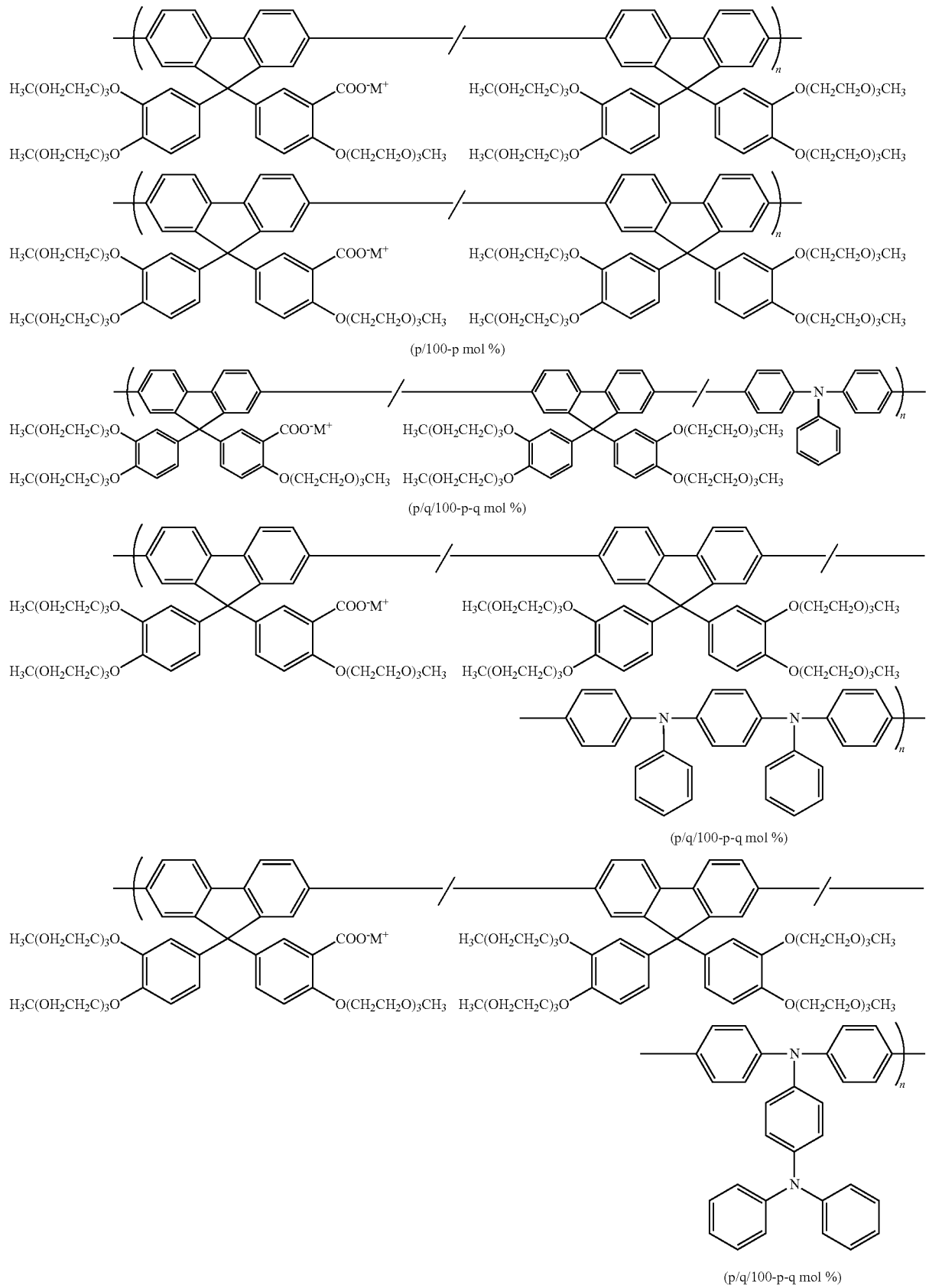

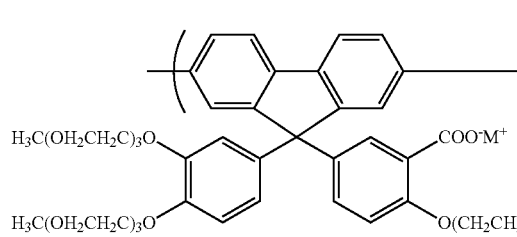
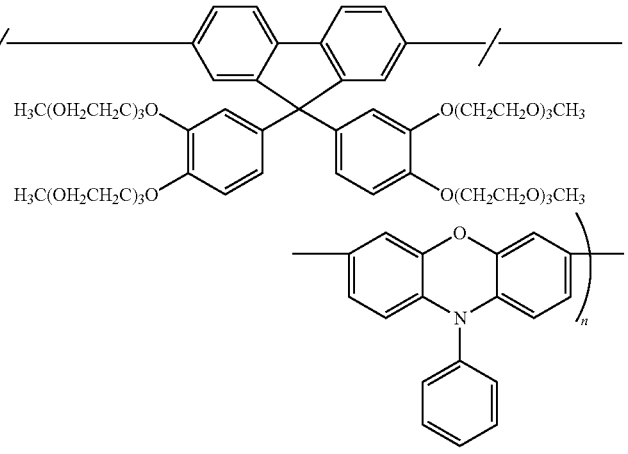

(p/q/100-p-q mol %)

—Method for Manufacturing Polymer Compound—

Next, a method for manufacturing the polymer compound according to the present invention will be described. Examples of a preferred method for manufacturing the polymer compound according to the present invention may include a method including: a method in which a compound represented by General Formula (17) and/or a compound represented by Formula (20) are employed as raw materials, and polymerized (a polymer compound manufacturing method 1); and a method in which a polymer compound containing no ionic group is synthesized in the first process, and a polymer compound containing an ionic group is synthesized from the polymer compound containing no ionic group in the second process (a polymer compound manufacturing method 2). The compound represented by Formula (17) and/or the compound represented by Formula (20) can be manufactured to be used as needed.

[Chemical Formula 40]

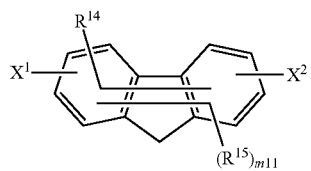

(17)

(In Formula (17), $R^{14}$ represents the group represented by Formula (2), the group represented by Formula (3), the group represented by Formula (18), or the group represented by Formula (20); $R^{15}$ represents the group represented by Formula (4); m11 represents an integer of 0 or more; and $X^1$ and $X^2$ each independently represent a group involved in condensation polymerization. When $R^{15}$ is plurally present, they may be the same or different. A hydrogen atom in Formula (17) may be replaced with a substituent other than $R^{14}$ or $R^{15}$.)

[Chemical Formula 41]

$$—R^{16}\text{-}\{(Q^4)_{n4}\text{-}Y^4\}_{m12} \quad (18)$$

(In Formula (18), $R^{16}$ represents a single bond or a (1+m12)-valent organic group that optionally has a substituent; $Q^4$ represents a divalent organic group; $Y^4$ represents —$CO_2R^x$, $SO_3R^x$, $SO_2R^x$, —$PO_3(R^x)_2$, or —$B(R^x)_2$; n4 represents an integer of 0 or more; $R^x$ represents a hydrogen atom, an alkyl group having 1 to 30 carbon atoms that optionally has a substituent, or an aryl group having 6 to 50 carbon atoms that optionally has a substituent; and m12 represents an integer of 1 or more, and when $R^{16}$ is a single bond, m12 represents 1. When $Q^4$, $Y^4$, n4, and $R^x$ are each plurally present, they may be the same or different.)

[Chemical Formula 42]

$$—R^{17}\text{-}\{(Q^5)_{n5}\text{-}Y^5\}_{m13} \quad (19)$$

(In Formula (19), $R^{17}$ represents a single bond or a (1+m13)-valent organic group that optionally has a substituent; $Q^5$ represents a divalent organic group; $Y^5$ represents a halogenated alkyl group, a halogen atom, —$N(R^\delta)_2$, —$P(R^\delta)_2$, or —$SR^\delta$; n5 represents an integer of 0 or more; $R^\delta$ represents a hydrogen atom, an alkyl group having 1 to 30 carbon atoms that optionally has a substituent, or an aryl group having 6 to 50 carbon atoms that optionally has a substituent; and m13 represents an integer of 1 or more, and when $R^{17}$ is a single bond, m13 represents 1. When $Q^5$, $Y^5$, n5, and $R^\delta$ are each plurally present, they may be the same or different.)

[Chemical Formula 43]

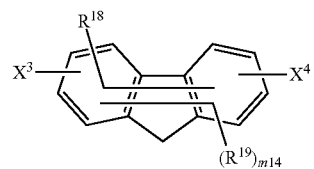

(20)

(In Formula (20), $R^{18}$ represents the group represented by Formula (8), the group represented by Formula (9), the group represented by Formula (21), or the group represented by Formula (22); $R^{19}$ represents the group represented by Formula (4); m14 represents an integer of 0 or more; and $X^3$ and $X^4$ each independently represent a group involved in condensation polymerization. When $R^{19}$ is plurally present, they may be the same or different. A hydrogen atom in Formula (20) may be replaced with a substituent other than $R^{18}$ or $R^{19}$.)

[Chemical Formula 44]

(21)

(In Formula (21), $R^{20}$ represents a (1+m15+m16)-valent organic group that optionally has a substituent; $Q^4$, n4, $Y^4$, $Q^3$, n3, and $Y^3$ are the same as the corresponding definitions above; m15 and m16 each independently represent an integer of 1 or more; and when $Q^4$, n4, $Y^4$, $Q^3$, n3, and $Y^3$ are each plurally present, they may be the same or different.)

[Chemical Formula 45]

(22)

(In Formula (22), $R^{21}$ represents a (1+m17+m18)-valent organic group that optionally has a substituent; $Q^5$, n5, $Y^5$, $Q^3$, n3, and $Y^3$ are the same as the corresponding definitions above; m15 and m16 each independently represent an integer of 1 or more; and when $Q^5$, n5, $Y^5$, $Q^3$, n3, and $Y^3$ are each plurally present, they may be the same or different.)

—Compound Represented by Formula (17)—

In Formula (17), $R^{14}$ represents the group represented by Formula (2), the group represented by Formula (3), the group represented by Formula (18), or the group represented by Formula (20); and $R^{15}$ represents the group represented by Formula (4). m11 is an integer of 0 or more, and $X^1$ and $X^2$ each independently represent a group involved in condensation polymerization. m11 is preferably 0 to 3 and more preferably 0 to 2. Examples of the group other than $R^{14}$ or $R^{15}$ may include the same as the substituent exemplified in the description with respect to Formula (1). When the substituent is plurally present, they may be the same or different.

—Group Represented by Formula (18)—

In Formula (18), $R^{16}$ represents a single bond or a (1+m12)-valent organic group that optionally has a substituent. The group represented by Formula (18) is a monovalent group.

In Formula (18), examples of the (1+m12)-valent organic group that optionally has a substituent represented by $R^3$ may include: a group remaining after removing m12 hydrogen atoms from an alkyl group having 1 to 20 carbon atoms that optionally has a substituent, such as a methyl group, an ethyl group, a propyl group, an isopropyl group, a butyl group, an isobutyl group, a sec-butyl group, a tert-butyl group, a pentyl group, a hexyl group, a cyclohexyl group, a heptyl group, an octyl group, a nonyl group, a decyl group, a lauryl group, and a group in which at least one hydrogen atom in these groups is substituted with a substituent; a group remaining after removing m12 hydrogen atoms from an aryl group having 6 to 30 carbon atoms that optionally has a substituent, such as a phenyl group, a 1-naphthyl group, a 2-naphthyl group, a 1-anthracenyl group, a 2-anthracenyl group, a 9-anthracenyl group, and a group in which at least one hydrogen atom in these groups is substituted with a substituent; a group remaining after removing m12 hydrogen atoms from an alkoxy group having 1 to 50 carbon atoms that optionally has a substituent, such as a methoxy group, an ethoxy group, a propyloxy group, a butoxy group, a pentyloxy group, a hexyloxy group, a nonyloxy group, a dodecyloxy group, a cyclopropyloxy group, a cyclobutyloxy group, a cyclopentyloxy group, a cyclohexyloxy group, a cyclononyloxy group, a cyclododecyloxy group, a norbornyloxy group, an adamantyloxy group, and a group in which at least one hydrogen atom in these groups is substituted with a substituent; a group remaining after removing m12 hydrogen atoms from an amino group having a substituent containing a carbon atom; and a group remaining after removing m12 hydrogen atoms from a silyl group having a substituent containing a carbon atom. The number of carbons of the substituent is not included in the above number of carbons. Because the synthesis of the raw material monomer is simplified, preferred examples are a group remaining after removing m12 hydrogen atoms from an alkyl group, a group remaining after removing m12 hydrogen atoms from an aryl group, or a group remaining after removing m12 hydrogen atoms from an alkoxy group.

Examples of the substituent may include the same as the substituent exemplified in the description with respect to Formula (1). When the substituent is plurally present, they may be the same or different.

In Formula (18), m12 represents an integer of 1 or more, and when $R^{16}$ is a single bond, m12 represents 1. Because the synthesis is simplified, m12 is preferably 1 to 4 and more preferably 1 to 3.

In Formula (18), examples of the divalent organic group represented by $Q^4$ may include: a divalent chain saturated hydrocarbon group having 1 to 50 carbon atoms that optionally has a substituent, such as a methylene group, an ethylene group, a 1,2-propylene group, a 1,3-propylene group, a 1,2-butylene group, a 1,3-butylene group, a 1,4-butylene group, a 1,5-pentylene group, a 1,6-hexylene group, a 1,9-nonylene group, a 1,12-dodecylene group, and a group in which at least one hydrogen atom in these groups is substituted with a substituent; a divalent chain unsaturated hydrocarbon group having 2 to 50 carbon atoms that optionally has a substituent, such as an alkenylene group having 2 to 50 carbon atoms that optionally has a substituent, such as an ethenylene group, a propenylene group, a 3-butenylene group, a 2-butenylene group, a 2-pentenylene group, a 2-hexenylene group, a 2-nonenylene group, a 2-dodecenylene group, and a group in which at least one hydrogen atom in these groups is substituted with a substituent, and an ethynylene group; a divalent saturated cyclic hydrocarbon group having 3 to 50 carbon atoms that optionally has a substituent, such as a cyclopropylene group, a cyclobutylene group, a cyclopentylene group, a cyclohexylene group, a cyclononylene group, a cyclododecylene group, a norbornylene group, an adamantylene group, and a group in which at least one hydrogen atom in these groups is substituted with a substituent; an arylene group having 6 to 50 carbon atoms that optionally has a substituent, such as a 1,3-phenylene group, a 1,4-phenylene group, a 1,4-naphthylene group, a 1,5-naphthylene group, a 2,6-naphthylene group, a biphenyl-4,4'-diyl group, and a group in which at least one hydrogen atom in these groups is substituted with a substituent; an alkyleneoxy group having 1 to 50 carbon atoms that optionally has a substituent, such as a methyleneoxy group, an ethyleneoxy group, a propyleneoxy group, a butyleneoxy group, a pentyleneoxy group, a hexyleneoxy group, and a group in which at least one hydrogen atom in these groups is substituted with a substituent (that is, a divalent organic group represented by formula: —$R^d$—O— (where $R^d$ is an alkylene group having 1 to 50 carbon atoms that optionally has a substituent, such as a methylene group, an ethylene group, a propylene group, a butylene group, a pentylene group, a hexylene group, and a group in which at least one hydrogen atom in these groups is substituted with a substituent)); an imino group having a substituent containing a carbon atom; and a silylene group having a substituent containing a carbon atom. The number of carbons of the substituent is not included in the above number of carbons. Because the synthesis is simplified, preferred examples are the divalent chain saturated hydrocarbon group, the arylene group, and the alkyleneoxy group.

The group exemplified as the divalent organic group represented by $Q^4$ may have a substituent, and examples of the substituent may include the same as the substituent exemplified in the description with respect to Formula (1). When the substituent is plurally present, they may be the same or different.

In Formula (18), $Y^4$ represents —$CO_2R^x$, —$SO_3R^x$, —$SO_2R^x$, —$PO_3(R^x)_2$, or —$B(R^x)^2$. $R^x$ represents a hydrogen atom, an alkyl group having 1 to 30 carbon atoms that optionally has a substituent, or an aryl group having 6 to 50 carbon atoms that optionally has a substituent. The number of carbons of the substituent is not included in the above number of carbons. Examples of the substituent may include the same as the substituent exemplified in the description with respect to Formula (1). When the substituent is plurally present, they may be the same or different. Examples of $R^x$ may include: an alkyl group having 1 to 20 carbon atoms such as a methyl group, an ethyl group, a propyl group, an isopropyl group, a butyl group, an isobutyl group, a sec-butyl group, a tert-butyl group, a pentyl group, a hexyl group, a cyclohexyl group, a heptyl group, an octyl group, a nonyl group, a decyl group, and a lauryl group; an aryl group having 6 to 30 carbon atoms such as a phenyl group, a 1-naphthyl group, a 2-naphthyl group, a 1-anthracenyl group, a 2-anthracenyl group, and a 9-anthracenyl group.

In Formula (18), n4 represents an integer of 0 or more, and in view of the synthesis of the raw material monomer, n4 is preferably an integer of from 0 to 8 and more preferably an integer of from 0 to 2.

—Group Represented by Formula (19)—

In Formula (19), $R^{17}$ represents a single bond or a (1+m13)-valent organic group that optionally has a substituent. The group represented by Formula (19) is a monovalent group.

In Formula (19), examples of the (1+m13)-valent organic group that optionally has a substituent represented by $R^{17}$ may include: a group remaining after removing m13 hydrogen atoms from an alkyl group having 1 to 20 carbon atoms that optionally has a substituent, such as a methyl group, an ethyl group, a propyl group, an isopropyl group, a butyl group, an isobutyl group, a sec-butyl group, a tert-butyl group, a pentyl group, a hexyl group, a cyclohexyl group, a heptyl group, an octyl group, a nonyl group, a decyl group, a lauryl group, and a group in which at least one hydrogen atom in these groups is substituted with a substituent; a group remaining after removing m13 hydrogen atoms from an aryl group having 6 to 30 carbon atoms that optionally has a substituent, such as a phenyl group, a 1-naphthyl group, a 2-naphthyl group, a 1-anthracenyl group, a 2-anthracenyl group, a 9-anthracenyl group, and a group in which at least one hydrogen atom in these groups is substituted with a substituent; a group remaining after removing m13 hydrogen atoms from an alkoxy group having 1 to 50 carbon atoms that optionally has a substituent, such as a methoxy group, an ethoxy group, a propyloxy group, a butoxy group, a pentyloxy group, a hexyloxy group, a nonyloxy group, a dodecyloxy group, a cyclopropyloxy group, a cyclobutyloxy group, a cyclopentyloxy group, a cyclohexyloxy group, a cyclononyloxy group, a cyclododecyloxy group, a norbornyloxy group, an adamantyloxy group, and a group in which at least one hydrogen atom in these groups is substituted with a substituent; a group remaining after removing m13 hydrogen atoms from an amino group having a substituent containing a carbon atom; and a group remaining after removing m13 hydrogen atoms from a silyl group having a substituent containing a carbon atom. The number of carbons of the substituent is not included in the above number of carbons. Because the synthesis of the raw material monomer is simplified, preferred examples are a group remaining after removing m13 hydrogen atoms from an alkyl group, a group remaining after removing m13 hydrogen atoms from an aryl group, and a group remaining after removing m13 hydrogen atoms from an alkoxy group.

Examples of the substituent may include the same as the substituent exemplified in the description with respect to Formula (1). When the substituent is plurally present, they may be the same or different.

In Formula (19), m13 represents an integer of 1 or more, and when $R^{17}$ is a single bond, m13 represents 1. Because the synthesis is simplified, m13 is preferably 1 to 4 and more preferably 1 to 3.

In Formula (19), examples of the divalent organic group represented by $Q^5$ may include: a divalent chain saturated hydrocarbon group having 1 to 50 carbon atoms that optionally has a substituent, such as a methylene group, an ethylene group, a 1,2-propylene group, a 1,3-propylene group, a 1,2-butylene group, a 1,3-butylene group, a 1,4-butylene group, a 1,5-pentylene group, a 1,6-hexylene group, a 1,9-nonylene group, a 1,12-dodecylene group, and a group in which at least one hydrogen atom in these groups is substituted with a substituent; a divalent chain unsaturated hydrocarbon group having 2 to 50 carbon atoms that optionally has a substituent, such as an alkenylene group having 2 to 50 carbon atoms that optionally has a substituent, such as an ethenylene group, a propenylene group, a 3-butenylene group, a 2-butenylene group, a 2-pentenylene group, a 2-hexenylene group, a 2-nonenylene group, a 2-dodecenylene group, and a group in which at least one hydrogen atom in these groups is substituted with a substituent, and an ethynylene group; a divalent saturated cyclic hydrocarbon group having 3 to 50 carbon atoms that optionally has a substituent, such as a cyclopropylene group, a cyclobutylene group, a cyclopentylene group, a cyclohexylene group, a cyclononylene group, a cyclododecylene group, a norbornylene group, an adamantylene group, and a group in which at least one hydrogen atom in these groups is substituted with a substituent; an arylene group having 6 to 50 carbon atoms that optionally has a substituent, such as a 1,3-phenylene group, a 1,4-phenylene group, a 1,4-naphthylene group, a 1,5-naphthylene group, a 2,6-naphthylene group, a biphenyl-4,4'-diyl group, and a group in which at least one hydrogen atom in these groups is substituted with a substituent; an alkyleneoxy group having 1 to 50 carbon atoms that optionally has a substituent, such as a methyleneoxy group, an ethyleneoxy group, a propyleneoxy group, a butyleneoxy group, a pentyleneoxy group, a hexyleneoxy group, and a group in which at least one hydrogen atom in these groups is substituted with a substituent (that is, a divalent organic group represented by formula: —$R^d$—O— (where $R^d$ is an alkylene group having 1 to 50 carbon atoms that optionally has a substituent, such as a methylene group, an ethylene group, a propylene group, a butylene group, a pentylene group, a hexylene group, and a group in which at least one hydrogen atom in these groups is substituted with a substituent)); an imino group having a substituent containing a carbon atom; and a silylene group having a substituent containing a carbon atom. The number of carbons of the substituent is not included in the above number of carbons.

Because the synthesis is simplified, preferred examples are the divalent chain saturated hydrocarbon group, the arylene group, and the alkyleneoxy group.

The group exemplified as the divalent organic group represented by $Q^5$ may have a substituent, and examples of the substituent may include the same as the substituent exemplified in the description with respect to Formula (1). When the substituent is plurally present, they may be the same or different.

In Formula (19), $Y^5$ represents a halogenated alkyl group, a halogen atom, $-N(R^\delta)_2$, $-P(R^\delta)_2$, or $-SR^\delta$. $R^\delta$ represents a hydrogen atom, an alkyl group having 1 to 30 carbon atoms that optionally has a substituent, or an aryl group having 6 to 50 carbon atoms that optionally has a substituent. The number of carbons of the substituent is not included in the above number of carbons. Examples of the substituent may include the same as the substituent exemplified in the description with respect to Formula (1). When the substituent is plurally present, they may be the same or different. Examples of $R^\delta$ may include: an alkyl group having 1 to 20 carbon atoms such as a methyl group, an ethyl group, a propyl group, an isopropyl group, a butyl group, an isobutyl group, a sec-butyl group, a tert-butyl group, a pentyl group, a hexyl group, a cyclohexyl group, a heptyl group, an octyl group, a nonyl group, a decyl group, and a lauryl group; and an aryl group having 6 to 30 carbon atoms such as a phenyl group, a 1-naphthyl group, a 2-naphthyl group, a 1-anthracenyl group, a 2-anthracenyl group, and a 9-anthracenyl group. The alkyl group in the halogenated alkyl group may be the same as the alkyl group described above. The halogen atom with respect to the halogenation in the halogenated alkyl group may be the same as the halogen atom described above. Examples of the halogenated alkyl group may include a halogenated methyl group, a halogenated ethyl group, a halogenated propyl group, and a halogenated butyl group.

In Formula (19), n5 represents an integer of 0 or more, and in view of the synthesis of the raw material monomer, n5 is preferably an integer of from 0 to 8 and more preferably an integer of from 0 to 2.

Group Represented by Formula (20)

In Formula (20), $R^{18}$ represents the group represented by Formula (8), the group represented by Formula (9), the group represented by Formula (21), or the group represented by Formula (22); and $R^{19}$ represents the group represented by Formula (4). m14 represents an integer of 0 or more, and $X^3$ and $X^4$ each independently represent a group involved in condensation polymerization. m14 is preferably 1 to 4 and more preferably 1 to 3. Examples of the substituent other than $R^{18}$ or $R^{19}$ may include the same as the substituent exemplified in the description with respect to Formula (1). When the substituent is plurally present, they may be the same or different.

Group Represented by Formula (21)

In Formula (21), $R^{20}$ represents a (1+m15+m16)-valent organic group that optionally has a substituent. The group represented by Formula (21) is a monovalent group.

In Formula (21), examples of the (1+m15+m16)-valent organic group that optionally has a substituent represented by $R^{20}$ may include: a group remaining after removing (m15+m16) hydrogen atoms from an alkyl group having 1 to 20 carbon atoms that optionally has a substituent, such as a methyl group, an ethyl group, a propyl group, an isopropyl group, a butyl group, an isobutyl group, a sec-butyl group, a tert-butyl group, a pentyl group, a hexyl group, a cyclohexyl group, a heptyl group, an octyl group, a nonyl group, a decyl group, a lauryl group, and a group in which at least one hydrogen atom in these groups is substituted with a substituent; a group remaining after removing (m15+m16) hydrogen atoms from an aryl group having 6 to 30 carbon atoms that optionally has a substituent, such as a phenyl group, a 1-naphthyl group, a 2-naphthyl group, a 1-anthracenyl group, a 2-anthracenyl group, a 9-anthracenyl group, and a group in which at least one hydrogen atom in these groups is substituted with a substituent; a group remaining after removing (m15+m16) hydrogen atoms from an alkoxy group having 1 to 50 carbon atoms that optionally has a substituent, such as a methoxy group, an ethoxy group, a propyloxy group, a butoxy group, a pentyloxy group, a hexyloxy group, a nonyloxy group, a dodecyloxy group, a cyclopropyloxy group, a cyclobutyloxy group, a cyclopentyloxy group, a cyclohexyloxy group, a cyclononyloxy group, a cyclododecyloxy group, a norbornyloxy group, an adamantyloxy group, and a group in which at least one hydrogen atom in these groups is substituted with a substituent; a group remaining after removing (m15+m16) hydrogen atoms from an amino group having a substituent containing a carbon atom; and a group remaining after removing (m15+m16) hydrogen atoms from a silyl group having a substituent containing a carbon atom. The number of the carbons of the substituent is not included in the above number of carbons. Because the synthesis of the raw material monomer is simplified, preferred examples are a group remaining after removing (m15+m16) hydrogen atoms from an alkyl group, a group remaining after removing (m15+m16) hydrogen atoms from an aryl group, or a group remaining after removing (m15+m16) hydrogen atoms from an alkoxy group.

Examples of the substituent may include the same as the substituent exemplified in the description with respect to Formula (1). When the substituent is plurally present, they may be the same or different.

In Formula (21), m15 and m16 each independently represent an integer of 1 or more (e.g., 1, 2, or 3 for each).

In Formula (21), $Q^4$, n4, $Y^4$, $Q^3$, n3, and $Y^3$ are the same as the corresponding definitions above, and when $Q^4$, n4, $Y^4$, $Q^3$, n3, and $Y^3$ are each plurally present, they may be the same or different.

—Group Represented by Formula (22)—

In Formula (22), $R^{21}$ represents a (1+m17+m18)-valent organic group that optionally has a substituent. The group represented by Formula (22) is a monovalent group.

In Formula (22), examples of the (1+m17+m18)-valent organic group that optionally has a substituent represented by $R^{21}$ may include: a group remaining after removing (m17+m18) hydrogen atoms from an alkyl group having 1 to 20 carbon atoms that optionally has a substituent, such as a methyl group, an ethyl group, a propyl group, an isopropyl group, a butyl group, an isobutyl group, a sec-butyl group, a tert-butyl group, a pentyl group, a hexyl group, a cyclohexyl group, a heptyl group, an octyl group, a nonyl group, a decyl group, a lauryl group, and a group in which at least one hydrogen atom in these groups is substituted with a substituent; a group remaining after removing (m17+m18) hydrogen atoms from an aryl group having 6 to 30 carbon atoms that optionally has a substituent, such as a phenyl group, a 1-naphthyl group, a 2-naphthyl group, a 1-anthracenyl group, a 2-anthracenyl group, a 9-anthracenyl group, and a group in which at least one hydrogen atom in these groups is substituted with a substituent; a group remaining after removing (m17+m18) hydrogen atoms from an alkoxy group having 1 to 50 carbon atoms that optionally has a substituent, such as a methoxy group, an ethoxy group, a propyloxy group, a butoxy group, a pentyloxy group, a hexyloxy group, a nonyloxy group, a dodecyloxy group, a cyclopropyloxy group, a cyclobutyloxy group, a cyclopentyloxy group, a cyclohexyloxy group, a cyclononyloxy group, a cyclododecyloxy group, a norbornyloxy group, an adamantyloxy group, and a group in which at least one hydrogen atom in these groups is substituted with a substituent; a group remaining after removing (m17+m18) hydrogen atoms from an amino group having a substituent containing a carbon atom; and a group remaining after removing (m17+m18) hydrogen atoms from a silyl group having a substituent containing a carbon atom. The number of the carbons of the substituent is not included in the above number of carbons. Because the synthesis of the raw material monomer is simplified, preferred examples are a group remaining after removing (m17+m18) hydrogen atoms from an alkyl group, a group remaining after removing (m17+m18) hydrogen atoms from an aryl group, and a group remaining after removing (m17+m18) hydrogen atoms from an alkoxy group.

Examples of the substituent may include the same as the substituent exemplified in the description with respect to Formula (1). When the substituent is plurally present, they may be the same or different.

In Formula (22), m17 and m18 each independently represent an integer of 1 or more (e.g., 1, 2, or 3 for each).

In Formula (22), $Q^5$, n5, $Y^5$, $Q^3$, n3, and $Y^3$ are the same as the corresponding definitions above, and when $Q^5$, n5, $Y^5$, $Q^3$, n3, and $Y^3$ are each plurally present, they may be the same or different.

When, together with one or more structural units selected from the group consisting of the structural unit represented by Formula (1), the structural unit represented by Formula (7), the structural unit represented by Formula (10), and the structural unit represented by Formula (11), a structural unit other than the structural unit represented by Formula (1), the structural unit represented by Formula (7), the structural unit represented by Formula (10), or the structural unit represented by Formula (11) is contained in the polymer compound according to the present invention, a polymer compound further having a structural unit represented by -$A_a$- can be manufactured by condensation polymerizing a compound represented by Formula (23) in addition to the compounds represented by Formulae (17) and (20).

$$X^5\text{-}A_a\text{-}X^6 \quad (23)$$

(In Formula (23), $A_a$ represents a divalent aromatic group that optionally has a substituent represented by the above $Ar^1$ or a divalent aromatic amine residue that optionally has a substituent, and $X^5$ and $X^6$ each independently represent a group involved in condensation polymerization.)

Examples of the group involved in condensation polymerization represented by $X^1$, $X^2$, $X^3$, $X^4$, $X^5$, and $X^6$ may include a hydrogen atom, a halogen atom, an alkyl sulfonate group, an aryl sulfonate group, an arylalkyl sulfonate group, a boric acid ester residue, a sulfonium methyl group, a phosphonium methyl group, a phosphonate methyl group, a monohalogenated methyl group, —B(OH)$_2$, a formyl group, a cyano group, and a vinyl group.

Examples of the halogen atom which can be selected as the group involved in condensation polymerization may include a fluorine atom, a chlorine atom, a bromine atom, and an iodine atom.

Examples of the alkyl sulfonate group which can be selected as the group involved in condensation polymerization may include a methane sulfonate group, an ethane sulfonate group, and a trifluoromethane sulfonate group.

Examples of the aryl sulfonate group which can be selected as the group involved in condensation polymerization may include a benzene sulfonate group and a p-toluene sulfonate group.

Examples of the arylalkyl sulfonate group which can be selected as the group involved in condensation polymerization may include a benzyl sulfonate group.

Examples of the boric acid ester residue which can be selected as the group involved in condensation polymerization may include groups represented by the following formulae.

[Chemical Formula 46]

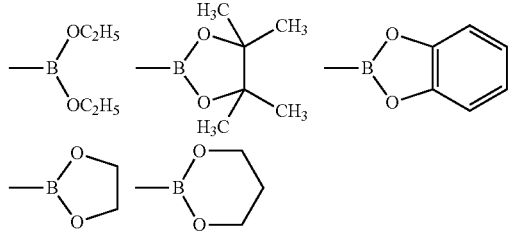

Examples of the sulfoniummethyl group which can be selected as the group involved in condensation-polymerization may include groups represented by the following formulae:

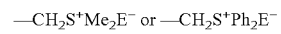

(where E represents a halogen atom, and Ph represents a phenyl group; the same is applicable hereinafter).

Examples of the phosphoniummethyl group which can be selected as the group involved in condensation-polymerization may include a group represented by the following formula:

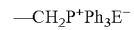

(where E represents the same meaning as described above).

Examples of the phosphonate methyl group which can be selected as the group involved in condensation polymerization may include a group represented by the following formula:

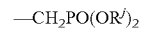

(where $R^j$ represents an alkyl group, an aryl group, or an arylalkyl group).

Examples of the monohalogenated methyl group which can be selected as the group involved in condensation polymerization may include a fluorinated methyl group, a chlorinated methyl group, a brominated methyl group, and an iodinated methyl group.

The group preferred as the group involved in condensation polymerization varies depending on the types of polymerization reactions. For example, when a zero-valent nickel complex for the Yamamoto coupling reaction or the like is used, examples of the group may include a halogen atom, an alkyl sulfonate group, an aryl sulfonate group, and an arylalkyl sulfonate group. When a nickel catalyst or a palladium catalyst for the Suzuki coupling reaction or the like is used, examples of the group may include an alkyl sulfonate group, a halogen atom, a boric acid ester residue, and —B(OH)$_2$. When an oxidation polymerization is conducted using an oxidant or conducted electrochemically, examples of the group may include a hydrogen atom.

Examples of the polymer compound manufacturing method 1 described above may include polymer compound manufacturing methods 1-1 and 1-2.

The polymer compound manufacturing method 1-1 is a method for manufacturing a polymer compound having the structural unit represented by Formula (1) including polymerizing an organic compound represented by the following formula (17A):

[Chemical Formula 47]

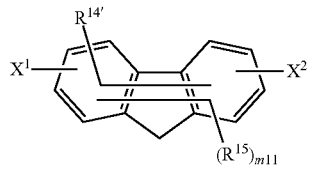

(17A)

(in Formula (17A), $R^{14'}$ represents the group represented by Formula (2) or the group represented by Formula (3); $R^{15}$, m11, and $X^1$ and $X^2$ are the same as the corresponding definitions above; a hydrogen atom in Formula (17A) may be replaced with a substituent other than $R^{14'}$ or $R^{15}$) to obtain a polymer compound having the structural unit represented by Formula (1).

The details of the groups in the organic compound represented by Formula (17A) are the same as those of the organic compound represented by Formula (17). In the manufacturing method 1-1, not only the organic compound represented by Formula (17A), but also one or two or more types of other organic compounds selected from the group consisting of the organic compound represented by Formula (17), the organic compound represented by Formula (20), and the organic compound represented by Formula (23) may be further polymerized. In the manufacturing method 1-1, $R^{14'}$, $R^{15}$, and m11 in the organic compound represented by Formula (17A) correspond to $R^4$, $R^2$, and m1 in the organic compound represented by Formula (1), respectively.

The polymer compound manufacturing method 1-2 is a method for manufacturing a polymer compound having the structural unit represented by Formula (7) including polymerizing an organic compound represented by the following formula (20A):

[Chemical Formula 48]

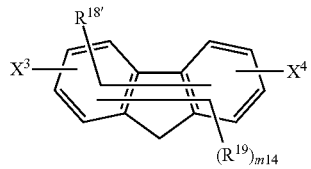

(20A)

(in Formula (20A), $R^{18'}$ represents the group represented by Formula (8) or the group represented by Formula (9); $R^{19}$, m14, and $X^3$ and $X^4$ are the same as the corresponding definitions above; a hydrogen atom in Formula (20A) may be replaced with a substituent other than $R^{18'}$ or $R^{19}$) to obtain a polymer compound having the structural unit represented by Formula (7).

The details of the groups represented by Formula (20A) are the same as those of the organic compound represented by Formula (20). In the manufacturing method 1-2, not only the organic compound represented by Formula (20A), but also one or two or more types of organic compounds selected from the group consisting of the organic compound represented by Formula (17), the organic compound represented by Formula (20), and the organic compound represented by Formula (23) may be further polymerized. In the manufacturing method 1-2, $R^{18'}$, $R^{19}$, and m14 in the organic compound represented by Formula (20A) correspond to $R^6$, $R^7$, and m5 in the organic compound represented by Formula (7), respectively.

Examples of the polymer compound manufacturing method 2 described above may include polymer compound manufacturing methods 2-1 and 2-2.

The polymer compound manufacturing method 2-1 is a method for manufacturing a polymer compound having the structural unit represented by Formula (1) including: (i) polymerizing an organic compound represented by the following Formula (17B):

[Chemical Formula 49]

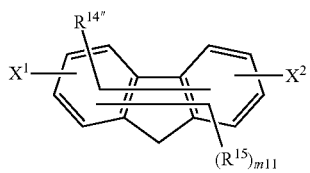

(17B)

(in Formula (17B), $R^{14''}$ represents the group represented by Formula (18) or the group represented by Formula (19). $R^{15}$, m11, and $X^1$ and $X^2$ are the same as the corresponding definitions above. A hydrogen atom in Formula (17B) may be replaced with a substituent other than $R^{14''}$ or $R^{15}$.) to obtain a polymer compound represented by the following Formula (17B'):

[Chemical Formula 50]

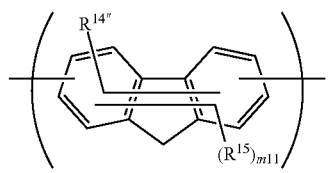

(17B')

(in Formula (17B'), $R^{14''}$ represents the group represented by Formula (18) or the group represented by Formula (19). $R^{15}$ and m11 are the same as the corresponding definitions above. A hydrogen atom in Formula (17B') may be replaced with a substituent other than $R^{14''}$ or $R^{15}$); and (ii) ionizing the polymer compound having the structural unit represented by Formula (17B') to obtain a polymer compound having the structural unit represented by Formula (1). The present invention also provides a polymer compound having the structural unit represented by Formula (17B'). The structural unit represented by Formula (17B') is a divalent structural unit.

The details of the groups in the organic compounds represented by Formula (17B) and (17B') are the same as those of the organic compound represented by Formula (17). In the process (i) of the manufacturing method 2-1, not only the organic compound represented by Formula (17B), but also one or two or more types of organic compounds selected from the group consisting of the organic compound represented by Formula (17), the organic compound represented by Formula (20), and the organic compound represented by Formula (23) may be further polymerized. In the manufacturing method 2-1, $R^{14''}$, $R^{15}$, and m11 in the organic compounds represented by Formulae (17B) and (17B') correspond to $R^1$, $R^2$, and m1 in the organic compound having the structural unit represented by Formula (1), respectively.

In the process (ii) of the manufacturing method 2-1, the polymer compound having the structural unit represented by Formula (17B') is ionized, thereby, in $R^{14'''}$, converting the group represented by Formula (18) or the group represented by Formula (19) (a non-ionic group) into the group represented by Formula (2) or the group represented by Formula (3) (an ionic group).

The manufacturing method 2-2 is a method for manufacturing a polymer compound having the structural unit represented by Formula (7) including: (i') polymerizing an organic compound represented by the following Formula (20B):

[Chemical Formula 51]

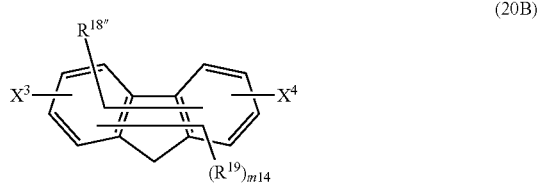

(20B)

(in Formula (20B), $R^{18'''}$ represents the group represented by Formula (21) or the group represented by Formula (22). $R^{19}$, m14, and $X^3$ and $X^4$ are the same as the corresponding definitions above. A hydrogen atom in Formula (20B) may be replaced with a substituent other than $R^{18'''}$ or $R^{19}$) to obtain a polymer compound represented by the following Formula (20B'):

[Chemical Formula 52]

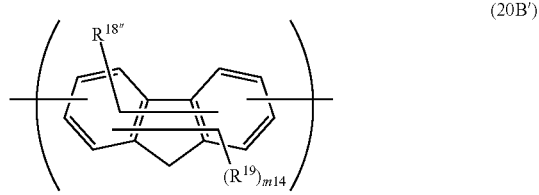

(20B')

(in Formula (20B'), $R^{18'''}$ represents the group represented by Formula (21) or the group represented by Formula (22). $R^{19}$ and m14 are the same as the corresponding definitions above. A hydrogen atom in Formula (20B') may be replaced with a substituent other than $R^{18'''}$ or $R^{19}$); and (ii') ionizing the polymer compound having the structural unit represented by Formula (20B') to obtain a polymer compound having the structural unit represented by Formula (7). The present invention also provides a polymer compound having the structural unit represented by Formula (20B'). The structural unit represented by Formula (20B') is a divalent structural unit.

The details of the groups in the organic compounds represented by Formula (20B) and (20B') may be the same as those of the organic compound represented by Formula (20). In the process (i) of the manufacturing method 2-2, not only the organic compound represented by Formula (20B), but also one or two or more types of organic compounds selected from the group consisting of the organic compound represented by Formula (17), the organic compound represented by Formula (20), and the organic compound represented by Formula (23) may be further polymerized. In the manufacturing method 2-2, $R^{18'''}$, $R^{19}$, and m14 in the organic compounds represented by Formulae (20B) and (20B') correspond to $R^6$, $R^7$, and m5 in the organic compound having the structural unit represented by Formula (7), respectively.

In the process (ii') of the manufacturing method 2-2, the polymer compound having the structural unit represented by Formula (20B') is ionized, thereby, in $R^{18'''}$, converting the group represented by Formula (21) or the group represented by Formula (22) (a non-ionic group) into the group represented by Formula (8) or the group represented by Formula (9) (an ionic group).

Examples of the ionization in the process (ii) of the manufacturing method 2-1 and the process (ii') of the manufacturing method 2-2 may include cationization and anionization. Examples of the ionization may include a method in which the polymer compound obtained in the process (i) is caused to react with a reagent such as a metal hydroxide, a metal carbonate, and alkylammonium hydroxide or a reagent such as an alkyl halide and $SbF_5$, as needed dissolved in water or an organic solvent, at a temperature of the melting point of the organic solvent or higher and the boiling point of the organic solvent or lower.

When the polymer compound according to the present invention is manufactured, a polymerization method may be employed in which, for example, a compound (monomer) represented by General Formula (17) or (20) having a plurality of groups involved in condensation polymerization is dissolved in an organic solvent as needed and is caused to react using an alkali or an appropriate catalyst, at a temperature of the melting point of the organic solvent or higher and the boiling point of the organic solvent or lower. Examples of such a polymerization method may include publicly known methods described in, for example, "Organic Reactions, vol. 14, pp. 270-490 (1965), published by John Wiley & Sons, Inc.," "Organic Syntheses, Collective Volume VI, pp. 407-411 (1988), published by John Wiley & Sons, Inc.," "Chemical Review (Chem. Rev.), vol. 95, p. 2457 (1995)," "Journal of Organometallic Chemistry (J. Organomet. Chem.), vol. 576, p. 147 (1999)," and "Macromolecular Chemistry, Macromolecular Symposium (Macromol. Chem., Macromol. Symp.) vol. 12, p. 229 (1987)."

When the polymer compound according to the present invention is manufactured, a known condensation polymerization reaction may be employed according to the group involved in condensation polymerization. Examples of such a polymerization method may include: a method of polymerizing the relevant monomer by the Suzuki coupling reaction; a method of polymerizing the relevant monomer by the Grignard reaction; a method of polymerizing the relevant monomer by a Ni(0) complex; a method of polymerizing the relevant monomer by an oxidant such as $FeCl_3$; a method of oxidative polymerizing the relevant monomer electrochemically; and a method of decomposing an intermediate polymer having an appropriate leaving group. Among such polymerization reactions, the method of polymerizing by the Suzuki coupling reaction, the method of polymerizing by the Grignard reaction, and the method of polymerizing by a zerovalent nickel complex are preferred, because the structure of the obtained ionic polymer can be easily controlled.

A preferred embodiment of the method for manufacturing the polymer compound according to the present invention is a method for manufacturing the polymer compound including: using a raw material monomer including a group selected from the group consisting of a halogen atom, an alkyl sulfonate group, an aryl sulfonate group, and an arylalkyl sulfonate group as the group involved in condensation polymerization; and condensation polymerizing the raw material monomer in the presence of a zero-valent nickel complex. Examples of the raw material monomer used for such a method may include a dihalogenated compound, a bis(alkyl sulfonate) compound, a bis(aryl sulfonate) compound, a bis (arylalkyl sulfonate) compound, a halogen-alkyl sulfonate compound, a halogen-aryl sulfonate compound, a halogen-arylalkyl sulfonate compound, an alkyl sulfonate-aryl sulfonate compound, an alkyl sulfonate-arylalkyl sulfonate compound, and an aryl sulfonate-arylalkyl sulfonate compound.

Another preferred embodiment of the method for manufacturing the polymer compound is a method for manufacturing the polymer compound including: using a raw material monomer including a group selected from the group consisting of a halogen atom, an alkyl sulfonate group, an aryl sulfonate group, an arylalkyl sulfonate group, —B(OH)$_2$, and a boric acid ester residue as the group involved in condensation polymerization, the raw material monomer in which the ratio between the sum (J) of the number of moles of a halogen atom, an alkyl sulfonate group, an aryl sulfonate group, and an arylalkyl sulfonate group that all raw material monomers have and the sum (K) of the number of moles of —B(OH)$_2$ and a boric acid ester residue that all raw material monomers have is substantially 1 (usually, K/J is in a range of 0.7 to 1.2); and condensation polymerizing the raw material monomer in the presence of a nickel catalyst or a palladium catalyst.

The organic solvent varies depending on the used compounds and the reaction. For the organic solvent, in order to suppress a side reaction, an organic solvent subjected thoroughly to deoxygenation treatment is generally preferred to be used. When the polymer compound is manufactured, it is preferred that the reaction is progressed using such an organic solvent in an inert atmosphere. The organic solvent is preferably subjected to a dehydration treatment as well as the deoxygenation treatment, provided that this may not be the case for the reaction in a two-phase system with water such as the Suzuki coupling reaction.

Examples of the organic solvent may include: a saturated hydrocarbon such as pentane, hexane, heptane, octane, and cyclohexane; an unsaturated hydrocarbon such as benzene, toluene, ethylbenzene, and xylene; alcohols such as methanol, ethanol, propanol, isopropanol, butanol, and tert-butyl alcohol; carboxylic acids such as formic acid, acetic acid, and propionic acid; ethers such as dimethyl ether, diethyl ether, methyl tert-butyl ether, tetrahydrofuran, tetrahydropyran, and dioxane; amines such as trimethylamine, triethylamine, N,N, N',N'-tetramethylethylenediamine, and pyridine; and amides such as N,N-dimethylformamide, N,N-dimethylacetamide, N,N-diethylacetamide, and N-methylmorpholine oxide. These organic solvents may be used alone or in combination of two or more types thereof. Among such organic solvents, in view of the reactivity, ethers are more preferred, and tetrahydrofuran and diethyl ether are further preferred. In view of the reaction rate, toluene and xylene are preferred.

When the polymer compound is manufactured, it is preferred that an alkali or an appropriate catalyst is added in order to cause the raw material monomer to react. Such an alkali or a catalyst may be selected according to an employed polymerization method or the like. Such an alkali and a catalyst are preferably those capable of being thoroughly dissolved in the solvent used for the reaction. Examples of the method for mixing the alkali or the catalyst may include a method in which while stirring a reaction mixture in an inert atmosphere such as argon and nitrogen, a solution of the alkali or the catalyst is slowly added thereto and a method in which the reaction mixture is slowly added to a solution of the alkali or the catalyst.

Regarding the polymer compound according to the present invention, if a polymerization-active group remains at the position of a terminal group as it is, there is such a probability that the light-emitting characteristics and the life characteristics of the obtained light-emitting device might lower. Therefore, the terminal group may be protected with a stable group. When the terminal group is protected with a stable group and the polymer compound according to the present invention is a conjugated compound, the polymer compound has preferably a conjugated bond in conjunction with a conjugated structure of the main chain of the polymer compound. Examples of such a structure may include a structure being bonded with an aryl group or a heterocyclic group through a carbon-carbon bond. Examples of such a stable group for protecting the terminal group may include a monovalent aromatic group.

Examples of a preferred method for manufacturing the polymer compound containing an ionic group may include a method in which in the first process, a polymer compound having no cationic group is polymerized, and in the second process, a polymer compound containing a cationic group is manufactured from the former polymer compound. Examples of the method for polymerizing the polymer compound having no cationic group in the first process may include the condensation polymerization reaction described above. Examples of the reaction in the second process may include a method in which the polymer compound obtained in the first process and a reagent such as a metal hydroxide, a metal carbonate, and alkylammonium hydroxide are dissolved in water or an organic solvent as needed and allowed to react at a temperature of the melting point of the organic solvent or higher and the boiling point of the organic solvent or lower.

Examples of another preferred method for manufacturing the polymer compound containing an ionic group may include a method in which in the first process, a polymer compound having no anionic group is polymerized, and in the second process, a polymer compound containing an anionic group is manufactured from the former polymer compound. Examples of the method for polymerizing the polymer compound having no anionic group in the first process may include the condensation polymerization reaction described above. Examples of the reaction in the second process may include a method in which a reagent such as an alkyl halide and SbF$_5$ is dissolved in water or an organic solvent as needed and allowed to react at a temperature of the melting point of the organic solvent or higher and the boiling point of the organic solvent or lower.

Impurities may be removed from the polymer compound containing an ionic group as needed through a process such as washing with water or an organic solvent and reprecipitation.

It is preferable that a layer containing the polymer compound according to the present invention is substantially non-luminescent when it is used for an electroluminescent device. Here, that a layer containing a given polymer compound is substantially non-luminescent means as follows. First, in Example 35 below, an electroluminescent device A is prepared in the same manner as Example 35 except that a polymer compound of interest is used in place of a non-conjugated polymer compound 1. On the other hand, an electroluminescent device C1 is prepared according to the description of Comparative Example 1. The electroluminescent device A and the electroluminescent device C1 are different only in that the electroluminescent device A has a layer containing the given polymer compound, while the electroluminescent device C1 has no layer containing the given polymer compound. Next, a forward voltage of 10 V is applied to the electroluminescent device A and the electroluminescent device C1 to measure a luminescent spectrum. A wavelength λ giving a maximum peak in the luminescent spectrum obtained with respect to the electroluminescent device C1 is measured. While assuming the luminescence intensity at the wavelength λ as 1, the luminescent spectrum obtained with respect to the electroluminescent device C1 is normalized and is integrated relative to the wavelength to calculate a normalized luminescence amount $S_0$. While assuming the luminescence intensity at the wavelength λ as 1, the luminescent spectrum obtained with respect to the electroluminescent device A is also normalized and is integrated relative to the wavelength to calculate a normalized luminescence amount S. When the value calculated by formula of $(S-S_0)/S_0 \times 100\%$ is 30% or less, that is, when an increment of the normalized luminescence amount of the electroluminescent device A having the layer containing the given polymer compound from the normalized luminescence amount of the electroluminescent device C1 not having the layer containing the given polymer compound is 30% or less, the used layer containing the given polymer compound is regarded as substantially non-luminescent. The value calculated by formula of $(S-S_0)/S_0 \times 100$ is preferably 15% or less and more preferably 10% or less.

<Electronic Device>

Next, an electronic device according to the present invention will be described.

The electronic device according to the present invention includes a layer containing a polymer compound having one or more structural units selected from the group consisting of the structural unit represented by Formula (1) and the structural unit represented by Formula (7) as a charge injection layer and/or a charge transport layer.

Examples of the electronic device according to the present invention may include an electroluminescent device and a photovoltaic cell. When the electronic device is used for the electroluminescent device (that may be referred to as the "electroluminescent device according to the present invention" below), the electronic device includes a light-emitting layer. When the electronic device is used for the photovoltaic cell (that may be referred to as the "photovoltaic cell according to the present invention" below), the electronic device includes a charge separation layer.

<Electroluminescent Device>

The electroluminescent device according to the present invention includes, for example, a cathode, an anode, a light-emitting layer positioned between the cathode and the anode, and a layer that is positioned between the light-emitting layer and the cathode or the anode and contains the polymer compound used in the present invention. The electroluminescent device according to the present invention may include a substrate as an optional constituent and may have a constitution in which the cathode, the anode, the light-emitting layer, the layer containing the polymer compound used in the present invention, and any optional constituents are provided on the surface of the substrate.

In one embodiment of the electroluminescent device according to the present invention, the anode is provided on the substrate, the light-emitting layer is stacked thereon, the layer containing the polymer compound according to the present invention is stacked thereon, and the cathode is stacked thereon. In another embodiment, the anode is stacked on the substrate, the layer containing the polymer compound according to the present invention is stacked thereon, the light-emitting layer is stacked thereon, and the cathode is stacked thereon. In still another embodiment, the anode is stacked on the substrate, the layer containing the polymer compound according to the present invention is stacked thereon, the light-emitting layer is stacked thereon, the layer containing the polymer compound according to the present invention is stacked thereon, and the cathode is stacked thereon. In still another embodiment, the cathode is stacked on the substrate, the layer containing the polymer compound according to the present invention is stacked thereon, the light-emitting layer is stacked thereon, and the anode is stacked thereon. In still another embodiment, the cathode is stacked on the substrate, the light-emitting layer is stacked thereon, the layer containing the polymer compound according to the present invention is stacked thereon, and the anode is stacked thereon. In further another embodiment, the cathode is stacked on the substrate, the layer containing the polymer compound according to the present invention is stacked thereon, the light-emitting layer is stacked thereon, the layer containing the polymer compound according to the present invention is stacked thereon, and the anode is stacked thereon. In these embodiments, layers having other functions such as a protective layer, a buffer layer, and a reflective layer may be further provided. The constitution of the electroluminescent device will be described separately in detail below. The electroluminescent device is further covered with a sealing film or a sealing substrate to form a light-emitting device with the electroluminescent device cut off from outside air.

The layer containing the polymer compound according to the present invention may be mixed with a known macromolecular or low molecular charge transport material, electroconductive carbons such as graphene, fullerene, and carbon nanotubes, an electroconductive compound such as a metal, an alloy, a metal oxide, and a metal sulfide, and a mixture thereof. As the charge transport material, those used for a hole transport layer or an electron transport layer, which will be described later, may be used. As the metal, alloy, metal oxide, and metal sulfide, those used for an anode or cathode, which will be described later, may be used. In addition, organic materials having neither a light-emitting function nor a charge transport function may be mixed without impairing the light-emitting function as the electroluminescent device.

The electroluminescent device according to the present invention may be an electroluminescent device of any type of what is called the bottom emission type that emits light from the substrate side, what is called the top emission type that emits light from the side opposite the substrate, and the double-sided emission type.

Examples of a method for forming the layer containing the polymer compound may include a film forming method using a solution containing the polymer compound.

Examples of a solvent for use in such film formation from a solution may include solvents having a solubility parameter of 9.3 or more such as water, alcohols, ethers, esters, nitrile compounds, nitro compounds, alkyl halides, aryl halides, thiols, sulfides, sulfoxides, thioketones, amides, and carboxylic acids. Examples of the solvents may include (the value in parentheses denotes the value of the solubility parameter of each solvent) water (21.0), methanol (12.9), ethanol (11.2), 2-propanol (11.5), 1-butanol (9.9), t-butyl alcohol (10.5), acetonitrile (11.8), 1,2-ethanediol (14.7), N,N-dimethylformamide (11.5), dimethyl sulfoxide (12.8), acetic acid (12.4), nitrobenzene (11.1), nitromethane (11.0), 1,2-dichloroethane (9.7), dichloromethane (9.6), chlorobenzene (9.6), bromobenzene (9.9), dioxane (9.8), propylene carbonate (13.3), pyridine (10.4), carbon disulfide (10.0), and mixed solvents of these solvents (for the values of the solubility parameter, see Solvent Handbook, 14th printing, published by Kodansha Ltd. Publishers). Here, a description will be made on the mixed solvents composed of two solvents (designated as a solvent 1 and a solvent 2). The solubility parameter ($\delta_m$) of the mixed solvent is determined by the equation: $\delta_m = \delta_1 \times \phi_1 + \delta_2 \times \phi_2$ (where $\delta_1$ is the solubility parameter of the solvent 1, $\phi_1$ is the volume fraction of the solvent 1, $\delta_2$ is the solubility parameter of the solvent 2, and $\phi_2$ is the volume fraction of the solvent 2.).

Examples of the film forming method from a solution may include application methods such as a spin coating method, a casting method, a micro gravure printing method, a gravure printing method, a bar coating method, a roll coating method, a wire bar coating method, a dip coating method, a slit coating method, a cap coating method, a spray coating method, a screen printing method, a flexographic printing method, an offset printing method, an inkjet printing method, and a nozzle coating method.

Because the optimum thickness of the layer containing the polymer compound varies depending on the polymer compound used, the thickness may be selected so as to give adequate values of drive voltage and light-emitting efficiency. The thickness is preferably from 1 nm to 1 μm, more preferably from 2 nm to 500 nm, and further more preferably from 2 nm to 200 nm. In view of protecting the light-emitting layer, the thickness is preferably from 5 nm to 1 μm.

The electroluminescent device includes a cathode and an anode and includes a light-emitting layer between the cathode and the anode. It may have another constituent.

For example, the electroluminescent device may include, between the anode and the light-emitting layer, one or more of a hole injection layer and a hole transport layer. When the hole injection layer is present, the device may include one or more hole transport layers between the light-emitting layer and the hole injection layer.

On the other hand, the device may include one or more of an electron injection layer and an electron transport layer between the cathode and the light-emitting layer. When the electron injection layer is present, the device may include one or more electron transport layers between the light-emitting layer and the electron injection layer.

The layer containing a composition used in the present invention can be used for the hole injection layer, the hole transport layer, the electron injection layer, the electron transport layer, or the like. When the layer containing the composition is used for the hole injection layer or the hole transport layer, the first electrode serves as the anode, and the second electrode serves as the cathode. When the layer containing the composition is used for the electron injection layer or the electron transport layer, the first electrode serves as the cathode and the second electrode serves as the anode.

The anode is an electrode for supplying holes to the hole injection layer, the hole transport layer, the light-emitting layer, or the like, while the cathode is an electrode for supplying electrons to the electron injection layer, the electron transport layer, the light-emitting layer, or the like.

The light-emitting layer refers to a layer having a function of accepting holes from the anode or a layer adjacent on the anode side and accepting electrons from the cathode or a layer adjacent on the cathode side when an electric field is applied, a function of moving the accepted charges by the force of the electric field, and a function of providing a recombination site for electrons and holes to cause light emission.

The electron injection layer is a layer adjacent to the cathode and a layer having a function of receiving holes from the anode and refers to a layer having further as needed any of a function of transporting electrons, a function of blocking holes injected from the anode, and a function of supplying electrons to the light-emitting layer. The electron transport layer is a layer mainly having a function of transporting electrons and refers to a layer having further as needed any of a function of receiving electrons from the cathode, a function of blocking holes injected from the anode, and a function of supplying electros to the light-emitting layer.

The hole injection layer is a layer adjacent to the anode and a layer having a function of receiving holes from the anode and refers to a layer having further as needed any of a function of transporting holes, a function of supplying holes to the light-emitting layer, and a function of blocking electrons injected from the cathode. The hole transport layer is a layer mainly having a function of transporting holes and refers to a layer having further as needed any of a function of receiving holes from the anode, a function of supplying holes to the light-emitting layer, and a function of blocking electrons injected from the cathode.

The electron transport layer and the hole transport layer may be collectively referred to as a charge transport layer. The electron injection layer and the hole injection layer may be collectively referred to as a charge injection layer.

In other words, the electroluminescent device according to the present invention may have the following layer structure (a) or may have a layer structure obtained by omitting one or more of the hole injection layer, the hole transport layer, the electron transport layer, and the electron injection layer from the layer structure (a). In the layer structure (a), the layer containing the polymer compound according to the present invention can be used as one or more layers selected from the group consisting of the hole injection layer, the hole transport layer, the electron injection layer, and the electron transport layer.

(a) Anode-Hole injection layer-(Hole transport layer)-Light-emitting layer-(Electron transport layer)-Electron injection layer-Cathode The symbol "-" means that the layers are stacked adjacent to one another. The "(hole transport layer)" means a layer structure including one or more hole transport layers. The "(electron transport layer)" means a layer structure including one or more electron transport layers. The same is applicable to the description of the following layer structures.

Furthermore, the electroluminescent device according to the present invention can include two light-emitting layers within one layered structure. In this case, the electroluminescent device can include a layer structure (b) described below or a layer structure obtained by omitting one or more of the hole injection layer, the hole transport layer, the electron transport layer, the electron injection layer, and an electrode from the layer structure (b). In the layer structure (b), the layer containing the polymer compound according to the present invention can be used for a layer located between the anode and a light-emitting layer that is closest to the anode or used for a layer located between the cathode and a light-emitting layer that is closest to the cathode.

(b) Anode-Hole injection layer-(Hole transport layer)-Light-emitting layer-(Electron transport layer)-Electron injection layer-Electrode-Hole injection layer-(Hole transport layer)-Light-emitting layer-(or Electron transport layer)-Electron injection layer-Cathode Furthermore, the electroluminescent device according to the present invention can include three or more light-emitting layers within one layer structure. In this case, the electroluminescent device can include a layer structure (c) described below or a layer structure obtained by omitting one or more of the hole injection layer, the hole transport layer, the electron transport layer, the electron injection layer, and an electrode from the layer structure (c). In the layer structure (c), the layer containing the polymer compound according to the present invention can be used for a layer located between the anode and a light-emitting layer that is closest to the anode or used for a layer located between the cathode and a light-emitting layer that is closest to the cathode.

(c) Anode-Hole injection layer-(Hole transport layer)-Light-emitting layer-(Electron transport layer)-Electron injection layer-Repeating unit A-Repeating unit A . . . -Cathode The "repeating unit A" indicates a unit of a layer structure of Electrode-Hole injection layer-(Hole transport layer)-Light-emitting layer-(Electron transport layer)-Electron injection layer.

Preferred examples of the layer structure of the electroluminescent device according to the present invention may include the following structures. In the following layer structures, the layer containing the polymer compound according to the present invention can be used for one or more layers selected from the group consisting of the hole injection layer, the hole transport layer, the electron injection layer, and the electron transport layer.

(a) Anode-Hole injection layer-Light-emitting layer-Cathode
(b) Anode-Light-emitting layer-Electron injection layer-Cathode
(c) Anode-Hole injection layer-Light-emitting layer-Electron injection layer-Cathode
(d) Anode-Hole injection layer-Hole transport layer-Light-emitting layer-Cathode
(e) Anode-Hole injection layer-Hole transport layer-Light-emitting layer-Electron injection layer-Cathode
(f) Anode-Light-emitting layer-Electron transport layer-Electron injection layer-Cathode
(g) Anode-Hole injection layer-Light-emitting layer-Electron transport layer-Electron injection layer-Cathode
(h) Anode-Hole injection layer-Hole transport layer-Light-emitting layer-Electron transport layer-Electron injection layer-Cathode The layer containing the polymer compound according to the present invention is preferably the electron injection layer or the electron transport layer. When the layer containing the polymer compound is the electron injection layer or the electron transport layer, the first electrode is the cathode.

The electroluminescent device according to the present invention may be further provided with an insulating layer adjacent to an electrode in order to improve adhesion with the electrode and improve the injection of charges from the electrode. A thin buffer layer may be provided on the interface of the charge transport layer and the light-emitting layer. The order and number of the layers to be stacked and the thickness of the layers may be selected taking light-emitting efficiency and device life into consideration.

Next, the material and forming method of the layers constituting the electroluminescent device according to the present invention will be described in detail.

—Substrate—

As a substrate constituting the electroluminescent device according to the present invention, any one is usable so long as it does not chemically change when an electrode is formed thereon and an organic layer is formed thereon. For example, substrates made from glass, plastics, polymer films, metal films, silicon, or the like and substrates obtained by laminating these materials may be used. Such substrates are commercially available or can be produced by known methods.

When the electroluminescent device according to the present invention constitutes a pixel of a display device, the substrate may have thereon a circuit for driving the pixel or have a planarized film on this drive circuit. When the planarized film is provided, the center line average roughness (Ra) of the planarized film satisfies preferably Ra<10 nm.

Ra can be measured based on JIS-B0601-2001 of Japanese Industrial Standards (JIS) with reference to JIS-B0651 to JIS-B0656, JIS-B0671-1, or the like.

—Anode—

In view of hole supply property to an organic semiconductor material used for the hole injection layer, the hole transport layer, an interlayer, the light-emitting layer, or the like, the anode constituting the electroluminescent device according to the present invention has preferably a work function of 4.0 eV or more on the surface of the anode on the light-emitting layer side.

As the material of the anode, electroconductive compounds such as metals, alloys, metal oxides, and metal sulfides, and mixtures thereof can be used. Specific examples may include electroconductive metal oxides such as tin oxide, zinc oxide, indium oxide, indium tin oxide (ITO), indium zinc oxide (IZO), and molybdenum oxide; metals such as gold, silver, chromium, and nickel; and mixtures of these electroconductive metal oxides and metals.

The anode may have a single layer structure composed of one or two or more of these materials or a multilayered structure composed of a plurality of layers having the same composition or different compositions. When it has a multilayered structure, it is more preferred to dispose a material having a work function of 4.0 eV or more on the outermost layer on the light-emitting layer side.

As a method for forming the anode, known methods can be used. Examples of the method may include a vacuum deposition method, a sputtering method, an ion plating method, a plating method, and a method by film formation from a solution (that may use a mixed solution with a macromolecular binder).

The thickness of the anode is usually from 10 nm to 10 μm, preferably from 40 nm to 500 nm.

In view of preventing faulty electric connection such as short circuit, the center line average roughness (Ra) of the surface of the anode on the light-emitting layer side satisfies preferably Ra<10 nm and more preferably Ra<5 nm.

Furthermore, the anode may be subjected to a surface treatment with a solution containing an electron accepting compound such as UV ozone, a silane coupling agent, or 2,3,5,6-tetrafluoro-7,7,8,8-tetracyanoquinodimethane after being formed by the above method. The surface treatment improves electric connection with a layer to be brought into contact with the anode.

When the anode is used as a light reflective electrode of the electroluminescent device according to the present invention, the anode preferably has a multilayered structure composed of a combination of a light reflective layer made of a highly light reflective metal and a high work function material layer containing a material having a work function of 4.0 eV or more.

Specific examples of the structure of the anode may include:

| | |
|---|---|
| Ag—MoO$_3$, | (i) |
| (Ag—Pd—Cu alloy)-(ITO and/or IZO), | (ii) |
| (Al—Nd alloy)-(ITO and/or IZO), | (iii) |
| (Mo—Cr alloy)-(ITO and/or IZO), | (iv) |
| and | |
| (Ag—Pd—Cu alloy)-(ITO and/or IZO)-MoO$_3$. | (v) |

In order to achieve a sufficient light reflectance, the thickness of the highly light reflective metal layer such as Al, Ag, an Al alloy, a Ag alloy, a Cr alloy, or the like is preferably 50 nm or more and more preferably 80 nm or more. The thickness of the high work function material layer such as ITO, IZO, and $MoO_3$ is usually within a range from 5 nm to 500 nm.

—Hole Injection Layer—

In the electroluminescent device according to the present invention, examples of the material for forming the hole injection layer other than the polymer compound according to the present invention may include: carbazole derivatives, triazole derivatives, oxazole derivatives, oxadiazole derivatives, imidazole derivatives, fluorene derivatives, polyarylalkane derivatives, pyrazoline derivatives, pyrazolone derivatives, phenylenediamine derivatives, arylamine derivatives, starburst type amines, phthalocyanine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidyne-based compounds, porphyrin-based compounds, polysilane-based compounds, poly(N-vinylcarbazole) derivatives, organic silane derivatives, and polymers containing them; electroconductive metal oxides such as vanadium oxide, tantalum oxide, tungsten oxide, molybdenum oxide, ruthenium oxide, and aluminum oxide; electroconductive polymers and oligomers such as polyaniline, aniline-based copolymers, thiophene oligomers, and polythiophene; organic electroconductive materials such as poly(3,4-ethylenedioxythiophene) polystyrenesulfonic acid and polypyrrole and polymers containing them; amorphous carbon; acceptor organic compounds such as tetracyanoquinodimethane derivatives (for example, 2,3,5,6-tetrafluoro-7,7,8,8-tetracyanoquinodimethane), 1,4-naphthoquinone derivatives, diphenoquinone derivatives, and polynitro compounds; and silane coupling agents such as octadecyltrimethoxysilane.

The above materials may be used as a single component or a composition composed of a plurality of components. The hole injection layer may have a single layered structure composed only of the above material or a multilayered structure composed of a plurality of layers having the same or different compositions. In addition, materials exemplified as materials usable in the hole transport layer or the interlayer can also be used for the hole injection layer.

As a method for preparing the hole injection layer, known methods can be used. When the material used for the preparation of the hole injection layer is an inorganic material, the vacuum deposition method, the sputtering method, the ion plating, or the like can be employed. When the material is a low molecular organic material, the vacuum deposition method, a transfer method such as laser transfer or heat transfer, the method by film formation from a solution (that may use a mixed solution with a macromolecular binder), or the like can be employed. When a hole injection material is a macromolecular organic material, the method by film formation from a solution can be employed.

When the hole injection material is a low molecular organic material such as a pyrazoline derivative, an arylamine derivative, a stilbene derivative, and a triphenyldiamine derivative, the hole injection layer is preferably formed by the vacuum deposition method.

The hole injection layer may also be formed using a mixed solution containing a polymer compound binder and the low molecular organic material dispersed therein.

The polymer compound binder to be mixed is preferably a compound that does not extremely hinder charge transport, and a compound not exhibiting strong absorption to visible light is suited for use. Specific examples of the polymer compound binder may include poly(N-vinylcarbazole), polyaniline and derivatives thereof, polythiophene and derivatives thereof, poly(p-phenylenevinylene) and derivatives thereof, poly(2,5-thienylene vinylene) and derivatives thereof, polycarbonates, polyacrylates, polymethyl acrylate, polymethyl methacrylate, polystyrene, polyvinyl chloride, and polysiloxane.

The solvent for use in the film formation from a solution may be any solvent that can dissolve the hole injection material. Examples of the solvent may include: water; chlorine-containing solvents such as chloroform, methylene chloride, and dichloromethane; ether solvents such as tetrahydrofuran; aromatic hydrocarbon solvents such as toluene and xylene; ketone solvents such as acetone and methyl ethyl ketone; and ester solvents such as ethyl acetate, butyl acetate, and ethyl cellosolve acetate.

Examples of the film forming method from a solution may include application methods including: coating methods such as the spin coating method from a solution, the casting method, the bar coating method, the roll coating method, the wire bar coating method, the dip coating method, the slit coating method, a capillary coating method, the spray coating method, and a nozzle coating method; and printing methods such as the micro gravure printing method, the gravure printing method, the screen printing method, the flexographic printing method, the offset printing method, a reverse printing method, and the inkjet printing method. Because of the simplicity of pattern forming, preferred examples may include the printing methods such as the gravure printing method, the screen printing method, the flexographic printing method, the offset printing method, the reverse printing method, the inkjet printing method and the nozzle coating method.

When an organic compound layer such as the hole transport layer and the light-emitting layer is formed after the formation of the hole injection layer, and particularly when both layers are formed by an application method, a layered structure may not be formed, because the layer applied first dissolves in a solvent contained in a solution for a layer applied later. In such a case, a method for insolubilizing a lower layer may be employed. Examples of the insolubilizing method may include: a method of cross-linking a polymer compound through a cross-linking group added thereto, thereby insolubilizing the lower layer; a method of mixing with a low molecular compound having an aromatic-ring-containing cross-linking group, typified by aromatic bisazide, as a cross-linking agent and cross-linking it to insolubilize the lower layer; a method of mixing a low molecular compound having an aromatic-ring-free cross-linking group, typified by an acrylate group, as a cross-linking agent and cross-linking it to insolubilize the lower layer; a method of exposing the lower layer to ultraviolet light to cause cross-linking, thereby insolubilizing the lower layer in an organic solvent to be used in the formation of an upper layer; and a method of heating the lower layer to cause cross-linking, thereby insolubilizing it in an organic solvent to be used in the formation of the upper layer. The heating temperature when the lower layer is heated is usually from 100° C. to 300° C. The heating time is usually from 1 minute to 1 hour.

As another method for stacking the upper layer without dissolving the lower layer, there is a method using solutions different in polarity for the formation of the adjacent layers. For example, there is a method using a water soluble polymer compound for the lower layer and an oil soluble polymer compound for the upper layer to prevent the lower layer from dissolving even by the application of the upper layer.

The optimum thickness of the hole injection layer varies depending on the material used and may be selected so as to give adequate values of drive voltage and light-emitting efficiency. The thickness is usually 1 nm to 1 µm, preferably from 2 nm to 500 nm, and more preferably from 10 nm to 100 nm.

—Hole Transport Layer—

In the electroluminescent device according to the present invention, examples of a material constituting the hole transport layer other than the polymer compound according to the present invention may include: carbazole derivatives, triazole derivatives, oxazole derivatives, oxadiazole derivatives, imidazole derivatives, fluorene derivatives, polyarylalkane derivatives, pyrazoline derivatives, pyrazolone derivatives, phenylenediamine derivatives, arylamine derivatives, starburst type amines, phthalocyanine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidyne-based compounds, porphyrin-based compounds, polysilane-based compounds, poly(N-vinylcarbazole) derivatives, organic silane derivatives, and polymers containing them; electroconductive polymers and oligomers such as polyaniline, aniline-based copolymers, thiophene oligomers, and polythiophene; and organic electroconductive materials such as polypyrrole.

The above materials may be used as a single component or a composition composed of a plurality of components. The hole transport layer may have a single layered structure composed only of the above material or a multilayered structure composed of a plurality of layers having the same or different compositions. In addition, materials exemplified as materials usable in the hole injection layer can also be used for the hole transport layer.

As a method for preparing the hole transport layer and the interlayer, for example, the same as the method for the film formation of the hole injection layer can be employed. Examples of the film forming method from a solution may include application methods and printing methods such as the spin coating method, the casting method, the bar coating method, the slit coating method, the spray coating method, the nozzle coating method, the gravure printing method, the screen printing method, the flexographic printing method, and the inkjet printing method. When a sublimation compound material is used, examples of the method may include the vacuum deposition method and the transfer method. Examples of the solvent for use in the film formation from a solution may include the solvents exemplified in the film forming method for the hole injection layer.

When an organic compound layer such as the light-emitting layer is formed by an application method after the formation of the hole transport layer, and when a lower layer dissolves in a solvent contained in a solution for a layer applied later, the lower layer can be insolubilized by the same method as exemplified in the film forming method for the hole injection layer.

The optimum thickness of the hole transport layer varies depending on the material used and may be selected so as to give adequate values of drive voltage and light-emitting efficiency. The thickness is usually 1 nm to 1 µm, preferably from 2 nm to 500 nm, and more preferably from 5 nm to 100 nm.

—Light-Emitting Layer—

In the electroluminescent device according to the present invention, when the light-emitting layer contains the polymer compound, conjugated polymer compounds such as polyfluorene derivatives, polyparaphenylene vinylene derivatives, polyphenylene derivatives, polyparaphenylene derivatives, polythiophene derivatives, polydialkylfluorenes, polyfluorenebenzothiadiazole, and polyalkylthiophenes are suited for use as the polymer compound.

The light-emitting layer containing the polymer compound may contain a macromolecular dye compound such as a perylene dye, a coumarin dye, and a rhodamine dye, and a low molecular dye compound such as rubrene, perylene, 9,10-diphenylanthracene, tetraphenylbutadiene, nile red, coumarin 6, and quinacridone. In addition, the light-emitting layer may contain a naphthalene derivative, anthracene or a derivative thereof, perylene or a derivative thereof, a dye based on polymethine, xanthene, coumarin, and cyanine, a metal complex of 8-hydroxyquinoline or a derivative thereof, an aromatic amine, tetraphenylcyclopentadiene or a derivative thereof, tetraphenylbutadiene or a derivative thereof, and a metal complex emitting phosphorescence such as tris(2-phenylpyridine)iridium.

The light-emitting layer of the electroluminescent device according to the present invention may include a composition composed of a non-conjugated polymer compound and a luminous organic compound such as the above organic dye or the above metal complex. Examples of the non-conjugated polymer compound may include polyethylene, polyvinyl chloride, polycarbonate, polystyrene, polymethyl methacrylate, polybutyl methacrylate, polyester, polysulfone, polyphenylene oxide, polybutadiene, poly(N-vinylcarbazole), hydrocarbon resins, ketone resins, phenoxy resins, polyamide, ethyl cellulose, vinyl acetate, ABS resins, polyurethane, melamine resins, unsaturated polyester resins, alkyd resins, epoxy resins, and silicone resins. The non-conjugated polymer compound may include, on the side chain thereof, a structure of one or more derivatives or compounds selected from the group consisting of carbazole derivatives, triazole derivatives, oxazole derivatives, oxadiazole derivatives, imidazole derivatives, fluorene derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidyne compounds, porphyrin compounds, and organic silane derivatives.

When the light-emitting layer contains a low molecular compound, examples of the low molecular compound may include low molecular dye compounds such as rubrene, perylene, 9,10-diphenylanthracene, tetraphenylbutadiene, nile red, coumarin 6, carbazole, and quinacridone, naphthalene derivatives, anthracene and derivatives thereof, perylene and derivatives thereof, dyes based on polymethine, xanthene, coumarin, cyanine, and indigo, metal complexes of 8-hydroxyquinoline and derivatives thereof, metal complexes of phthalocyanine and derivatives thereof, aromatic amines, tetraphenylcyclopentadiene and derivatives thereof, and tetraphenylbutadiene and derivatives thereof.

When the light emitting layer contains a metal complex emitting phosphorescence, examples of the metal complex may include tris(2-phenylpyridine)iridium, thienylpyridine ligand-containing iridium complexes, phenylquinoline ligand-containing iridium complexes, and triazacyclononane skeleton-containing terbium complexes.

The above materials may be used as a single component or a composition composed of a plurality of components. The light-emitting layer may have a single layered structure composed one or two or more of the above materials or a multilayered structure composed of a plurality of layers having the same or different compositions.

As a film forming method for the light-emitting layer, the same as the method for the film formation of the hole injection layer may be employed. Examples of the film forming method from a solution may include application methods and printing methods such as the spin coating method, the casting method, the bar coating method, the slit coating method, the spray coating method, the nozzle coating method, the gravure printing method, the screen printing method, the flexographic printing method, and the inkjet printing method. When a sublimation compound material is used, examples of the method may include the vacuum deposition method and a transfer method.

Examples of the solvent for use in the film formation from a solution may include the solvents exemplified in the film forming method for the hole injection layer.

When an organic compound layer such as the electron transport layer is formed by an application method after the formation of the light-emitting layer, and when a lower layer dissolves in a solvent contained in a solution for a layer applied later, the lower layer can be insolubilized by the same method as exemplified in the film forming method for the hole injection layer.

The optimum thickness of the light-emitting layer varies depending on the material used and may be selected so as to give adequate values of drive voltage and light-emitting efficiency. The thickness is usually 5 nm to 1 μm, preferably from 10 nm to 500 nm, and more preferably from 30 nm to 200 nm.

—Electron Transport Layer—

In the electroluminescent device according to the present invention, known materials that constitute the electron transport layer other than the polymer compound according to the present invention can be used. Examples of the material may include triazole derivatives, oxazole derivatives, oxadiazole derivatives, imidazole derivatives, fluorene derivatives, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, anthraquinodimethane derivatives, anthrone derivatives, thiopyran dioxide derivatives, carbodiimide derivatives, fluorenylidenemethane derivatives, distyrylpyrazine derivatives, aromacyclic tetracarboxylic anhydrides such as naphthalene and perylene, phthalocyanine derivatives, various metal complexes typified by metal complexes of a 8-quinolinol derivative, metal phthalocyanines, and metal complexes having benzoxazole or benzothiazole as a ligand, organic silane derivatives, metal complexes of 8-hydroxyquinoline or a derivative thereof, polyquinoline and derivatives thereof, polyquinoxaline and derivatives thereof, and polyfluorene and derivatives thereof. Of these materials, triazole derivatives, oxadiazole derivatives, benzoquinone and derivatives thereof, anthraquinone and derivatives thereof, metal complexes of 8-hydroxyquinoline or a derivative thereof, polyquinoline and derivatives thereof, polyquinoxaline and derivatives thereof, and polyfluorene and derivatives thereof are preferred.

The above materials may be used as a single component or a composition composed of a plurality of components. The electron transport layer may have a single layered structure composed one or two or more of the above materials or a multilayered structure composed of a plurality of layers having the same or different compositions. In addition, materials exemplified as materials usable in the electron injection layer can also be used for the electron transport layer.

As a film forming method for the electron transport layer, for example, the same as the method for the film formation of the hole injection layer may be employed. Examples of the film forming method from a solution may include application methods and printing methods such as the spin coating method, the casting method, the bar coating method, the slit coating method, the spray coating method, the nozzle coating method, the gravure printing method, the screen printing method, the flexographic printing method, and the inkjet printing method. When a sublimation compound material is used, examples of the method may include the vacuum deposition method and a transfer method.

Examples of the solvent for use in the film formation from a solution may include the solvents exemplified in the film forming method for the hole injection layer.

When an organic compound layer such as the electron injection layer is formed by an application method after the formation of the electron transport layer, and when a lower layer dissolves in a solvent contained in a solution for a layer applied later, the lower layer can be insolubilized by the same method as exemplified in the film forming method for the hole injection layer.

The optimum thickness of the electron transport layer varies depending on the material used and may be selected so as to give adequate values of drive voltage and light-emitting efficiency. The thickness is usually 1 nm to 1 μm, preferably from 2 nm to 500 nm, and more preferably from 5 nm to 100 nm.

—Electron Injection Layer—

In the electroluminescent device according to the present invention, known materials that constitute the electron injection layer other than the polymer compound according to the present invention can be used. Examples of the material may include triazole derivatives, oxazole derivatives, oxadiazole derivatives, imidazole derivatives, fluorene derivatives, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, anthraquinodimethane derivatives, anthrone derivatives, thiopyran dioxide derivatives, carbodiimide derivatives, fluorenylidenemethane derivatives, distyrylpyrazine derivatives, aromacyclic tetracarboxylic anhydrides such as naphthalene and perylene, phthalocyanine derivatives, various metal complexes typified by metal complexes of a 8-quinolinol derivative, metal phthalocyanines, and metal complexes having benzoxazole or benzothiazole as a ligand, and organic silane derivatives.

The above materials may be used as a single component or a composition composed of a plurality of components. The electron injection layer may have a single layered structure composed only of the above material or a multilayered structure composed of a plurality of layers having the same or different compositions. In addition, materials exemplified as materials usable in the electron transport layer and a hole block layer can also be used for the electron injection layer.

As a film forming method for the electron injection layer, for example, the same as the method for the film formation of the hole injection layer may be employed. Examples of the film forming method from a solution may include application methods and printing methods such as the spin coating method, the casting method, the bar coating method, the slit coating method, the spray coating method, the nozzle coating method, the gravure printing method, the screen printing method, the flexographic printing method, and the inkjet printing method. When a sublimation compound material is used, examples of the method may include the vacuum deposition method and a transfer method.

Examples of the solvent for use in the film formation from a solution may include the solvents exemplified in the film forming method for the hole injection layer.

The optimum thickness of the electron injection layer varies depending on the material used and may be selected so as to give adequate values of drive voltage and light-emitting efficiency. The thickness is usually 1 nm to 1 μm, preferably from 2 nm to 500 nm, and more preferably from 5 nm to 100 nm.

—Cathode—

In the electroluminescent device according to the present invention, the cathode may have a single layered structure composed of a single material or a plurality of materials, or a multilayered structure composed of a plurality of layers. When the cathode has a single layer structure, examples of the material of the cathode may include low resistance metals such as gold, silver, copper, aluminum, chromium, tin, lead, nickel, and titanium, alloys containing these metals, electroconductive metal oxides such as tin oxide, zinc oxide, indium oxide, indium tin oxide (ITO), indium zinc oxide (IZO), and molybdenum oxide, and mixtures of the electroconductive metal oxide and the metal exemplified above, and among them, aluminum and alloys containing aluminum are preferred. When the cathode has a multilayered structure, it has preferably a two-layer structure including a first cathode layer and a cover cathode layer or a three-layer structure including a first cathode layer, a second cathode layer, and a cover cathode layer. The first cathode layer as used herein refers to a layer present on the side closest to the light-emitting layer among the cathodes. The cover cathode layer refers to a layer that covers the first cathode layer in a two-layer structure and covers the first cathode layer and the second cathode layer in a three-layer structure. In view of electron supplying capacity, the material of the first cathode layer has preferably a work function of 3.5 eV or less. Oxides, fluorides, carbonates, complex oxides, or the like of a metal having a work function of 3.5 eV or less are also suited for use as the first cathode layer material. As the material of the cover cathode layer, metals, metal oxides, or the like having a low resistivity and highly corrosion-resistant to water are suited for use.

As the first cathode layer material, one or more materials selected from the group consisting of alkali metals, alkaline earth metals, alloys containing one or more of these metals, oxides, halides, carbonates, and complex oxides of the metals, and mixtures thereof are usable. Examples of the alkali metals or oxides, halides, carbonates, or complex oxides thereof may include lithium, sodium, potassium, rubidium, cesium, lithium oxide, sodium oxide, potassium oxide, rubidium oxide, cesium oxide, lithium fluoride, sodium fluoride, potassium fluoride, rubidium fluoride, cesium fluoride, lithium carbonate, sodium carbonate, potassium carbonate, rubidium carbonate, cesium carbonate, potassium molybdate, potassium titanate, potassium tungstate, and cesium molybdate. Examples of the alkaline earth metals or oxides, halides, carbonates, or complex oxides thereof may include magnesium, calcium, strontium, barium, magnesium oxide, calcium oxide, strontium oxide, barium oxide, magnesium fluoride, calcium fluoride, strontium fluoride, barium fluoride, magnesium carbonate, calcium carbonate, strontium carbonate, barium carbonate, barium molybdate, and barium tungstate. Examples of the alloy containing one or more alkali metals or alkaline earth metals may include a Li—Al alloy, a Mg—Ag alloy, an Al—Ba alloy, a Mg—Ba alloy, a Ba—Ag alloy, and a Ca—Bi—Pb—Sn alloy. Compositions made of the material exemplified as the first cathode layer material and the material exemplified as the material constituting the electron injection layer can be used for the first cathode layer.

Examples of the material of the second cathode layer may include the same materials as those of the first cathode layer.

Examples of the cover cathode layer material may include low resistance metals such as gold, silver, copper, aluminum, chromium, tin, lead, nickel, and titanium, alloys containing these metals, metal nanoparticles, metal nanowires, electroconductive metal oxides such as tin oxide, zinc oxide, indium oxide, indium tin oxide (ITO), indium zinc oxide (IZO), and molybdenum oxide, mixtures of these electroconductive metal oxides and metals, and nanoparticles of the electroconductive metal oxides, and electroconductive carbons such as graphene, fullerene, and carbon nanotubes.

Examples of the cathode having a multilayered structure may include: a two-layer structure including a first cathode layer and a cover cathode layer such as Mg/Al, Ca/Al, Ba/Al, NaF/Al, KF/Al, RbF/Al, CsF/Al, $Na_2CO_3$/Al, $K_2CO_3$/Al, and $Cs_2CO_3$/Al; and a three-layer structure including a first cathode layer, a second cathode layer, and a cover cathode layer such as LiF/Ca/Al, NaF/Ca/Al, KF/Ca/Al, RbF/Ca/Al, CsF/Ca/Al, Ba/Al/Ag, KF/Al/Ag, KF/Ca/Ag, and $K_2CO_3$/Ca/Ag. The symbol "/" means that the layers are adjacent to each other. The material of the second cathode layer preferably has a reduction action on the material of the first cathode layer. The presence or absence and degree of the reduction action between materials can be estimated, for example, from bond dissociation energy ($\Delta rH°$) between compounds. More specifically, in the reduction reaction of the material constituting the first cathode electrode with the material constituting the second cathode layer, when they are a combination of materials to provide a positive bond dissociation energy, it can be said that the material of the second cathode layer has a reduction action on the material of the first cathode layer. With respect to the bond dissociation energy, it is possible to refer to, for example, "Handbook on Electrochemistry, 5th ed." (Maruzen Co., Ltd., published in 2000) and "Thermodynamic Database MALT" (Kagaku Gijutsu-Sha, published in 1992).

As a method for preparing the cathode, known methods can be used. Examples of the method may include the vacuum deposition method, the sputtering method, the ion plating method, and the method by film formation from a solution (that may contain a macromolecular binder). For the formation of the cathode by using metals, metal oxides, fluorides, or carbonates, the vacuum deposition method is frequently used. For the formation of the cathode by using metal oxides having a high boiling point, metal complex oxides, or electroconductive metal oxides such as indium tin oxide (ITO), the sputtering method or the ion plating method are frequently used. For the formation of the cathode by using in combination two or more of metals, metal oxides, fluorides, carbonates, metal oxides having a high boiling point, metal complex oxides, and electroconductive metal oxides, a co-deposition method, the sputtering method, the ion plating method, or the like are used. For the formation of the cathode by using metal nanoparticles, metal nanowires, or electroconductive metal oxide nanoparticles, the method by film formation from a solution is frequently used. In particular, for the formation of the cathode by using compositions of low molecular organic compounds and metals, metal oxides, fluorides, or carbonates, the co-deposition method is suited.

The optimum thickness of the cathode varies depending on the material and the layer structure used and may be selected so as to give adequate values of drive voltage, light-emitting efficiency, and device life. The thickness of the first cathode layer is usually 0.5 nm to 20 nm, and the thickness of the cover cathode layer is usually 10 nm to 1 μm. For example, when Ba or Ca is used for the first cathode layer, and Al is used for the cover cathode layer, the thickness of Ba or Ca is preferably from 2 nm to 10 nm, and the thickness of Al is preferably from 10 nm to 500 nm. When NaF or KF is used for the first cathode layer, and Al is used for the cover cathode layer, the thickness of NaF or KF is preferably from 1 nm to 8 nm, and the thickness of Al is preferably from 10 nm to 500 nm.

In the electroluminescent device according to the present invention using the cathode as a light transmitting electrode, a visible light transmittance of the cover cathode layer is preferably 40% or more and more preferably 50% or more. This visible light transmittance can be achieved by using a transparent electroconductive metal oxide such as indium tin oxide (ITO), indium zinc oxide (IZO), or molybdenum oxide as the cover cathode layer material, or adjusting the thickness of the cover cathode layer to be 30 nm or less by using a low resistance metal such as gold, silver, copper, aluminum, chromium, tin, and lead, and an alloy containing such metals.

For the purpose of improving the light transmittance from the cathode side, an antireflection layer may be disposed on the cover cathode layer of the cathode. Materials used for the antireflection layer have preferably a refractive index of from 1.8 to 3.0. Examples of the materials capable of satisfying this refractive index may include ZnS, ZnSe, and $WO_3$. Although the thickness of the antireflection layer varies depending on the combination of the materials, it is usually from 10 nm to 150 nm.

—Insulating Layer—

An insulating layer with a thickness of 5 nm or less that the electroluminescent device according the present invention optionally has functions of improving adhesion with an electrode, improving injection of charges from the electrode, and preventing mixing with a layer adjacent to it. Examples of the material of the insulating layer may include metal fluorides, metal oxides, and organic insulating materials (polymethyl methacrylate or the like). Examples of the electroluminescent device provided with the insulating layer with a thickness of 5 nm or less may include a device provided with the insulating layer with a thickness 5 nm or less adjacent to the cathode and an device provided with the insulating layer with a thickness of 5 nm or less adjacent to the anode.

—Other Constituents—

The device may be further provided with a sealing member on the side opposite the substrate across the light emitting layer or the like. In addition, it may have optional constituents for constituting a display device including filters such as a color filter and a fluorescence conversion filter and circuits and wirings necessary for the driving of pixels.

—Method for Manufacturing Electroluminescent Device—

The electroluminescent device according to the present invention can be manufactured, for example, by successively stacking layers on a substrate. More specifically, the electroluminescent device can be manufactured by providing the anode on the substrate, stacking layers such as the hole injection layer and the hole transport layer one after another, stacking thereon the light-emitting layer, stacking thereon layers such as the electron transport layer and the electron injection layer, and stacking the cathode thereon. Another manufacturing method includes providing the cathode on the substrate, stacking thereon layers such as the electron injection layer, the electron transport layer, the light-emitting layer, the hole transport layer, and the hole injection layer one after another, and then stacking the anode thereon to manufacture the electroluminescent device. A still another manufacturing method includes facing and joining the anode or an anode-side base material obtained by stacking layers on the anode and the cathode or a cathode side base material obtained by stacking layers on the cathode to manufacture the electroluminescent device.

—Application of Electroluminescent Device—

A display device can be manufactured using the electroluminescent device according to the present invention. The display device has the electroluminescent device as a pixel unit. As a form of the arrangement of pixel units, a usual arrangement in display devices such as television may be employed and a form of the arrangement in which a number of pixels may be arranged on a common substrate can be employed. In the device of the present invention, pixels arranged on the substrate can be formed in a pixel area defined by a bank. In addition, the electroluminescent device according to the present invention can be used for planar or curved illumination devices.

<Photovoltaic Cell>

A photovoltaic cell according to the present invention includes, for example, an anode, a cathode, a charge separation layer located between the anode and the cathode, and a layer that is located between the charge separation layer and the anode or cathode, and contains the polymer compound according to the present invention. The photovoltaic cell according to the present invention may have a substrate as an optional constituent and it may include, on the surface of the substrate, the anode, the cathode, the charge separation layer, and the layer containing the polymer compound according to the present invention, and optional constituents.

In one embodiment of the photovoltaic cell according to the present invention, the cathode is provided on the substrate, the charge separation layer is stacked thereon, the layer containing the polymer compound according to the present invention is stacked thereon, and the anode is stacked thereon. In another embodiment, the cathode is provided on the substrate, the layer containing the polymer compound according to the present invention is stacked thereon, the charge separation layer is stacked thereon, and the anode is stacked thereon. In still another embodiment, the cathode is provide on the substrate, the layer containing the polymer compound according to the present invention is stacked thereon, the charge separation layer is stacked thereon, the layer containing the polymer compound according to the present invention is stacked thereon, and the anode is stacked thereon. In still another embodiment, the anode is provided on the substrate, the layer containing the polymer compound according to the present invention is stacked thereon, the charge separation layer is stacked thereon, and the anode is stacked thereon. In still another embodiment, the anode is provided on the substrate, the charge separation layer is stacked thereon, the layer containing the polymer compound according to the present invention is stacked thereon, and the cathode is stacked thereon. In further another embodiment, the anode is stacked on the substrate, the layer containing the polymer compound according to the present invention is stacked thereon, the charge separation layer is stacked thereon, the layer containing the polymer compound according to the present invention is stacked thereon, and the cathode is stacked thereon. In these embodiments, layers other than the layer containing the polymer compound according to the present invention or the charge separation layer may be further provided. The constitution of the photovoltaic cell will be described in detail below.

The layer containing the polymer compound according to the present invention may contain a known electron donating compound and/or electron accepting compound, metal nanoparticles, or metal oxide nanoparticles.

Examples of a method for forming the layer containing the polymer compound may include a method for film formation using a solution containing the polymer compound.

Examples of a solvent for use in such film formation from a solution may include solvents having a solubility parameter of 9.3 or more out of water, alcohols, ethers, esters, carboxylic acids, alkyl halides, heterocyclic aromatic compounds, thiols, sulfides, thioketones, sulfoxides, nitro compounds, nitrile compounds, and mixed solvents of these solvents. The examples and solubility parameters of the solvents are described above.

Examples of the film forming method from a solution may include application methods such as the spin coating method, the casting method, the micro gravure printing method, the gravure printing method, the bar coating method, the roll coating method, the wire bar coating method, the dip coating method, the slit coating method, the cap coating method, the spray coating method, the screen printing method, the flexographic printing method, the offset printing method, the inkjet printing method, and the nozzle coating method.

Because the optimum thickness of the layer containing the polymer compound varies depending on the polymer compound used, the thickness may be selected so as to give an adequate value of photovoltaic efficiency. The thickness is preferably from 1 nm to 1 µm, more preferably from 2 nm to 500 nm, and further more preferably from 2 nm to 200 nm.

The photovoltaic cell including the layer containing the polymer compound according to the present invention includes the anode, the cathode, and the charge separation layer located between the anode and the cathode and preferably includes the layer containing the polymer compound according to present invention either one of or both between the charge separation layer and the anode and between the charge separation layer and the anode. More preferably, the photovoltaic cell includes the layer containing the polymer compound between the cathode and the charge separation layer.

The charge separation layer of the photovoltaic cell according to the present invention preferably contains an electron donating compound and an electron accepting compound.

The charge separation layer may contain one compound alone or two or more compounds in combination for each of the electron donating compound and the electron accepting compound. The electron donating compound and the electron accepting compound are relatively determined depending on the energy level thereof.

Examples of the electron donating compound may include pyrazoline derivatives, arylamine derivatives, stilbene derivatives, triphenyldiamine derivatives, and conjugated polymer compounds. Examples of the conjugated polymer compounds may include oligothiophene and derivatives thereof, polyfluorene and derivatives thereof, polyvinylcarbazole and derivatives thereof, polysilane and derivatives thereof, polysiloxane derivatives having, on the side chain or main chain thereof, an aromatic amine, polyaniline and derivatives thereof, polypyrrole and derivatives thereof, polyphenylenevinylene and derivatives thereof, and polythienylenevinylene and derivatives thereof.

Examples of the electron accepting compound may include oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, metal complexes of 8-hydroxyquinoline and derivatives thereof, polyquinoline and derivatives thereof, polyquinoxaline and derivatives thereof, polyfluorene and derivatives thereof, fullerenes such as $C_{60}$ and derivatives thereof, phenanthrene derivatives such as bathocuproine, metal oxides such as titanium oxide, and carbon nanotubes. As the electron accepting compound, titanium oxide, carbon nanotubes, fullerene, and fullerene derivatives are preferred, and fullerene and fullerene derivatives are particularly preferred.

The thickness of the charge separation layer is usually from 1 nm to 100 µm, more preferably from 2 nm to 1000 nm, further more preferably from 5 nm to 500 nm, and still more preferably from 20 nm to 200 nm.

<Method for Manufacturing Charge Separation Layer>

Any method can be employed for the method for manufacturing the charge separation layer and examples thereof may include film formation from a solution and film formation by the vacuum deposition method.

For the film formation from a solution, it is possible to use application methods such as the spin coating method, the casting method, the microgravure coating method, the gravure coating method, the bar coating method, the roll coating method, the wire bar coating method, the dip coating method, the spray coating method, the screen printing method, the gravure printing method, the flexographic printing method, the offset printing method, the inkjet printing method, a dispenser printing method, the nozzle coating method, and the capillary coating method. Among these, the spin coating method, the flexographic printing method, the gravure printing method, the inkjet printing method, and the dispenser printing method are preferred.

The photovoltaic cell including the layer containing the polymer compound according to the present invention is usually formed on a substrate. Any substrate is usable so long as it does not change upon formation of an electrode and formation of an organic material layer. Examples of the material of the substrate may include glass, plastics, polymer films, and silicon. When the substrate employed is opaque, the electrode on the opposite side (that is, an electrode distant from the substrate) is preferably transparent or translucent.

Examples of the transparent or translucent electrode material may include electroconductive metal oxide films and translucent thin metal films. Specific examples may include a film prepared using an electroconductive material composed of indium oxide, zinc oxide, tin oxide, and complexes thereof such as indium tin oxide (ITO), and indium zinc oxide, NESA, gold, platinum, silver, and copper. Among these, ITO, indium zinc oxide, and tin oxide are preferred. Examples of a method for forming the electrode may include the vacuum deposition method, the sputtering method, the ion plating method, and the plating method.

As an electrode material, organic transparent electroconductive films such as polyaniline and derivatives thereof and polythiophene and derivatives thereof may be used. Furthermore, as the electrode material, metals and electroconductive polymers can be used. One of a pair of electrodes is preferably made of a material having a small work function. Examples may include metals such as lithium, sodium, potassium, rubidium, cesium, magnesium, calcium, strontium, barium, aluminum, scandium, vanadium, zinc, yttrium, indium, cerium, samarium, europium, terbium, and ytterbium, alloys of two or more thereof, alloys of one or more of the above metals and one or more of gold, silver, platinum, copper, manganese, titanium, cobalt, nickel, tungsten, and tin, and graphite and graphite interlayer compounds. Examples of the alloys may include a magnesium-silver alloy, a magnesium-indium alloy, a magnesium-aluminum alloy, an indium-silver alloy, a lithium-aluminum alloy, a lithium-magnesium alloy, a lithium-indium alloy, and a calcium-aluminum alloy.

As means for improving the photovoltaic efficiency, an additional intermediate layer other than the charge separation layer may be used in addition to the layer containing the polymer compound according to the present invention. Examples of a material used as the intermediate layer may include halides and oxides of alkali metals or alkaline earth metals such as lithium fluoride. Additional examples may include fine particles of inorganic semiconductor such as titanium oxide and PEDOT (poly-3,4-ethylenedioxythiophene).

<Usage of Cell>

When the photovoltaic cell according to the present invention is exposed to light such as sunlight on the side of the transparent or translucent electrode, photovoltaic power is generated between the electrodes so that it can be operated as an organic thin-film solar cell. A plurality of organic thin-film solar cells integrated can be used as an organic thin film solar cell module.

By being exposed to light on the side of the transparent or translucent electrode while applying or not applying a voltage between the electrodes, a photocurrent flows so that it can be operated as an organic optical sensor. A plurality of organic light sensors integrated can be used as an organic image sensor.

<Solar Cell Module>

The organic thin-film solar cell can have basically a similar module structure to a conventional solar cell module. In the solar cell module, a cell is usually formed on a supporting substrate such as a metal, ceramic, or the like and it is covered with a filling resin, a protective glass, or the like to capture light from the side opposite the supporting substrate. Alternatively, the cell is formed on the supporting substrate made of a transparent material such as reinforced glass to capture light from the transparent supporting substrate side. Specifically, module structures called a super straight type, a substrate type, and a potting type, and a substrate-integrated module structure used in amorphous silicon solar cells, or the like are known. The organic thin-film solar cell according to the present invention can select these module structures as needed, depending on a purpose of use, a place of use, and an environment.

A typical module of the superstrate type or the substrate type has a structure in which cells are arranged at a given interval between the supporting substrates each of which is transparent and subjected to an antireflection treatment on one side or on both sides thereof; adjacent cells are connected to each other by metal leads or flexible wiring; and a current collecting electrode is placed at an outer peripheral portion to allow the electric power thus generated to be taken to the outside. In order to protect the cells or improve current collecting efficiency, various plastic materials such as ethylene vinyl acetate (EVA) may be provided in the form of a film or a filling resin between the substrate and cells according to the purposes.

When the module is used in a place where the covering of the surface with a hard material is not required, for example, a place with less external impact, it is possible to form a surface protective layer from a transparent plastic film or cure the filling resin to impart a protective function thereto, thereby eliminating one of the supporting substrates. The supporting substrate is fixed, at the periphery thereof, with a metal frame in a sandwich form so as to ensure sealing of the inside and rigidity of the module. The space between the supporting substrate and the frame is hermetically sealed with a sealing material. A solar cell can also be formed on a curved surface if the cell itself, the supporting substrate, the filling material, or the sealing material is made of a flexible material.

In a solar cell using a flexible substrate such as a polymer film, the cell body can be manufactured by sequentially forming unit cells while delivering a roll-shaped substrate, cutting into a desired size, and then sealing a peripheral portion with a flexible, moisture-resistant material. It is also possible to manufacture a module structure called "SCAF" described in "Solar Energy Materials and Solar Cells", 48, p 383-391. Furthermore, a solar cell using a flexible substrate can also be used after being bonded and fixed to curved glass or the like.

EXAMPLES

The present invention will be described more specifically below based on the examples and comparative example, however, the present invention is not limited to the following examples.

The weight-average molecular weight (Mw) and the number-average molecular weight (Mn) of a polymer compound were determined as a polystyrene-equivalent weight-average molecular weight and a polystyrene-equivalent number-average molecular weight, respectively, by using gel permeation chromatography (GPC) ("HLC-8220GPC" manufactured by Tosoh Corporation). A sample to be measured was dissolved in tetrahydrofuran to give a concentration of about 0.5% by weight and 50 µL of the resulting solution was injected into GPC. Tetrahydrofuran was used as a mobile phase of GPC and was fed at a flow rate of 0.5 mL/min. Structural analysis of the polymer compound was conducted by $^1$H-NMR analysis using a 300 MHz NMR spectrometer manufactured by Varian, Inc. The measurement was conducted after dissolving the sample in a deuterated solvent (a solvent in which a hydrogen atom, in the molecules thereof, has been substituted with a deuterium atom) capable of dissolving the sample therein so as to give a concentration of 20 mg/mL. The orbital energy of HOMO of the polymer compound was determined by measuring the ionization potential of the polymer compound and regarding the resulting ionization potential as the orbital energy. The orbital energy of LUMO was determined by determining a difference in energy between HOMO and LUMO and regarding the sum of the difference and the ionization potential measured above as the orbital energy of the LUMO. The ionization potential was measured using a photoelectron spectrometer ("AC-2" manufactured by Riken Keiki Co., Ltd.). The difference in energy between HOMO and LUMO was determined by measuring an absorption spectrum of the polymer compound using an ultraviolet-visible-near infrared spectrophotometer ("Cary5E" manufactured by Varian, Inc.) through its absorption edge.

Example 1

Synthesis of Compound A

After a reaction vessel was purged with a nitrogen gas, 2,7-dibromo-9-fluorenone (92.0 g, 272 mmol) and diethyl ether (3.7 L) were mixed and cooled to 0° C. To the mixture was added dropwise a 1 mol/L diethyl ether solution of methylmagnesium iodide (0.5 L, 545 mmol), and the mixture was stirred for 3 hours. To the resultant reaction mixture was added an aqueous ammonium chloride solution to remove the aqueous layer, and the organic layer was dried over anhydrous sodium sulfate and concentrated under reduced pressure. The resultant crude product was purified with silica gel column chromatography to obtain a compound A (92.81 g, 262 mmol, with a yield of 96%).

[Chemical Formula 53]

Compound A

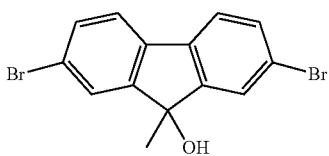

Example 2

Synthesis of Compound B

After a reaction vessel was purged with a nitrogen gas, the compound A (83.0 g, 234 mmol), p-toluene sulfonate monohydrate (4.49 g, 23.6 mmol), and chloroform (2.5 L) were refluxed for 1 hour, and to the resultant reaction mixture was added an aqueous ammonium chloride solution to remove the aqueous layer. The organic layer was dried over anhydrous sodium sulfate and concentrated under reduced pressure to obtain a compound B (73.6 g, 219 mmol, with a yield of 93%).

[Chemical Formula 54]

Compound B

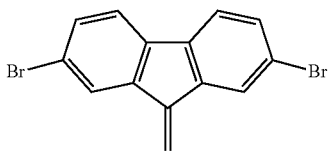

Example 3

Synthesis of Compound C

After a reaction vessel was purged with a nitrogen gas, the compound B (70.0 g, 208 mmol), ethyl salicylate (104 g, 625 mmol), mercaptoacetic acid (4.20 g, 45.6 mmol), and methane sulfonate (1214 g) were stirred at 70° C. for 8 hours. The resultant reaction mixture was added dropwise to iced water. The precipitated solid was collected by filtration and washed with methanol. The crude product was purified with silica gel column chromatography to obtain a compound C (52.14 g, 104 mmol, with a yield of 50%).

[Chemical Formula 55]

Compound C

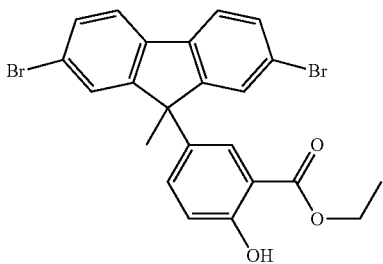

Example 4

Synthesis of Compound D

After a reaction vessel was purged with a nitrogen gas, the compound C (41.2 g, 82.0 mmol), 2-[2-(2-methoxyethoxy)ethoxy]-ethyl-p-toluene sulfonate (75.8 g, 238 mmol), dimethylformamide (214 g), potassium carbonate (54.4 g, 394 mmol), and 1,4,7,10,13,16-hexaoxacyclooctadecane (also referred to as "18-crown-6") (4.68 g, 18 mmol) were stirred at 105° C. for 2 hours. The resultant reaction mixture was added to water and extracted with ethyl acetate. The organic layer was dried over anhydrous sodium sulfate and concentrated under reduced pressure, and the resultant crude product was purified with silica gel column chromatography to obtain a compound D (40.2 g, 62.0 mmol, with a yield of 76%).

$^1$H NMR (400 MHz, CDCl$_3$, rt)

δ (ppm) 1.37 (3H), 1.84 (3H), 3.36 (3H), 3.53 (2H), 3.58-3.79 (6H), 3.73 (2H), 4.12 (2H), 4.34 (2H), 6.80 (1H), 6.90 (1H), 7.28 (2H), 7.48 (2H), 7.58 (2H), 7.70 (1H).

[Chemical Formula 56]

Compound D

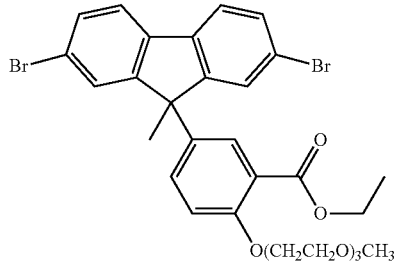

Example 5

Synthesis of Compound E

After a reaction vessel was purged with a nitrogen gas, the compound D (28.4 g, 43.8 mmol), bis(pinacolato)diboron (24.30 g, 95.7 mol), [1,1'-bis(diphenylphosphino)ferrocene] palladium (II) dichloride dichloromethane adduct (0.35 g, 0.4 mmol), 1,1'-bis(diphenylphosphino)ferrocene (0.24 g, 0.4 mmol), potassium acetate (25.60 g, 260 mmol), and 1,4-dioxane (480 mL) were stirred at 120° C. for 17 hours. The resultant reaction mixture was filtered and washed with ethyl acetate. The filtrate was concentrated under reduced pressure, purified with silica gel column chromatography, and then purified by recrystallization to obtain a compound E (18.22 g, 24.5 mmol, with a yield of 56%).

$^1$H NMR (400 MHz, CDCl$_3$, rt)

δ (ppm) 1.30-1.47 (27H), 1.88 (3H), 3.35 (3H), 3.53 (2H), 3.60-3.69 (4H), 3.73 (2H), 3.84 (2H), 4.10 (2H), 4.34 (2H), 6.74 (1H), 6.87 (1H), 7.58 (2H), 7.72-7.89 (5H).

[Chemical Formula 57]

Compound E

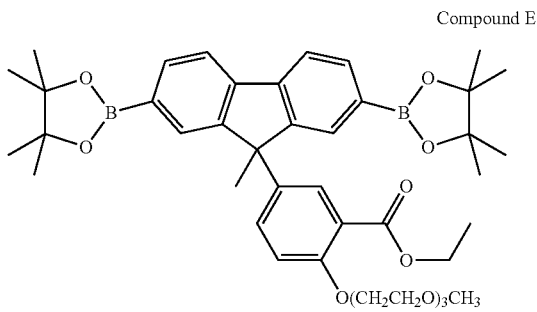

Example 6

Synthesis of Polymer compound A

After forming an argon gas atmosphere within a reaction vessel, the compound D (0.47 g), the compound E (0.48 g), dichlorobis(triphenylphosphine)palladium (0.6 mg), tetrabutylammonium bromide (6 mg), toluene (6 mL), and a 2 mol/L aqueous sodium carbonate solution (2 mL) were stirred at 105° C. for 6 hours. Phenylboronic acid (35 mg) was then added to the mixture, and the mixture was stirred at 105° C. for 14 hours. To the resultant reaction mixture were added sodium diethyldithiocarbamate trihydrate (0.65 g) and water (13 mL), and the mixture was stirred at 80° C. for 2 hours. The mixture was added dropwise to ethanol, and the precipitate was collected by filtration and dried. The solid was dissolved in chloroform and purified with alumina and silica gel chromatography. The eluent was added dropwise to methanol, and the precipitate was collected by filtration and dried to obtain a polymer compound A (0.57 g). Polystyrene-equivalent number-average molecular weight of the polymer compound A was $2.0 \times 10^4$. The polymer compound A is composed of a structural unit represented by Formula (A).

[Chemical Formula 58]

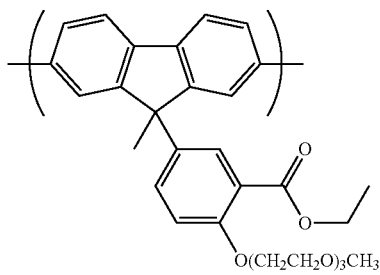

(A)

Example 7

Synthesis of Cesium Salt of Polymer Compound A (Conjugated Polymer Compound 1)

After forming an argon gas atmosphere within a reaction vessel, the polymer compound A (0.20 g), tetrahydrofuran (18 mL), methanol (9 mL), cesium hydroxide monohydrate (97 mg), and water (1 mL) were stirred at 65° C. for 2 hours. To the mixture was then added methanol (52 mL), and the mixture was stirred at 65° C. for 6 hours. The resultant reaction mixture was concentrated and dried. To the solid was added methanol, and the mixture was filtered. The filtrate was added dropwise to isopropanol, and the solid was collected by filtration and dried to obtain a conjugated polymer compound 1 (0.20 g). The conjugated polymer compound 1 is composed of a structural unit represented by Formula (B).

[Chemical Formula 59]

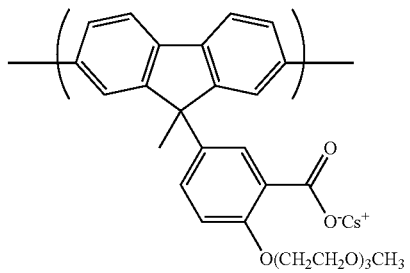

(B)

Example 8

Synthesis of Polymer compound B

After forming an argon gas atmosphere within a reaction vessel, the compound D (0.528 g), the compound E (0.493 g), dichlorobis(triphenylphosphine)palladium (0.56 mg), N,N'-bis(4-bromophenyl)-N,N'-bis(4-tert-butyl-2,6-dimethylphenyl)-1,4-phenylenediamine (35.8 mg), methyltrioctylammonium chloride ("Aliquat 336" (registered trademark) manufactured by Sigma-Aldrich Co.) (8.10 mg, 0.0200 mmol), toluene (20 mL), and a 2 mol/L aqueous sodium carbonate solution (10 mL) were stirred at 105° C. for 6 hours. Phenylboronic acid (35 mg) was then added to the mixture, and the mixture was stirred at 105° C. for 14 hours. To the resultant reaction mixture were added sodium diethyldithiocarbamate trihydrate (0.72 g) and water (14 mL), and the mixture was stirred at 80° C. for 2 hours. The mixture was added dropwise to methanol, and the precipitate was collected by filtration and dried. The resultant solid was dissolved in chloroform and purified with alumina and silica gel chromatography. The eluent was concentrated and dried. The concentrate was dissolved in toluene and added dropwise to methanol. The precipitate was collected by filtration and dried to obtain a polymer compound B (0.31 g). Polystyrene-equivalent number-average molecular weight of the polymer compound B was $1.8 \times 10^4$. The polymer compound B is composed of a structural unit represented by Formula (C).

[Chemical Formula 60]

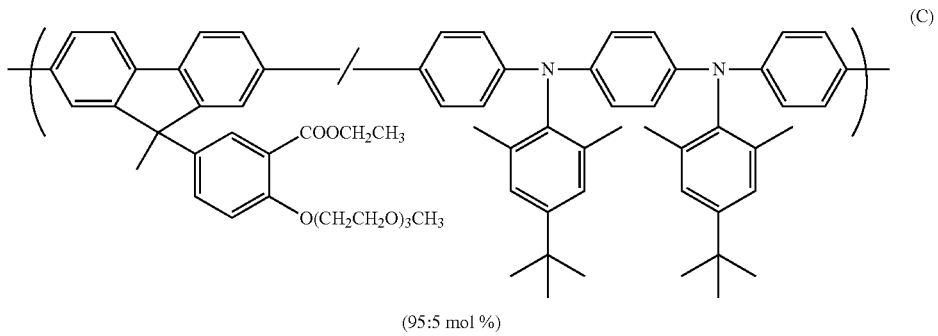

(95:5 mol %)

Example 9

Synthesis of Cesium Salt of Polymer Compound B (Conjugated Polymer Compound 2)

After forming an argon gas atmosphere within a reaction vessel, the polymer compound B (0.15 g), tetrahydrofuran (20 mL), methanol (10 mL), cesium hydroxide monohydrate (103 mg), and water (1 mL) were stirred at 65° C. for 2 hours. To the mixture was then added methanol (20 mL), and the mixture was stirred at 65° C. for 2 hours. The resultant reaction mixture was concentrated and dried. To the solid was added methanol, and the mixture was filtered. The filtrate was added dropwise to isopropanol, and the solid was collected by filtration and dried to obtain a conjugated polymer compound 2 (0.15 g). The conjugated polymer compound 2 is composed of a structural unit represented by Formula (D).

[Chemical Formula 62]

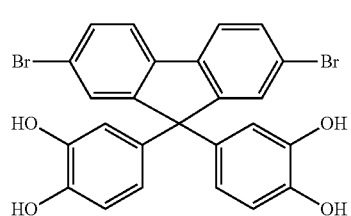

Compound F

[Chemical Formula 61]

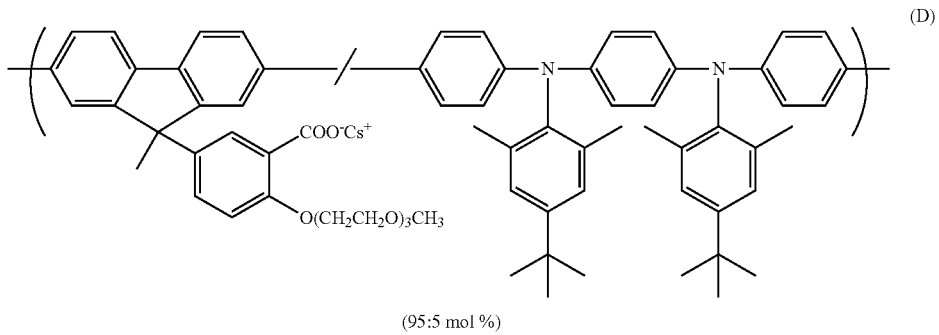

(95:5 mol %)

Example 10

Synthesis of Compound F

After forming a nitrogen gas flow within a reaction vessel, 2,7-dibromo-9-fluorenone (121.9 g), catechol (883.1 g), 3-mercapto propionic acid (4.87 g), and concentrated sulfuric acid (18.4 g) were mixed, and the mixture was stirred at 125° C. for 2 hours. The resultant mixture was left to be cooled and added to iced water, and the resultant solid was filtered. The resultant solid was dissolved in ethanol. The ethanol solution was added to hexane, and the resultant solid was collected by filtration to obtain a compound F (168.1 g).

Example 11

Synthesis of Compound G

After forming a nitrogen gas flow within a reaction vessel, the compound F (138.4 g), 2-[2-(2-methoxyethoxy)ethoxy]-ethyl p-toluene sulfonate (408.6 g), potassium carbonate (358.5 g), and acetonitrile (2.5 L) were mixed, and the mixture was refluxed under heating for 3 hours. After being left to be cooled, the resultant reaction mixture was collected by filtration, and the filtrate was concentrated under reduced pressure and purified with silica gel column chromatography to obtain a compound G (109.4).

[Chemical Formula 63]

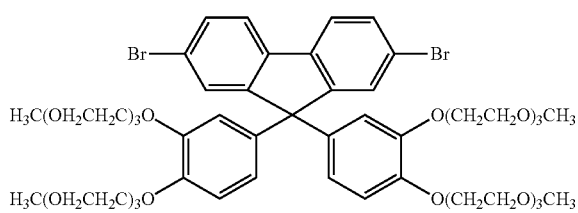

Compound G

Example 12

Synthesis of Compound H

After a reaction vessel was purged with a nitrogen gas, the compound G (101.2 g), bis(pinacolato)diboron (53.1 g), [1,1'-bis(diphenylphosphino)ferrocene]dichloropalladium (II) dichloromethane complex (3.7 g), 1,1'-bis(diphenylphosphino)ferrocene (5.4 g), potassium acetate (90.6 g), and dioxane (900 mL) were mixed, heated to 110° C., and refluxed under heating for 8 hours. After being left to be cooled, the resultant reaction solution was collected by filtration, and the filtrate was concentrated under reduced pressure and purified with silica gel column chromatography to obtain a compound H (51.4 g).

[Chemical Formula 64]

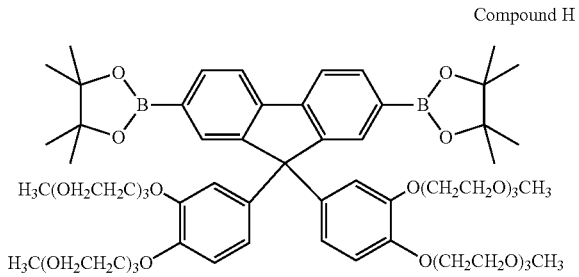

Compound H

Example 13

Synthesis of Polymer Compound C

After a reaction vessel was purged with a nitrogen gas, the compound E (0.360 g), the compound H (0.273 g), the compound G (0.493 g), N,N'-bis(4-bromophenyl)-N,N'-bis(4-tert-butyl-2,6-dimethylphenyl)-1,4-phenylenediamine (35.8 mg), methyltrioctylammonium chloride ("Aliquat 336" (registered trademark) manufactured by Sigma-Aldrich Co.) (8.10 mg), bis(triphenylphosphine)dichloropalladium (1.12 mg), a 2 mol/L aqueous sodium carbonate solution (15 mL), and toluene (20 mL) were stirred at 105° C. for 6 hours. Phenylboronic acid (39 mg) was then added to the mixture, and the mixture was stirred at 105° C. for 6 hours. To the resultant reaction mixture were added sodium diethyldithiocarbamate trihydrate (0.72 g) and water (14 mL), and the mixture was stirred at 80° C. for 2 hours. The resultant mixture was added dropwise to methanol, and the precipitate was collected by filtration and dried. The resultant solid was dissolved in chloroform and purified with alumina and silica gel chromatography. The eluent was concentrated and dried. The concentrate was dissolved in toluene and added dropwise to methanol, and the precipitate was collected by filtration to obtain a polymer compound C (0.41 g). Polystyrene-equivalent number-average molecular weight of the polymer compound C was $2.0 \times 10^4$. The polymer compound C is composed of a structural unit represented by Formula (E).

[Chemical Formula 65]

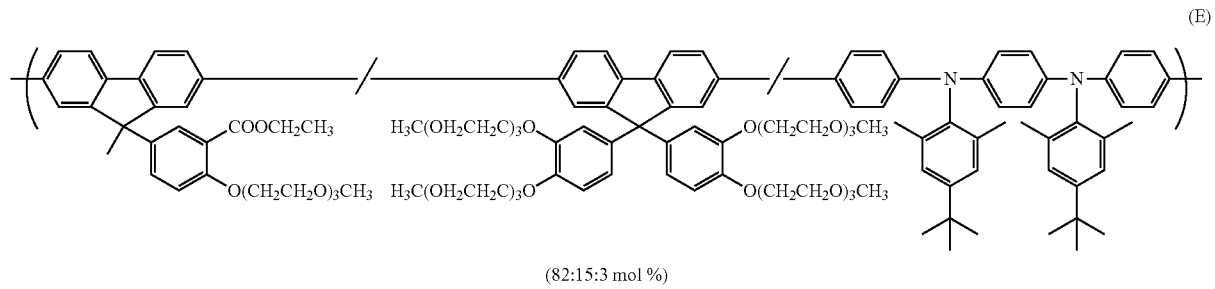

(E)

(82:15:3 mol %)

Example 14

Synthesis of Cesium Salt of Polymer Compound C (Conjugated Polymer Compound 3)

After forming an argon gas atmosphere within a reaction vessel, the polymer compound C (0.15 g), tetrahydrofuran (20 mL), methanol (10 mL), cesium hydroxide monohydrate (103 mg), and water (1 mL) were stirred at 65° C. for 2 hours. To the mixture was then added methanol (20 mL), and the mixture was stirred at 65° C. for 2 hours. The resultant reaction mixture was concentrated and dried. To the solid was added methanol, and the mixture was filtered. The filtrate was added dropwise to isopropanol, and the solid was collected by filtration and dried to obtain a conjugated polymer compound 3 (0.17 g). The conjugated polymer compound 3 is composed of a structural unit represented by Formula (F).

[Chemical Formula 66]

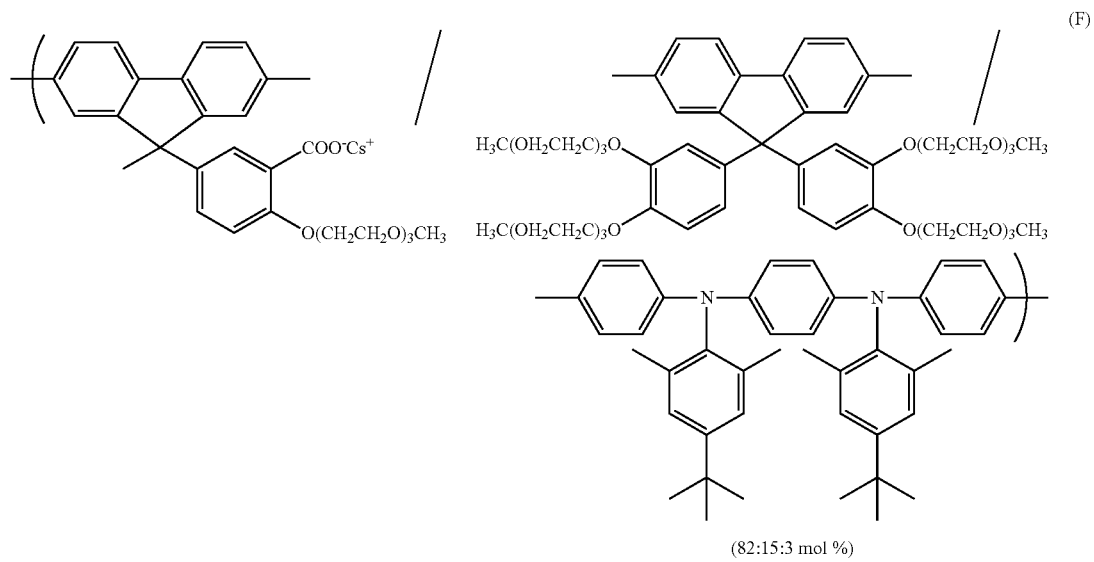

(F)

(82:15:3 mol %)

Example 15

Synthesis of Polymer Compound D

After a reaction vessel was purged with a nitrogen gas, the compound H (0.715 g), the compound D (0.426 g), methyltrioctylammonium chloride ("Aliquat 336" (registered trademark) manufactured by Sigma-Aldrich Co.) (6.60 mg), bis(triphenylphosphine)dichloropalladium (0.460 mg), a 2 mol/L aqueous sodium carbonate solution (10 mL), and toluene (20 mL) were mixed and stirred at 105° C. Toluene (20 mL) was stirred at 105° C. for 5 hours, then phenylboronic acid (32 mg) was added, and the mixture was stirred at 105° C. for 6 hours. To the resultant reaction mixture were added sodium diethyldithiocarbamate trihydrate (0.72 g) and water (14 mL), and the mixture was stirred at 80° C. for 2 hours. The mixture was added dropwise to methanol, and the precipitate was collected by filtration and dried. The resultant solid was dissolved in chloroform and purified with alumina and silica gel chromatography. The eluent was concentrated and dried. The concentrate was dissolved in toluene and added dropwise to methanol. The precipitate was collected by filtration to obtain a polymer compound D (0.55 g). Polystyrene-equivalent number-average molecular weight of the polymer compound D was $2.3 \times 10^4$. The polymer compound D is composed of a structural unit represented by Formula (G).

[Chemical Formula 67]

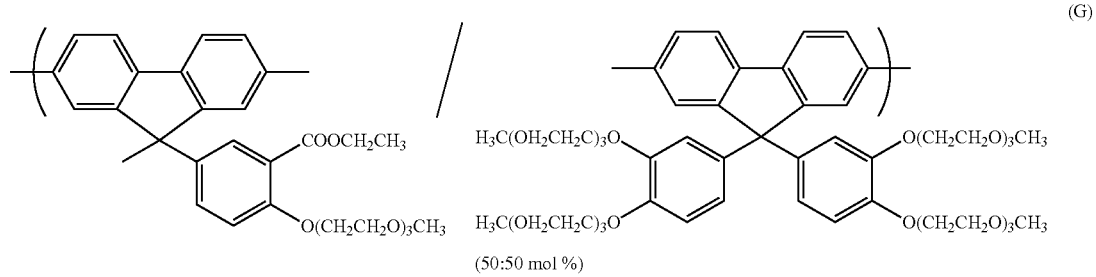

(G)

(50:50 mol %)

Example 16

Synthesis of Cesium Salt of Polymer Compound D (Conjugated Polymer Compound 4)

After forming an argon gas atmosphere within a reaction vessel, the polymer compound D (0.15 g), tetrahydrofuran (20 mL), methanol (10 mL), cesium hydroxide monohydrate (103 mg), and water (1 mL) were stirred at 65° C. for 2 hours. To the mixture was then added methanol (20 mL), and the mixture was stirred at 65° C. for 2 hours. The resultant reaction mixture was concentrated and dried. To the solid was added methanol, and the mixture was filtered. The resultant filtrate was concentrated and dried, and the resultant solid was washed with water and dried to obtain a conjugated polymer compound 12 (0.14 g). The conjugated polymer compound 4 is composed of a structural unit represented by Formula (H).

[Chemical Formula 68]

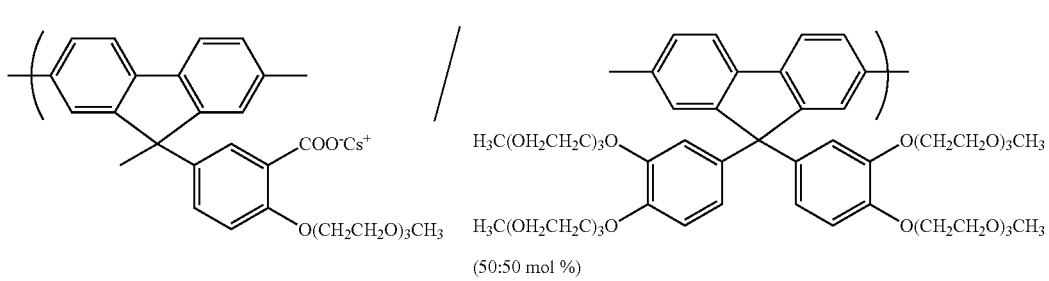

(50:50 mol %)

Example 17

Synthesis of Polymer compound E

After a reaction vessel was purged with a nitrogen gas, the compound E (0.534 g, 0.712 mmol), the compound D (0.472 g, 0.720 mmol), bis(4-bromophenyl)[4-(1-methylpropyl)phenyl]amine (38.2 mg, 0.082 mmol), methyltrioctylammonium chloride ("Aliquat 336" (registered trademark) manufactured by Sigma-Aldrich Co.) (8.10 mg, 0.0200 mmol), bis(triphenylphosphine)dichloropalladium (0.560 mg, 0.800 μmol), a 17.5% by weight aqueous sodium carbonate solution (10 mL), and toluene (20 mL) were put in a two-necked flask and stirred at 105° C. Four hours later, bis(triphenylphosphine)dichloropalladium (0.560 mg, 0.800 μmol), a 17.5% by weight aqueous sodium carbonate solution (5 mL), and phenylboronic acid (39.0 mg, 0.320 mmol) were added, and the mixture was stirred for 6 hours. To the resultant reaction mixture were added sodium diethyldithiocarbamate trihydrate (0.72 g)(720 mg) and water (14 mL), and the mixture was stirred at 80° C. for 2 hours. The resultant reaction solution was added to methanol (300 mL), and the precipitated solid was collected by filtration, washed with water (50 mL), and dried. The resultant solid was dissolved in chloroform (20 mL) and purified with a silica gel column and an alumina column. The column eluent was concentrated and dried, then dissolved in toluene (20 mL), and filtered. The filtrate was concentrated and added dropwise to methanol, and the precipitate was collected by filtration and dried to obtain a polymer compound E (611 mg). Polystyrene-equivalent number-average molecular weight of the polymer compound E was $3.8 \times 10^4$. The polymer compound E is composed of a structural unit represented by Formula (1).

[Chemical Formula 69]

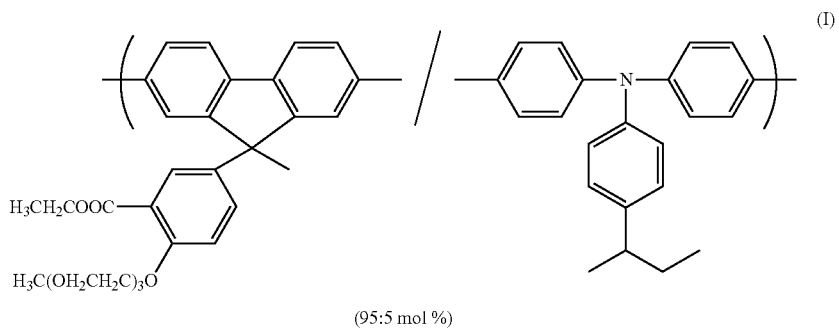

(95:5 mol %)

Bis(4-bromophenyl)[4-(1-methylpropyl)phenyl]amine was synthesized by a known method described in WO2002-45184.

Example 18

Synthesis of Cesium Salt of Polymer Compound E (Conjugated Polymer Compound 5)

After a reaction vessel was purged with a nitrogen gas, the polymer compound E (200 mg), cesium hydroxide monohydrate (137 mg, 0.816 mmol), tetrahydrofuran (20 mL), methanol (10 mL), and water (1.6 mL) were mixed and stirred at 65° C. for 2 hours. To the mixture was then added methanol (20 mL), and the mixture was stirred for 2 hours. The reaction mixture was concentrated and dried. To the solid was added methanol, and the mixture was filtered. The filtrate was concentrated. The concentrated filtrate was added dropwise to isopropanol, and the precipitated solid was collected by filtration and dried to obtain a conjugated polymer compound 5 (142 mg). The conjugated polymer compound 5 is composed of a structural unit represented by Formula (J).

[Chemical Formula 70]

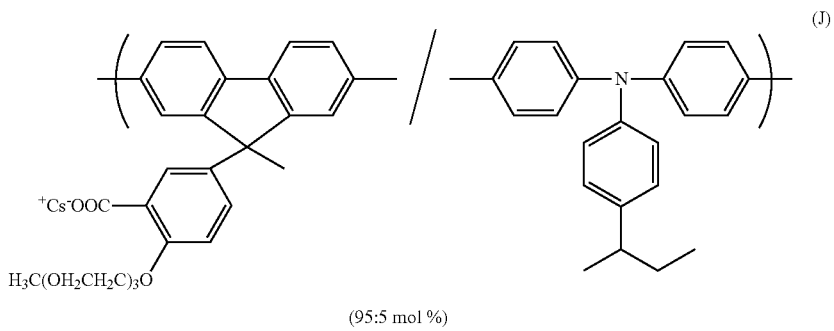

(95:5 mol %)

Example 19

Synthesis of Polymer Compound F

After a reaction vessel was purged with a nitrogen gas, the compound E (534 mg, 0.712 mmol), the compound D (493 mg, 0.752 mmol), 2,4-bis(4-bromophenyl)-6-(4-hexylphenyl)-1,3,5-triazine (26.7 mg, 0.480 mmol), methyltrioctylammonium chloride ("Aliquat 336" (registered trademark) manufactured by Sigma-Aldrich Co.) (8.10 mg, 0.0200 mmol), bis(triphenylphosphine)dichloropalladium (0.560 mg, 0.800 μmol), a 17.5% by weight aqueous sodium carbonate solution (10 mL), and toluene (20 mL) were mixed and stirred at 105° C. for 4 hours. Bis(triphenylphosphine)dichloropalladium (0.560 mg, 0.800 μmol), phenylboronic acid (39.0 mg, 0.320 mmol), and toluene (3.0 mL) were then added to the mixture, and the mixture was stirred for 3 hours. To the resultant reaction mixture were added sodium diethyldithiocarbamate trihydrate (720 mg) and water (14 mL), and the mixture was stirred at 80° C. for 2 hours. The resultant reaction solution was added dropwise to methanol, and the precipitated solid was collected by filtration. The solid was dissolved in chloroform (40 mL) and passed through a silica gel column and an alumina column. The eluent was concentrated and dried. The resultant solid was dissolved in toluene (30 mL) and filtered. The filtrate was concentrated. The concentrated filtrate was added dropwise to methanol. The precipitated solid was collected by filtration and dried to obtain a polymer compound F (412 mg). Polystyrene-equivalent number-average molecular weight of the polymer compound F was $4.2 \times 10^4$. The polymer compound F is composed of a structural unit represented by Formula (K).

[Chemical Formula 71]

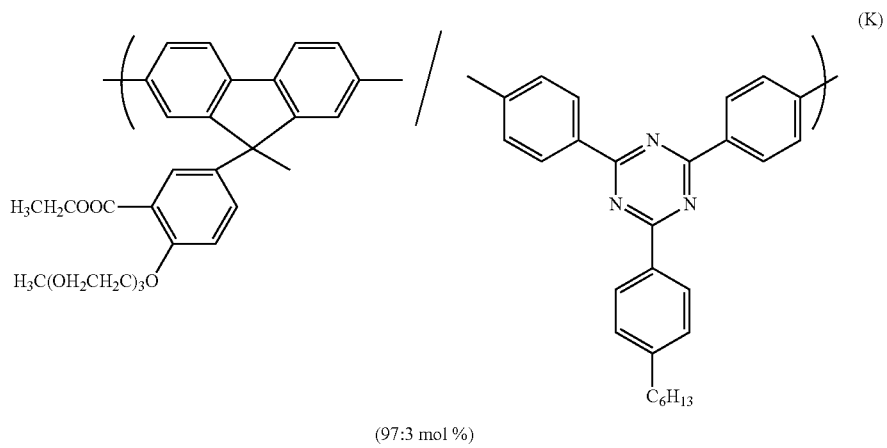

(97:3 mol %)

2,4-Bis(4-bromophenyl)-6-(4-hexylphenyl)-1,3,5-triazine was synthesized by a known method described in, for example, WO2009-131255.

Example 20

Synthesis of Cesium Salt of Polymer Compound F (Conjugated Polymer Compound 6)

After a reaction vessel was purged with a nitrogen gas, the polymer compound F (200 mg), cesium hydroxide monohydrate (137 mg, 0.816 mmol), tetrahydrofuran (20 mL), methanol (10 mL), and water (1.6 mL) were mixed and stirred at 65° C. for 1 hour. To the mixture was then further added methanol (100 mL), and the mixture was stirred for 2 hours. The resultant solution was concentrated and dried. The solid was dissolved in methanol (80 mL) and filtered. The filtrate was concentrated and added dropwise to isopropanol, and the precipitated solid was collected by filtration and dried to obtain a conjugated polymer compound 6 (207 mg). The conjugated polymer compound 6 is composed of a structural unit represented by Formula (L).

[Chemical Formula 72]

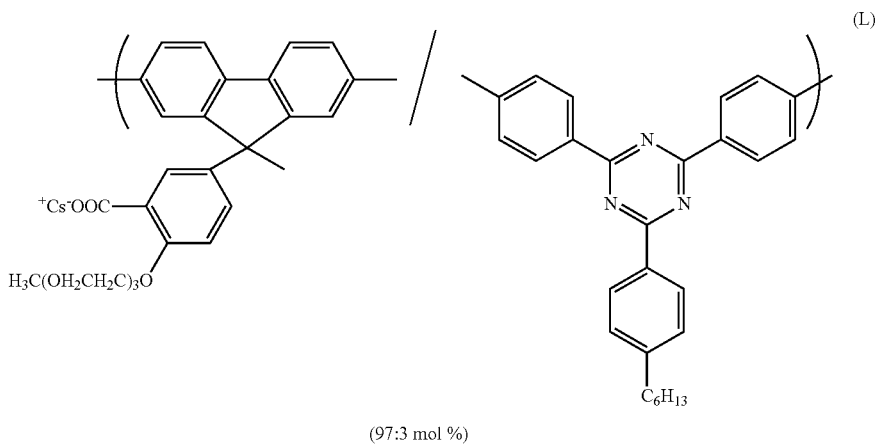

(L)

(97:3 mol %)

Example 21

Synthesis of Compound I

After a reaction vessel was purged with a nitrogen gas, 2,7-dibromo-9-fluorenone (82.3 g, 244 mmol) and tetrahydrofuran (3.8 L) were mixed and cooled to 0° C. To the mixture was added dropwise a 1 mol/L tetrahydrofuran solution of iso-butylmagnesium bromide (0.475 L, 475 mmol), and the mixture was stirred for 1 hour. To the resultant reaction mixture was added an aqueous ammonium chloride solution to remove the aqueous layer, and the organic layer was dried over anhydrous sodium sulfate and concentrated under reduced pressure. The resultant crude product was purified with silica gel column chromatography to obtain a target compound I (51.9 g, 131 mmol, with a yield of 54%).

$^1$H NMR (400 MHz, CDCl$_3$, rt)

δ (ppm) 0.60 (6H), 1.17 (1H), 2.04 (1H), 2.09 (2H), 7.43-7.51 (4H), 7.62 (2H).

[Chemical Formula 73]

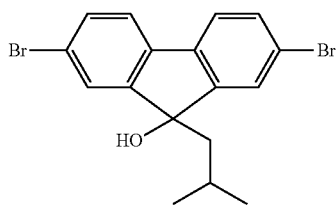

Compound I

Example 22

Synthesis of Compound J

After a reaction vessel was purged with a nitrogen gas, the compound I (49.6 g, 125 mmol), methane toluene sulfonic acid (99.1 g, 1032 mmol), and chloroform (0.51 L) were refluxed for 1 hour. To the resultant reaction mixture was added an aqueous ammonium chloride to remove the aqueous layer. The organic layer was dried over anhydrous sodium sulfate and concentrated under reduced pressure to obtain a target compound J (36.4 g, 96.3 mmol, with a yield of 77%)

$^1$H NMR (400 MHz, CDCl$_3$, rt)

δ (ppm) 1.27 (6H), 3.41 (1H), 6.60 (1H), 7.45-7.60 (4H), 7.80 (1H), 7.97 (1H).

[Chemical Formula 74]

Compound J

Example 23

Synthesis of Compound K

After a reaction vessel was purged with a nitrogen gas, the compound J (36.4 g, 96.3 mmol), ethyl salicylate (32.0 g, 193 mmol), mercaptoacetic acid (1.86 g, 20.2 mmol), and methane sulfonic acid (465 g) were stirred at 70° C. for 6 hours. The resultant reaction mixture was added dropwise to iced water, and the precipitated solid was collected by filtration and washed with methanol. The crude product was purified with silica gel column chromatography to obtain a target compound K (39.6 g, 72.8 mmol, with a yield of 75.6%).

$^1$H NMR (400 MHz, CDCl$_3$, rt)

δ (ppm) 0.53 (6H), 0.98 (1H), 1.44 (3H), 2.41 (2H), 4.44 (2H), 6.74 (1H), 6.80 (1H), 7.30 (2H), 7.47 (2H), 7.60 (2H), 7.84 (1H), 10.8 (1H).

[Chemical Formula 75]

Compound K

Example 24

Synthesis of Compound L

After a reaction vessel was purged with a nitrogen gas, the compound K (39.6 g, 72.8 mmol), 2-[2-(2-methoxyethoxy)ethoxy]-ethyl-p-toluene sulfonate (67.1 g, 210 mmol), dimethylformamide (198 g), potassium carbonate (48.2 g, 349 mmol), and 1,4,7,10,13,16-hexaoxacyclooctadecane (also referred to as "18-crown-6") (3.82 g, 14.5 mmol) were stirred at 105° C. for 1 hour. The resultant reaction mixture was added to water and extracted with ethyl acetate. The organic layer was dried over anhydrous sodium sulfate and concentrated under reduced pressure, and the resultant crude product was purified with silica gel column chromatography to obtain a target compound L (47.4 g, 68.6 mmol, with a yield of 94%).

$^1$H NMR (400 MHz, CDCl$_3$, rt)

δ (ppm) 0.51 (2H), 1.00 (1H), 1.38 (3H), 2.44 (2H), 3.36 (3H), 3.53 (2H), 3.58-3.73 (6H), 3.72 (2H), 4.13 (2H), 4.34 (2H), 6.75 (1H), 6.85 (1H), 7.32 (2H), 7.48 (2H), 7.58 (2H), 7.70 (1H).

[Chemical Formula 76]

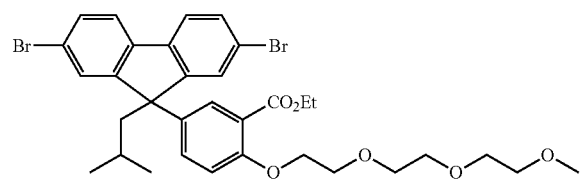

Compound L

Example 25

Synthesis of Compound M

After a reaction vessel was purged with a nitrogen gas, the compound L (18.0 g, 26.1 mmol), bis(pinacolato)diboron (14.7 g, 57.4 mol), [1,1'-bis(diphenylphosphino)ferrocene] palladium (II)dichloride with one molecule of dichloromethane (0.21 g, 0.26 mmol), 1,1'-bis(diphenylphosphino)ferrocene (0.14 g, 0.26 mmol), potassium acetate (15.4 g, 156 mmol), and 1,4-dioxane (290 mL) were stirred at 120° C. for 24 hours. The resultant reaction mixture was filtered and washed with ethyl acetate. The filtrate was concentrated under reduced pressure, purified with silica gel column chromatography, and then purified by recrystallization to obtain a target compound M (11.6 g, 14.8 mmol, with a yield of 57%).

$^1$H NMR (400 MHz, CDCl$_3$, rt)

δ (ppm) 0.44 (6H), 0.99 (1H), 1.30-1.43 (27H), 2.55 (2H), 3.35 (3H), 3.53 (2H), 3.60-3.69 (4H), 3.74 (2H), 3.85 (2H), 4.08 (2H), 4.34 (2H), 6.70 (1H), 6.79 (1H), 7.56 (2H), 7.75-7.83 (5H).

[Chemical Formula 77]

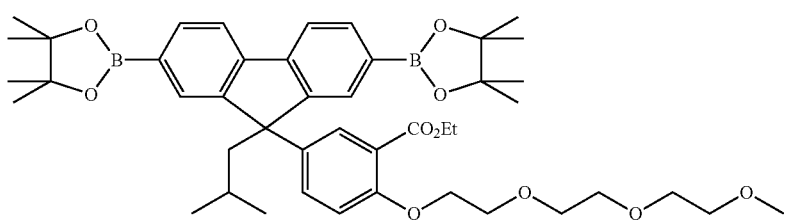

Example 26

Synthesis of Polymer Compound G

After a reaction vessel was purged with a nitrogen gas, the compound M (573.6 mg, 0.728 mmol), the compound L (567 mg, 0.800 mmol), methyltrioctylammonium chloride ("Aliquat 336" (registered trademark) manufactured by Sigma-Aldrich Co.) (0.20 g, manufactured by Sigma-Aldrich Co.) (8.10 mg, 0.0200 mmol), bis(triphenylphosphine)dichloropalladium (0.560 mg, 0.798 μmol), 17.5% by weight Na$_2$CO$_3$ aq. (10 mL), and toluene (20 mL) were put in a two-necked flask and stirred at 105° C. Four hours later, bis(triphenylphosphine)dichloropalladium (0.560 mg, 0.798 μmol), a 17.5% by weight aqueous sodium carbonate solution (3.0 mL), and phenylboronic acid (39.0 mg, 0.320 mmol), and toluene (3.0 mL) were added, and the mixture was stirred for 6 hours. To the resultant reaction mixture was added an aqueous sodium diethyldithiocarbamate trihydrate solution (720 mg), and the mixture was stirred at 80° C. for 2 hours. The resultant reaction solution was added to methanol to precipitate a solid. The resultant solid was collected by filtration, dissolved in chloroform (40 mL), and passed through a silica gel column and an alumina column. The resultant solution was concentrated and dried, dissolved in toluene (30 mL), and filtered. The filtrate was concentrated. This solution was added dropwise to methanol, and the resultant precipitate was collected. The resultant solid was dried to obtain a polymer compound G (0.44 g). Polystyrene-equivalent number-average molecular weight of the polymer compound G was 3.5×10$^4$. The polymer compound G is composed of a structural unit represented by Formula (M).

[Chemical Formula 78]

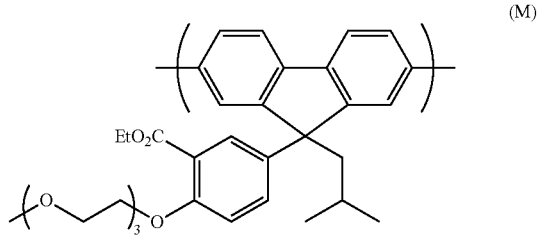

(M)

Example 27

Synthesis of Cesium Salt of Polymer Compound G (Conjugated Polymer Compound 7)

After forming an argon gas atmosphere within a reaction vessel, the polymer compound G (0.20 g), tetrahydrofuran (20 mL), methanol (10 mL), cesium hydroxide monohydrate (126 mg), and water (1 mL) were stirred at 65° C. for 4 hours. The resultant reaction mixture was concentrated and dried. The resultant solid was washed with water and dried to obtain a conjugated polymer compound 7 (0.21 g). The conjugated polymer compound 7 is composed of a structural unit represented by Formula (N).

[Chemical Formula 79]

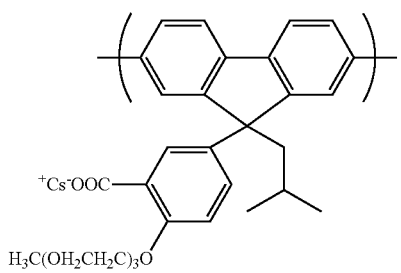

(N)

Example 28

Synthesis of Lithium Salt of Polymer Compound G (Conjugated Polymer Compound 8)

After forming an argon gas atmosphere within a reaction vessel, the polymer compound G (0.15 g), tetrahydrofuran (10 mL), methanol (7 mL), lithium hydroxide monohydrate (23.6 mg), and water (0.3 mL) were stirred at 65° C. for 4 hours. The resultant reaction mixture was concentrated and dried. The resultant solid was washed with water and dried to obtain a conjugated polymer compound 8 (0.13 g). The conjugated polymer compound 8 is composed of a structural unit represented by Formula (O).

[Chemical Formula 80]

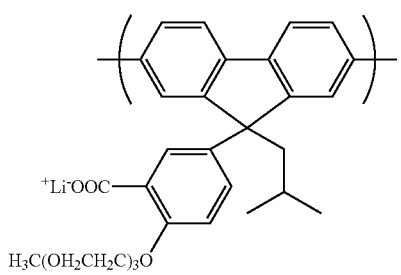

(O)

Example 29

Synthesis of Compound L

After a reaction vessel was purged with a nitrogen gas, dimethyl-5-iodoisophthalate (101.1 g) and dehydrated tetrahydrofuran (284 mL) were mixed and cooled to −20° C. To the mixture was added dropwise isopropyl magnesium chloride (a 1M tetrahydrofuran solution) (336 mL), and the mixture was stirred for 30 minutes. To the reaction solution was added 2,7-dibromo-9-fluorenone (70.9 g), and the reaction solution was stirred for 3 hours. To the resultant reaction mixture was added an aqueous ammonium chloride solution (560 mL). After adding methyl-tert-butyl ether (560 mL), the reaction mixture was returned to room temperature, and the organic layer was extracted by separation. The organic layer was dried over sodium sulfate and filtered, and the filtrate was concentrated. Toluene (650 g) was added to the resultant solid to be mixed therewith, and the mixture was filtered. The resultant solid was washed with hexane and dried to obtain a compound L (100.8 g).

[Chemical Formula 81]

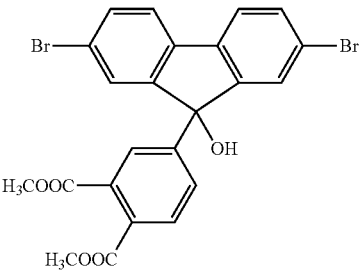

Compound L

Example 30

Synthesis of Compound M

After a reaction vessel was purged with a nitrogen gas, the compound L (95.9 g), catechol (59.0 g), mercaptoacetic acid (3.45 mL), and methane sulfonic acid (725 mL) were mixed and stirred at 75° C. for 3 hours. After being left to be cooled, the resultant mixture was left to be cooled and added to iced water, and the resultant solid was collected by filtration. The resultant solid was washed with methanol and dried to obtain a compound M (107.8 g).

[Chemical Formula 82]

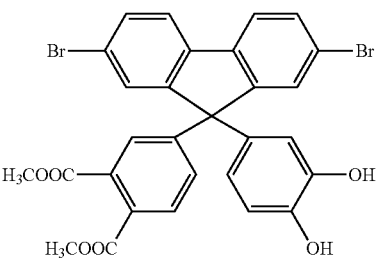

Compound M

Example 31

Synthesis of Compound N

After forming a nitrogen gas flow within a reaction vessel, the compound M (66.2 g), 2-[2-(2-methoxyethoxy)ethoxy]-ethyl p-toluene sulfonate (97.6 g), potassium carbonate (70.1 g), and N,N'-dimethylformamide (264 mL) were mixed and refluxed under heating at 105° C. for 2 hours. After being left to be cooled, the resultant reaction mixture was added to iced water and extracted with ethyl acetate, and the organic layer was collected. The collected organic layer was dried over sodium sulfate and collected by filtration. The filtrate was concentrated under reduced pressure and purified with silica gel column chromatography to obtain a compound N (114 g).

[Chemical Formula 83]

Compound N

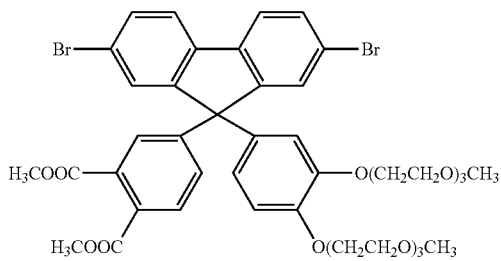

Example 32

Synthesis of Compound O

After a reaction vessel was purged with a nitrogen gas, the compound N (25.3 g), bis(pinacolato)diboron (15.4 g), [1,1'-bis(diphenylphosphino)ferrocene]palladium (II)dichloride (0.23 g), 1,1'-bis(diphenylphosphino)ferrocene (0.15 g), potassium acetate (16.3 g), and 1,4-dioxane (420 mL) were stirred at 120° C. for 24 hours. The resultant reaction mixture was filtered and washed with ethyl acetate. The filtrate was concentrated under reduced pressure, purified with silica gel column chromatography, and then purified by recrystallization to obtain a target compound O (11.4 g).

[Chemical Formula 84]

Compound O

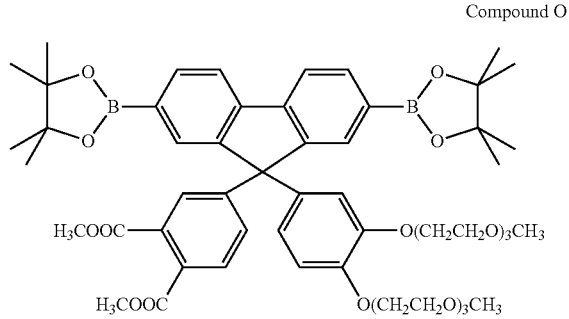

Example 33

Synthesis of Polymer Compound H

After a reaction vessel was purged with a nitrogen gas, the compound N (0.63 g), the compound O (0.62 g), methyltrioctylammonium chloride ("Aliquat 336" (registered trademark) manufactured by Sigma-Aldrich Co.) (0.20 g, manufactured by Sigma-Aldrich Co.) (7 mg), bis(triphenylphosphine)dichloropalladium (0.56 mg), a 12.0% by weight aqueous sodium carbonate solution (2.7 mL), and toluene (20 mL) were put in a two-necked flask and stirred at 105° C. Nine hours later, bis(triphenylphosphine)dichloropalladium (0.6 mg), a 12.0% by weight aqueous sodium carbonate solution (1 mL), and phenylboronic acid (33.4 mg), and toluene (1.5 mL) were added, and the mixture was stirred for 16 hours. To the resultant reaction mixture was added an aqueous sodium diethyldithiocarbamate trihydrate solution (720 mg), and the mixture was stirred at 80° C. for 2 hours. The resultant reaction solution was added to methanol to precipitate a solid. The resultant solid was collected by filtration, dissolved in chloroform (45 mL), and extracted by separation. The organic layer was concentrated and dried, dissolved in chloroform (22 mL), and passed through a silica gel column and an alumina column. The resultant solution was concentrated and dried, dissolved in chloroform (20 mL), and filtered. The filtrate was concentrated. This solution was added dropwise to methanol, and the resultant precipitate was collected. The resultant solid was dried to obtain a polymer compound H (0.59 g). Polystyrene-equivalent number-average molecular weight of the polymer compound H was $3.5 \times 10^4$. The polymer compound H is composed of a structural unit represented by Formula (P).

[Chemical Formula 85]

(P)

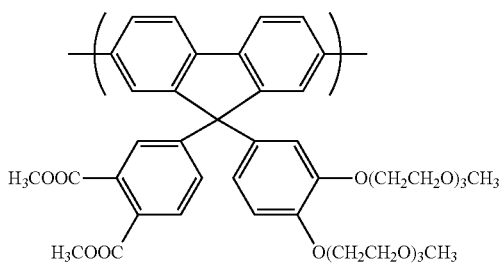

Example 34

Synthesis of Cesium Salt of Polymer Compound H (Conjugated Polymer Compound 9)

After forming an argon gas atmosphere within a reaction vessel, the polymer compound H (0.20 g), tetrahydrofuran (4.2 mL), methanol (4.8 mL), cesium hydroxide monohydrate (178 mg), and water (0.8 mL) were stirred at 65° C. for 4 hours. To the mixture was further added methanol (5.0 mL), and the mixture was stirred for 2 hours. The resultant reaction mixture was concentrated and added dropwise to isopropanol. The precipitated solid was collected by filtration and dried to obtain a conjugated polymer compound 9 (0.20 g). The conjugated polymer compound 9 is composed of a structural unit represented by Formula (Q).

[Chemical Formula 86]

(Q)

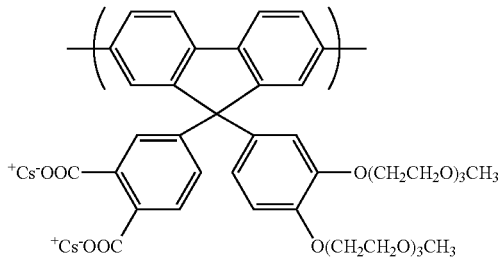

Reference Example 1

Synthesis of Polyurethane Sodium Salt
(Non-Conjugated Polymer Compound 1)

After a reaction vessel was purged with a nitrogen gas, 1,3-butanediol (1.0 g), dibutyltin dilaurate (7.5 mg), and dimethylolpropionic acid (0.5 g) were put in a 100 mL flask. DMF (50 mL) was added to the mixture, and the mixture was stirred at 90° C. for 30 minutes. To the mixture was then added isophorone diisocyanate (3.3 g), and the mixture was heated at 90° C. for 3 hours. A solution containing a polymer compound obtained in this stage was subjected to GPC measurement according to the above-described method to measure the molecular weight of the polymer compound. Polystyrene-equivalent number-average molecular weight of the polymer compound was $1.9\times10^3$, and polystyrene-equivalent weight-average molecular weight of the polymer compound was $3.0\times10^3$. The resultant reaction solution was cooled to 60° C. and neutralized through the addition of a 1M aqueous sodium hydroxide solution. The reaction solution was stirred at 60° C. further for 1 hour, and the solvent was distilled off from the reaction solution to obtain a white solid (2.0 g). The resultant white solid is referred to as a non-conjugated polymer compound 1. The non-conjugated polymer compound 1 is composed of a structural unit represented by Formula (1).

[Chemical Formula 87]

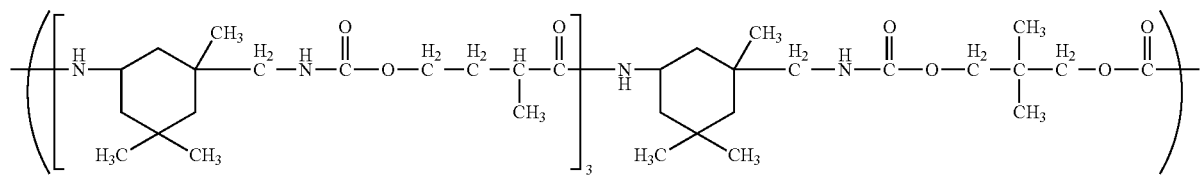

(I)

Example 35

Preparation of Electroluminescent Device 1

Onto an ITO anode (thickness: 45 nm), which had been patterned for film formation on the surface of a glass substrate, a solution of a hole injection material was applied to form a hole injection layer with a film thickness of 60 nm by the spin coating method. The glass substrate on which the hole injection layer had been formed was heated at 200° C. for 10 minutes in an inert gas atmosphere (in a nitrogen atmosphere) to insolubilize the hole injection layer. The resulting substrate was left to be cooled to room temperature to obtain a substrate having the hole injection layer thereon.

As the solution of the hole injection material, AQ-1200, which is a polythiophene/sulfonic acid-based hole injection material purchased from Plextronics, Inc., was used.

Next, a hole-transporting polymer material and xylene were mixed to obtain a composition for forming a hole transport layer containing a 0.7% by weight hole-transporting polymer material.

The hole-transporting polymer material was synthesized according to the following process.

After making the gas within a reaction vessel an inert gas atmosphere, 2,7-dibromo-9,9-di(octyl)-fluorene (1.4 g), 2,7-bis(4,4,5,5-tetramethyl-1,3,2-dioxaborolan-2-yl)-9,9-di(octyl)fluorene (6.4 g), N,N'-bis(4-bromophenyl)-N,N'-bis(4-butylphenyl)-1,4-phenylenediamine (4.1 g), bis(4-bromophenyl)benzocyclobutene amine (0.6 g), tetraethylammonium hydroxide (1.7 g), palladium acetate (4.5 mg), tri(2-methoxyphenyl) phosphine (0.03 g), and toluene (100 mL) were mixed, and the resultant mixture was stirred at 100° C. for 2 hours. To the mixture was then added phenylboronic acid (0.06 g), and the resultant mixture was stirred for 10 hours. After being left to be cooled, the aqueous layer was removed. After adding an aqueous sodium diethyldithiocarbamate solution and stirring the mixture, the aqueous layer was removed, and the organic layer was washed with water and a 3% by volume aqueous acetic acid solution. After pouring the organic layer into methanol to precipitate a solid, the solid collected by filtration was dissolved in toluene again and passed through a silica gel column and an alumina column. The eluted toluene solution containing the solid was collected. The collected toluene solution was poured into methanol to precipitate the solid. The precipitated solid was collected by filtration and vacuum dried at 50° C. to obtain a hole-transporting polymer material. Polystyrene-equivalent weight-average molecular weight of the hole-transporting polymer material was $3.0\times10^5$.

Onto the hole injection layer of the substrate on which the hole injection layer had been formed obtained as described above, the composition for forming a hole transport layer was applied by the spin coating method to form an applied film with a thickness of 20 nm. The substrate having the applied film was heated at 180° C. for 60 minutes in an inert gas atmosphere (in a nitrogen atmosphere) to insolubilize the applied film. The substrate was then left to be cooled to room temperature to obtain a substrate having the hole transport layer thereon.

Next, a light-emitting polymer material and xylene were mixed to obtain a composition for forming a light-emitting layer containing a 1.4% by weight light-emitting polymer material.

The light-emitting polymer material was synthesized according to the following process.

After making the gas within a reaction vessel an inert gas atmosphere, 2,7-dibromo-9,9-di(octyl)-fluorene (9.0 g), N,N'-bis(4-bromophenyl)-N,N'-bis(4-tert-butyl-2,6-dimethylphenyl) 1,4-phenylenediamine (1.3 g), 2,7-bis(4,4,5,5-tetramethyl-1,3,2-dioxaborolan-2-yl)-9,9-di(4-hexyphenyl) fluorene (13.4 g), tetraethylammonium hydroxide (43.0 g), palladium acetate (8 mg), tri(2-methoxyphenyl) phosphine (0.05 g), and toluene (200 mL) were mixed, and the resultant mixture was stirred at 90° C. for 8 hours. To the mixture was then added phenylboronic acid (0.22 g), and the resultant mixture was stirred for 14 hours. After being left to be cooled, the aqueous layer was removed. After adding an aqueous sodium diethyldithiocarbamate solution and stirring the mixture, the aqueous layer was removed, and the organic layer was washed with water and a 3% by volume aqueous acetic acid solution. After pouring the organic layer into methanol to precipitate a solid, the solid collected by filtration was dissolved in toluene again and passed through a silica gel column and an alumina column. The eluted toluene solution containing the solid was collected. The collected toluene solution was poured into methanol to precipitate the solid. The precipitated solid was vacuum dried at 50° C. to obtain a light-emitting polymer material (12.5 g). According to gel permeation chromatography, polystyrene-equivalent weight-average molecular weight of the obtained light-emitting polymer material was $3.1 \times 10^5$.

Onto the hole transport layer of the substrate on which the hole transport layer had been formed obtained as described above, the composition for forming a light-emitting layer was applied by the spin coating method to form an applied film with a thickness of 80 nm. The substrate having the applied film was heated at 130° C. for 10 minutes in a nitrogen atmosphere to evaporate the solvent and left to be cooled to room temperature to obtain a substrate having the light-emitting layer thereon.

Methanol and the conjugated polymer compound 1 were mixed to obtain a solution containing a 0.2% by weight conjugated polymer compound 1. Onto the light-emitting layer of the substrate on which the light-emitting layer had been formed as described above, the solution was applied by the spin coating method to obtain an applied film with a thickness of 10 nm. The substrate having the applied film was heated at 130° C. for 10 minutes in a nitrogen atmosphere to evaporate the solvent and left to be cooled to room temperature to obtain a substrate having the conjugated polymer compound 1.

The substrate having the layer containing the conjugated polymer compound 1 obtained as described above was inserted into a vacuum deposition apparatus, and an Al film with a thickness of 80 nm was formed on the layer by the vacuum deposition method to form a cathode. Thus, a layered structure 1 was prepared.

The layered structure 1 thus prepared was taken out of the vacuum deposition apparatus and sealed with a sealing glass and a two-part mixing type epoxy resin in a nitrogen atmosphere to obtain an electroluminescent device 1.

Example 36

Preparation of Electroluminescent Device 2

An electroluminescent device 2 was obtained in the same manner as Example 35 except that the conjugated polymer compound 2 was used in place of the conjugated polymer compound 1 in Example 35.

Example 37

Preparation of Electroluminescent Device 3

An electroluminescent device 3 was obtained in the same manner as Example 35 except that the conjugated polymer compound 3 was used in place of the conjugated polymer compound 1 in Example 35.

Example 38

Preparation of Electroluminescent Device 4

An electroluminescent device 4 was obtained in the same manner as Example 35 except that the conjugated polymer compound 4 was used in place of the conjugated polymer compound 1 in Example 35.

Example 39

Preparation of Electroluminescent Device 5

An electroluminescent device 5 was obtained in the same manner as Example 35 except that the conjugated polymer compound 5 was used in place of the conjugated polymer compound 1 in Example 35.

Example 40

Preparation of Electroluminescent Device 6

An electroluminescent device 6 was obtained in the same manner as Example 35 except that the conjugated polymer compound 6 was used in place of the conjugated polymer compound 1 in Example 35.

Example 41

Preparation of Electroluminescent Device 7

An electroluminescent device 7 was obtained in the same manner as Example 35 except that the conjugated polymer compound 7 was used in place of the conjugated polymer compound 1 in Example 35.

Example 42

Preparation of Electroluminescent Device 8

An electroluminescent device 8 was obtained in the same manner as Example 35 except that the conjugated polymer compound 8 was used in place of the conjugated polymer compound 1 in Example 35.

Example 43

Preparation of Electroluminescent Device 9

An electroluminescent device 9 was obtained in the same manner as Example 35 except that the conjugated polymer compound 9 was used in place of the conjugated polymer compound 1 in Example 35.

Example 44

Preparation of Electroluminescent Device 5

An electroluminescent device 10 was obtained in the same manner as Example 35 except that Ag was used in place of Al in Example 35.

Comparative Example 1

Preparation of Electroluminescent Device C1

An electroluminescent device C1 was obtained in the same manner as Example 35 except that the cathode was directly formed without forming the layer containing the conjugated polymer compound 1 in Example 35.

Comparative Example 2

Preparation of Electroluminescent Device C2

An electroluminescent device C2 was obtained in the same manner as Example 44 except that the cathode was directly formed without forming the layer containing the conjugated polymer compound 1 in Example 44.

Comparative Example 3

Preparation of Electroluminescent Device C3

An electroluminescent device C3 was obtained in the same manner as Example 35 except that the non-conjugated polymer compound 1 was used in place of the conjugated polymer compound 1 in Example 35.

[Measurement]

A forward voltage of 10 V was applied to the electroluminescent devices 1 to 10 and C1 to C3 obtained as described above to measure light-emitting brightness and light-emitting efficiency. The results are indicated in Table 1.

TABLE 1

| | Conjugated polymer compound | Cathode | Light-emitting brightness (cd/m$^2$) | Light-emitting efficiency (cd/A) |
|---|---|---|---|---|
| Example 35 (Electroluminescent device 1) | Conjugated polymer compound 1 | Al | 4716.4 | 4.20 |
| Example 36 (Electroluminescent device 2) | Conjugated polymer compound 2 | Al | 2987.9 | 3.56 |
| Example 37 (Electroluminescent device 3) | Conjugated polymer compound 3 | Al | 4800.0 | 4.08 |
| Example 38 (Electroluminescent device 4) | Conjugated polymer compound 4 | Al | 4745.2 | 4.09 |
| Example 39 (Electroluminescent device 5) | Conjugated polymer compound 5 | Al | 207.8 | 1.35 |
| Example 40 (Electroluminescent device 6) | Conjugated polymer compound 6 | Al | 95.9 | 0.65 |
| Example 41 (Electroluminescent device 7) | Conjugated polymer compound 7 | Al | 4493.8 | 5.44 |
| Example 42 (Electroluminescent device 8) | Conjugated polymer compound 8 | Al | 8671.3 | 6.18 |
| Example 43 (Electroluminescent device 9) | Conjugated polymer compound 9 | Al | 3608.6 | 4.87 |
| Example 44 (Electroluminescent device 10) | Conjugated polymer compound 1 | Ag | 29.7 | 0.71 |
| Comparative Example 1 (Electroluminescent device C1) | Absent | Al | 1.5 | 0.01 |
| Comparative Example 2 (Electroluminescent device C2) | Absent | Ag | 12.8 | 0.5 |
| Comparative Example 3 (Electroluminescent device C3) | Non-conjugated polymer compound 1 | Al | 0.7 | 0.01 |

The invention claimed is:

1. An electronic device including a layer comprising a polymer compound comprising one or more structural units selected from the group consisting of a structural unit represented by formula (1) and a structural unit represented by formula (7) as a charge injection layer and/or a charge transport layer, wherein the structural unit represented by formula (1) is:

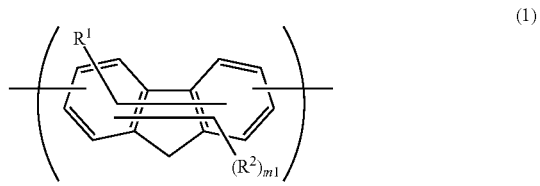

(1)

wherein
R$^1$ represents a group represented by formula (2) or formula (3);
R$^2$ represents a group represented by formula (4);
m1 represents an integer of 0 or more;
when R$^2$ is plurally present, they may be the same or different; and
a hydrogen atom in formula (1) may be replaced with a substituent other than R$^1$ or R$^2$;

wherein the group represented by formula (2) is:

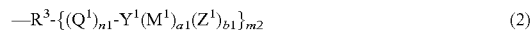

(2)

wherein
R$^3$ represents a single bond, or a (1+m2)-valent organic group that optionally has a substituent;
Q$^1$ represents a divalent organic group;
Y$^1$ represents $-CO_2^-$, $-SO_3^-$, $-SO_2^-$, $-PO_3^{2-}$ or $-B(R^\alpha)_3^-$;
M$^1$ represents Cs$^+$;
Z$^1$ represents F$^-$, Cl$^-$, Br$^-$, I$^-$, OH$^-$, B(R$^a$)$_4^-$, R$^a$SO$_3^-$, R$^a$COO$^-$, ClO$^-$, ClO$_2^-$, ClO$_3^-$, ClO$_4^-$, SCN$^-$, CN$^-$, NO$_3^-$, SO$_4^{2-}$, HSO$_4^-$, PO$_4^{3-}$, HPO$_4^{2-}$, H$_2$PO$_4^-$, BF$_4^-$, or PF$_6^-$;
n1 represents an integer of 0 or more;
a1 represents an integer of 1 or more, and b1 represents an integer of 0 or more, wherein a1 and b1 are selected such that a charge of the group represented by formula (2) is zero;
R$^\alpha$ represents an alkyl group having 1 to 30 carbon atoms that optionally has a substituent, or an aryl group having 6 to 50 carbon atoms that optionally has a substituent;
R$^a$ represents an alkyl group having 1 to 30 carbon atoms that optionally has a substituent, or an aryl group having 6 to 50 carbon atoms that optionally has a substituent;
m2 represents an integer of 1 or more, and when R$^3$ is a single bond, m2 represents 1; and
when Q$^1$, Y$^1$, Z$^1$, n1, a1 and b1 are each plurally present, they each may be the same or different;

wherein the group represented by formula (3) is:

(3)

wherein
R$^4$ represents a single bond, or a (1+m3)-valent organic group that optionally has a substituent;
Q$^2$ represents a divalent organic group;
Y$^2$ represents a carbocation, an ammonium cation, a phosphonium cation, a sulfonium cation, or an iodonium cation;
M$^2$ represents F$^-$, Cl$^-$, Br$^-$, I$^-$, OH$^-$, B(R$^b$)$_4^-$, R$^b$SO$_3^-$, R$^b$COO$^-$, ClO$^-$, ClO$_2^-$, ClO$_3^-$, ClO$_4^-$, SCN$^-$, CN$^-$, NO$_3^-$, SO$_4^{2-}$, HSO$_4^-$, PO$_4^{3-}$, HPO$_4^{2-}$, H$_2$PO$_4^-$, BF$_4^-$ or PF$_6^-$;
Z$^2$ represents a metallic cation, or represents an ammonium cation that optionally has a substituent;
n2 represents an integer of 0 or more;

a2 represents an integer of 1 or more, and b2 represents an integer of 0 or more, wherein a2 and b2 are selected such that a charge of the group represented by formula (3) is zero;

$R^b$ represents an alkyl group having 1 to 30 carbon atoms that optionally has a substituent, or an aryl group having 6 to 50 carbon atoms that optionally has a substituent;

m3 represents an integer of 1 or more, and when $R^4$ is a single bond, m3 represents 1; and when $Q^2$, $Y^2$, $M^2$, $Z^2$, n2, a2 and b2 are each plurally present, they each may be the same or different;

wherein the group represented by formula (4) is:

(4)

wherein $R^5$ represents a single bond, or a (1+m4)-valent organic group that optionally has a substituent;

$Q^3$ represents a divalent organic group;

$Y^3$ represents a cyano group, or a group represented by formula (5) or formula (6);

n3 represents an integer of 0 or more;

m4 represents an integer of 1 or more, and when $R^5$ is a single bond, m4 is 1; and when $Q^3$, $Y^3$ and n3 are each plurally present, they each may be the same or different;

wherein the group represented by formula (5) or formula (6) are:

(5)

(6)

wherein

R' represents a divalent hydrocarbon group that optionally has a substituent;

R" represents a hydrogen atom, a monovalent hydrocarbon group that optionally has a substituent, a carboxyl group, a sulfo group, a hydroxy group, a mercapto group, —$NR^C_2$, a cyano group or —$C(=O)NR^C_2$;

R''' represents a trivalent hydrocarbon group that optionally has a substituent;

a3 in formula (5) represents an integer of 3 to 10;

a3 in formula (6) represents an integer of 1 or more;

$R^c$ represents an alkyl group having 1 to 30 carbon atoms that optionally has a substituent, or an aryl group having 6 to 50 carbon atoms that optionally has a substituent; and when R', R" and R''' are each plurally present, they each may be the same or different; and wherein the structural unit represented by formula (7) is:

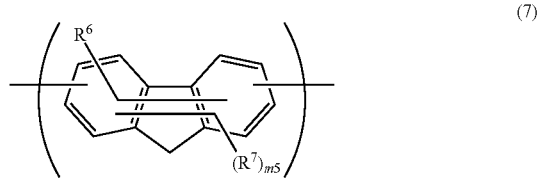

(7)

wherein $R^6$ represents a group represented by formula (8) or formula (9);

$R^7$ represents the group represented by formula (4), wherein $R^5$, $Q^3$, n3, and m4 are represented as defined above, $Y^3$ represents a cyano group or a group represented by formula (5) or formula (6), wherein a3 in formula (5) or formula (6) represents an integer of 1 or more, R', R", R''', and Rc are represented as defined above, and when $Q^3$, $Y^3$, n3, R', R", and R''' are plurally present, they may each be the same or different;

m5 represents an integer of 0 or more;

when $R^7$ is plurally present, they may be the same or different; and a hydrogen atom in formula (7) may be replaced with a substituent other than $R^6$ or $R^7$;

wherein the group represented by formula (8) is:

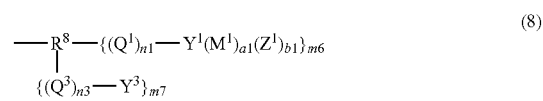

(8)

wherein $R^8$ represents a (1+m6+m7)-valent organic group that optionally has a substituent;

$M^1$ represents a metallic cation, or represents an ammonium cation that optionally has a substituent;

$Y^3$ represents a cyano group or a group represented by formula (5) or formula (6), wherein a3 in formula (5) or formula (6) represents an integer of 1 or more, R', R", R''', and Rc are represented as defined above, and when R', R", and R''' are plurally present, they may each be the same or different;

$Q^1$, $Q^3$, $Y^1$, $Z^1$, n1, n3, a1 and b1 are the same as the corresponding definitions above;

m6 and m7 each independently represent an integer of 1 or more; and when $Q^1$, $Q^3$, $Y^1$, $Y^3$, $M^1$, $Z^1$, n1, n3, a1 and b1 are each plurally present, they each may be the same or different;

wherein the group represented by formula (9) is:

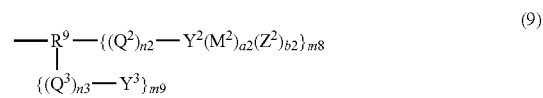

(9)

wherein $R^9$ represents a (1+m8+m9)-valent organic group that optionally has a substituent;

$Y^3$ represents a cyano group or a group represented by formula (5) or formula (6), wherein a3 in formula (5) or formula (6) represents an integer of 1 ore more, R', R", R''', and Rc are represented as defined above, and when R', R", and R''' are plurally present, they may each be the same or different;

$Q^2$, $Q^3$, $Y^2$, $M^2$, $Z^2$, n2, n3, a2 and b2 are the same as the corresponding definitions above;

m8 and m9 each independently represent an integer of 1 or more; and when $Q^2$, $Q^3$, $Y^2$, $Y^3$, $M^2$, $Z^2$, n2, n3, a2, b2 are each plurally present, they each may be the same or different.

2. The electronic device according to claim 1, wherein the polymer compound comprises one or more structural units selected from the group consisting of a structural unit represented by formula (10) and a structural unit represented by formula (11), wherein the structural unit represented by formula (10) is:

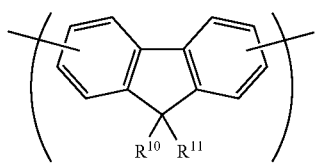
(10)

wherein
- $R^{10}$ represents the group represented by formula (2) or formula (3);
- $R^{11}$ represents the group represented by formula (4) as defined in formula (1) above; and
- a hydrogen atom in formula (10) may be replaced with a substitutent other than $R^{10}$ or $R^{11}$; and wherein the structural unit represented by formula (11) is:

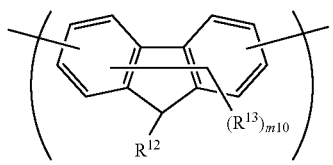
(11)

wherein
- $R^{12}$ represents the group represented by formula (8) or formula (9);
- $R^{13}$ represents the group represented by formula (4) as defined in formula (7) above;
- m10 represents an integer of 0 or more;
- when $R^{13}$ is plurally present, they may be the same or different; and
- a hydrogen atom in formula (11) may be replaced with a substituent other than $R^{12}$ or $R^{13}$.

3. The electronic device according to claim 1, wherein the layer comprising the polymer compound is an electron injection layer and/or an electron transport layer.

4. The electronic device according to claim 1, which is an electroluminescent device.

5. A polymer compound comprising one or more structural units selected from the group consisting of a structural unit represented by formula (1) and a structural unit represented by formula (7), wherein the structural unit represented by formula (1) is:

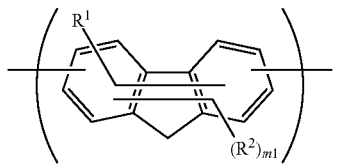
(1)

wherein
- $R^1$ represents a group represented by formula (2) or formula (3);
- $R^2$ represents a group represented by formula (4);
- m1 represents an integer of 0 or more;
- when $R^2$ is plurally present, they may be the same or different; and
- a hydrogen atom in formula (1) may be replaced with a substituent other than $R^1$ or $R^2$;

wherein the group represented by formula (2) is:

$$-R^3-\{(Q^1)_{n1}-Y^1(M^1)_{a1}(Z^1)_{b1}\}_{m2} \quad (2)$$

wherein
- $R^3$ represents a single bond, or a (1+m2)-valent organic group that optionally has a substituent;
- $Q^1$ represents a divalent organic group;
- $Y^1$ represents $-CO_2^-$, $-SO_3^-$, $-SO_2^-$, $-PO_3^{2-}$ or $-B(R^\alpha)_3^-$;
- $M^1$ represents $Cs^+$;
- $Z^1$ represents $F^-$, $Cl^-$, $Br^-$, $I^-$, $OH^-$, $B(R^a)_4^-$, $R^aSO_3^-$, $R^aCOO^-$, $ClO^-$, $ClO_2^-$, $ClO_3^-$, $ClO_4^-$, $SCN^-$, $CN^-$, $NO_3^-$, $SO_4^{2-}$, $HSO_4^-$, $PO_4^{3-}$, $HPO_4^{2-}$, $H_2PO_4^-$, $BF_4^-$, or $PF_6^-$;
- n1 represents an integer of 0 or more;
- a1 represents an integer of 1 or more, and b1 represents an integer of 0 or more, wherein a1 and b1 are selected such that a charge of the group represented by formula (2) is zero;
- $R^\alpha$ represents an alkyl group having 1 to 30 carbon atoms that optionally has a substituent, or an aryl group having 6 to 50 carbon atoms that optionally has a substituent;
- $R^a$ represents an alkyl group having 1 to 30 carbon atoms that optionally has a substituent, or an aryl group having 6 to 50 carbon atoms that optionally has a substituent;
- m2 represents an integer of 1 or more, and when $R^3$ is a single bond, m2 represents 1; and
- when $Q^1$, $Y^1$, $Z^1$, n1, a1 and b1 are each plurally present, they each may be the same or different;

wherein the group represented by formula (3) is:

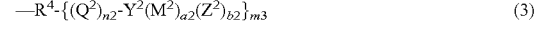
$$-R^4-\{(Q^2)_{n2}-Y^2(M^2)_{a2}(Z^2)_{b2}\}_{m3} \quad (3)$$

wherein
- $R^4$ represents a single bond, or a (1+m3)-valent organic group that optionally has a substituent;
- $Q^2$ represents a divalent organic group;
- $Y^2$ represents a carbocation, an ammonium cation, a phosphonium cation, a sulfonium cation, or an iodonium cation;
- $M^2$ represents $F^-$, $Cl^-$, $Br^-$, $I^-$, $OH^-$, $B(R^b)_4^-$, $R^bSO_3^-$, $R^bCOO^-$, $ClO^-$, $ClO_2^-$, $ClO_3^-$, $ClO_4^-$, $SCN^-$, $CN^-$, $NO_3^-$, $SO_4^{2-}$, $HSO_4^-$, $PO_4^{3-}$, $HPO_4^{2-}$, $H_2PO_4^-$, $BF_4^-$ or $PF_6^-$;
- $Z^2$ represents a metallic cation, or represents an ammonium cation that optionally has a substituent;
- n2 represents an integer of 0 or more;
- a2 represents an integer of 1 or more, and b2 represents an integer of 0 or more, wherein a2 and b2 are selected such that a charge of the group represented by formula (3) is zero;
- $R^b$ represents an alkyl group having 1 to 30 carbon atoms that optionally has a substituent, or an aryl group having 6 to 50 carbon atoms that optionally has a substituent;
- m3 represents an integer of 1 or more, and when $R^4$ is a single bond, m3 represents 1; and
- when $Q^2$, $Y^2$, $M^2$, $Z^2$, n2, a2 and b2 are each plurally present, they each may be the same or different;

wherein the group represented by formula (4) is:

$$-R^5-\{(Q^3)_{n3}-Y^3\}_{m4} \quad (4)$$

wherein
- $R^5$ represents a single bond, or a (1+m4)-valent organic group that optionally has a substituent;
- $Q^3$ represents a divalent organic group;

Y³ represents a cyano group, or a group represented by formula (5) or formula (6);

n3 represents an integer of 0 or more;

m4 represents an integer of 1 or more, and when R⁵ is a single bond, m4 is 1; and when Q³, Y³ and n3 are each plurally present, they each may be the same or different;

wherein the group represented by formula (5) or formula (6) are:

(5)

(6)

wherein

R' represents a divalent hydrocarbon group that optionally has a substituent;

R" represents a hydrogen atom, a monovalent hydrocarbon group that optionally has a substituent, a carboxyl group, a sulfo group, a hydroxy group, a mercapto group, —NR$^c_2$, a cyano group or —C(=O)NR$^c_2$;

R''' represents a trivalent hydrocarbon group that optionally has a substituent;

a3 in formula (5) represents an integer of 3 to 10;

a3 in formula (6) represents an integer of 1 or more;

R$^c$ represents an alkyl group having 1 to 30 carbon atoms that optionally has a substituent, or an aryl group having 6 to 50 carbon atoms that optionally has a substituent; and when R', R" and R''' are each plurally present, they each may be the same or different; and wherein the structural unit represented by formula (7) is:

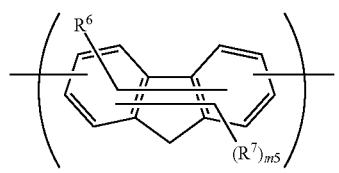

(7)

wherein

R⁶ represents a group represented by formula (8) or formula (9);

R⁷ represents the group represented by formula (4), wherein

R⁵, Q³, n3, and m4 are represented as defined above, Y³ represents a cyano group or a group represented by formula (5) or formula (6), wherein a3 in formula (5) or formula (6) represents an integer of 1 or more, R', R", R''', and Rc are represented as defined above, and when Q³, Y³, n3, R', R", and R''' are plurally present, they may each be the same or different;

m5 represents an integer of 0 or more;

when R⁷ is plurally present, they may be the same or different; and a hydrogen atom in formula (7) may be replaced with a substituent other than R⁶ or R⁷;

wherein the group represented by formula (8) is:

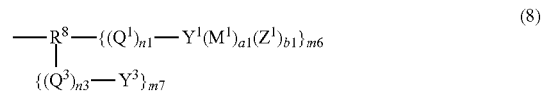

(8)

wherein

R⁸ represents a (1+m6+m7)-valent organic group that optionally has a substituent;

M¹ represents a metallic cation, or represents an ammonium cation that optionally has a substituent;

Y³ represents a cyano group or a group represented by formula (5) or formula (6), wherein a3 in formula (5) or formula (6) represents an integer of 1 or more, R', R", R''', and Rc are represented as defined above, and when R', R", and R''' are plurally present, they may each be the same or different;

Q¹, Q³, Y¹, Z¹, n1, n3, a1 and b1 are the same as the corresponding definitions above;

m6 and m7 each independently represent an integer of 1 or more; and when Q¹, Q³, Y¹, Y³, M¹, Z¹, n1, n3, a1 and b1 are each plurally present, they each may be the same or different;

wherein the group represented by formula (9) is:

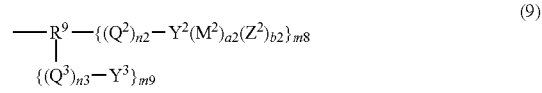

(9)

wherein

R⁹ represents a (1+m8+m9)-valent organic group that optionally has a substituent;

Y³ represents a cyano group or a group represented by formula (5) or formula (6), wherein a3 in formula (5) or formula (6) represents an integer of 1 or more, R', R", R''', and Rc are represented as defined above, and when R', R", and R''' are plurally present, they may each be the same or different;

Q², Q³, Y², M², Z², n2, n3, a2 and b2 are the same as the corresponding definitions above;

m8 and m9 each independently represent an integer of 1 or more; and when Q², Q³, Y², Y³, M², Z², n2, n3, a2 and b2 are each plurally present, they each may be the same or different.

6. The polymer compound according to claim 5, wherein the polymer compound comprises one or more structural units selected from the group consisting of a structural unit represented by formula (10) and a structural unit represented by formula (11), wherein the structural unit represented by formula (10) is:

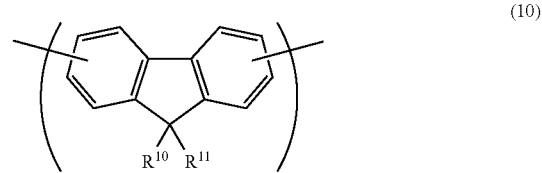

(10)

wherein

R¹⁰ represents the group represented by formula (2) or formula (3);

R¹¹ represents the group represented by formula (4) as defined in formula (1) above; and a hydrogen atom in formula (10) may be replaced with a substituent other than $R^{10}$ or $R^{11}$; and wherein the structural unit represented by formula (11) is:

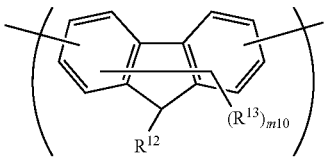

(11)

wherein
$R^{12}$ represents the group represented by formula (8) or formula (9);
$R^{13}$ represents the group represented by formula (4) as defined in formula (7) above;
m10 represents an integer of 0 or more;
when $R^{13}$ is plurally present, they may be the same or different; and
a hydrogen atom in formula (11) may be replaced with a substituent other than $R^{12}$ or $R^{13}$.

7. A method of producing a polymer compound comprising a structural unit represented by formula (1), which includes polymerizing an organic compound represented by formula (17A) to obtain the polymer compound comprising the structural unit represented by formula (1), wherein the organic compound represented by formula (17A) is:

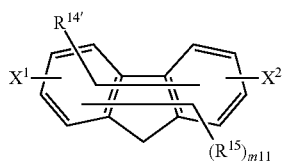

(17A)

wherein
$R^{14'}$ represents a group represented by formula (2), or a group represented by formula (3);
$R^{15}$ represents a group represented by formula (4);
m11 represents an integer of 0 or more;
$X^1$ and $X^2$ each independently represent a group involved in a fused polymerization;
when $R^{15}$ is plurally present, they may be the same or different; and
a hydrogen atom in formula (17A) may be replaced with a substituent other than $R^{14'}$ or $R^{15}$;
wherein the group represented by formula (2) is:

(2)

wherein
$R^3$ represents a single bond, or a (1+m2)-valent organic group that optionally has a substituent;
$Q^1$ represents a divalent organic group;
$Y^1$ represents $-CO_2^-$, $-SO_3^-$, $-SO_2^-$, $-PO_3^{2-}$ or $-B(R^\alpha)_3^-$;
$M^1$ represents $Cs^+$;
$Z^1$ represents $F^-$, $Cl^-$, $Br^-$, $I^-$, $OH^-$, $B(R^a)_4^-$, $R^aSO_3^-$, $R^aCOO^-$, $ClO^-$, $ClO_2^-$, $ClO_3^-$, $ClO_4^-$, $SCN^-$, $CN^-$, $NO_3^-$, $SO_4^{2-}$, $HSO_4^-$, $PO_4^{3-}$, $HPO_4^{2-}$, $H_2PO_4^-$, $BF_4^-$, or $PF_6^-$;
n1 represents an integer of 0 or more;
a1 represents an integer of 1 or more, and b1 represents an integer of 0 or more, wherein a1 and b1 are selected such that a charge of the group represented by formula (2) is zero;
$R^\alpha$ represents an alkyl group having 1 to 30 carbon atoms that optionally has a substituent, or an aryl group having 6 to 50 carbon atoms that optionally has a substituent;
$R^a$ represents an alkyl group having 1 to 30 carbon atoms that optionally has a substituent, or an aryl group having 6 to 50 carbon atoms that optionally has a substituent;
m2 represents an integer of 1 or more, and when $R^3$ is a single bond, m2 represents 1; and
when $Q^1$, $Y^1$, $Z^1$, n1, a1 and b1 are each plurally present, they each may be the same or different;
wherein the group represented by formula (3) is:

(3)

wherein
$R^4$ represents a single bond, or a (1+m3)-valent organic group that optionally has a substituent;
$Q^2$ represents a divalent organic group;
$Y^2$ represents a carbocation, an ammonium cation, a phosphonium cation, a sulfonium cation, or an iodonium cation;
$M^2$ represents $F^-$, $Cl^-$, $Br^-$, $I^-$, $OH^-$, $B(R^b)_4^-$, $R^bSO_3^-$, $R^bCOO^-$, $ClO^-$, $ClO_2^-$, $ClO_3^-$, $ClO_4^-$, $SCN^-$, $CN^-$, $NO_3^-$, $SO_4^{2-}$, $HSO_4^-$, $PO_4^{3-}$, $HPO_4^{2-}$, $H_2PO_4^-$, $BF_4^-$ or $PF_6^-$;
$Z^2$ represents a metallic cation, or represents an ammonium cation that optionally has a substituent;
n2 represents an integer of 0 or more;
a2 represents an integer of 1 or more, and b2 represents an integer of 0 or more, wherein a2 and b2 are selected such that a charge of the group represented by formula (3) is zero;
$R^b$ represents an alkyl group having 1 to 30 carbon atoms that optionally has a substituent, or an aryl group having 6 to 50 carbon atoms that optionally has a substituent;
m3 represents an integer of 1 or more, and when $R^4$ is a single bond, m3 represents 1; and
when $Q^2$, $Y^2$, $M^2$, $Z^2$, n2, a2 and b2 are each plurally present, they each may be the same or different;
wherein the group represented by formula (4) is:

(4)

wherein
$R^5$ represents a single bond, or a (1+m4)-valent organic group that optionally has a substituent;
$Q^3$ represents a divalent organic group;
$Y^3$ represents a cyano group, or a group represented by formula (5) or formula (6);
n3 represents an integer of 0 or more;
m4 represents an integer of 1 or more, and when $R^5$ is a single bond, m4 is 1; and
when $Q^3$, $Y^3$ and n3 are each plurally present, they each may be the same or different;
wherein the group represented by formula (5) or formula (6) are:

(5)

(6)

wherein

R' represents a divalent hydrocarbon group that optionally has a substituent;

R'' represents a hydrogen atom, a monovalent hydrocarbon group that optionally has a substituent, a carboxyl group, a sulfo group, a hydroxy group, a mercapto group, —$NR^c_2$, a cyano group or —$C(=O)NR^c_2$;

R''' represents a trivalent hydrocarbon group that optionally has a substituent;

a3 in formula (5) represents an integer of 3 to 10;

a3 in formula (6) represents an integer of 1 or more;

$R^c$ represents an alkyl group having 1 to 30 carbon atoms that optionally has a substituent, or an aryl group having 6 to 50 carbon atoms that optionally has a substituent; and when R', R'' and R''' are each plurally present, they each may be the same or different; and wherein the structural unit represented by formula (1) is:

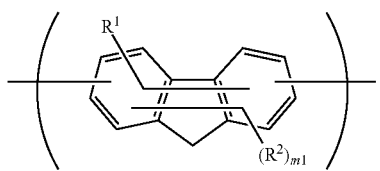 (1)

wherein $R^1$ represents the group represented by formula (2) or formula (3);

$R^2$ represents the group represented by formula (4);

m1 represents an integer of 0 or more;

when $R^2$ is plurally present, they may be the same or different; and a hydrogen atom in formula (1) may be replaced with a substituent other than $R^1$ or $R^2$.

8. A method of producing a polymer compound comprising a structural unit represented by formula (1), which includes:

(i) polymerizing an organic compound represented by formula (17B) to obtain a polymer compound comprising a structural unit represented by formula (17B'); and (ii) ionizing the polymer compound comprising the structural unit represented by formula (17B') to obtain the polymer compound comprising the structural unit represented by formula (1);

wherein the organic compound represented by formula (17B) is:

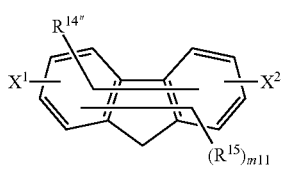 (17B)

wherein $R^{14''}$ represents a group represented by formula (18), or a group represented by formula (19);

$R^{15}$ represents a group represented by formula (4);

m11 represents an integer of 0 or more;

$X^1$ and $X^2$ each independently represent a group involved in a fused polymerization;

when $R^{15}$ is plurally present, they may be the same or different; and a hydrogen atom in formula (17B) may be replaced with a substituent other than $R^{14''}$ or $R^{15}$;

wherein the group represented by formula (18) is:

—$R^{16}$-{$(Q^4)_{n4}$-$Y^4$}$_{m12}$ (18)

wherein $R^{16}$ represents a single bond, or a (1+m12)-valent organic group that optionally has a substituent;

$Q^4$ represents a divalent organic group;

$Y^4$ represents —$CO_2R^x$, —$SO_3R^x$, —$SO_2R^x$, —$PO_3(R^x)_2$ or —$B(R^x)_2$;

n4 represents an integer of 0 or more;

$R^x$ represents a hydrogen atom, an alkyl group having 1 to 30 carbon atoms that optionally has a substituent, or an aryl group having 6 to 50 carbon atoms that optionally has a substituent;

m12 represents an integer of 1 or more, and when $R^{16}$ is a single bond, m12 represents 1; and when $Q^4$, $Y^4$, n4 and $R^x$ are each plurally present, they each may be the same or different;

wherein the group represented by formula (19) is:

—$R^{17}$-{$(Q^5)_{n5}$-$Y^5$}$_{m13}$ (19)

wherein $R^{17}$ represents a single bond, or a (1+m13)-valent organic group that optionally has a substituent;

$Q^5$ represents a divalent organic group;

$Y^5$ represents a halogenated alkyl group, a halogen atom, —$N(R^\delta)_2$, —$P(R^\delta)_2$ or —$SR^\delta$;

n5 represents an integer of 0 or more;

$R^\delta$ represents a hydrogen atom, an alkyl group having 1 to 30 carbon atoms that optionally has a substituent, or an aryl group having 6 to 50 carbon atoms that optionally has a substituent;

m13 represents an integer of 1 or more, and when $R^{17}$ is a single bond, m13 represents 1; and when $Q^5$, $Y^5$, n5 and $R^\delta$ are each plurally present, they each may be the same or different;

wherein the group represented by formula (4) is:

—$R^5$-{$(Q^3)_{n3}$-$Y^3$}$_{m4}$ (4)

wherein $R^5$ represents a single bond, or a (1+m4)-valent organic group that optionally has a substituent;

$Q^3$ represent a divalent organic group;

$Y^3$ represents a cyano group, or a group represented by formula (5) or formula (6);

n3 represents an integer of 0 or more;

m4 represents an integer of 1 or more, and when $R^5$ is a single bond, m4 is 1; and when $Q^3$, $Y^3$ and n3 are each plurally present, they each may be the same or different;

wherein the group represented by formula (5) or formula (6) are:

—O—(R'O)$_{a3}$—R'' (5)

(6)

wherein
R' represents a divalent hydrocarbon group that optionally has a substituent;
R" represents a hydrogen atom, a monovalent hydrocarbon group that optionally has a substituent, a carboxyl group, a sulfo group, a hydroxy group, a mercapto group, —$NR^c_2$, a cyano group or —$C(=O)NR^c_2$;
R'" represents a trivalent hydrocarbon group that optionally has a substituent;
a3 in formula (5) represents an integer of 3 to 10;
a3 in formula (6) represents an integer of 1 or more;
$R^c$ represents an alkyl group having 1 to 30 carbon atoms that optionally has a substituent, or an aryl group having 6 to 50 carbon atoms that optionally has a substituent; and
when R', R" and R'" are each plurally present, they each may be the same or different;
wherein the organic compound represented by formula (17B') is:

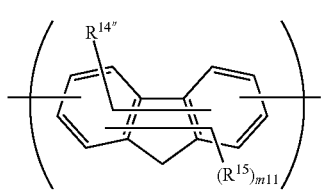

(17B')

wherein
$R^{14"}$ represents the group represented by formula (18), or the group represented by formula (19);
$R^{15}$ and m11 are the same as the corresponding definitions above; and
a hydrogen atom in formula (17B') may be replaced with a substituent other than $R^{14"}$ or $R^{15}$;
wherein the structural unit represented by formula (1) is:

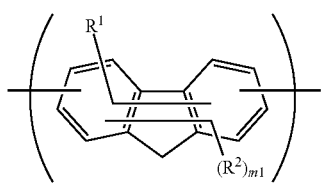

(1)

wherein
$R^1$ represents a group represented by formula (2) or formula (3);
$R^2$ represents the group represented by formula (4);
m1 represents an integer of 0 or more;
when $R^2$ is plurally present, they may be the same or different; and
a hydrogen atom in formula (1) may be replaced with a substituent other than $R^1$ or $R^2$;
wherein the group represented by formula (2) is:

(2)

wherein
$R^3$ represents a single bond, or a (1+m2)-valent organic group that optionally has a substituent;
$Q^1$ represents a divalent organic group;
$Y^1$ represents —$CO_2^-$, —$SO_3^-$, —$SO_2^-$, —$PO_3^{2-}$ or —$B(R^\alpha)_3^-$;

$M^1$ represents $Cs^+$;
$Z^1$ represents $F^-$, $Cl^-$, $Br^-$, $I^-$, $OH^-$, $B(R^a)_4^-$, $R^aSO_3^-$, $R^aCOO^-$, $ClO^-$, $ClO_2^-$, $ClO_3^-$, $ClO_4^-$, $SCN^-$, $CN^-$, $NO_3^-$, $SO_4^{2-}$, $HSO_4^-$, $PO_4^{3-}$, $HPO_4^{2-}$, $H_2PO_4^-$, $BF_4^-$, or $PF_6^-$;
n1 represents an integer of 0 or more;
a1 represents an integer of 1 or more, and b1 represents an integer of 0 or more, wherein a1 and b1 are selected such that a charge of the group represented by formula (2) is zero;
$R^\alpha$ represents an alkyl group having 1 to 30 carbon atoms that optionally has a substituent, or an aryl group having 6 to 50 carbon atoms that optionally has a substituent;
$R^a$ represents an alkyl group having 1 to 30 carbon atoms that optionally has a substituent, or an aryl group having 6 to 50 carbon atoms that optionally has a substituent;
m2 represents an integer of 1 or more, and when $R^3$ is a single bond, m2 represents 1; and
when $Q^1$, $Y^1$, $Z^1$, n1, a1 and b1 are each plurally present, they each may be the same or different;
wherein the group represented by formula (3) is:

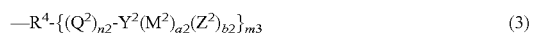

(3)

wherein
$R^4$ represents a single bond, or a (1+m3)-valent organic group that optionally has a substituent;
$Q^2$ represents a divalent organic group;
$Y^2$ represents a carbocation, an ammonium cation, a phosphonium cation, a sulfonium cation, or an iodonium cation;
$M^2$ represents $F^-$, $Cl^-$, $Br^-$, $I^-$, $OH^-$, $B(R^b)_4^-$, $R^bSO_3^-$, $R^bCOO^-$, $ClO^-$, $ClO_2^-$, $ClO_3^-$, $ClO_4^-$, $SCN^-$, $CN^-$, $NO_3^-$, $SO_4^{2-}$, $HSO_4^-$, $PO_4^{3-}$, $HPO_4^{2-}$, $H_2PO_4^-$, $BF_4^-$ or $PF_6^-$;
$Z^2$ represents a metallic cation, or represents an ammonium cation that optionally has a substituent;
n2 represents an integer of 0 or more;
a2 represents an integer of 1 or more, and b2 represents an integer of 0 or more, wherein a2 and b2 are selected such that a charge of the group represented by formula (3) is zero;
$R^b$ represents an alkyl group having 1 to 30 carbon atoms that optionally has a substituent, or an aryl group having 6 to 50 carbon atoms that optionally has a substituent;
m3 represents an integer of 1 or more, and when $R^4$ is a single bond, m3 represents 1; and
when $Q^2$, $Y^2$, $M^2$, $Z^2$, n2, a2 and b2 are each plurally present, they each may be the same or different.

9. A method of producing a polymer compound comprising a structural unit represented by formula (7), which includes polymerizing an organic compound represented by formula (20A) to obtain the polymer compound comprising the structural unit represented by formula (7),
wherein the organic compound represented by formula (20A) is:

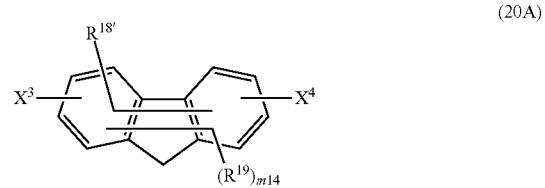

(20A)

wherein
R$^{18'}$ represents a group represented by formula (8), or a group represented by formula (9);
R$^{19}$ represents a group represented by formula (4);
m14 represents an integer of 0 or more;
X$^3$ and X$^4$ each independently represent a group involved in a fused polymerization;
when R$^{19}$ is plurally present, they may be the same or different; and
a hydrogen atom in formula (20A) may be replaced with a substituent other than R$^{18'}$ or R$^{19}$;
wherein the group represented by formula (8) is:

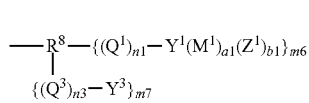 (8)

wherein
R$^8$ represents a (1+m6+m7)-valent organic group that optionally has a substituent;
Q$^1$ represents a divalent organic group;
Q$^3$ represents a divalent organic group;
Y$^1$ represents —CO$_2^-$, —SO$_3^-$, —SO$_2^-$, —PO$_3^{2-}$ or —B(R$^\alpha$)$_3^-$;
Y$^3$ represents a cyano group, or a group represented by formula (5) or formula (6);
M$^1$ represents a metallic cation, or represents an ammonium cation that optional has a substituent;
Z$^1$ represents F$^-$, Cl$^-$, Br$^-$, I$^-$, OH$^-$, B(R$^a$)$_4^-$, R$^a$SO$_3^-$, R$^a$COO$^-$, ClO$^-$, ClO$_2^-$, ClO$_3^-$, ClO$_4^-$, SCN$^-$, CN$^-$, NO$_3^-$, SO$_4^{2-}$, HSO$_4^-$, PO$_4^{3-}$, HPO$_4^{2-}$, H$_2$PO$_4^-$, BF$_4^-$, or PF$_6^-$;
n1 represents an integer of 0 or more;
a1 represents an integer of 1 or more, and b1 represents an integer of 0 or more, wherein a1 and b1 are selected such that a charge of the group represented by formula (2) is zero;
n3 represents an integer of 0 or more;
R$^\alpha$ represents an alkyl group having 1 to 30 carbon atoms that optionally has a substituent, or an aryl group having 6 to 50 carbon atoms that optionally has a substituent;
R$^a$ represents an alkyl group having 1 to 30 carbon atoms that optionally has a substituent, or an aryl group having 6 to 50 carbon atoms that optionally has a substituent;
m6 and m7 each independently represent an integer of 1 or more; and
when Q$^1$, Q$^3$, Y$^1$, Y$^3$, M$^1$, Z$^1$, n1, n3, a1 and b1 are each plurally present, they each may be the same or different;
wherein the group represented by formula (5) or formula (6) are:

—O—(R'O)$_{a3}$—R'' (5)

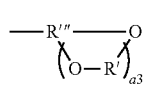 (6)

wherein
R' represents a divalent hydrocarbon group that optionally has a substituent;
R'' represents a hydrogen atom, a monovalent hydrocarbon group that optionally has a substituent, a carboxyl group, a sulfo group, a hydroxy group, a mercapto group, —NR$^c_2$, a cyano group or —C(=O)NR$^c_2$;
R''' represents a trivalent hydrocarbon group that optionally has a substituent;
a3 represents an integer of 1 or more;
R$^c$ represents an alkyl group having 1 to 30 carbon atoms that optionally has a substituent, or an aryl group having 6 to 50 carbon atoms that optionally has a substituent; and
when R', R'' and R''' are each plurally present, they each may be the same or different;
wherein the group represented by formula (9) is:

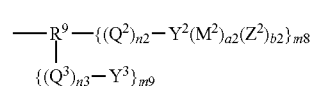 (9)

wherein
R$^9$ represents a (1+m8+m9)-valent organic group that optionally has a substituent;
Q$^3$, Y$^3$ and n3 are the same as the corresponding definitions above;
Q$^2$ represents a divalent organic group;
Y$^2$ represents a carbocation, an ammonium cation, a phosphonium cation, a sulfonium cation, or an iodonium cation;
M$^2$ represents F$^-$, Cl$^-$, Br$^-$, I$^-$, OH$^-$, B(R$^b$)$_4^-$, R$^b$SO$_3^-$, R$^b$COO$^-$, ClO$^-$, ClO$_2^-$, ClO$_3^-$, ClO$_4^-$, SCN$^-$, CN$^-$, NO$_3^-$, SO$_4^{2-}$, HSO$_4^-$, PO$_4^{3-}$, HPO$_4^{2-}$, H$_2$PO$_4^-$, BF$_4^-$ or PF$_6^-$;
Z$^2$ represents a metallic cation, or represents an ammonium cation that optionally has a substituent;
n2 represents an integer of 0 or more;
a2 represents an integer of 1 or more, and b2 represents an integer of 0 or more, wherein a2 and b2 are selected such that a charge of the group represented by formula (3) is zero;
R$^b$ represents an alkyl group having 1 to 30 carbon atoms that optionally has a substituent, or an aryl group having 6 to 50 carbon atoms that optionally has a substituent;
m8 and m9 each independently represent an integer of 1 or more; and
when Q$^2$, Q$^3$, Y$^2$, Y$^3$, M$^2$, Z$^2$, n2, n3, a2 and b2 are each plurally present, they each may be the same or different;
wherein the group represented by formula (4) is:

—R$^5$-{(Q$^3$)$_{n3}$-Y$^3$}$_{m4}$ (4)

wherein
R$^5$ represents a single bond, or a (1+m4)-valent organic group that optionally has a substituent;
Q$^3$, Y$^3$ and n3 are the same as the corresponding definitions above;
m4 represents an integer of 1 or more, and when R$^5$ is a single bond, m4 is 1; and
when Q$^3$, Y$^3$ and n3 are each plurally present, they each may be the same or different;

wherein the structural unit represented by formula (7) is:

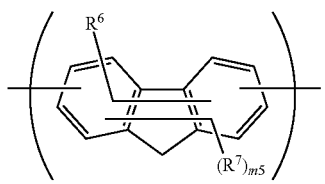

(7)

wherein
R$^6$ represents the group represented by formula (8) or formula (9);
R$^7$ represents the group represented by formula (4);
m5 represents an integer of 0 or more;
when R$^7$ is plurally present, they may be the same or different; and
a hydrogen atom in formula (7) may be replaced with a substituent other than R$^6$ or R$^7$.

10. A method of producing a polymer compound comprising a structural unit represented by formula (7), which includes:
(i') polymerizing an organic compound represented by formula (20B) to obtain a polymer compound comprising a structural unit represented by formula (20B'); and
(ii') ionizing the polymer compound comprising the structural unit represented by formula (20B') to obtain the polymer compound comprising the structural unit represented by formula (7),
wherein the organic compound represented by formula (20B) is:

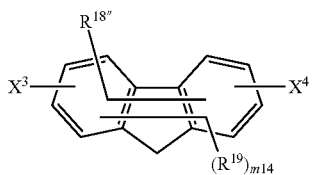

(20B)

wherein
R$^{18''}$ represents a group represented by formula (21), or a group represented by formula (22);
R$^{19}$ represents a group represented by formula (4);
m14 represents an integer of 0 or more;
X$^3$ and X$^4$ each independently represent a group involved in a fused polymerization;
when R$^{19}$ is plurally present, they may be the same or different; and
a hydrogen atom in formula (20B) may be replaced with a substituent other than R$^{18''}$ or R$^{19}$;
wherein the group represented by formula (21) is:

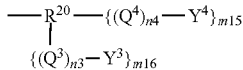

(21)

wherein
R$^{20}$ represents a (1+m15+m16)-valent organic group that optionally has a substituent;
Q$^4$ represents a divalent organic group;

Y$^4$ represents —CO$_2$R$^x$, —SO$_3$R$^x$, —SO$_2$R$^x$, —PO$_3$(R$^x$)$_2$ or —B(R$^x$)$_2$;
n4 represents an integer of 0 or more;
Q$^3$ represents a divalent organic group;
Y$^3$ represents a cyano group, or a group represented by formula (5) or formula (6);
n3 represents an integer of 0 or more;
R$^x$ represents a hydrogen atom, an alkyl group having 1 to 30 carbon atoms that optionally has a substituent, or an aryl group having 6 to 50 carbon atoms that optionally has a substituent;
m15 and m16 each independently represent an integer of 1 or more; and
when Q$^4$, n4, Y$^4$, Q$^3$, n3 and Y$^3$ are each plurally present, they each may be the same or different;
wherein the group represented by formula (5) or formula (6) are:

(5)

(6)

wherein
R' represents a divalent hydrocarbon group that optionally has a substituent;
R'' represents a hydrogen atom, a monovalent hydrocarbon group that optionally has a substituent, a carboxyl group, a sulfo group, a hydroxy group, a mercapto group, —NR$^c_2$, a cyano group or —C(=O)NR$^c_2$;
R''' represents a trivalent hydrocarbon group that optionally has a substituent;
a3 represents an integer of 1 or more;
R$^c$ represents an alkyl group having 1 to 30 carbon atoms that optionally has a substituent, or an aryl group having 6 to 50 carbon atoms that optionally has a substituent; and
when R', R'' and R''' are each plurally present, they each may be the same or different;
wherein the group represented by formula (22) is:

(22)

wherein
R$^{21}$ represents a (1+m17+m18)-valent organic group that optionally has a substituent;
Q$^3$, Y$^3$ and n3 are the same as the corresponding definitions above;
Q$^5$ represents a divalent organic group;
Y$^5$ represents a halogenated alkyl group, a halogen atom, —N(R$^\delta$)$_2$, —P(R$^\delta$)$_2$ or —SR$^\delta$;
n5 represents an integer of 0 or more;
R$^\delta$ represents a hydrogen atom, an alkyl group having 1 to 30 carbon atoms that optionally has a substituent, or an aryl group having 6 to 50 carbon atoms that optionally has a substituent;
m17 and m18 each independently represent an integer of 1 or more; and
when Q$^5$, n5, Y$^5$, Q$^3$, n3 and Y$^3$ are each plurally present, they each may be the same or different;

wherein the group represented by formula (4) is:

$$—R^5-\{(Q^3)_{n3}-Y^3\}_{m4} \qquad (4)$$

wherein
R$^5$ represents a single bond, or a (1+m4)-valent organic group that optionally has a substituent;
Q$^3$, Y$^3$ and n3 are the same as the corresponding definitions above;
m4 represents an integer of 1 or more, and when R$^5$ is a single bond, m4 is 1; and
when Q$^3$, Y$^3$ and n3 are each plurally present, they each may be the same or different;
wherein the organic compound represented by formula (20B') is:

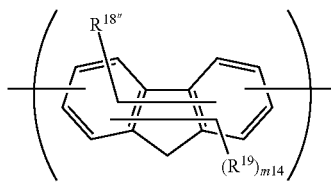

(20B')

wherein
R$^{18''}$ represents the group represented by formula (21), or the group represented by formula (22);
R$^{19}$ and m14 are the same as the corresponding definitions above; and
a hydrogen atom in formula (20B') may be replaced with a substituent other than R$^{18''}$ or R$^{19}$;
wherein the structural unit represented by formula (7) is:

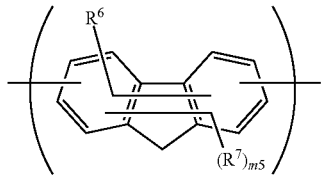

(7)

wherein
R$^6$ represents a group represented by formula (8) or formula (9);
R$^7$ represents the group represented by formula (4);
m5 represents an integer of 0 or more;
when R$^7$ is plurally present, they may be the same or different; and
a hydrogen atom in formula (7) may be replaced with a substituent other than R$^6$ or R$^7$;
wherein the group represented by formula (8) is:

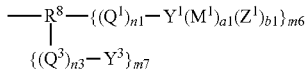

(8)

wherein
R$^8$ represents a (1+m6+m7)-valent organic group that optionally has a substituent;

Q$^3$, Y$^3$ and n3 are the same as the corresponding definitions above;
Q$^1$ represents a divalent organic group;
Y$^1$ represents —CO$_2^-$, —SO$_3^-$, —SO$_2^-$, —PO$_3^{2-}$ or —B(R$^\alpha$)$_3^-$;
M$^1$ represents a metallic cation, or represents an ammonium cation that optionally has a substituent;
Z$^1$ represents F$^-$, Cl$^-$, Br$^-$, I$^-$, OH$^-$, B(R$^a$)$_4^-$, R$^a$SO$_3^-$, R$^a$COO$^-$, ClO$^-$, ClO$_2^-$, ClO$_3^-$, ClO$_4^-$, SCN$^-$, CN$^-$, NO$_3^-$, SO$_4^{2-}$, HSO$_4^-$, PO$_4^{3-}$, HPO$_4^{2-}$, H$_2$PO$_4^-$, BF$_4^-$ or PF$_6^-$;
n1 represents an integer of 0 or more;
a1 represents an integer of 1 or more, and b1 represents an integer of 0 or more, wherein a1 and b1 are selected such that a charge of the group represented by formula (2) is zero;
R$^\alpha$ represents an alkyl group having 1 to 30 carbon atoms that optionally has a substituent, or an aryl group having 6 to 50 carbon atoms that optionally has a substituent;
R$^a$ represents an alkyl group having 1 to 30 carbon atoms that optionally has a substituent, or an aryl group having 6 to 50 carbon atoms that optionally has a substituent;
m6 and m7 each independently represent an integer of 1 or more; and
when Q$^1$, Q$^3$, Y$^1$, Y$^3$, M$^1$, Z$^1$, n1, n3, a1 and b1 are each plurally present, they each may be the same or different;
wherein the group represented by formula (9) is:

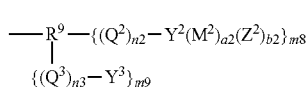

(9)

wherein
R$^9$ represents a (1+m8+m9)-valent organic group that optionally has a substituent;
Q$^3$, Y$^3$ and n3 are the same as the corresponding definitions above;
Q$^2$ represents a divalent organic group;
Y$^2$ represents a carbocation, an ammonium cation, a phosphonium cation, a sulfonium cation, or an iodonium cation;
M$^2$ represents F$^-$, Cl$^-$, Br$^-$, I$^-$, OH$^-$, B(R$^b$)$_4^-$, R$^b$SO$_3^-$, R$^b$COO$^-$, ClO$^-$, ClO$_2^-$, ClO$_3^-$, ClO$_4^-$, SCN$^-$, CN$^-$, NO$_3^-$, SO$_4^{2-}$, HSO$_4^-$, PO$_4^{3-}$, HPO$_4^{2-}$, H$_2$PO$_4^-$, BF$_4^-$ or PF$_6^-$;
Z$^2$ represents a metallic cation, or represents an ammonium cation that optionally has a substituent;
n2 represents an integer of 0 or more;
a2 represents an integer of 1 or more, and b2 represents an integer of 0 or more, wherein a2 and b2 are selected such that a charge of the group represented by formula (3) is zero;
R$^b$ represents an alkyl group having 1 to 30 carbon atoms that optionally has a substituent, or an aryl group having 6 to 50 carbon atoms that optionally has a substituent;
m8 and m9 each independently represent an integer of 1 or more; and
when Q$^2$, Q$^3$, Y$^2$, Y$^3$, M$^2$, Z$^2$, n2, n3, a2 and b2 are each plurally present, they each may be the same or different.

* * * * *